US008722639B2

(12) United States Patent
Krause et al.

(10) Patent No.: US 8,722,639 B2
(45) Date of Patent: *May 13, 2014

(54) MEANS AND METHODS FOR THE TREATMENT OF HEARING LOSS AND PHANTOM HEARING

(75) Inventors: Karl-Heinz Krause, Geneva (CH); Botond Banfi, North Liberty, IA (US)

(73) Assignee: University of Geneva, Geneva (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/336,147

(22) Filed: Dec. 23, 2011

(65) Prior Publication Data

US 2012/0252868 A1  Oct. 4, 2012

Related U.S. Application Data

(62) Division of application No. 11/628,419, filed as application No. PCT/EP2005/006061 on Jun. 6, 2005, now Pat. No. 8,088,359.

(30) Foreign Application Priority Data

Jun. 4, 2004  (EP) ..................................... 04013266

(51) Int. Cl.
| | |
|---|---|
| *C12N 9/00* | (2006.01) |
| *C12N 9/02* | (2006.01) |
| *C12N 1/20* | (2006.01) |
| *C12N 15/00* | (2006.01) |
| *C12N 15/11* | (2006.01) |
| *C07H 21/04* | (2006.01) |

(52) U.S. Cl.
USPC ....... 514/44 A; 435/135; 435/189; 435/252.3; 435/320.1; 536/23.2

(58) Field of Classification Search
None
See application file for complete search history.

(56) References Cited

U.S. PATENT DOCUMENTS

| | | | |
|---|---|---|---|
| 6,846,672 B2 | 1/2005 | Lambeth et al. | 435/325 |
| 7,029,673 B2 | 4/2006 | Lambeth et al. | 424/94.4 |
| 7,056,704 B2 | 6/2006 | Tuschl et al. | 435/91.1 |
| 7,078,196 B2 | 7/2006 | Tuschl et al. | 435/91.1 |
| 7,202,052 B2 | 4/2007 | Lambeth et al. | 435/25 |
| 7,202,053 B2 | 4/2007 | Lambeth et al. | 435/25 |
| 7,226,769 B2 | 6/2007 | Lambeth et al. | 435/192 |
| 2004/0001818 A1 | 1/2004 | Aird et al. | 424/94.4 |
| 2004/0009901 A1 | 1/2004 | Holmdahl et al. | 514/8 |
| 2005/0255487 A1 | 11/2005 | Khvorova et al. | 435/6 |
| 2008/0108583 A1 | 5/2008 | Feinstein | 514/44 A |
| 2009/0156524 A1 | 6/2009 | Feinstein et al. | 514/44 R |
| 2010/0273854 A1 | 10/2010 | Kalinski et al. | 514/44 A |

FOREIGN PATENT DOCUMENTS

| | | |
|---|---|---|
| EP | 0914821 | 5/1999 |
| EP | 1410798 | 4/2004 |
| WO | WO 97/19679 | 6/1997 |
| WO | WO 00/44895 | 8/2000 |
| WO | WO 02/30453 | 4/2002 |
| WO | WO 02/66047 | 8/2002 |
| WO | WO 02/79224 | 10/2002 |
| WO | WO 03/87399 | 10/2003 |
| WO | WO 2004/007689 | 1/2004 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Amarzguioui et al., "Tolerance for mutations and chemical modifications in a siRNA," *Nucleic Acids Research*, 31(2):589-595, 2003.
Babior et al., "The neutrophil NADPH oxidase," *Arch. Biochem. Biophys.*, 397:342-344, 2002.
Babior, "NADPH oxidase: an update," *Blood*, 93:1464-1476, 1999.
Banfi et al., "A $Ca^{2+}$-activated NADPH oxidase in testis, spleen, and lymph nodes," *J Biol. Chem.*, 276:37594-37601, 2001.
Banfi et al., "A mammalian H+ channel generated through alternative splicing of the NADPH oxidase homolog NOH-1," *Science*, 287:138-142, 2000.
Banfi et al., "NOX3, a superoxide-generating NADPH oxidase of the inner ear," J. Biol. Chem., 279:46065-46072, 2004.
Banfi et al., "Two novel proteins activate superoxide generation by the NADPH oxidase Noxi," J. Biol. Chem., 278:3510-3513, 2003.
Bedard and Krause, "The NOX family of ROS-generating NADPH oxidases: Physiology and Pathophysiology," *Physiol. Rev.*, 87:245-313, 2007.
Bokoch and Knaus, "NADPH oxidases: not just for leukocytes anymore!" *Trends Biochem. Sci.*, 28:502-508, 2003.
Borghi et al., "Possible role of HMG-CoA reducatse inhibitors for the treatment of sudden sensorineural hearing loss (SSHL)," *Medical Hypotheses*, 58(5):399-402, 2002.
Braasch et al., "RNA interference in mammalian cells by chemically-modified RNA," *Biochemistry*, 42:7967-7975, 2003.
Caillou et al., "Expression of reduced nicotinamide adenine dinucleotide phosphate oxidase (ThoX, LNOX, Duox) genes and proteins in human thyroid tissues," *J. Clin. Endocrinol. Metab.*, 86:3351-3358, 2001.
Caplen et al., "Specific inhibition of gene expression by small double-stranded RNAs in invertebrate vertebrate systems," *Proc. Natl. Acad. Sci.*, 98(17):9472-9747, 2001.
Chakraborty, "Potentiality of small interfering RNAs (siRNA) as rcent therapeutic targets for gene-silencing," *Current Drug Targets*, 8(3):469-82, 2007.

(Continued)

*Primary Examiner* — Christian Fronda
(74) *Attorney, Agent, or Firm* — Parker Highlander PLLC

(57) ABSTRACT

This invention relates to modulators of NADPH oxidase as a medicament for the treatment and/or prevention of hearing loss and/or phantom hearing. Such modulators preferably act by inhibiting NADPH oxidase activity, wherein the NADPH oxidase comprises or consists of the amino acid sequence of any one of SEQ ID NO: 1, 3 or 5, or (ii) is encoded by a nucleic acid comprising or consisting of the sequence of any one of SEQ ID NO: 2, 4, 6, 23 or 24, or (iii) is a fragment of the protein according to (i) or (ii) and exhibits NADPH oxidase activity, or (iv) has a sequence at least 75% identical with the protein according to (i) or (ii) or with the fragment according to (iii) and exhibits NADPH oxidase activity. Also provided are pharmaceutical compositions, medical uses and diagnostic uses of compounds of the invention.

20 Claims, 10 Drawing Sheets

(56) References Cited

OTHER PUBLICATIONS

Figure 1:
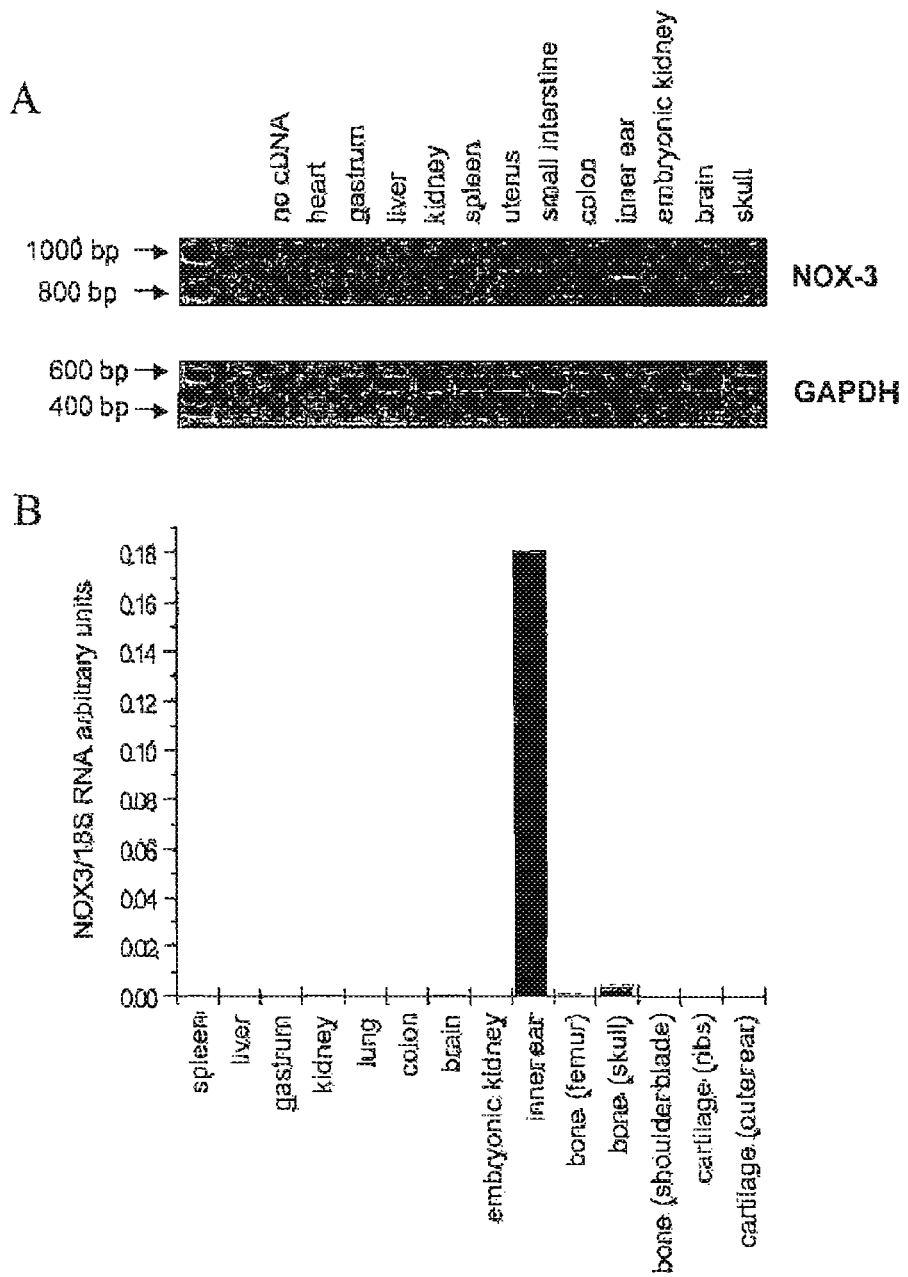

Chalk et al., "Improved and automated prediction of effective siRNA," *Biochem. Biophys. Res. Commun.*, 319(1):264-274, 2004.

Cheng et al., "Homologs of gp91phox: cloning and tissue expression of Nox3, Nox4, and Nox5," *Gene*, 269:131-140, 2001.

Chiu and Rana, "RNAi in human cells: Basic structural and function features of small interfering RNA," *Molecular Cell*, 19:549-561, 2002.

Chiu and Rana, "SiRNA function in RNAi: a chemical modification analysis," *RNA*, 9:1034-1048, 2003.

Clerici et al., "Direct detection of ototoxicant-induced reactive oxygen species generation in cochlear explants," *Hear. Res.*, 98:116-124, 1996.

Czauderna et al., "Structural variations and stabilizing modification of synthetic siRNA in mammalian cells," *Nucleic Acids Research*, 31(11):2705-2716, 2003.

Darlington and Smith, "Vestibulotoxicity following aminoglycoside antibiotics and its prevention," *Curr. Opin. Investig. Drugs*, 4:841-846, 2003.

De Deken et al., "Cloning of two human thyroid cDNAs encoding new members of the NADPH oxidase family," *J. Biol. Chem.*, 275:23227-23233, 2000.

Elbashir et ai., "Duplexes of 21-nucleotide mediated RNA intereference in cultured mammalian cells," *Nature*, 411:494-498, 2001.

Elbashir et al., "Analysis of gene function in somatic mammalian cells using small interfering RNAs," *Methods*, 26:199-213, 2002.

European Search Report, issued in European patent Application No. EP 08004076, dated Jul. 4, 2008.

Fire et al., "Potent and scientific genetic interference by double-stranded RNA in *Caenorhabditis elegans*," *Nature*, 391:806-811, 1998.

Geiszt et al., "Identification of renox, an NAD(P)H oxidase in kidney," *Proc. Natl. Acad. Sci. USA*, 97:8010-8014, 2000.

Geiszt et al., "Proteins Homologous to p47$^{phox}$ support superoxide production by NAD(P)H oxidase 1 in colon epithelial cells," *J. Biol. Chem.*, 278:20006-20012, 2003.

Henderson et al., "The role of antioxidants in protection from impulse noise," *Ann. N.Y. Acad. Sci.*, 884:368-380, 1999.

Holen et al., "Positional effects of short interfering RNAs targeting the human coagulation trigger tissue factor," *Nucleic Acids Research*, 30(8):1757-1766, 2002.

Holen et al., "Similar behavior of single-strand and double-strand siRNAs suggests they act through a common RNAi pathway," *Nucleic Acids Research*, 31(9):2401-2407, 2003.

Holland et al., "Endothelial cell oxidant production: effect of NADPH oxidase inhibitors," *Endothelium*, 7:109-119, 2000.

Jones et al., "Effect of trans-bullar gentamicin treatment on guinea pig angular and linear vestibulo-ocular reflexes," *Exp. Brain Res.*, 153:293-306, 2003.

Kikuchi et al., "NADPH oxidase subunit, gp91$^{phox}$ homologue, preferentially expressed in human colon epithelial cells," *Gene*, 254:237-243, 2000.

Kopke et al., "Toxins and trauma share common pathways in hair cell death," *Ann. N.Y. Acad. Sci.*, 884:171-191, 1999.

Kopke et al., "Use of organotypic cultures of Corti's organ to study the protective effects of antioxidant molecules on cisplatin-induced damage of auditory hair cells," *Am. J Otol.*, 18:559-571, 1997.

Krause et al., "Tissue distribution and putative physiological function of NOX family NADPH oxidases," *Jpn. J Infect. Dis.*, 57: S28-S29, 2004.

Kurreck, "siRNA efficiency: Structure or sequence—That is the Question," *J. Biomed. Biotech.*, 2006(4): 83757, 2006.

Lalucque and Silar, "NADPH oxidase: an enzyme for multicellularity?" *Trends Microbiol.*, 11:9-12, 2003.

Lambeth, "Nox/Duox family of nicotinamide adenine dinucleotide (phosphate) oxidases," *Curr. Opin. Hematol.*, 9:11-17, 2002.

Levenkova et al., "Gene specific siRNA selector," *Bioinformatics*, 20(3):430-432, 2004.

Maak et al., "Oxygen free radical release in human failing myocardium is associated with increased activity of Rac1-GTPase and represents a target for statin treatment," *Circulation*, 108:1567-1574, 2003.

Mahato et al., "Modulation of gene expression by antisense and antigene oligodeoxynucleotides and small interfering RNA," *Expert Opinion on Drug Delivery*, 2(10):3-28, 2005.

Malgrange et al., "Expression of growth factors and their receptors in the postnatal rat cochlea," *Neurochem. Res.*, 23:1133-1138, 1998.

McFadden et al., "Cu/Zn SOD deficiency potentiates hearing loss and cochlear pathology in aged 129,CD-1 mice," *J. Comp. Neurol.*, 413:101-112, 1999.

Mocsai et al., "Differential effects of tyrosine kinase inhibitors and an inhibitor of the mitogen-activated protein kinase cascade on degranulation and superoxide production of human neutrophil granulocytes," *Biochem. Pharmacol.*, 54:781-789, 1997.

Mukherjea et al., "Transtympanic Administration of short interfering (si)RNA for the NOX3 isoform of NADPH oxidase protects against cisplatin-induced hearing loss in the rat," *Antioxidants & Redox Signaling*, 13(5):589-598, 2010.

Naito et al., "siDirect: highly effective, target-specific siRNA design software for mammalian RNA interference," *Nucleic Acids Research*, 32: W124-W129, 2004. Web Server Issue DOI: 10.1093/nar/gkh442.

NCBI Entrez protein database entry NP_056533, (2009).

Neri et al., "Tinnitus and oxidative stress in a selected series of elderly patients," *Arch. Gerontol. Geriatr.*, Suppl. 8:219-223, 2002.

Novotny et al., "Treatment of tinnitus with phenothiazines," abstract XP002353104, Database accession No. EMB-1986243373, *Ceskoslovenska Otolaryngologie*, 35:291-5, 1986.

Office Communication issued in U.S. Appl. No. 11/628,419, dated Oct. 12, 2010.

Office Communication issued in U.S. Appl. No. 11/628,419, dated Jan. 6, 2011.

Office Communication issued in U.S. Appl. No. 11/628,419, dated Jun. 23, 2011.

Ohinata et al., "Intense noise induces formation of vasoactive lipid peroxidation products in the cochlea," *Brain Res.*, 878:163-173, 2000.

Ohlemiller et al., "Early elevation of cochlear reactive oxygen species following noise exposure," *Audiol. Neurootol.*, 4:229-236, 1999.

Paffenholz et al., "Vestibular defects in head-tilt mice result from mutations in NOX3, encoding a NADPH oxidase," *Genes & Development*, 15(5):486-491, 2004.

PCT International Preliminary Report on Patentability, issued in International application No. PCT/EP2005/006061, dated Dec. 4, 2006.

PCT International Search Report and Written Opinion, issued in International application No. PCT/EP2005/006061, dated Apr. 5, 2006.

Prakash, "Positional effect of chemical modifications on short interference RNA activity in mammalian cells," *J. Med. Chem.*, 48(13):4247-53, 2005.

Scherer and Rossi, "Therapeutic applications of RNA interference: Recent advances in siRNA design," *Advances in Genetics*, 52:1-21, 2004.

Schneider et al., "*Gingko biloba* (Rökan) therapy in tinnitus patients and measurable interactions between tinnitus and vestibular disturbances," *Int. Tinnitus J.*, 6:56-62, 2000.

Seifert and Schachtele, "Studies with protein kinase C inhibitors presently available cannot elucidate the role of protein kinase C in the activation of NADPH oxidase," *Biochem. Biophys. Res. Commun.*, 152:585-592, 1988.

Sergi et al., "Cisplatin ototoxicity in the guinea pig: vestibular and cochlear damage," *Hear. Res.*, 182:56-64, 2003.

Sha and Schacht, "Formation of reactive oxygen species following bioactivation of gentamicin," *Free Radic. Biol. Med.*, 26:341-347, 1999.

Sioud et al., "Potential design rules and enzymatic synthesis of siRNAs," *Methods in Molec. Biol.*, 252:457-468, 2004.

Suh et al., "Cell transformation by the superoxide-generating oxidase Mox1," *Nature*, 401:79-82, 1999.

(56) References Cited

OTHER PUBLICATIONS

Takeya et al., "Novel human homologues of p47$^{phox}$ and p67$^{phox}$ participate in activation of superoxide-producing NADPH oxidases," *J. Biol. Chem.*, 278:25234-25246, 2003.

Takumida and Anniko, "Simultaneous detection of both nitric oxide and reactive oxygen species in guinea pig vestibular sensory cells," *ORL J. Otorhinolaryngol. Relat. Spec.*, 64:143-147, 2002.

Takumida et al., "Neuroprotection of vestibular sensory cells from gentamicin ototoxicity obtained using nitric oxide synthase inhibitors, reactive oxygen species scavengers, brain-derived neurotrophic factors and calpain inhibitors," *Acta Otolaryngol.*, 123:8-13, 2003.

Tsunawaki et al., "Fungal metabolite gliotoxin inhibits assembly of the human respiratory burst NADPH oxidase," *Infect Immun.*, 72:3373-3382, 2004.

Tuschl, "RNA interference and small interfering RNAs," *Chembiochem*, 2:239-245, 2001.

Van Campen et al., "Oxidative DNA damage is associated with intense noise exposure in the rat," *Hear. Res.*, 164:29-38, 2002.

Wang et al., "Identification of a novel partner of Duox," *J. Biol. Chem.*, 280:3096-3103, 2005.

Yanai et al., "Expression of mouse osteocalcin transcripts, OG1 and OG2, is differently regulated in bone tissues and osteoblast cultures," *J. Bone Miner. Metab.*, 19:345-351, 2001.

Yoshida et al., "Fungal gliotoxin targets the onset of superoxide-generating NADPH oxidase of human neutrophils," *Biochem. Biophys. Res. Commun.*, 268:716-723, 2000.

Zamore, "RNA interference: listening to the sound of silence," *Nature Structural Biology*, 8(9):746-750, 2001.

\* cited by examiner

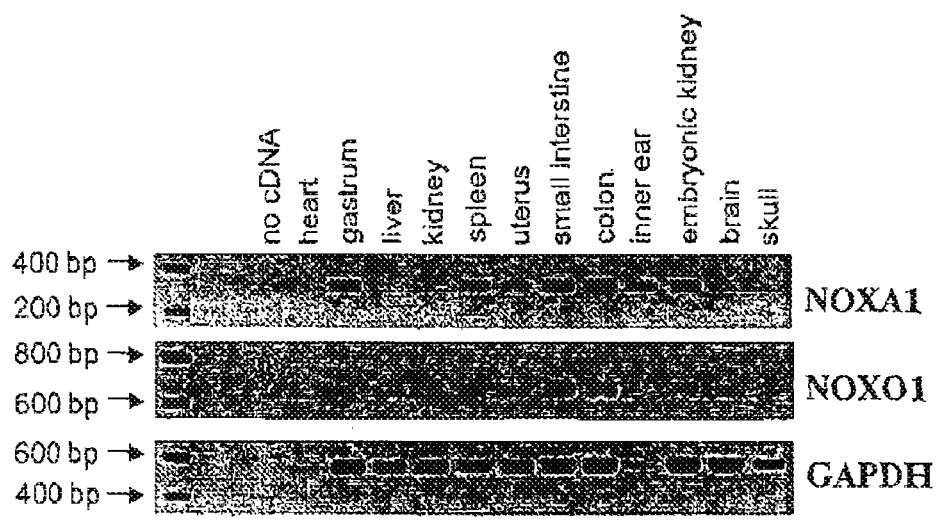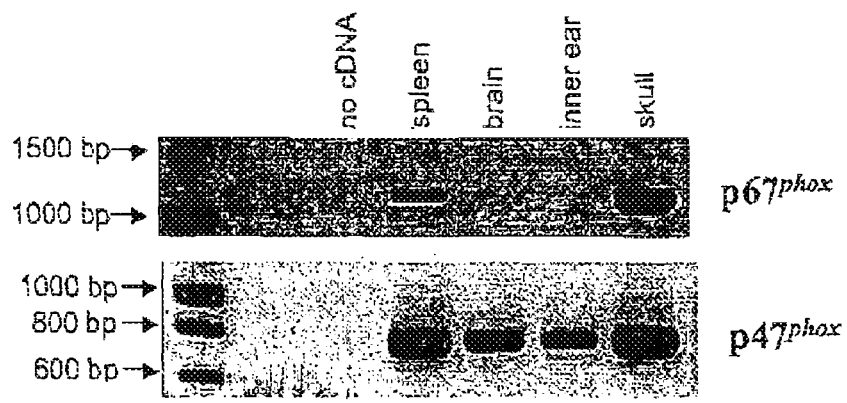
Figure 2

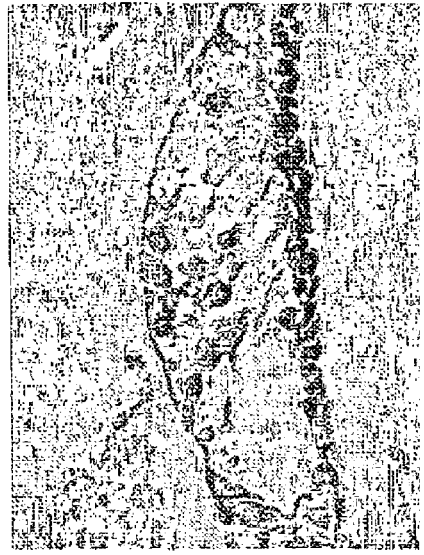
Figure 4A-D

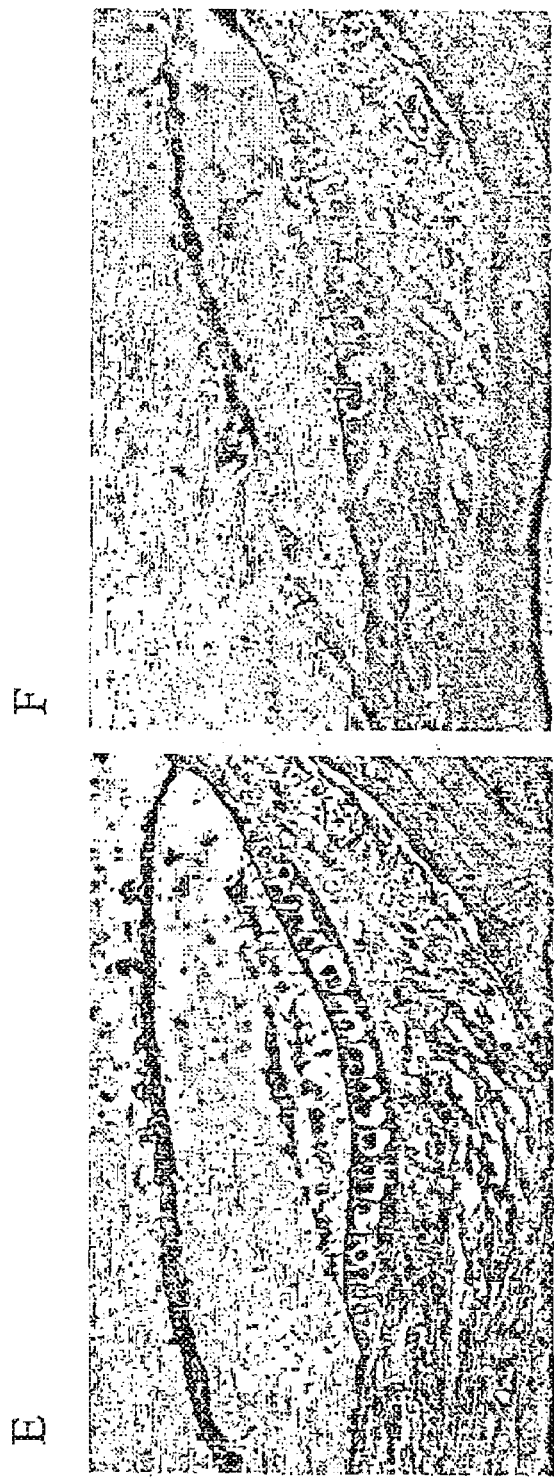
Figure 4E-F

MEANS AND METHODS FOR THE TREATMENT OF HEARING LOSS AND PHANTOM HEARING

This application is a divisional of co-pending U.S. application Ser. No. 11/628,419 filed Oct. 3, 2007, which is a national phase application under 35 U.S.C. §371 of International Application No. PCT/EP2005/006061 filed Jun. 6, 2005, which claims priority to European Application No. 04013266.4 filed Jun. 4, 2004, the entire text and figures of which disclosures are incorporated herein by reference without disclaimer.

This invention relates to a method of identifying a modulator of an NADPH oxidase, whereby said modulator is suitable as a lead compound and/or as a medicament for the treatment and/or prevention of hearing loss and/or phantom hearing, the method comprising the steps of (a) contacting a test compound with a protein, wherein said protein (i) comprises or consists of the amino acid sequence of any one of SEQ ID NO: 1, 3 or 5, or (ii) is encoded by a nucleic acid comprising or consisting of the sequence of any one of SEQ ID NO: 2, 4, 6, 23 or 24, or (iii) is a fragment of the protein according to (i) or (ii) and exhibits NADPH oxidase activity, or (iv) has a sequence at least 75% identical with the protein according to (i) or (ii) or with the fragment according to (iii) and exhibits NADPH oxidase activity, and optionally with one or more NADPH oxidase subunits, under conditions allowing binding of said test compound to said protein or, if present, said subunit(s); (b) optionally determining whether said test compound binds to said protein or, if present, said subunit(s); and (c) determining whether (ca) said test compound, upon contacting in step (a); or (cb) said test compound, upon binding in step (b) modulates the expression and/or activity of said protein or, if present, said subunit(s). Also provided are pharmaceutical compositions, medical uses and diagnostic uses of compounds of the invention.

In this specification, a number of documents is cited. The disclosure of these documents, including manufacturer's manuals, is herewith incorporated by reference in its entirety.

Hearing impairment is a widespread and severe sensory deficit. It is the third most prevalent major chronic disability in the over 65-year-old age group, but also found in younger persons. Slightly more than 1 percent of people under the age of 17 have hearing loss, the prevalence rises to 12 percent between the ages of 45 and 64, to 24 percent between the ages of 65 and 74, and up to 39 percent for ages over 75. There are three major causes of hearing loss: noise-dependent hearing loss, drug-associated hearing loss and age-associated hearing loss. Interestingly, there appears to be a common mechanism to three major causes of hearing loss, namely destruction of sensory epithelium and cochlear neurons through reactive oxygen species. In terms of treatment, no efficient drug treatment or prophylaxis of hearing loss are available at this point and the only option at present is the use of hearing aids. This situation is further aggravated by the limited understanding of the molecular processes involved in hearing loss and the scarcity of suitable molecular targets for therapeutic intervention.

The inner ear is a highly complex structure involved in hearing and balancing. The conversion of sound into electrical signals occurs within the cochlea, in the organ of Corti, and the electrical signals are conducted by the axons of spiral ganglion neurons to the brain. The linear movement of the head is sensed by the otolith organs (utricle and saccule) and the rotation movements by the ampullas of the semicircular canals. The signals generated in the vestibular system are transmitted by the vestibular ganglion neurons to the central nervous system.

Hearing impairment due to loss of cochlear function occurs frequently, if not invariably over lifetime. Noise and ototoxic chemicals may lead to a precocious, rapid hearing loss, while age itself leads to a more insidious, chronic loss of hearing. Research over the last decades has identified reactive oxygen species (ROS[1]) as the major factor mediating hearing loss [1]. ROS is generated within the cochlea after exposure to ototoxic drugs (e.g. cisplatin [2, 3], aminoglycoside antibiotics [3]) or to noise [4]. Signs of oxidative stress, such as DNA damage and lipid peroxidation, have been documented in vivo in response to those challenges [5, 6], as well as in cochlear aging [7]. The vestibular system is also damaged by ototoxic drugs [8, 9] in a process that includes excessive ROS production [10, 11].

[1] The abbreviations used are: bp, base pair; DPI, diphenylene iodonium; DUOX, dual domain oxidase; 5-FU, 5-Fluorouracil; GAPDH, glyceraldehyde-3-phosphate dehydrogenase; gp91$^{phox}$, 91-kDa glycoprotein subunit of the phagocyte NADPH oxidase; NOX, NADPH oxidase; NOXA1, NOX activator 1; NOXO1, NOX organizer 1; PMA, phorbol 12-myristate 13-acetate; PCR, polymerase chain reaction; ROS, reactive oxygen species; RT-PCR, reverse transcription-PCR; SOD, superoxide dismutase.

While the role of oxidative stress in inner ear damage is well established, its source is poorly understood. A role of non-enzymatic generation of ROS by ototoxic compounds has been suggested [12]. The possibility that a superoxide-generating enzyme could be localized within the inner ear, and thereby account for the oxidative damage of this organ, has received little attention.

Over the last decade, it has been proven that the expression of superoxide-generating NADPH oxidases is not restricted to phagocytes. Beside the well-known catalytic subunit of the phagocyte NADPH oxidase, gp91$^{phox}$/NOX2 (for review see [13]), six other superoxide-producing enzymes have been identified in mammals [14, 15]. For most NOX and DUOX enzymes, a predominant tissue localization has been described, e.g. colon epithelium for NOX1 [16, 17], kidney cortex for NOX4 [18], lymphoid organs and testis for NOX5 [19], and the thyroid gland for DUOX1 and DUOX2 [20, 21]. For NOX3, with the exception of some very low level expression in the embryonic kidney [22], no convincing tissue localization had been found so far.

Our knowledge of the activation mechanisms of members of the NOX/DUOX family varies considerably among individual enzymes. NOX1 and gp91$^{phox}$/NOX2 are subunit-dependent enzymes that need to assemble with an activator subunit (NOXA1 and p67$^{phox}$, respectively) and an organizer subunit (NOXO1 and p47$^{phox}$, respectively) to generate superoxide [23-26]. NOX5, DUOX1 and DUOX2, on the other hand, have N-terminal Ca$^{2+}$-binding motifs (EF-hand domains), and so far one of them, NOX5, has been shown to be activated by increased Ca$^{2+}$ concentration [27]. The mechanism of NOX4 activation is less clear. There are indications that it might be a constitutively active enzyme [18].

Tinnitus; also referred to as phantom hearing, is a common and in some instances invalidating medical complaint. Presently, the pathophysiology of the disease is poorly understood and there is not proven causative treatment available. There is however evidence that reactive oxygen species might play a role in the pathophysiology of tinnitus (Neri S. Tinnitus and oxidative stress in a selected series of elderly patients. Arch Gerontol Geriatr. 2002; 35 Suppl:219-23) and there are at least some reports that suggest a beneficial effect of antioxidant medication such as Gingko extract on the course of the disease (e.g. Schneider D et al. Gingko biloba (Rokan) therapy in tinnitus patients and measurable interactions between tinnitus and vestibular disturbances. Int Tinnitus J. 2000; 6(1):56-62). Thus, NOX3 might also be involved in the pathophysiology of tinnitus and the use of a NOX3 modulator or inhibitor is an interesting new concept for the treatment of tinnitus.

US-A1 20040001818 and WO-A1 0230453 describe methods of inhibiting angiogenesis, endothelial cell migration or endothelial cell proliferation using NADPH oxidase inhibitors.

EP-A2 1410798 describes a pharmaceutical composition comprising and uses of inhibitors of the production or the release of reactive oxygen metabolites (ROMs) and of compounds effective to scavenge ROMs. The uses are directed to the manufacture of a medicament for the treatment of Adult Respiratory Distress Syndrome (ARDS); ischemia or reperfusion injury, infectious disease, autoimmune or inflammatory diseases, and neurodegenerative diseases. Compounds effective to inhibit enzymatic ROM production or release comprise NADPH oxidase inhibitors.

EP-A2 0914821 relates to a method for diagnosis of atherosclerosis involving measurement of NADPH oxidase activity.

WO-A2 9719679 describes the use of NADPH oxidase inhibitors for the manufacture of a medicament for prevention of atherosclerosis.

US-A1 20040009901 relates to a method of treating a mammal having an autoimmune condition involving NADPH oxidase deficiency. Also, a method for identifying an agent that enhances NADPH oxidase activity is described.

WO-A2 02079224 relates to human peptides and proteins that are related to NADPH oxidase subfamily and methods for identifying modulators thereof. The proteins are described as being substantially similar to p47phox.

WO-A2 04007689 describes regulatory proteins for Nox enzymes, which are referred to as p41Nox proteins, and nucleic acid sequences encoding these proteins. Furthermore, a method for identifying a compound that modulates superoxide production is rescribed, the method involving administration of the protein. The envisaged medical indications relate to abnormal cell growth and proliferation and include cancer, prostatic hypertrophy and atherosclerosis.

NCBI Entrez protein database entry NP_056533 comprises the amino acid sequence of human NADPH oxidase 3 (NOX3). The sequence is 568 amino acids in length. The database entry recites similarity to gp91phox.

In view of the limited understanding of processes leading to hearing loss and phantom hearing, the technical problem underlying the present invention was therefore the provision of means and methods for the development of drugs for treatment of hearing loss and phantom hearing.

Accordingly, this invention relates to a method of identifying a modulator of an NADPH oxidase, whereby said modulator is suitable as a lead compound and/or as a medicament for the treatment and/or prevention of hearing loss and/or phantom hearing, the method comprising the steps of (a) contacting a test compound with a protein, wherein said protein (i) comprises or consists of the amino acid sequence of any one of SEQ ID NO: 1, 3 or 5, or (ii) is encoded by a nucleic acid comprising or consisting of the sequence of any one of SEQ ID NO: 2, 4, 6, 23 or 24, or (iii) is a fragment of the protein according to (i) or (ii) and exhibits NADPH oxidase activity, or (iv) has a sequence at least 75% identical with the protein according to (i) or (ii) or with the fragment according to (iii) and exhibits NADPH oxidase activity, and optionally with one or more NADPH oxidase subunits, under conditions allowing binding of said test compound to said protein or, if present, said subunit(s); (b) optionally determining whether said test compound binds to said protein or, if present, said subunit(s); and (c) determining whether (ca) said test compound, upon contacting in step (a); or (cb) said test compound, upon binding in step (b) modulates the expression and/or activity of said protein or, if present, said subunit(s).

The term "modulator" designates a compound modulating the activity of a target molecule, preferably by performing one or more of the following effects: (i) the transcription of the gene encoding the protein to be modulated is modulated, (ii) the translation of the mRNA encoding the protein to be modulated is modulated, (iii) the protein performs its biochemical function with modulated efficiency in presence of the modulator, and (iv) the protein performs its cellular function with modulated efficiency in presence of the modulator. It is understood that the term "modulator" includes inhibitors and activators at all regulatory levels mentioned above.

The term "NADPH oxidase" comprises any NADPH oxidase. It includes NOX enzymes such as NOX1, NOX2, NOX3, NOX4 and NOX5 as well as DUOX enzymes such as DUOX1 and DUOX2 (see references 13 to 27).

The term "lead compound" designates a compound which is a drug candidate and which may require chemical modifications in order to optimize its pharmacological properties and eventually become a drug to be formulated as a medicament. Methods of optimization are known in the art and further detailed below.

The term "hearing loss" according to the invention embraces drug-, noise- and age-related hearing loss. Age-related hearing loss is also referred to as presbyacusis. The term "phantom hearing", also known as "tinnitus", is a common and in some instances invalidating medical complaint.

The term "protein" recited in the main claim extends to homologues having at least 75% sequence identity. Preferably, the sequence identity level is 80% or 85%, more preferred 90% or 95%, and yet more preferred 98% or 99%. For the purpose of determining the level of sequence identity, two nucleotide or protein sequences can be aligned electronically using suitable computer programs known in the art. Such programs comprise BLAST (Altschul et al. (1990), J. Mol. Biol. 215, 403-410), variants thereof such as WU-BLAST (Altschul & Gish (1996), Methods Enzymol. 266, 460-480), FASTA (Pearson & Lipman (1988), Proc. Natl. Acad. Sci. USA 85, 2444-2448) or implementations of the Smith-Waterman algorithm (SSEARCH, Smith & Waterman (1981), J. Mol. Biol. 147, 195-197). These programs, in addition to providing a pairwise sequence alignment, also report the sequence identity level (usually in percent identity) and the probability for the occurrence of the alignment by chance (P-value). Programs such as CLUSTALW (Higgins et al. (1994), Nucleic Acids Res. 22, 4673-4680) can be used to align more than two sequences.

The optional presence of one or more NADPH oxidase subunits relates inter alia to embodiments, wherein not only modulators exerting their effect exclusively directly on the NADPH oxidase are to be identified, but also modulators which act by interfering with the association of the NADPH oxidase with said subunit(s) are to be identified. Such modulators may be compounds binding to regions of the NADPH oxidase and/or of the subunit(s) involved in subunit association. In other words, a test compound identified by the method of the invention which interferes with association (e.g. binds to regions of the NADPH oxidase and/or of the subunit(s) involved in subunit association) is an example of a test compound according to the invention which either modulates expression and/or activity of the protein defined in the main embodiment or modulates the expression and/or activity of said subunit(s).

Also embraced by the invention is a method as defined above, wherein test compounds may be identified which modulate the expression and/or activity of both the protein defined in the main embodiment and said subunits.

In the following, the interactions of an NADPH oxidase with its subunits is exemplified for the NADPH oxidase 3 (NOX3). NOX3 activity requires the widely distributed membrane NOX subunit $p22^{phox}$. However, in the absence of further, viz. cytoplasmic subunits, no high level, but only low level ROS generation occurs. In contrast in the presence of the combination of one activator subunit (either NOXA1 or p67phox/NOXA2) and one organizer subunit (either NOXO1 or $p47^{phox}$/NOXO2) NOX3 is capable of generating high levels of ROS. In addition, the NOX3 activity most likely also involves the ubiquitous GTP-binding protein Rac. The interaction sites between the partners are depicted in the following scheme.

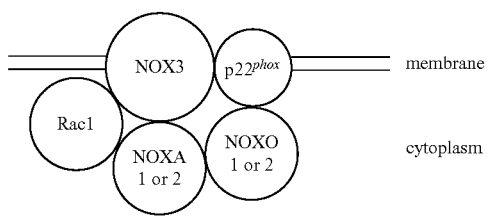

A key interaction is the binding of the activator domain of the activator subunits (amino acids 202-212 for hNOXA1 and amino acids 200-210 for $hp67^{phox}$/NOXA2) to NOX3. It is not clear whether there is a direct interaction of the organizer subunits with NOX3, but there is an indirect interaction with NOX3 through binding to $p22^{phox}$ via the tandem SH3 domain (amino acids 158-217 and 233-289 for hNOXO1 and amino acids 156-216 and 226-286 for $hp47^{phox}$/NOXO2) and through binding to an SH3 domain of the activator subunit (amino acids 402-463 for hNOXA1 and amino acids 457-513 for $hp67^{phox}$/NOXA2) through its proline-rich region (amino acids 321-331 for hNOXO1 and 360-370 for $hp47^{phox}$/NOXO2). The precise site of interaction between NOX3 and $p22^{phox}$, as well as the sites of interaction of Rac1 with NOX3 and the activator subunits (NOXA1 or $p67^{phox}$) are not known. The table below provides a compilation of the interaction sites.

| binding region of the subunit | target |
|---|---|
| activator region of activator subunit (aa 202-212 for hNOXA1 and aa 200-210 for $hp67^{phox}$/NOXA2) | NOX3 |
| tandem SH3 domain of organizer subunit (aa 158-217 and aa 233-289 for hNOXO1 and aa 156-216 and 226-286 for $hp47^{phox}$/NOXO2) | $p22^{phox}$ |
| proline-rich region of organizer subunit (aa 321-331 for hNOXO1 and 360-370 for $hp47^{phox}$/NOXO2) | SH3 domain of activator subunit (aa 402-463 for hNOXA1 and aa 457-513 for $hp67^{phox}$/NOXA2) |

The optional determination of binding test compounds in step (b) relates to any biophysical binding assay, which may be used to identify binding test molecules prior to performing the functional assay with the binding test molecules only. Suitable biophysical binding assays are known in the art and comprise fluorescence polarization (FP) assay, fluorescence resonance energy transfer (FRET) assay and surface plasmon resonance (SPR) assay. Step (b) is particularly advantageous if said biophysical assay is more amenable to high throughput than the functional assay.

Step (c) relates to the above mentioned functional assay. Determining whether a test compound, or a binding test compound, modulates the expression of a target protein may be accomplished by measuring the expression level. In a more preferred embodiment, the expression level to be determined is the mRNA expression level. Methods for the determination of mRNA expression levels are known in the art and comprise Real Time PCR, Northern blotting and hybridization on microarrays or DNA chips equipped with one or more probes or probe sets specific for transcripts encoding proteins of the NADPH oxidase family.

In another more preferred embodiment, the expression level to be determined is the protein expression level. The skilled person is aware of methods for the quantitation of proteins. Amounts of purified protein in solution can be determined by physical methods, e.g. photometry. Methods of quantifying a particular protein in a mixture rely on specific binding, e.g. of antibodies. Specific detection and quantitation methods exploiting the specificity of antibodies comprise immunohistochemistry (in situ) and surface plasmon resonance. Western blotting combines separation of a mixture of proteins by electrophoresis and specific detection with antibodies.

The present invention also relates to a method of identifying a modulator of an NADPH oxidase, whereby said modulator is suitable as a lead compound and/or as a medicament for the treatment and/or prevention of hearing loss and/or phantom hearing, the method comprising the steps of (a) contacting a test compound with a protein, wherein said protein (i) comprises or consists of the amino acid sequence of any one of SEQ ID NO: 1, 3 or 5, or (ii) is encoded by a nucleic acid comprising or consisting of the sequence of any one of SEQ ID NO: 2, 4, 6, 23 or 24, or (iii) is a fragment of the protein according to (i) or (ii) and exhibits NADPH oxidase activity, or (iv) has a sequence at least 75% identical with the protein according to (i) or (ii) or with the fragment according to (iii) and exhibits NADPH oxidase activity, under conditions allowing binding of said test compound to said protein; and (b) determining whether said test compound, upon contacting in step (a) modulates the expression and/or activity of said protein.

The present invention also relates to a method of identifying a modulator of an NADPH oxidase, whereby said modulator is suitable as a lead compound and/or as a medicament for the treatment and/or prevention of hearing loss and/or phantom hearing, the method comprising the steps of (a) contacting a test compound with a protein, wherein said protein (i) comprises or consists of the amino acid sequence of any one of SEQ ID NO: 1, 3 or 5, or (ii) is encoded by a nucleic acid comprising or consisting of the sequence of any one of SEQ ID NO: 2, 4, 6, 23 or 24, or (iii) is a fragment of the protein according to (i) or (ii) and exhibits NADPH oxidase activity, or (iv) has a sequence at least 75% identical with the protein according to (i) or (ii) or with the fragment according to (iii) and exhibits NADPH oxidase activity, under conditions allowing binding of said test compound to said protein; (b) determining whether said test compound, upon contacting in step (a) modulates the expression and/or activity of said protein; and (c) performing clinical trials with said modulator.

In a preferred embodiment of the method of the invention, said contacting comprises contacting with one or more NADPH oxidase subunits, under conditions allowing binding of said test compounds to said subunit(s), and wherein said determining comprises determining whether said test compound modulates the expression and/or activity of said subunit(s).

In a further preferred embodiment the method further comprises, prior to step (b), the step of (b') determining whether said test compound binds to said protein or, if present, said subunit(s), wherein said determining in step (b) is effected upon binding in step (b'). The method according to this preferred embodiment comprises both determining of whether a test compound, upon contacting in step (a), modulates expression and/or activity and the determining of whether a test compound, upon binding in step (b'), modulates expression and/or activity. The term "expression and/or activity" relate to, as defined herein above, the expression and/or activity of the protein as defined in the main embodiment and/or of said subunit(s).

Quantitation of the modulation of the activity of an NADPH oxidase may be effected by quantifing the reactive oxygen species production. Accordingly, said modulation preferably involves modulating the ROS production of said protein, and determining in step (c) comprises quantifying ROS production. Methods of quantifying ROS are known in the art and are further exemplified in Example 4 enclosed herewith.

The inventors for the first time demonstrated high-level expression of the NADPH oxidase NOX3 in the inner ear. Thereby, a protein suitable as a target for therapeutic intervention in hearing loss and phantom hearing is provided.

Vestibular and cochlear sensory epithelia develop from a common ectodermal thickening at the head region, called placode [34]. The otic placode also gives rise to the neurons that will form the inner ear ganglia [35]. The data presented in the Examples and Figures enclosed herewith suggest that the expression of NOX3 mRNA may follow this pattern.

Furthermore, the inventors demonstrated for the first time that NOX3 is a superoxide-generating enzyme. It is also demonstrated that the pattern of subunit- and stimulus-dependence that is distinct from other known NOX family NADPH oxidases. NOX3, as opposed to NOX1 and NOX2, produces low levels of superoxide upon PKC activation without the need of subunits. While the activation of phagocyte NADPH oxidase is thought to occur through PKC-dependent phosphorylation of $p47^{phox}$ [13], this, obviously, cannot be the mechanism of the subunit-independent activation of NOX3. At this point, there are numerous possible pathways how PKC might activate NOX3 (e.g. direct phosphorylation of NOX3, activation of the small GTPase protein Rac1, or changes in the lipid environment). The subunit-independent ROS-generation by NOX3 is of low level in the transfected cells. Given the localization of NOX3 in the inner ear, close to or within highly ROS-sensitive cells, it is tempting to speculate that low, rather than high level superoxide generation is the default mode of NOX3 function.

However, NOX3 activity can be massively enhanced by known NOX organizer and regulator/activator subunits. Searches of mouse and human genomic databases suggest that there are probably no other close homologues of $p47^{phox}$ and $p67^{phox}$ than NOXO1 and NOXA1, respectively. Thus, if NOX3 functions in a subunit-dependent manner in vivo, it would have to use subunits of other NOX enzymes.

Based on PCR data shown in FIG. 2, NOX3 could potentially interact with NOXA1 and/or $p47^{phox}$ in the inner ear. However, it cannot be excluded that, under specific circumstances or in a very limited number of cells, other NOX subunits may also be expressed in the inner ear.

Therefore, in a preferred embodiment, said NADPH oxidase subunit(s) is/are the activating subunit(s) NOXA1 and/or $p67^{phox}$/NOXA2, and/or the organising subunit(s) NOXO1 and/or $p47^{phox}$/NOXO2.

In a further preferred embodiment said protein and, if present, said subunit(s) is/are comprised in a membrane preparation. Membrane preparations according to the invention may be membrane fractions obtained, for example, by centrifugation upon cell disruption. Alternatively, said membrane preparation is obtained by reconstituting the protein(s) according to the main embodiment with membrane- or micelle-forming amphiphilic lipids.

In a further preferred embodiment said protein and, if present, said subunit(s) is/are comprised in a cell transfected with a nucleic acid encoding said protein. This embodiment relates to a cellular screen.

In a further preferred embodiment of the method of the invention, said protein and, if present, said subunit(s) is/are comprised in a non-human animal. This embodiment relates to an in vivo screen. While less amenable to high throughput, the in vivo screen offers the advantage of the assessment of the disease state of the non-human animal. Accordingly, in a more preferred embodiment, the modulation of ROS production involves improving the hearing of said animal and determining in step (c) involves quantifying said hearing.

In a further preferred embodiment, prior to said contacting, (a') an ototoxic agent and/or an agent increasing the activity and/or the expression of said protein or subunit(s), is brought into contact with said protein or subunit(s) is/are administered to said cell or said animal. Administration of an ototoxic agent and/or an agent increasing the activity and/or the expression of said protein or subunit(s) may be used as a means of modelling (at the cellular level), or inducing/enhancing (at the organismic level) the disease or disease-related conditions.

Interestingly, while there is almost no literature on the physiological function of ROS in the inner ear, there is a considerable number of studies on the pathological effect of excessive ROS production in this organ (for reviews see [1] and [4]). It has been shown in several publications that specific ototoxic drugs (such as platinum derivatives or aminoglycoside antibiotics) lead to accumulation of ROS in both the cochlea [3] and the vestibular system [8, 11, 36], and noise trauma has been demonstrated to be a prominent cause of ROS production in the cochlea [37]. A permanent increase of ROS concentration, in turn, leads primarily to the death of sensory epithelial cells, and, to a lesser extent, to the death of innervating neurons [1]. Based on the surprising observations presented herein and relating to its localization and its capacity to generate ROS, NOX3 is likely to be a major source of ROS in the inner ear. The unexpected observation that cisplatin markedly enhances NOX3-dependent superoxide production, evokes the possibility that NOX3 is a mediator of cisplatin-dependent ototoxicity. Time course and dose-response of the cisplatin-dependent NOX3 activation is compatible with the time course [2] and dose-response [38] of cisplatin toxicity to inner ear sensory cells.

In a more preferred embodiment, said ototoxic agent is selected from the group consisting of salicylates, non-steroidal antiinflammatories, antibiotics, diuretics, cytostatics, quinine derivatives and gastroprotective drugs.

Salicylates include Aspirine and methyl-salicylates.

Non-steroidal antiinflammatories include diclofenac, etocolac, fenprofen, ibuprofen, indomethacin, naproxen, piroxicam and sulindac.

Preferred antibiotics are aminoglycosides such as amikacin, gentamycin, kanamycin, neomycin, netilmicin, streptomycin and tobramycin. Further preferred antibiotics include erythromycin, vancomycin, minocycline, polymixin B, amphotericin B and capreomycin.

Exemplary diuretics according to the invention are bendroflumethazide, bumetadine, chlorthalidone, ethacrynic acid and furosemide.

Cytostatics, or antineoplastic drugs according to the invention include bleomycine, bromocriptine, carboplatinum, cisplatin, methotrexate, nitrogen mustard, vinblastin and vincristine.

Quinine derivatives, being used as antimalarial and antiarrhythmic drugs, include chloroquine phosphate, quinacrine hydrochloride and quinine sulphate.

Misoprostol is among the envisaged gastroprotective drugs.

In a preferred embodiment of the method of the invention, said NADPH oxidase is NOX3. In a further preferred embodiment said NADPH oxidase is the protein defined in claim 1.

In a further preferred embodiment, the method of the invention further comprises the step of formulating said modulator with a pharmaceutically acceptable carrier. By "pharmaceutically acceptable carrier" is meant a non-toxic solid, semisolid or liquid filler, diluent, encapsulating material or formulation auxiliary of any type.

More preferred, and prior to said formulating, the affinity, specificity and/or pharmacological properties of the modulator are optimized and/or clinical trials are performed with said modulator or the optimized modulator.

Accordingly, the present invention also relates to a method of identifying a modulator of an NADPH oxidase, whereby said modulator is suitable as a lead compound and/or as a medicament for the treatment and/or prevention of hearing loss and/or phantom hearing, the method comprising the steps of (a) contacting a test compound with a protein, wherein said protein (i) comprises or consists of the amino acid sequence of any one of SEQ ID NO: 1, 3 or 5, or (ii) is encoded by a nucleic acid comprising or consisting of the sequence of any one of SEQ ID NO: 2, 4, 6, 23 or 24, or (iii) is a fragment of the protein according to (i) or (ii) and exhibits NADPH oxidase activity, or (iv) has a sequence at least 75% identical with the protein according to (i) or (ii) or with the fragment according to (iii) and exhibits NADPH oxidase activity, under conditions allowing binding of said test compound to said protein; (b) determining whether said test compound, upon contacting in step (a) modulates the expression and/or activity of said protein; and (c) performing clinical trials with said modulator.

Methods for the optimization of the pharmacological properties of compounds identified in screens, generally referred to as lead compounds, are known in the art and comprise a method of modifying a compound identified as a lead compound to achieve: (i) modified site of action, spectrum of activity, organ specificity, and/or (ii) improved potency, and/or (iii) decreased toxicity (improved therapeutic index), and/or (iv) decreased side effects, and/or (v) modified onset of therapeutic action, duration of effect, and/or (vi) modified pharmacokinetic parameters (resorption, distribution, metabolism and excretion), and/or (vii) modified physicochemical parameters (solubility, hygroscopicity, color, taste, odor, stability, state), and/or (viii) improved general specificity, organ/tissue specificity, and/or (ix) optimized application form and route by (i) esterification of carboxyl groups, or (ii) esterification of hydroxyl groups with carbon acids, or (iii) esterification of hydroxyl groups to, e.g. phosphates, pyrophosphates or sulfates or hemi succinates, or (iv) formation of pharmaceutically acceptable salts, or (v) formation of pharmaceutically acceptable complexes, or (vi) synthesis of pharmacologically active polymers, or (vii) introduction of hydrophilic moieties, or (viii) introduction/exchange of substituents on aromates or side chains, change of substituent pattern, or (ix) modification by introduction of isosteric or bioisosteric moieties, or (x) synthesis of homologous compounds, or (xi) introduction of branched side chains, or (xii) conversion of alkyl substituents to cyclic analogues, or (xiii) derivatisation of hydroxyl group to ketales, acetales, or (xiv) N-acetylation to amides, phenylcarbamates, or (xv) synthesis of Mannich bases, imines, or (xvi) transformation of ketones or aldehydes to Schiff's bases, oximes, acetales, ketales, enolesters, oxazolidines, thiozolidines or combinations thereof; said method optionally further comprising the steps of the above described methods.

The various steps recited above are generally known in the art. They include or rely on quantitative structure-action relationship (QSAR) analyses (Kubinyi, "Hausch-Analysis and Related Approaches", VCH Verlag, Weinheim, 1992), combinatorial biochemistry, classical chemistry and others (see, for example, Holzgrabe and Bechtold, Deutsche Apotheker Zeitung 140(8), 813-823, 2000).

Individuals to be selected for said clinical trials comprise healthy individuals, individuals with a disposition or at risk to develop hearing loss or phantom hearing and patients suffering from hearing loss or phantom hearing. Hearing loss is understood to comprise drug-, noise- and age-related hearing loss.

Moreover, the present invention also relates to a pharmaceutical composition comprising (a) an antibody, aptamer, or a fragment or derivative thereof binding specifically the protein defined in the main embodiment; (b) an antisense nucleic acid, an siRNA, or a ribozyme binding specifically a nucleic acid encoding said protein; (c) a iodonium derivative and/or a substituted catechol such as apocynin; (d) a compound comprising the fragment of SEQ ID NO: 11 from position 202 to position 212, the fragment of SEQ ID NO: 1.1 from position 402 to position 463, the fragment of SEQ ID NO: 15 from position 200 to position 210, the fragment of SEQ ID NO: 15 from position 457 to position 513, the fragment of SEQ ID NO: 7 from position 158 to position 217, the fragment of SEQ ID NO: 7 from position 233 to position 289, the fragment of SEQ ID NO: 7 from position 321 to position 331, the fragment of SEQ ID NO: 19 from position 156 to position 216, the fragment of SEQ ID NO: 19 from position 226 to position 286, the fragment of SEQ ID NO: 19 from position 360 to position 370; and/or (e) a nucleic acid comprising a sequence encoding any of the fragments according to (d). The fragments according to (d) are regions of the sequences of the respective SEQ ID NOs known or expected to be involved in subunit association.

Said compounds according to (d) may furthermore comprise a cell-penetrating peptide. The term "cell-penetrating peptide" relates to a peptide which is capable of entering into cells. This capability may be exploited for the delivery of fragments defined in (d) to cells.

For example, said compounds may be peptides or polypeptides comprising both a fragment as defined in (d) above and a cell-penetrating peptide. Alternatively, other means of functionally linking a fragments as defined in (d) and a cell-penetrating peptide are envisaged. Preferably, said compounds comprising both a fragment as defined in (d) above and a cell-penetrating peptide act as dominant negative cell-permeating inhibitors.

Said cell-penetrating peptides according to the invention include Tat-derived cell-penetrating peptides [46, 47], Antennapedia peptides or penetratins [48, 49] such as the peptide having the sequence Arg-Gln-lle-Lys-lle-Trp-Phe-Gln-Asn- Arg-Arg-Met-Lys-Trp-Lys-Lys (SEQ ID NO: 25), peptides derived from HSV-1 VP22 [50], transportans [51], MAP peptides [52] such as the peptide with the sequence KLALKLA-LKALKAALKLA (SEQ ID NO: 26), signal sequence-based cell-penetrating peptides (NLS) [53], hydrophobic membrane translocating sequence (MTS) peptides [53] and arginine-rich transporters for drugs. According to an overview of cell-penetrating peptides is provided in [45], CPPs are divided into two classes: the first class consists of amphipathic helical peptides, such as transportan and model amphipathic peptide (MAP), where lysine (Lys) is the main contributor to the positive charge, while the second class includes arginine (Arg)-rich peptides, such as TAT and Antp or penetratin.

The nucleic acids according to (e) include the sequences with the SEQ ID NOs: 12, 16, 8 and 20 as well those fragments thereof which comprise a sequence encoding any of the fragments according to (d). Said nucleic acid may optionally comprise a sequence encoding a cell-penetrating peptide.

Also embraced by the present invention are pharmaceutical compositions comprising fragments of proteins orthologous or homologous to hNOXA1, hNOXO1, hp47phox/NOXO2 or hp67phox/NOXA2, whereby said fragments align with the fragments of hNOXA1, hNOXO1, hp47phox/NOXO2 or hp67phox/NOXA2 recited under (d), as are pharmaceutical compositions comprising nucleic acids encoding these aligning fragments. It is understood that these pharmaceutical compositions are considered equivalents of the above described embodiment directed to pharmaceutical compositions. Said orthologous or homologous proteins include the respective murine proteins, i.e., proteins having an amino acid sequence set forth in any one of SEQ ID NO: 13, 17, 9 or 21. The nucleic acids encoding the latter are set forth in SEQ ID NO: 14, 18, 10 and 22.

Two nucleotide or protein sequences can be aligned electronically using suitable computer programs known in the art. Such programs comprise BLAST (Altschul et al. (1990), J. Mol. Biol. 215, 403-410), variants thereof such as WU-BLAST (Altschul & Gish (1996), Methods Enzymol. 266, 460-480), FASTA (Pearson & Lipman (1988), Proc. Natl. Acad. Sci. USA 85, 2444-2448) or implementations of the Smith-Waterman algorithm (SSEARCH, Smith & Waterman (1981), J. Mol. Biol. 147, 195-197). These programs, in addition to providing a pairwise sequence alignment, also report the sequence identity level (usually in percent identity) and the probability for the occurrence of the alignment by chance (P-value). Programs such as CLUSTALW (Higgins et al. (1994), Nucleic Acids Res. 22, 4673-4680) can be used to align more than two sequences.

Furthermore embraced by the present invention are pharmaceutical compositions comprising (a) peptidomimetic compound(s) which has been obtained by using any of the fragments according to (d) as a lead compound.

Pharmaceutical compositions comprising a nucleic acid according to (e) and/or the above described equivalents thereof are also envisaged to be used for gene therapy. For this purpose, the nucleic acid may be part of an expression, a gene transfer or gene targeting vector. Gene therapy, which is based on introducing therapeutic genes into cells by ex-vivo or in-vivo techniques is one of the most important applications of gene transfer. Transgenic mice expressing a neutralizing antibody directed against nerve growth factor have been generated using the "neuroantibody" technique; Capsoni, Proc. Natl. Acad. Sci. USA 97 (2000), 6826-6831 and Biocca, Embo J. 9 (1990), 101-108. Suitable vectors, methods or gene-delivering systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Onodua, Blood 91 (1998), 30-36; Verzeletti, Hum. Gene Ther. 9 (1998), 2243-2251; Verma, Nature 389 (1997), 239-242; Anderson, Nature 392 (Supp. 1998), 25-30; Wang, Gene Therapy 4 (1997), 393-400; Wang, Nature Medicine 2 (1996), 714-716; WO 94/29469; WO 97/00957; U.S. Pat. No. 5,580,859; U.S. Pat. No. 5,589,466; U.S. Pat. No. 4,394,448 or Schaper, Current Opinion in Biotechnology 7 (1996), 635-640, and references cited therein. The nucleic acid molecules according to (e) may be designed for direct introduction or for introduction via liposomes, viral vectors (e.g. adenoviral, retroviral), electroporation, ballistic (e.g. gene gun) or other delivery systems into the cell. Additionally, a baculoviral system can be used as eukaryotic expression system for the nucleic acid molecules of the invention. The introduction and gene therapeutic approach should, preferably, lead to the expression of a fragment according to (d) of the invention, whereby said expressed fragment is particularly useful in the treatment, amelioration and/or prevention of hearing loss and/or phantom hearing.

Said antibody, which is monoclonal antibody, polyclonal antibody, single chain antibody, or fragment thereof that specifically binds said peptide or polypeptide also including bispecific antibody, synthetic antibody, antibody fragment, such as Fab, a F(ab$_2$)', Fv or scFv fragments etc., or a chemically modified derivative of any of these (all comprised by the term "antibody"). Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of the peptide or polypeptide of the invention (Schier, Human Antibodies Hybridomas 7 (1996), 97-105; Malmborg, J. Immunol. Methods 183 (1995), 7-13). The production of chimeric antibodies is described, for example, in WO89/09622. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook (1989), loc. cit.

The term "monoclonal" or "polyclonal antibody" (see Harlow and Lane, (1988), loc. cit.) also relates to derivatives of said antibodies which retain or essentially retain their binding specificity. Whereas particularly preferred embodiments of said derivatives are specified further herein below, other preferred derivatives of such antibodies are chimeric antibodies comprising, for example, a mouse or rat variable region and a human constant region.

The term "scFv fragment" (single-chain Fv fragment) is well understood in the art and preferred due to its small size and the possibility to recombinantly produce such fragments.

Preferably, the antibody, aptamer, fragment or derivative thereof according to the invention specifically binds the target protein, (poly)peptide or fragment or epitope thereof whose presence or absence is to be monitored.

The term "specifically binds" in connection with the antibody used in accordance with the present invention means that the antibody etc. does not or essentially does not cross-react with (poly)peptides of similar structures. Cross-reactivity of a panel of antibodies etc. under investigation may be tested, for example, by assessing binding of said panel of antibodies etc. under conventional conditions (see, e.g., Harlow and Lane, (1988), loc. cit.) to the (poly)peptide of interest as well as to a number of more or less (structurally and/or functionally) closely related (poly)peptides. Only those antibodies that bind to the (poly)peptide/protein of interest but do not or do not essentially bind to any of the other (poly)peptides which are preferably expressed by the same tissue as the (poly)peptide of interest, are considered specific for the (poly)peptide/protein of interest and selected for further studies in accordance with the method of the invention.

In a particularly preferred embodiment of the method of the invention, said antibody or antibody binding portion is or is derived from a human antibody or a humanized antibody.

The term "humanized antibody" means, in accordance with the present invention, an antibody of non-human origin, where at least one complementarity determining region (CDR) in the variable regions such as the CDR3 and preferably all 6 CDRs have been replaced by CDRs of an antibody of human origin having a desired specificity. Optionally, the non-human constant region(s) of the antibody has/have been replaced by (a) constant region(s) of a human antibody. Methods for the production of humanized antibodies are described in, e.g., EP-A1 0 239 400 and WO90/07861.

The term "aptamer" as used herein refers to DNA or RNA molecules that have been selected from random pools based on their ability to bind other molecules. Aptamers have been selected which bind nucleic acid, proteins, small organic compounds, and even entire organisms. A database of aptamers is maintained at http://aptamer.icmb.utexas.edu/.

An antisense nucleic acid according to the invention is a nucleic acid molecule complementary to a nucleic acid molecule encoding a protein according to the main embodiment which may be used for the repression of expression of said protein. The construction of small interfering RNAs (siRNAs) (see, e.g. Zamore Nat Struct Biol 2001, 8(9):746-50 or Tuschl T. CHEMBIOCHEM. 2001, 2:239-245) or of appropriate ribozymes (see, e.g., EP-B1 0 291 533, EP-A1 0 321 201, EP-A2 0 360 257) which specifically cleave the (pre)-mRNA of a gene comprising a nucleic acid encoding said protein are also suitable for the repression of expression. The techniques underlying said repression of expression are well known in the art. Selection of appropriate target sites and corresponding ribozymes can be done as described for example in Steinecke et al. (Methods in Cell Biology (1995) 50:449-460). Standard methods relating to antisense technology have also been described (Melani at al., Cancer Res. (1991) 51:2897-2901). Said nucleic acid molecules may be chemically synthesized or transcribed by an appropriate vector containing a chimeric gene which allows for the transcription of said nucleic acid molecule in the cell. Such nucleic acid molecules may further contain ribozyme sequences as described above.

Iodonium derivatives or, more specifically, aryliodonium compounds include diphenylene iodonium (DPI, also referred to as iodoniumdiphenyl or iodonium biphenyl), di-2-thienyliodonium (also referred to as iodonium thiophene) and phenoxaiodonium. These compounds act as arylating agents and directly and irreversibly inhibit NOX enzymes.

Apocynin (4-hydroxy-3-methoxy-acetophenone) is a methoxy-substituted catechol and exerts its effect on NOX enzymes through the inhibition of subunit assembly.

Also embraced by the present invention are pharmaceutical compositions comprising (i) naphthoquinones such as plumbagin, acetylshikonin; (ii) inhibitors of HMG-CoA reductase including statins such as lovastatin, simvastatin, atorvastatin; (iii) gliotoxin; (iv) phenothiazines such as phenothiazine, trifluoperazine, and/or (v) a derivative of any one of (i) to (v).

Plumbagin is a naphtoquinone derived from *Plumbago Zeylanica* (Chitrak, an indian medicinal plant).

Gliotoxin is a metabolite of pathogenic fungi (*Aspergillus* and *Candida* spp) and has been implicated in infectious pathways. It exhibits immunosupressive action and antitumor activity and inhibits activation process of NOX2 (Yoshida et al., 2000) and the assembly of the enzyme (Tsunawaki et al., 2004). It is available from Sigma.

Statins are inhibitors of HMG-CoA. They decrease plasma cholesterol and block rac-1 dependent activation of NADPH oxidases (Maack et al. 2003). Furthermore, they inhibit myristoylation of rac.

Trifluoperazine is an inhibitor of PKC/calmodulin and prevents the activation of NADPH oxidases (Seifert and Scachtele, 1988, Holland et al., 2000).

The term derivative relates to compounds having the same core or backbone structure while one or more of the substituents are modified, for example by replacing a methyl group with a trifluoromethyl group. These modifications are such that the biological/pharmacological activity is not substantially altered. Said activity may be monitored by the assays disclosed herein.

The present invention also relates to a pharmaceutical composition consisting of (a) ortho-methoxy-substituted catechols such as apocynin, acetosyringone, vanillin, vanillic acid, syringaldehyde, syringic acid; and (b) a pharmaceutically acceptable carrier, excipient or diluent.

Also provided by the present invention is a pharmaceutical composition comprising (a) an ototoxic agent; and (b) a compound selected from the group consisting of: (i) an antibody, aptamer, or a fragment or derivative thereof binding specifically the protein defined in claim 1; (ii) an antisense nucleic acid, an siRNA, or a ribozyme binding specifically a nucleic acid encoding said protein; (iii) a compound comprising the fragment of SEQ ID NO: 11 from position 202 to position 212, the fragment of SEQ ID NO: 11 from position 402 to position 463, the fragment of SEQ ID NO: 15 from position 200 to position 210, the fragment of SEQ ID NO: 15 from position 457 to position 513, the fragment of SEQ ID NO: 7 from position 158 to position 217, the fragment of SEQ ID NO: 7 from position 233 to position 289, the fragment of SEQ ID NO: 7 from position 321 to position 331, the fragment of SEQ ID NO: 19 from position 156 to position 216, the fragment of SEQ ID NO: 19 from position 226 to position 286, the fragment of SEQ ID NO: 19 from position 360 to position 370, wherein said compound may furthermore comprise a cell-penetrating peptide; (iv) a nucleic acid comprising a sequence encoding any of the fragments according to (c), wherein said nucleic acid may optionally comprise a sequence encoding a cell-penetrating peptide; (v) aryliodonium compounds such as diphenylene iodonium (DPI), di-2-thienyliodonium, phenoxalodonium; (vi) naphthoquinones such as plumbagin, acetylshikonin; (vii) inhibitors of HMG-CoA reductase including statins such as lovastatin, simvastatin, atorvastatin; (viii) gliotoxin; (ix) phenothiazines such as phenothiazine, trifluoperazine, and/or (x) a derivative of any one of (v) to (ix). Said ototoxic agent may be any agent detailed herein above. Preferably, said ototoxic agent is a medicament, wherein said medicament causes ototoxicity as a side effect. Therefore, and in view of the disclosure of the mechanism of ototoxicity in this application, a combination therapy with a medicament with ototoxic side effect and an inhibitor of the protein defined in the main embodiment is provided. Also provided is the use of an ototoxic agent and of a compound as defined in (b) above for the manufacture of pharmaceutical composition, wherein said compound as defined in (b) prevents, alleviates or cures the ototoxic effect of said ototoxic agent.

In a preferred embodiment of said pharmaceutical composition, said ototoxic agent is an antibiotic.

In a more preferred embodiment of said pharmaceutical composition, said ototoxic agent is an aminoglycoside antibiotic, preferably gentamycin. This type of combination therapy is particularly envisaged for those regions or countries where aminoglycoside antibiotics such as gentamycin, owing to their low cost, are widely used.

The present invention also relates to the use of a modulator of the protein defined in the main embodiment for the preparation of a pharmaceutical composition for the treatment and/or prevention of hearing loss and/or phantom hearing, wherein said modulator is selected from the group consisting of (a) an antibody, aptamer, or a fragment or derivative thereof binding specifically said protein; (b) an antisense nucleic acid, an siRNA, or a ribozyme binding specifically a nucleic acid encoding said protein; (c) a known modulator of NOX3 and/or NADPH oxidases and/or electron transport proteins; (d) a compound comprising the fragment of SEQ ID NO: 11 from position 202 to position 212, the fragment of SEQ ID NO: 11 from position 402 to position 463, the fragment of SEQ ID NO: 15 from position 200 to position 210, the fragment of SEQ ID NO: 15 from position 457 to position 513, the fragment of SEQ ID NO: 7 from position 158 to position 217, the fragment of SEQ ID NO: 7 from position 233 to position 289, the fragment of SEQ ID NO: 7 from position 321 to position 331, the fragment of SEQ ID NO: 19 from position 156 to position 216, the fragment of SEQ ID NO: 19 from position 226 to position 286, the fragment of SEQ ID NO: 19 from position 360 to position 370; (e) a nucleic acid comprising a sequence encoding any of the fragments according to (d); and (f) a modulator identified by the method of any one of claims 1 to 13. The fragments according to (d) are regions of the sequences of the respective SEQ ID NOs known or expected to be involved in subunit association. Said compounds according to (d) may furthermore comprise a cell-penetrating peptide. The term "cell-penetrating peptide" is defined herein above.

The nucleic acids according to (e) include the sequences with the SEQ ID NOs: 12, 16, 8 and 20 as well those fragments thereof which comprise a sequence encoding any of the fragments according to (d). Said nucleic acid may optionally comprise a sequence encoding a cell-penetrating peptide.

Also embraced by the present invention are uses of fragments of proteins orthologous or homologous to hNOXA1, hNOXO1, hp47phox/NOXO2 or hp67phox/NOXA2, whereby said fragments align with the fragments of hNOXA1, hNOXO1, hp47phox/NOXO2 or hp67phox/NOXA2 recited under (d), as are uses of nucleic acids encoding these aligning fragments. It is understood that these uses are considered equivalents of the above described embodiment. Said orthologous or homologous proteins include the respective murine proteins, i.e., proteins having an amino acid sequence set forth in any one of SEQ ID NO: 13, 17, 9 or 21. The nucleic acids encoding the latter are set forth in SEQ ID NO: 14, 18, 10 and 22.

Furthermore embraced by the present invention are uses of (a) peptidomimetic compound(s) which has been obtained by using any of the fragments according to (d) as a lead compound.

Uses of a nucleic acid according to (e) and/or of the above described equivalents thereof are also envisaged for gene therapy.

The present invention also relates to the use of a cisplatin and/or hydrogen hexachloroplatinate for the preparation of a pharmaceutical composition for the treatment and/or prevention of tinnitus. Cisplatin and hydrogen hexachloroplatinate are activators of the protein defined the main embodiment. Surprisingly, in many incidences of tinnitus a positive response to a treatment with compounds known to induce oxidative stress in the inner ear is observed.

Also provided is a method of diagnosing hearing loss and/or phantom hearing and/or an individual's disposition or risk to develop said loss and/or said phantom hearing, comprising the steps of: (a) determining (a) polymorphism(s) in a NOX3 gene or cDNA and/or in a gene or cDNA encoding an NADPH oxidase subunit in a sample obtained from said individual; and (b) associating said polymorphism(s) with a disease state or disposition state. Preferably, said sample is a blood sample. Preferably, said NOX3 gene comprises or consists of the sequence set forth in SEQ ID NO: 23 or 24. Preferably said NOX3 cDNA (or equivalently mRNA) comprises or consists of the sequence set forth in SEQ ID NO: 2, 4 or 6. Preferably said cDNA encoding an NADPH oxidase subunit comprises or consists of the sequence set forth in any one of SEQ ID NOs: 8, 10, 12, 14, 16, 18, 20 or 22.

The term "polymorphism", or "nucleotide polymorphism" refers to the occurrence of one or more different nucleotides or bases at a given location on a chromosome. Usually, polymorphisms are distinguished from mutations based on their prevalence. Sometimes a threshold of 1% prevalence in a population of individuals is considered for separating polymorphisms (more frequent) from mutations (less frequent). A single nucleotide polymorphism (SNP) is a polymorphism of a single nucleotide or base. The SNP database maintained at NCBI (http://www.ncbi.nlm.nih.gov/SNP/) divides SNPs into SNPs in the proximity of a known locus and such that are 5' further away than 2 kb from the most 5' feature of a gene and 3' further away than 500 bases from the most 3' feature of a gene. SNPs in the proximity of a known locus are further divided into SNPs occurring at an mRNA location and such that do not. SNPs occurring at an mRNA location comprise coding and non-coding SNPs.

It is understood that the term "polymorphism(s) in a NOX3 gene and/or in a gene encoding an NADPH oxidase subunit" embraces polymorphisms in exons, introns and regulatory regions such as promoters. Polymorphisms in exons may be determined or analysed using genomic DNA or cDNA (or equivalently mRNA). Polymorphisms in introns or regulatory regions such as promoters may be determined or analysed using cDNA (or equivalently mRNA).

Said associating of polymorphism(s) with a disease state or disposition state refers to classifying of individuals and patients. The term "classifying" refers to the assignment of individuals or patients to two or more groups or classes. In other words, individuals, previously unclassified, get labelled by their respective class. The assigned class label may refer to parameters used for classification, e.g. polymorphisms, or may refer to parameters not used for classification because their values are not known beforehand, e.g. fast or slow response to therapy. In the first case, class discovery methods, e.g. clustering may be applied, whereas in the second case predictive classification methods are used. Classification may be done manually by a trained person or by a computer program provided with the values of the parameters used for class distinction. Patients have to give informed consent. Data have to be handled and kept secret in accordance with national laws.

The present invention also provides the use of a compound binding to the protein defined in the main embodiment or to a NADPH oxidase subunit for the preparation of a diagnostic composition for the diagnosis of hearing loss and/or phantom hearing and/or an individual's disposition or risk to develop said loss and/or said phantom hearing, wherein said compound is selected from the group consisting of (a) an antibody, aptamer, or a fragment or derivative thereof binding specifically said protein; and (b) a known modulator of NOX3 and/or NADPH oxidases and/or electron transport proteins.

In a preferred embodiment of the use according to the invention, said known modulator is selected from the group consisting of iodonium derivatives, substituted catechols such as apocynin, platinum derivatives and palladium derivatives.

Known modulators to be used for the preparation of a pharmaceutical composition according to the invention are selected from the group consisting of (i) aryliodonium compounds such as diphenylene iodonium (DPI), di-2-thienyliodonium, phenoxaiodonium; (ii) ortho-methoxy-substituted catechols such as apocynin, acetosyringone, vanillin, vanillic acid, syringaldehyde, syringic acid; (iii) naphthoquinones such as plumbagin, acetylshikonin; (iv) inhibitors of HMG-CoA reductase including statins such as lovastatin, simvastatin, atorvastatin; (v) gliotoxin; (vi) phenothiazines such as phenothiazine, trifluoperazine; and (vii) a derivative of any one of (i) to (vi). Said known modulators act as inhibitors of the protein defined in the main embodiment.

Known modulators to be used for the preparation of a diagnostic composition according to the invention are selected from the known modulators to be used for the preparation of a pharmaceutical composition and cisplatin and hexachloroplatinate as well as derivatives thereof. Cisplatin and hexachloroplatinate bind and activate the protein defined in the main embodiment and are therefore specifically envisaged for the manufacture of a diagnostic composition.

Cisplatin, as demonstrated by the inventors, is a preferred platinum derivative which modulates NOX3 activity. The platinum derivative hydrogen hexachloroplatinate and palladium derivatives are known to modulate the activity of NOX2 (phagocyte NADPH oxidase). In both cases, there are indications that modulation is a direct effect on the NOX enzymes.

Also envisaged is the use of a compound binding to a nucleic acid encoding the protein defined in the main embodiment or an NADPH oxidase subunit for the preparation of a diagnostic composition for the diagnosis of hearing loss and/or phantom hearing and/or an individual's disposition or risk to develop said loss and/or said phantom hearing, wherein said compound is a nucleic acid complementary to said nucleic acid and at least 15 nucleotides in length. This embodiment is directed to oligonucleotide probes for the detection of genomic DNA or mRNA. With regard to genomic DNA, also the detection and distinction of polymorphisms is envisaged.

Preferably, said compound is detectably labelled.

More preferred, said diagnosis to be performed involves imaging of the human or animal body.

In a preferred embodiment of the method or the use of the invention, said animal is a rodent. More preferred, said rodent is mouse or rat.

In a preferred embodiment of the method or the use of the present invention, said modulator is an inhibitor.

The term "inhibitor" designates a compound lowering the activity of a target molecule, preferably by performing one or more of the following effects: (i) the transcription of the gene encoding the protein to be inhibited is lowered, (ii) the translation of the mRNA encoding the protein to be inhibited is lowered, (iii) the protein performs its biochemical function with lowered efficiency in presence of the inhibitor, and (iv) the protein performs its cellular function with lowered efficiency in presence of the inhibitor.

Compounds falling in class (i) include compounds interfering with the transcriptional machinery and/or its interaction with the promoter of said gene and/or with expression control elements remote from the promoter such as enhancers. Compounds of class (ii) comprise antisense constructs and constructs for performing RNA interference well known in the art (see, e.g. Zamore (2001) or Tuschl (2001)). Compounds of class (iii) interfere with molecular function of the protein to be inhibited, in case of an NADPH oxidase with its enzymatic activity and/or its capability to associate with NADPH oxidase subunits. Accordingly, active site binding compounds, in particular compounds capable of binding to the active site of any NADPH oxidase, are envisaged, as are compounds interfering with the association of NADPH oxidase with said subunits. More preferred are compounds specifically binding to an active site of NADPH oxidase. Also envisaged are compounds binding to or blocking substrate binding sites of NADPH oxidase. Class (iv) includes compounds which do not necessarily directly bind to NADPH oxidase, but still interfere with NADPH oxidase activity, for example by binding to and/or inhibiting the function or inhibiting expression of members of a pathway which comprises NADPH oxidase. These members may be either upstream or downstream of NADPH oxidase within said pathway.

In a preferred embodiment, the inhibitor is a low molecular weight compound. Low molecular weight compounds are compounds of natural origin or chemically synthesized compounds, preferably with a molecular weight between 100 and 1000, more preferred between 200 and 750, and even more preferred between 300 and 600.

The efficiency of the inhibitor can be quantitized by comparing the level of activity in the presence of the inhibitor to that in the absence of the inhibitor. For example, as an activity measure may be used: the change in amount of mRNA formed, the change in amount of protein formed, the change in amount of substrate converted or product formed, and/or the change in the cellular phenotype or in the phenotype of an organism.

In a preferred embodiment, the level of activity is less than 90%, more preferred less than 80%, 70%, 60% or 50% of the activity in absence of the inhibitor. Yet more preferred are inhibitors lowering the level down to less than 25%, less than 10%, less than 5% or less than 1% of the activity in absence of the inhibitor.

The present invention also relates to a nucleic acid (i) comprising or consisting of the sequence of SEQ ID NO: 6, or (ii) encoding a protein comprising or consisting of the sequence of SEQ ID NO: 5, or (iii) encoding a fragment of the protein according to (ii), wherein said fragment exhibits NADPH oxidase activity, or (iv) encoding a protein having a sequence at least 95% identical with the protein according to (ii) or with the fragment according to (iii) and exhibiting NADPH oxidase activity.

Preferably, said protein having at least 95% sequence identity with the protein according to (ii) or with the fragment according to (iii), has 98% or 99% identity with said protein or fragment.

An alternative embodiment of the invention relates to a vector comprising the above defined nucleic acid.

The vector of the present invention may be, e.g., a plasmid, cosmid, virus, bacteriophage or another vector used e.g. conventionally in genetic engineering, and may comprise further genes such as marker genes which allow for the selection of said vector in a suitable host cell and under suitable conditions.

Furthermore, the vector of the present invention may, in addition to the nucleic acids of the invention, comprise expression control elements, allowing proper expression of the coding regions in suitable hosts. Such control elements are known to the artisan and may include a promoter, a splice cassette, translation initiation codon, translation and insertion site for introducing an insert into the vector. Preferably, the nucleic acid of the invention is operably linked to said expression control sequences allowing expression in eukaryotic or prokaryotic cells.

Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook (1989), loc. cit., and Ausubel, Current Protocols in Molecular Biology, Green Publishing Associates and Wiley Interscience, N.Y. (1989), (1994).

Alternatively, the nucleic acids and vectors of the invention can be reconstituted into liposomes for delivery to target cells. According to the invention relevant sequences can be transferred into expression vectors where expression of a particular (poly)peptide/protein is required. Typical cloning vectors include pBscpt sk, pGEM, pUC9, pBR322 and pGBT9. Typical expression vectors include pTRE, pCAL-n-EK, pESP-1, pOP13CAT.

Furthermore, a protein encoded by said nucleic acid is provided.

The present invention furthermore relates to host containing an aforementioned vector or an aforementioned nucleic acid, or an aforementioned protein. Said host may be produced by introducing said vector or nucleic acid into a host cell which upon its presence in the cell mediates the expression of a protein encoded by the nucleic acid of the invention or comprising a nucleic acid or a vector according to the invention wherein the nucleic acid and/or the encoded (poly) peptide/protein is foreign to the host cell.

By "foreign" it is meant that the nucleic acid and/or the encoded (poly)peptide/protein is either heterologous with respect to the host, this means derived from a cell or organism with a different genomic background, or is homologous with respect to the host but located in a different genomic environment than the naturally occurring counterpart of said nucleic acid. This means that, if the nucleic acid is homologous with respect to the host, it is not located in its natural location in the genome of said host, in particular it is surrounded by different genes. In this case the nucleic acid may be either under the control of its own promoter or under the control of a heterologous promoter. The vector or nucleic acid according to the invention which is present in the host may either be integrated into the genome of the host or it may be maintained in some form extrachromosomally. In this respect, it is also to be understood that the nucleic acid of the invention can be used to restore or create a mutant gene via homologous recombination.

The host can be any prokaryote or eukaryotic cell, such as a bacteria, an insect, fungal, plant or animal cell.

The term "prokaryote" is meant to include all bacteria which can be transformed or transfected with a DNA or RNA molecules for the expression of a protein of the invention. Prokaryotic hosts may include gram negative as well as gram positive bacteria such as, for example, E. coli, S. typhimurium, Serratia marcescens and Bacillus subtilis. The term "eukaryotic" is meant to include yeast cells, cells of higher plant, insect cells and preferably mammalian cells. Depending upon the host employed in a recombinant production procedure, the protein encoded by the nucleic acid of the present invention may be glycosylated or may be non-glycosylated. A nucleic acid of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook (1989), loc. cit.).

Preferably, said host is a cell. More preferred, the host is a human cell or human cell line.

Alternatively, said host is a transgenic non-human animal.

A method for the production of a transgenic non-human animal, for example transgenic mouse, comprises introduction of a nucleic acid or vector according to the invention into a germ cell, an embryonic cell, stem cell or an egg or a cell derived therefrom. The non-human animal can be used in accordance with a screening method of the invention described herein. Production of transgenic embryos and screening of those can be performed, e.g., as described by A. L. Joyner Ed., Gene Targeting, A Practical Approach (1993), Oxford University Press. The DNA of the embryonal membranes of embryos can be analyzed using, e.g., Southern blots with an appropriate probe. A general method for making transgenic non-human animals is described in the art, see for example WO 94/24274. For making transgenic non-human organisms (which include homologously targeted non-human animals), embryonal stem cells (ES cells) are preferred. Murine ES cells, such as AB-1 line grown on mitotically inactive SNL76/7 cell feeder layers (McMahon and Bradley, Cell 62: 1073-1085 (1990)) essentially as described (Robertson, E. J. (1987) in Teratocarcinomas and Embryonic Stem Cells: A Practical Approach. E. J. Robertson, ed. (Oxford: IRL Press), p. 71-112) may be used for homologous gene targeting. Other suitable ES lines include, but are not limited to, the E14 line (Hooper et al., Nature 326: 292-295 (1987)), the D3 line (Doetschman et al., J. Embryol. Exp. Morph. 87: 27-45 (1985)), the CCE line (Robertson et al., Nature 323: 445-448 (1986)), the AK-7 line (Zhuang et al., Cell 77: 875-884 (1994) which is incorporated by reference herein). The success of generating a mouse line from ES cells bearing a specific targeted mutation depends on the pluripotence of the ES cells (i.e., their ability, once injected into a host developing embryo, such as a blastocyst or morula, to participate in embryogenesis and contribute to the germ cells of the resulting animal). The blastocysts containing the injected ES cells are allowed to develop in the uteri of pseudopregnant non-human females and are born as chimeric mice. The resultant transgenic mice are chimeric for cells having either the recombinase or reporter loci and are backcrossed and screened for the presence of the correctly targeted transgene(s) by PCR or Southern blot analysis on tail biopsy DNA of offspring so as to identify transgenic mice heterozygous for either the recombinase or reporter locus/loci.

Methods for producing transgenic flies, such as *Drosophila melanogaster* are also described in the art, see for example U.S. Pat. No. 4,670,388, Brand & Perrimon, Development (1993) 118: 401-415; and Phelps & Brand, Methods (April 1998) 14: 367-379.

Transgenic worms such as *C. elegans* can be generated as described in Mello, et al., (1991) Efficient gene transfer in *C. elegans*: extrachromosomal maintenance and integration of transforming sequences. Embo J 10, 3959-70, Plasterk, (1995) Reverse genetics: from gene sequence to mutant worm. Methods Cell Biol 48, 59-80.

The invention also relates to transgenic non-human animals such as transgenic mouse, rats, hamsters, dogs, monkeys, rabbits, pigs, *C. elegans* and fish such as Torpedo fish comprising a nucleic acid according to the invention.

Also provided is an antibody or aptamer, or fragment or derivative thereof binding specifically to the protein encoded by said nucleic acid as is an antisense nucleic acid, an siRNA, or a ribozyme binding specifically said nucleic acid.

The Figures show:

FIG. 1: Tissue distribution of NOX3 mRNA. A) NOX3 mRNA expression was evaluated in 12 rat tissues by RT-PCR (upper panel); GAPDH mRNA was used as a reference transcript (lower panel). "No cDNA" represents negative control PCR devoid of added cDNA. The first lane of both panels shows DNA size markers. B) Quantification of NOX3 RNA in 14 mouse tissues using real time PCR. NOX3 mRNA expression is shown relative to 18S rRNA expression. The amounts of NOX3 and 18S PCR products were measured using SYBR Green.

FIG. 2: PCR detection of cDNAs encoding NOX activator and regulator subunits in the inner ear. A, RT-PCR amplification of NOXA1, NOXO1, and the reference GAPDH cDNA from the indicated rat tissues. B, RT-PCR amplification of $p67^{phox}$ and $p47^{phox}$ cDNA from the indicated rat tissues. The first lane of each panel shows DNA size markers.

Figure 3:
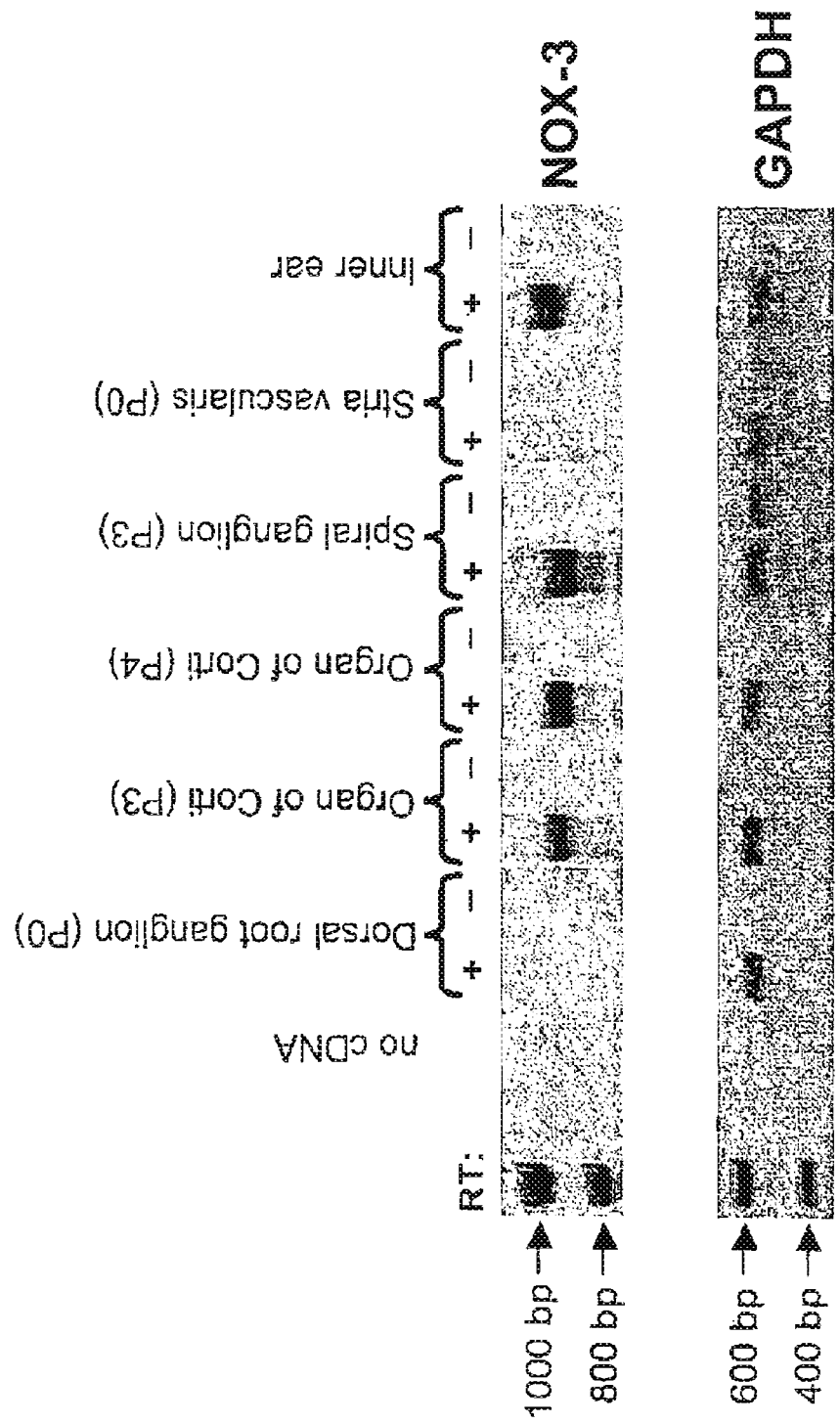

FIG. 3: Expression of NOX3 mRNA in specific regions of cochlea. The indicated regions of the rat inner ear were obtained by microdissection and NOX3 (upper panel) and GAPDH (lower panel) expression were assessed by RT-PCR. "+" symbols represent reverse transcribed (RT positive) samples; "-" symbols represent not reverse transcribed (RT negative) samples. P0, P3, and P4 indicate the postnatal days when samples were taken. Positive control inner ear sample was isolated from adult rat.

FIG. 4: Localization of NOX3 mRNA in inner ear by in situ hybridization. Mouse inner ear sections hybridized with digoxigenin-labeled antisense (A, C, and E) and sense (B, D, and F) probes of NOX3, shown at ×20 (A, B) and ×40 (C-F) magnifications. A, The antisense probe hybridized with the RNA of spiral ganglion neurons. B, The sense probe yielded only a weak, uniform signal and no labeling of spiral ganglion neurons. C, Hybridization of antisense NOX3 probe with the organ of Corti labeled the sensory epithelium. D, Hybridization of sense NOX3 probe with organ of Corti did not yield specific signals. E, Antisense NOX3 probe hybridized with the sensory epithelial cell layer of the saccule. F, Only a week uniform signal was observed with the sense NOX3 probe.

Figure 5:
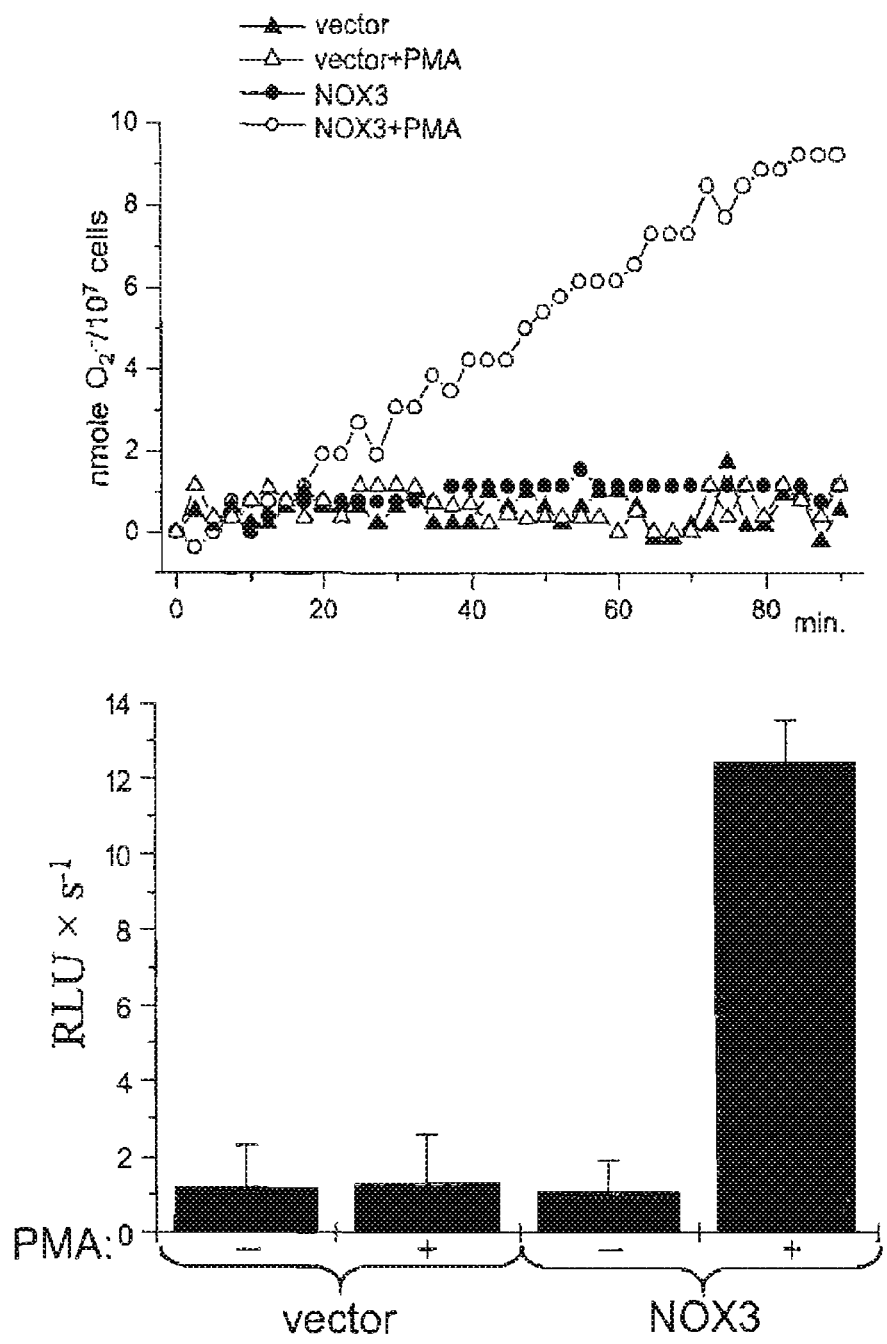

FIG. 5: NOX3-dependent superoxide production in the absence of other NOX subunits. HEK293 cells were transfected with either pcDNA3.1 vector or NOX3, and superoxide generation was measured as cytochrome C reduction (upper panel) or as luminol-amplified chemiluminescence (lower panel) in the presence or absence of 100 nM PMA, as indicated. Upper panel shows the result of a single experiment representative of three independent studies. Lower panel shows statistical analysis of peak superoxide production. Chemiluminescence signals were measured with relative light units (RLU) and normalized to 1 second and 150,000 cells.

FIG. 6: Subunit regulation of NOX3 activity. A, B, and C, HEK293 cells were transfected with different combinations of NOX3, NOXO1, NOXA1, $p47^{phox}$, and $p67^{phox}$, as indicated. Superoxide generation was measured as SOD sensitive cytochrome C reduction (lines and symbols) or as luminol-amplified chemiluminescence (bar graphs) in the presence or absence of PMA (100 nM), as indicated. Lines and symbols show typical experiments, representative of at least three independent studies. Bar graphs show statistical analysis of peak superoxide production. Chemiluminescence signals were measured with relative light units (RLU) and normalized to 1 second and 150,000 cells.

Figure 7:
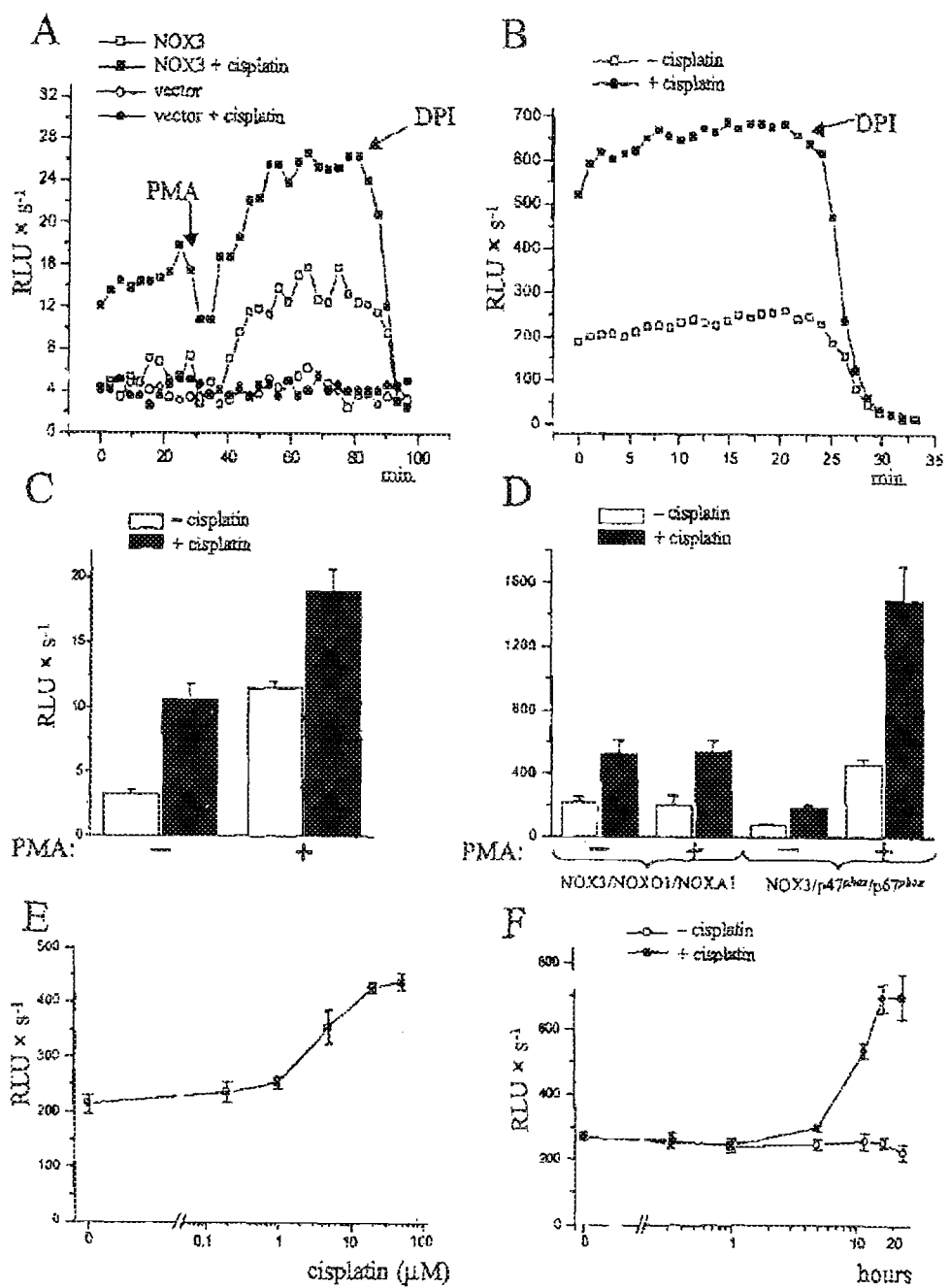

FIG. 7: Cisplatin enhances NOX3-dependent superoxide production. Superoxide production of transfected HEK293 cells were measured either as luminol-amplified chemiluminescence (B, D, E and F) or with a luminol-based superoxide detection kit, Diogenes (A and C). Cells were pre-incubated in the presence or absence of 20 μM cisplatin for 12 hours (A-E). A, HEK293 cells were transfected with NOX3 or control vector (pcDNA3.1) and incubated with or without cisplatin before superoxide measurement. 100 nM PMA and 5 μM DPI were added as indicated. Traces represent a typical experiment, representative of three independent studies. B, HEK293 cells stably expressing NOX3/NOXA1/NOXO1 were pre-incubated with or without cisplatin before superoxide measurement. 5 μM DPI was added as indicated. Traces show a typical experiment, representative of eight independent studies. C, Statistical analysis of peak superoxide production of NOX3 transfected HEK293 cells, after cisplatin- or control treatment, in the presence or absence of 100 nM PMA. D, Statistical analysis of peak superoxide production of HEK293 cells transfected with the indicated constructs and pre-incubated with or without cisplatin. The measurements were carried out in the absence or presence of 100 nM PMA, as indicated. E, Superoxide production of a HEK293 cell clone stably transfected with NOX3/NOXO1/NOXA1 after incubation with various concentrations of cisplatin for 12 hours. F, Superoxide production of a HEK293 cell clone stably transfected with NOX3/NOXO1/NOXA1 after incubation in the presence or absence of 20 μM cisplatin for the indicated periods of time.

The following examples illustrate the invention but should not be construed as being limiting.

EXAMPLE 1

Cloning of Mouse and Rat NOX3 cDNA

Experimental procedures. The first and the last exons of mouse and rat NOX3 genes were identified based on their homology with the human NOX3 gene using the Ensembl Genome Browser (www.ensembl.org). Inner ear samples of mouse (strain C57Bl6) and rat (strain Sprague-Dawley) were isolated and total RNA was purified as described [28]. Primers were designed and used to amplify the full length of coding sequences (mouse NOX3 forward 5'-atg ccg gtg tgc tgg att ctg aac-3' and reverse 5'-cta gaa gtt ttc ctt gtt gta ata gaa-3', rat NOX3 forward 5'-gtg ttg gta gta aga gaa gtg tca tg-3' and reverse 5'-c tag aag ttt tcc ttg ttg taa tag-3') with Taq DNA polymerase (Qiagen) under standard conditions. PCR products were subcloned into pcDNA3.1 vector (Invitrogen) and verified by sequencing.

Results. So far, NOX3 mRNA has only been detected in human embryonic kidney, but expression levels were very low [22, 30] and hence the physiological relevance questionable. We reasoned that the physiologically relevant localization of NOX3 might have been missed because previous studies had restricted their analysis to commercially available human RNA sources. To overcome these limitations, we decided to work in mouse and rat and to prepare RNA from tissues that had not been investigated so far. As hitherto only the human NOX3 sequence was known, we identified mouse and rat NOX3 genes by searching genomic DNA databases and designed—based on these results—mouse and rat NOX3 PCR primers.

We then prepared RNA from a variety of mouse and rat tissues, including bone (femur, skull, shoulder blade), cartilage (joints of ribs, outer ear), and inner ear and analyzed them for NOX3 expression by RT-PCR. As shown on FIG. 1A, high levels of NOX3 transcript were detected only in the rat inner ear sample (despite its relatively low mRNA content demonstrated by the low amount of GAPDH PCR product). Using primer pairs designed from the first and the last exons of the mouse and rat NOX3 gene, respectively, we amplified whole length mouse and rat NOX3 coding sequences from inner ear samples. The predicted amino acid sequences of both mouse and rat NOX3 showed 81% sequence identity with the human sequence and 93.5% identity with each other.

EXAMPLE 2

Tissue Distribution of NOX3

Experimental procedures. Total RNA was isolated from different organs of rat and mouse and from specific regions of the rat inner ear using the TRIzol reagent. With the exception of RNA purified from parts of the inner ear, samples were DNase treated, then further purified with RNeasy kit (Qiagen). 2 µg total RNA from each tissue was reverse transcribed using Superscript reverse transcriptase (Life Technologies, Inc.). PCR was carried out with Taq DNA polymerase using the following primers: mouse NOX3 forward 5'-gtg ata aca ggc tta aag cag aag gc-3', reverse 5'-cca ell tcc cct act tga ctt tag-3'; rat NOX3 forward 5'-gcg tgt gct gta gag gac cgt gga g-3', reverse 5'-gag cct gtc cct ctg ctc caa atg c-3'; mouse GAPDH forward 5'-ggg tgt gaa cca cga gaa at-3', reverse 5'-gtc atg agc cct tcc aca at −3'; rat GAPDH forward 5'-cgg tgt caa cgg att tgg ccg tat t-3', reverse 5'-act gtg gtc atg agc cct tcc acg a-3'; rat NOXO1 forward 5'-acc caa acc tct gga tct gga gcc c-3', reverse 5'-gga tgg cac tca tac agg ggc gag t-3'; rat NOXA1 forward 5'-tac tgg ccg tag cac gcg aag act g-3', reverse 5'-gga cct ccc agg ctt gca gtt tga a-3'; rat p47$^{phox}$ forward 5'-gca gga cct gtc gga gaa ggt ggt c-3', reverse 5'-tct gtc gct ggg cct ggg tta tct c-3'; rat p67$^{phox}$ forward 5'-aag cag aag agc agt tag cat tgg c-3', reverse 5'-gga gtg cct tcc aaa ttc ttg gct g-3'. Standard PCR conditions were used, and the number of PCR cycles was 30 (FIGS. 1 and 2) or 28 (FIG. 3) for the amplification of GAPDH and 35 for all other amplifications.

Quantitative PCR was carried out using ABI Prism 7900HT Sequence Detection System with standard temperature protocol and 2×SYBR Green PCR Master Mix reagent (Applied Biosystems, Worrington, UK) in 25 µl volume, in triplicates. 300 nM of the following primer pairs were used for the reactions: mouse 18S forward 5'-aca tcc aag gaa ggc agc ag-3' and reverse 5'-ttt tcg tca cta cct ccc cg-3'; mouse NOX3 forward 5'-cga cga att caa gca gat tgc-3', and reverse 5'-aag agt ctt tga cat ggc ttt gg-3'. All amplifications were carried out in a MicroAmp optical 96-well reaction plate with optical adhesive covers (PE Applied Biosystems). The accumulation of PCR products was detected by monitoring the increase in fluorescence of the reporter dye.

Results.

NOX3 is predominantly expressed in the inner ear—Based on the cDNA sequence of mouse NOX3, we designed primers for real time PCR to study quantitative expression of NOX3 RNA in different mouse tissues. 18S RNA was used as a reference gene. The results of real-time PCR demonstrated that NOX3 was predominantly expressed in the inner ear (FIG. 1B). Low amounts of NOX3 RNA could also be detected in skull, brain, and embryonic kidney. However, inner ear contained 50-fold of the NOX3 content of skull and 870-fold of the one of embryonic kidney (FIG. 1B).

Expression of cytoplasmic NOX subunits in the inner ear—NOX1 and gp91$^{phox}$/NOX2 require cytoplasmic organizer subunits (NOXO1, p47$^{phox}$) and activator subunits (NOXA1, p67$^{phox}$) to form a functional enzyme. As NOX3 shows a high degree of homology with NOX1 and gp91$^{phox}$/NOX2 [31], we considered that it might also be a subunit-dependent enzyme and therefore investigated expression of cytoplasmic NOX subunits in the inner ear. RT-PCR analysis (using 35 PCR cycles) showed that mRNA of the activator subunit NOXA1, as well as mRNA of the organizer subunit p47$^{phox}$ was expressed in the inner ear (FIG. 2). mRNA of the activator subunit, p67$^{phox}$, and the organizer subunit, NOXO1, could be detected only at very high cycle numbers (40 PCR cycles; data not shown). Since p47$^{phox}$ mRNA is expressed in phagocytic cells, its detection might be due to blood cell contamination. In contrast, NOXA1 is not expressed in blood cells [24] nor in tissues neighboring the inner ear (FIG. 2A); thus, it is most likely expressed within cells of the inner ear.

Expression of NOX3 in different parts of the cochlea—In order to identify regions of the inner ear that express NOX3, we isolated distinct parts of rat cochlea such as organ of Corti, stria vascularis, and spiral ganglia from newborn rats (postnatal day 1 to 4) as described previously [32]. As a control tissue, we used dorsal root ganglia. Total RNA was extracted from these tissues and tested for NOX3 and GAPDH housekeeping gene expression by RT-PCR. Results showed that NOX3 is expressed in spiral ganglia and in the organ of Corti, while stria vascularis and dorsal root ganglia were devoid of NOX3 mRNA (FIG. 3). Our experiments demonstrated that i) NOX3 is expressed only in selected structures of the cochlea (i.e. organ of Corti and spiral ganglia), and ii) its expression is not a general property of the peripheral nervous system (i.e. it was absent from dorsal root ganglia).

EXAMPLE 3

In Situ Hybridization

Experimental procedures. For in situ hybridization experiments digoxigenin-labelled antisense and sense (negative control) cRNA probes (nucleotides 560-849 of mNOX3) were generated and used as described previously [19] on decalcified, 7 µm thick inner ear sections.

Results. To further define the site of NOX3 expression, we performed in situ hybridization of adult mouse inner ear sections. The antisense NOX3 probe labeled spiral ganglion neurons (FIG. 4A) and cells of the organ of Corti (FIG. 4C). The cellular structures within the organ of Corti were not sufficiently well preserved to identify NOX3-expressing cells more precisely. The sense probe gave only a weak, uniform background signal demonstrating the specificity of the antisense hybridization (FIGS. 4 B and D). Specific labeling for NOX3 was also observed in the vestibular system, namely in the sensory epithelial cell layer of the saccule (FIG. 4 E, F).

EXAMPLE 4

Measurement of Reactive Oxygen Species

Experimental procedures.

Cell culture and transfection—HEK293 were maintained in Dulbecco's Modified Eagle's Medium/Ham's Nutrient Mixture F12 that was supplemented with 10% fetal calf serum, penicillin (100 units/ml), streptomycin (100 µg/ml), and 4 mmol/liter L-glutamine. NOX3-, NOXO1-, NOXA1-, $p47^{phox}$-, and $p67^{phox}$ cDNAs were subcloned into pcDNA3.1 (Invitrogen, Groningen, Netherlands) and transfected into HEK293 cells with the Effectene transfection system (Qiagen). To obtain stable clones, NOX3, NOXO1, NOXA1-transfected HEK293 cells were selected with 400 µg/ml G418 starting on the 2nd day after the transfection. After 14 days of selection, 24 surviving clones were tested for superoxide production. The positive clones were verified to express NOX3-, NOXO1-, and NOXA1 RNA by RT-RCR.

ROS generation was measured by the peroxidase-dependent luminol-amplified chemiluminescence technique (referred to as luminol-amplified chemiluminescence) in 96 well microplates using Luminometer Wallac 1420 Multilabel Counter (PerkinElmer Life Sciences). Measurements were performed in Hanks' balanced salt solution supplemented with 1 mg/ml D-glucose, 1 unit/ml horseradish peroxidase, and 250 µM luminol. In some experiments, phorbol ester (PMA) was added during the measurements to 100 nM final concentration. When the effect of cisplatin or 5-Fluorouracil (5-FU) was investigated, these compounds were pre-incubated with the cells for the indicated time and concentration in cell culture medium. Before ROS measurements, the cell culture medium was exchanged with the assay solution and chemiluminescence or absorption (see below) was measured at 37° C. After measurements cells were counted, and the results were normalized to 150,000 cells. Extracellular superoxide production was measured in 96-well microplates at 550 nm as the SOD-sensitive reduction of 100 µM ferricytochrome C (referred to as cytochrome C reduction technique). The $O^-_2$ production was calculated using an absorption coefficient of 21.1 $mM^{-1}$ $cm^{-1}$ and normalized to $10^7$ cells [29].

Results.

NOX3-dependent superoxide generation in the absence of subunits—To investigate its molecular function, we transiently expressed NOX3 in HEK293 cells, which do not show endogenous expression of the enzyme. Superoxide production was measured with cytochrome C reduction technique and with luminol-amplified chemiluminescence. Using either technique, NOX3-transfected cells generated low amounts of superoxide, but only in the presence of a protein kinase C activator (phorbol ester, PMA) (FIG. 5). Since both NOX1 and $gp91^{phox}$/NOX2 have an obligatory subunit requirement, the stimulus-dependent and subunit-independent activity of NOX3 is a unique and distinguishing feature of this NOX isoform.

Figure 6A:
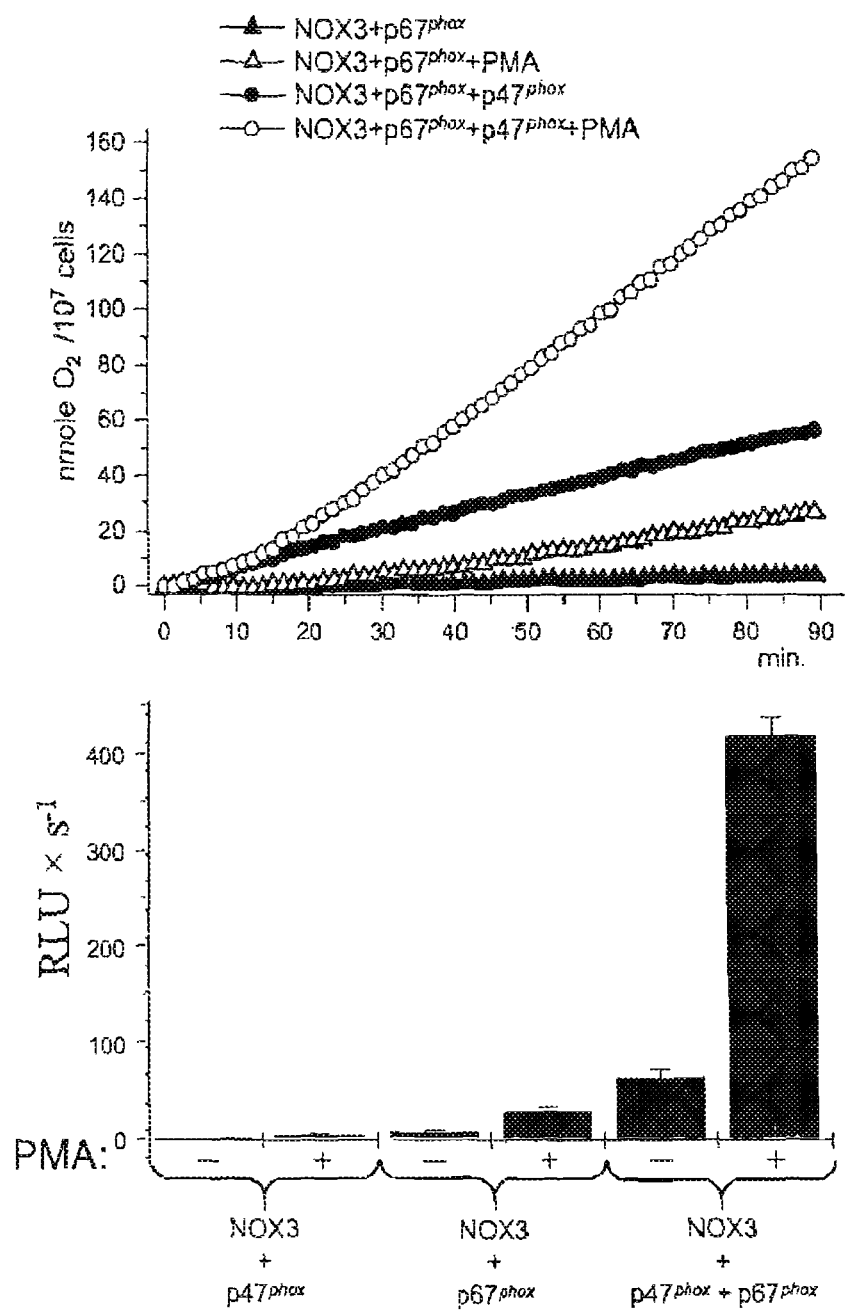

Regulation of NOX3 by the organizer and activator subunits of NOX1 and $gp91^{phox}$/NOX2—Since expression of NOX regulator and activator subunits was detected in the inner ear (see above, FIG. 2), we reasoned that they might influence NOX3 activity. Thus, we investigated superoxide generation by NOX3 upon co-transfection with cytoplasmic subunits. In the first series of experiments, NOX3 was co-transfected with the cytosolic subunits of the phagocyte NADPH oxidase, $p67^{phox}$ and $p47^{phox}$. In these transfectants, the NOX3-dependent superoxide generation was markedly increased, even without an added stimulus (FIG. 6A). The addition of PMA, however, led to a strong enhancement of NOX3 activity (FIG. 6A). HEK293 cells, transfected with $p47^{phox}$ and $p67^{phox}$ but devoid of NOX3, did not produce any superoxide (not shown). Interestingly $p67^{phox}$ alone, in the absence of $p47^{phox}$, was sufficient to double the PMA-induced superoxide generation of NOX3, while $p47^{phox}$, in the absence of $p67^{phox}$, did not modify NOX3 activity (compare FIG. 5 with FIG. 6A).

Figure 6B:
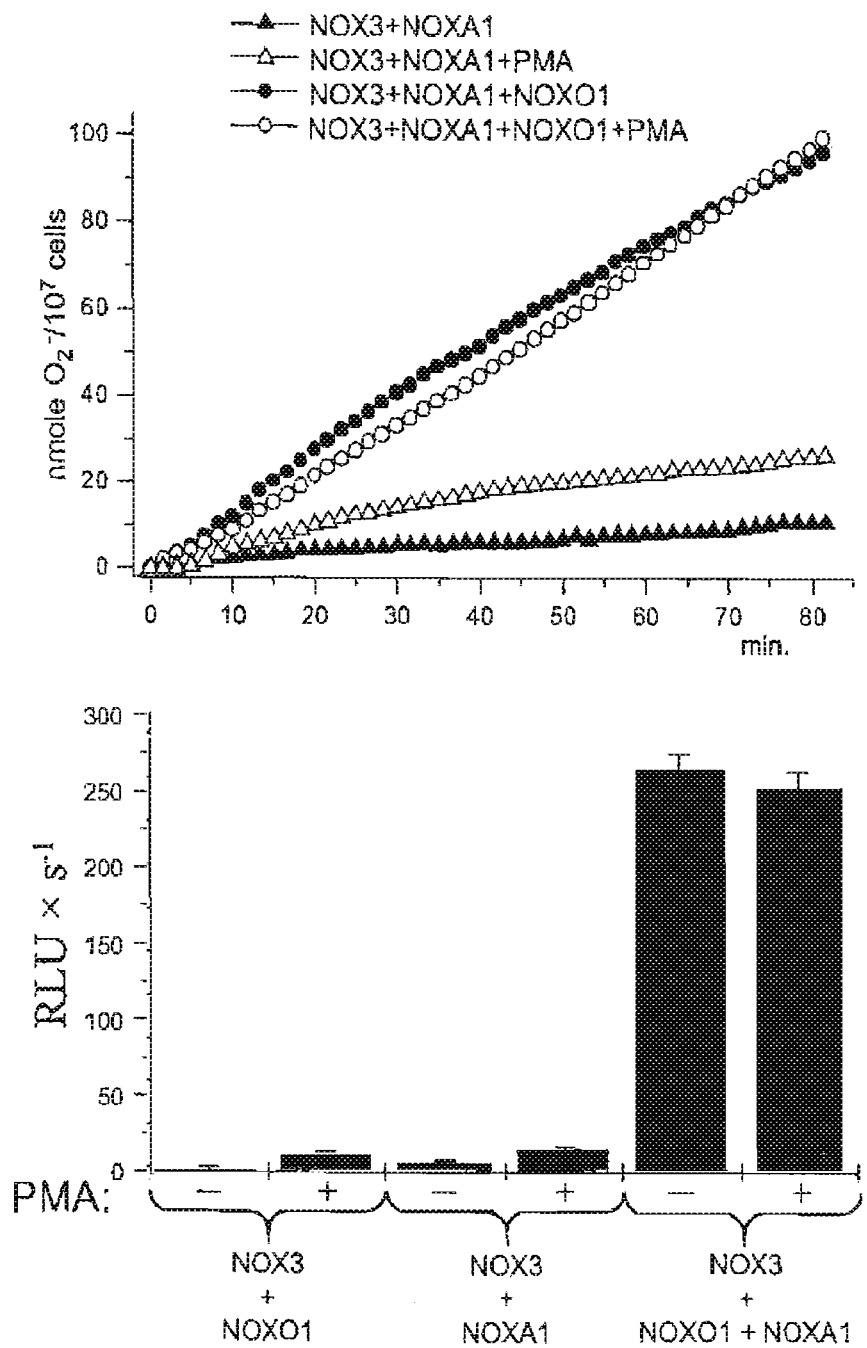

Next it was investigated whether NOX3 could be regulated by the NOXO1 and NOXA1 subunits, which are associated with NOX1 in the colon. Co-transfection of NOX3 with NOXO1 and NOXA1 resulted in a massive increase of superoxide production (FIG. 6B). The NOXO1/NOXA1-enhanced superoxide generation was insensitive to PMA (FIG. 6B). The co-expression of NOXA1 with NOX3, in the absence of NOXO1, had an enhancing effect on PMA-stimulated NOX3 activity. NOXO1 alone, however, did not influence NOX3-dependent superoxide production (FIG. 6B, lower panel).

Figure 6C:
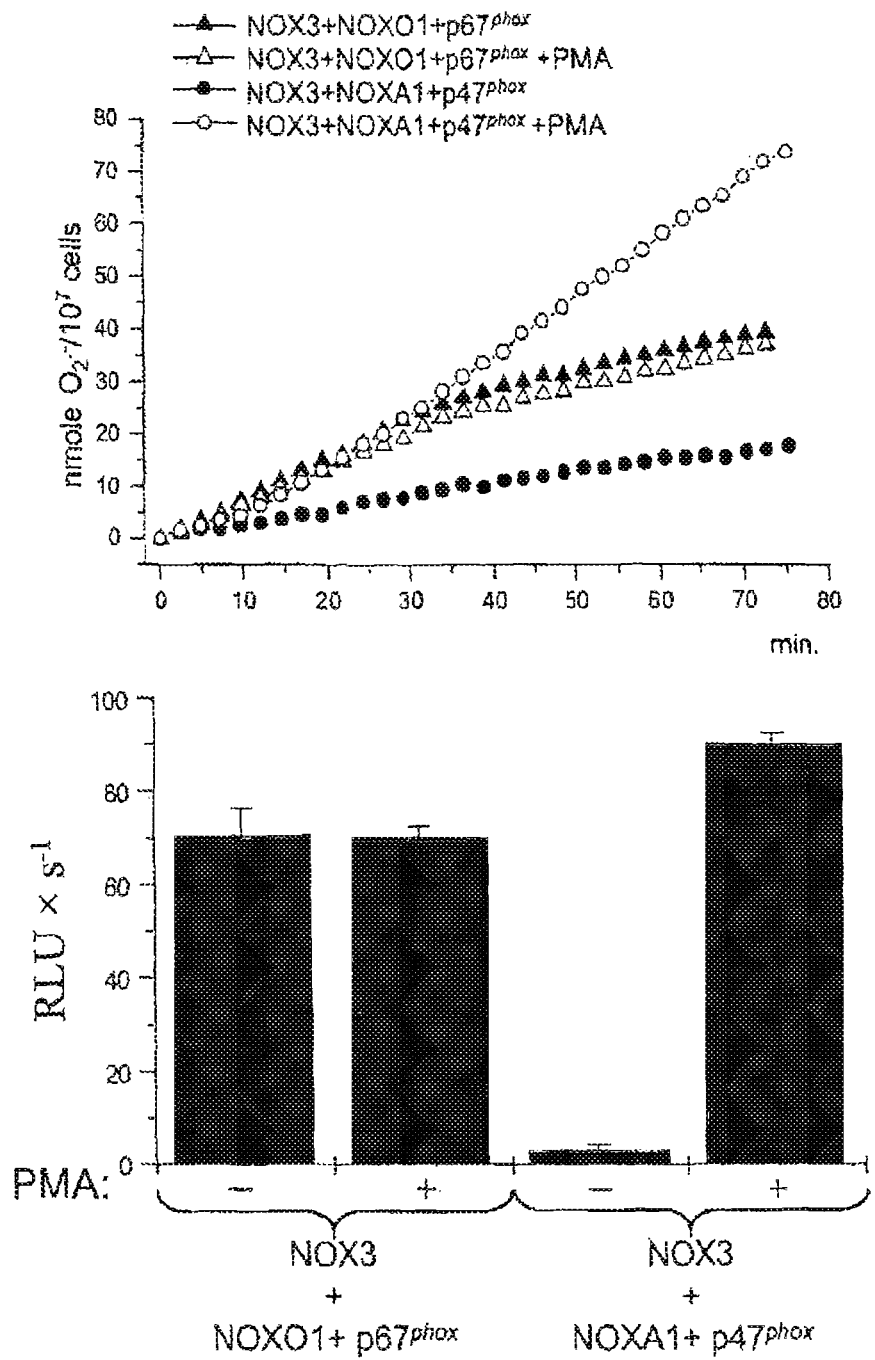

At a least on a biochemical level, there is promiscuity among the organizer and regulator subunits: NOXO1 is able to function with $p67^{phox}$, and NOXA1 with $p47^{phox}$ [24-26]. Therefore, we investigated which combinations of organizer and activator subunits are capable to regulate NOX3, and what kind of properties those complexes may have. Expression of NOXO1, $p67^{phox}$, and NOX3 in HEK293 cells, led to spontaneous superoxide generation that could not be further enhanced by PMA (FIG. 6C). However, when $p47^{phox}$, NOXA1, and NOX3 were expressed, superoxide production by HEK293 cells was largely PMA-dependent (FIG. 6C). Thus, the organizer subunit ($p47^{phox}$ versus NOXO1) determines whether NOX3 activity is PKC-dependent or independent.

Cisplatin enhances NOX3 activity—Cisplatin is an ototoxic drug that exerts its toxic effect, at least in part, through induction of ROS generation in the inner ear [2]. We therefore investigated the effect of this drug on NOX3 activity. HEK293 cells were transfected with NOX3 or with a control vector (pcDNA3.1) and incubated for 12 hours in the presence or absence of 20 µM cisplatin. Cisplatin alone elicited superoxide production in NOX3-transfected, but not in control-transfected cells (FIG. 7A, see traces before PMA addition and FIG. 7C). Addition of PMA further increased superoxide generation, while an NADPH oxidase inhibitor, diphenylene iodonium (DPI), blocked it completely (FIG. 7A).

When HEK293 cells were co-transfected with NOX3, NOXO1 and NOXA1, they produced ROS in a constitutive manner (see FIG. 6B). To investigate the effect of cisplatin under these conditions, we generated HEK293 clones stably expressing NOX3, NOXO1, and NOXA1 subunits. These clones produced superoxide constitutively and spontaneously as observed in the transient transfectants. Upon incubation with 20 µM cisplatin (12 hours), a marked increase of superoxide production was detected by the luminol-amplified chemiluminescence (FIGS. 7B and C), and also by cytochrome C reduction (not shown). The superoxide generation was insensitive to PMA and could be abolished by DPI (FIGS. 7B and D). As control we investigated the effect of another chemotherapeutic drugs 5-fluorouracil, which is devoid of ototoxicity; incubation of NOX3/NOXO1/NOXA1 expressing cells with this compound (100 µM, 17 hours) did not influence superoxide production (data not shown). HEK293 cells were also co-transfected with NOX3, $p47^{phox}$, and $p67^{phox}$, and incubated with 20 µM cisplatin for 12 hours.

Cisplatin enhanced the superoxide production of NOX3-, p47$^{phox}$-, and p67$^{phox}$-transfected cells by a factor of approximately 3.3 (FIG. 7D); this superoxide production could be blocked by addition of 5 μM DPI (not shown).

Next the concentration and time dependency of the cisplatin effect on NOX3 activity was investigated using a NOX3/NOXO1/NOXA1 transfected stable clone. After incubating the cells with various concentrations of cisplatin for 12 hours, superoxide production was measured (FIG. 7E). Cisplatin caused an increase of NOX3-dependent ROS generation already at 1 μM concentration, and 20 μM cisplatin had a maximal effect (FIG. 7E). The $EC_{50}$ of NOX3 activation by cisplatin was 3.6+/−1.4 μM.

In order to examine the time course of NOX3 activation by cisplatin, a NOX3/NOXO1/NOXA1 transfected stable clone was incubated with 20 μM cisplatin for various periods of time. Cisplatin enhanced NOX3 activity already after 5 hours treatment and reached its maximal effect after around 17 hours (FIG. 7F); the $t_{50}$ was 11.5+/−1.7 hours.

Further References

1. Kopke, R., et al., (1999) *Ann. N.Y. Acad. Sci.* 884, 171-191.
2. Kopke, R. D., et al., (1997) *Am. J. Otol.* 18, 559-571.
3. Clerici, W. J., Hensley, K., DiMartino, D. L., Butterfield, D. A., (1996) *Hear. Res.* 98, 116-124.
4. Henderson, D., et al., (1999) *Ann. N.Y. Acad. Sci.* 884, 368-380.
5. Ohinata, Y., et al., (2000) *Brain Res.* 878, 163-173.
6. Van Campen, L. E., et al., (2002) *Hear. Res.* 164, 29-38.
7. McFadden, S. L., et al., (1999) *J. Comp. Neurol.* 413, 101-112.
8. Sergi, B., Ferraresi, A., Troiani, D., Paludetti, G., Fetoni, A. R., (2003) *Hear. Res.* 182, 56-64.
9. Jones, G. E., Balaban, C. D., Jackson, R. L., Wood, K. A., Kopke, R. D., (2003) *Exp. Brain Res.* 153, 293-306.
10. Takumida, M., et al., (2003) *Acta Otolaryngol.* 123, 8-13.
11. Darlington, C. L., Smith, P. F., (2003) *Curr. Opin. Investig. Drugs.* 4, 841-846.
12. Sha, S. H. and J. Schacht, (1999) *Free Radic. Biol. Med.* 26, 341-347.
13. Babior, B. M., J. D. Lambeth, and W. Nauseef, (2002) *Arch. Biochem. Biophys.* 397, 342-344.
14. Bokoch, G. M., Knaus, U. G., (2003) *Trends Biochem. Sci.* 28, 502-508.
15. Lambeth, J. D., (2002) *Curr. Opin. Hematol.* 9, 11-17.
16. Suh, Y. A., et al., (1999) *Nature* 401, 79-82.
17. Banfi, B., et al., (2000) *Science* 287, 138-42.
18. Geiszt, M., et al., (2000) *Proc. Natl. Acad. Sci. USA.* 97, 8010-8014.
19. Banfi, B., et al., (2001) *J. Biol. Chem.* 276, 37594-37601.
20. De Deken, X., Wang, D., Many, M. C., Costagliola, S., Libert, F., Vassart, G., Dumont, J. E., and Miot, F., (2000) *J. Biol. Chem.* 275, 23227-23233.
21. Caillou, B., Dupuy, C., Lacroix, L., Nocera, M., Talbot, M., Ohayon, R., Deme, D., Bidert, J. M., Schlumberger, M., and Virion, A., (2001) *J. Clin. Endocrinol. Metab.* 86, 3351-3358.
22. Kikuchi, H., et al., (2000) *Gene* 254, 237-243.
23. Babior, B. M., (1999) *Blood* 93, 1464-1476.
24. Banfi, B., Clark, R. A., Steger, K., Krause, K. H., (2003) *J. Biol. Chem.* 278, 3510-3513.
25. Geiszt, M., Lekstrom, K., Witta, J., Leto, T. L., (2003) *J. Biol. Chem.* 278, 20006-20012.
26. Takeya, R., Ueno, N., Kami, K., Taura, M., Kohjima, M., Izaki, T., Nunoi, H., Sumimoto, H., (2003) *J. Biol. Chem.* 278, 25234-25246.
27. Banfi, B., Tirone, F., Durussel, I., Knisz, J., Moskwa, P., Molnar, G. Z., Krause, K. H., Cox, J. A., (2004) *J. Biol. Chem. in press.*
28. Yanai, T., et al., (2001) *J. Bone Miner. Metab.* 19, 345-351.
29. Mocsai, A., et al., (1997) *Biochem. Pharmacol.* 54, 781-789.
30. Cheng, G., et al., (2001) *Gene* 269, 131-140.
31. Lalucque, H., Silar, P., (2003) *Trends Microbiol.* 11, 9-12.
32. Maigrange, B., Rogister, B., Lefebvre, P. P., Mazy-Servais, C., Welcher, A. A., Bonnet, C., Hsu, R. Y., Rigo, J. M., Van De Water, T. R., Moonen, G., (1998) *Neurochem. Res.* 23, 1133-1138.
33. Riad-el Sabrouty, S., Blanchard, J. M., Marty, L., Jeanteur, P., Piechaczyk, M., (1989) *J. Mol. Evol.* 29, 212-222.
34. Fekete, D. M., Wu, D. K., (2002) *Curr. Opin. Neurobiol.* 12, 35-42.
35. Fritzsch, B. F., Barald, K. F., Lomax, M. I., (1998) in *Development of the Auditory System* (Rubel, E. W., Popper A. N., and Fay R. R. eds.), vol. 9., pp. 80-145, Springer-Verlag Press, New York.
36. Takumida, M., Anniko, M., (2002) *ORL J. Otorhinolaryngol. Relat. Spec.* 64, 143-147.
37. Ohlemiller, K. K., Wright, J. S., Dugan, L. L., (1999) *AudioL. Neurootol.* 4, 229-236.
38. Zhang, M., Liu, W., Ding, D., Salvi, R., (2003) *Neuroscience* 120, 191-205.
39. Paffenholz, R., Bergstrom, R. A., Pasutto, F., Wabnitz, P., Munroe, R. J., Jagla, W., Heinzmann, U., Marquardt, A., Bareiss, A., Laufs, J., Russ, A., Stumm, G., Schimenti, J. C., Bergstrom, D. E., (2004) *Genes Dev. in press.*
40. Tsunawaki S, Yoshida L S, Nishida S, Kobayashi T, Shimoyama T. Fungal metabolite gliotoxin inhibits assembly of the human respiratory burst NADPH oxidase. Infect Immun. 2004 June; 72(6):3373-82.
41. Yoshida L S, Abe S, Tsunawaki S. Fungal gliotoxin targets the onset of superoxide-generating NADPH oxidase of human neutrophils. Biochem Biophys Res Commun. 2000 Feb. 24; 268(3):716-23.
42. Maack C, Kartes T, Kilter H, Schafers H J, Nickenig G, Bohm M, Laufs U. Oxygen free radical release in human failing myocardium is associated with increased activity of rac1-GTPase and represents a target for statin treatment. Circulation. 2003 Sep. 30; 108(13):1567-74.
43. Seifert R, Schachtele C. Studies with protein kinase C inhibitors presently available cannot elucidate the role of protein kinase C in the activation of NADPH oxidase. Biochem Biophys Res Commun. 1988 Apr. 29; 152(2): 585-92.
44. Holland J A, O'Donnell R W, Chang M M, Johnson D K, Ziegler L M. Endothelial cell oxidant production: effect of NADPH oxidase inhibitors. Endothelium. 2000; 7(2): 109-19.
45. *Adv Drug Deliv Rev.* 2005 Feb. 28; 57(4):637-51. Epub 2004 Dec. 22.
46. A. D. Frankel, D. S. Bredt and C. O. Pabo, TAT protein from human immunodeficiency virus forms a metal-linked dimer, *Science* 240 (1988), pp. 70-73.
47. S. Futaki, T. Suzuki, W. Ohashi, T. Yagami, S. Tanaka, K. Ueda and Y. Sugiura, Arginine-rich peptides. An abundant source of membrane-permeable peptides having potential as carriers for intracellular protein delivery, *J. Biol. Chem.* 276 (2001), pp. 5836-5840.
48. Homeodomain of Antennapedia (Antp): W. J. Gehring, M. Affolter and T. Burglin, Homeodomain proteins, *Annu. Rev. Biochem.* 63 (1994), pp. 487-526.

49. D. Derossi, A. H. Joliot, G. Chassaing and A. Prochiantz, The third helix of the Antennapedia homeodomain translocates through biological membranes, *J. Biol. Chem.* 269 (1994), pp. 10444-10450.
50. A. Aints, H. Guven, G. Gahrton, C. I. Smith and M. S. Dilber, Mapping of herpes simplex virus-1 VP22 functional domains for inter- and subcellular protein targeting, *Gene Ther.* 8 (2001), pp. 1051-1056.
51. M. Pooga, M. Hallbrink, M. Zorko and U. Langel, Cell penetration by transportan, *FASEB J.* 12 (1998), pp. 67-77.
52. J. Oehlke, A. Scheller, B. Wiesner, E. Krause, M. Beyermann, E. Klauschenz, M. Meizig and M. Bienert, Cellular uptake of an alpha-helical amphipathic model peptide with the potential to deliver polar compounds into the cell interior non-endocytically, *Biochim. Biophys. Acta* 1414 (1998), pp. 127-139.
53. Y. Z. Lin, S. Y. Yao, R. A. Veach, T. R. Torgerson and J. Hawiger, Inhibition of nuclear translocation of transcription factor NF-kappa B by a synthetic peptide containing a cell membrane-permeable motif and nuclear localization sequence, *J. Biol. Chem.* 270 (1995), pp. 14255-14258.

The invention claimed is:

1. A method for reducing the expression of NOX3 in the inner ear of a subject comprising administering an effective amount of a siRNA inhibitor of NOX3, or of a pharmaceutical composition comprising an effective amount of a siRNA inhibitor of NOX3, to the subject, wherein NOX3 protein comprises or consists of the amino acid sequence of any one of SEQ ID NO: 1, 3 or 5.

2. The method of claim 1 wherein the expression of NOX3 in the inner ear is localized to spiral ganglion neurons and cells of the organ of Corti.

3. The method of claim 1 wherein the expression of NOX3 in the inner ear is localized to the sensory epithelial layer of the vestibular system.

4. The method of claim 1 wherein the NOX3 protein comprises the amino acid sequence of SEQ ID NO:1.

5. The method of claim 1, wherein the subject is is afflicted with or at risk of developing phantom hearing.

6. The method of claim 1, wherein the subject is afflicted with or at risk of developing drug-, noise- or age-related hearing loss.

7. The method of claim 1 wherein the level expression of NOX3 in the subject's inner ear results from treating the subject with an ototoxic agent.

8. The method of claim 7, wherein the ototoxic agent is selected from the group consisting of salicylates, non-steroidal antiinflammatories, antibiotics, diuretics, cytostatics, quinine derivatives and gastroprotective drugs.

9. The method of claim 8, wherein the ototoxic agent is a cytostatic.

10. The method of claim 9, wherein the cytostatic is bleomycine, bromocriptine, carboplatinum, cisplatin, methotrexate, nitrogen mustard, vinblastine or vincristine.

11. The method of claim 8, wherein the ototoxic agent is an antibiotic.

12. The method of claim 11, wherein the antibiotic is an aminoglycoside antibiotic.

13. The method of claim 12, wherein the aminoglycoside antibiotic is amikacin, gentamycin, kanamycin, neomycin, netilmycin, streptomycin or tobramycin.

14. The method of claim 11, wherein the antibiotic is erythromycin, vancomycin, minocycline, polymixin B, amphotericin B and capreomycin.

15. The method of claim 8, wherein the ototoxic agent is a salicylate.

16. The method of claim 15, wherein the salicylate is aspirin or methyl salicylate.

17. The method of claim 8, wherein the ototoxic agent is a non-steroidal anti-inflammatory agent.

18. The method of claim 17, wherein the non-steroidal anti-inflammatory agent is selected from the group consisting of diclofenac, etocolac, fenprofen, ibuprofen, indomethacin, naproxen, piroxicam and sulindac.

19. The method of claim 8, wherein the ototoxic agent is a quinine derivative.

20. The method of claim 19, wherein the quinine derivative is selected from the group consisting of chloroquine phosphate, quinacrine hydrochloride and quinine sulphate.

* * * * *

UNITED STATES PATENT AND TRADEMARK OFFICE
CERTIFICATE OF CORRECTION

PATENT NO. : 8,722,639 B2
APPLICATION NO. : 13/336147
DATED : May 13, 2014
INVENTOR(S) : Karl-Heinz Krause et al.

It is certified that error appears in the above-identified patent and that said Letters Patent is hereby corrected as shown below:

On the Title Page

Item (56) References Cited - Other Publications, delete the 9th reference on page 1 "Banfi et al., "Two novel proteins activate superoxide generation by the NADPH oxidase Noxi," J. Biol. Chem., 278:3510-3513, 2003." and replace with --Banfi et al., "Two novel proteins activate superoxide generation by the NADPH oxidase NOX1," J. Biol. Chem., 278:3510-3513, 2003.-- therefor.

Item (56) References Cited - Other Publications, delete the 16th reference on page 1 "Chakraborty, "Potentiality of small interfering RNAs (siRNA) as rcent therapeutic targets for gene-silencing," *Current Drug Targets*, 8(3):469-482, 2007." and replace with --Chakraborty, "Potentiality of small interfering RNAs (siRNA) as recent therapeutic targets for gene-silencing," *Current Drug Targets*, 8(3):469-482, 2007.-- therefor.

Item (56) References Cited - Other Publications, delete the 9th reference on page 2 "Elbashir et ai., "Duplexes of 21-nucleotide mediated RNA interference in cultured mammalian cells," *Nature*, 411:494-498, 2001." and replace with --Elbashir et al., "Duplexes of 21-nucleotide mediated RNA interference in cultured mammalian cells," *Nature*, 411:494-498, 2001.-- therefor.

Signed and Sealed this
Twelfth Day of August, 2014

Michelle K. Lee
*Deputy Director of the United States Patent and Trademark Office*

SEQUENCE LISTING

```
<160> NUMBER OF SEQ ID NOS: 26

<210> SEQ ID NO 1
<211> LENGTH: 568
<212> TYPE: PRT
<213> ORGANISM: Homo sapiens

<400> SEQUENCE: 1

Met Met Gly Cys Trp Ile Leu Asn Glu Gly Leu Ser Thr Ile Leu Val
1               5                   10                  15

Leu Ser Trp Leu Gly Ile Asn Phe Tyr Leu Phe Ile Asp Thr Phe Tyr
            20                  25                  30

Trp Tyr Glu Glu Glu Ser Phe His Tyr Thr Arg Val Ile Leu Gly
        35                  40                  45

Ser Thr Leu Ala Trp Ala Arg Ala Ser Ala Leu Cys Leu Asn Phe Asn
    50                  55                  60

Cys Met Leu Ile Leu Pro Val Ser Arg Asn Leu Ile Ser Phe Ile
65                  70                  75                  80

Arg Gly Thr Ser Ile Cys Cys Arg Gly Pro Trp Arg Arg Gln Leu Asp
                85                  90                  95

Lys Asn Leu Arg Phe His Lys Leu Val Ala Tyr Gly Ile Ala Val Asn
            100                 105                 110

Ala Thr Ile His Ile Val Ala His Phe Phe Asn Leu Glu Arg Tyr His
        115                 120                 125

Trp Ser Gln Ser Glu Glu Ala Gln Gly Leu Leu Ala Ala Leu Ser Lys
    130                 135                 140

Leu Gly Asn Thr Pro Asn Glu Ser Tyr Leu Asn Pro Val Arg Thr Phe
145                 150                 155                 160

Pro Thr Asn Thr Thr Thr Glu Leu Leu Arg Thr Ile Ala Gly Val Thr
                165                 170                 175

Gly Leu Val Ile Ser Leu Ala Leu Val Leu Ile Met Thr Ser Ser Thr
            180                 185                 190

Glu Phe Ile Arg Gln Ala Ser Tyr Glu Leu Phe Trp Tyr Thr His His
        195                 200                 205

Val Phe Ile Val Phe Phe Leu Ser Leu Ala Ile His Gly Thr Gly Arg
    210                 215                 220

Ile Val Arg Gly Gln Thr Gln Asp Ser Leu Ser Leu His Asn Ile Thr
225                 230                 235                 240

Phe Cys Arg Asp Arg Tyr Ala Glu Trp Gln Thr Val Ala Gln Cys Pro
                245                 250                 255

Val Pro Gln Phe Ser Gly Lys Glu Pro Ser Ala Trp Lys Trp Ile Leu
            260                 265                 270

Gly Pro Val Val Leu Tyr Ala Cys Glu Arg Ile Ile Arg Phe Trp Arg
        275                 280                 285
```

-continued

```
Phe Gln Gln Glu Val Val Ile Thr Lys Val Val Ser His Pro Ser Gly
            290                 295                 300

Val Leu Glu Leu His Met Lys Lys Arg Gly Phe Lys Met Ala Pro Gly
305                 310                 315                 320

Gln Tyr Ile Leu Val Gln Cys Pro Ala Ile Ser Ser Leu Glu Trp His
                325                 330                 335

Pro Phe Thr Leu Thr Ser Ala Pro Gln Glu Asp Phe Ser Val His
            340                 345                 350

Ile Arg Ala Ala Gly Asp Trp Thr Ala Ala Leu Leu Glu Ala Phe Gly
            355                 360                 365

Ala Glu Gly Gln Ala Leu Gln Glu Pro Trp Ser Leu Pro Arg Leu Ala
370                 375                 380

Val Asp Gly Pro Phe Gly Thr Ala Leu Thr Asp Val Phe His Tyr Pro
385                 390                 395                 400

Val Cys Val Cys Val Ala Ala Gly Ile Gly Val Thr Pro Phe Ala Ala
                405                 410                 415

Leu Leu Lys Ser Ile Trp Tyr Lys Cys Ser Glu Ala Gln Thr Pro Leu
            420                 425                 430

Lys Leu Ser Lys Val Tyr Phe Tyr Trp Ile Cys Arg Asp Ala Arg Ala
            435                 440                 445

Phe Glu Trp Phe Ala Asp Leu Leu Ser Leu Glu Thr Arg Met Ser
450                 455                 460

Glu Gln Gly Lys Thr His Phe Leu Ser Tyr His Ile Phe Leu Thr Gly
465                 470                 475                 480

Trp Asp Glu Asn Gln Ala Leu His Ile Ala Leu His Trp Asp Glu Asn
                485                 490                 495

Thr Asp Val Ile Thr Gly Leu Lys Gln Lys Thr Phe Tyr Gly Arg Pro
            500                 505                 510

Asn Trp Asn Asn Glu Phe Lys Gln Ile Ala Tyr Asn His Pro Ser Ser
            515                 520                 525

Ser Ile Gly Val Phe Phe Cys Gly Pro Lys Ala Leu Ser Arg Thr Leu
            530                 535                 540

Gln Lys Met Cys His Leu Tyr Ser Ser Ala Asp Pro Arg Gly Val His
545                 550                 555                 560

Phe Tyr Tyr Asn Lys Glu Ser Phe
                565
```

<210> SEQ ID NO 2
<211> LENGTH: 1707
<212> TYPE: DNA
<213> ORGANISM: Homo sapiens

<400> SEQUENCE: 2

```
atgatggggt gctggatttt gaatgagggt ctctccacca tattagtact ctcatggctg      60
ggaataaatt tttatctgtt tattgacacg ttctactggt atgaagagga ggagtctttc     120
cattacacac gagttatttt gggttcaaca ctggcttggg cacgagcatc cgcactgtgc     180
ctgaattta actgcatgct aattctaata cctgtcagtc gaaaccttat ttcattcata      240
agaggaacaa gtatttgctg cagaggaccg tggaggaggc aattagacaa aaaccctcaga    300
tttcacaaac tggtcgccta tgggatagct gttaatgcaa ccatccacat cgtggcgcat    360
ttcttcaacc tggaacgcta ccactggagc cagtccgagg aggcccaggg acttctggcc    420
gcactttcca gctgggcaa cacccctaac gagagctacc tcaaccctgt ccggaccttc    480
cccacaaaca caaccactga attgctaagg acaatagcag gcgtcaccgg tctggtgatc    540
```

```
tctctggctt tagtcttgat catgacctcg tcaactgagt tcatcagaca ggcctcctat      600
gagttgttct ggtacacaca ccatgttttc atcgtcttct ttctcagcct ggccatccat      660
gggacgggtc ggattgttcg aggccaaacc caagacagtc tctctctgca acatcacc       720 ttctgtagag accgctatgc agaatggcag acagtggccc aatgcccgt gcctcaattt       780 tctggcaagg aaccctcggc ttggaaatgg attttaggcc ctgtggtctt gtatgcatgt     840
gaaagaataa ttaggttctg gcgatttcaa caagaagttg tcattaccaa ggtggtaagc     900 caccccctctg gagtcctgga acttcacatg aaaaagcgtg gctttaaaat ggcgccaggg    960
cagtacatct tggtgcagtg cccagccata tcttcgctgg agtggcaccc cttcacccctt  1020 acctctgccc cccaggaaga cttttccagc gtgcacatcc gggcagcagg agactggaca    1080
gcagcgctac tggaggcctt tggggcagag ggacaggccc tccaggagcc ctggagcctg    1140
ccaaggctgg cagtggacgg gccctttgga actgccctga cagatgtatt tcactaccca    1200
gtgtgtgtgt gcgttgccgc ggggatcgga gtcactccct tcgctgctct tctgaaatct    1260
atatggtaca aatgcagtga ggcacagacc ccactgaagc tgagcaaggt gtatttctac    1320
tggatttgcc gggatgcaag agcttttgag tggtttgctg atctcttact ctccctggaa    1380
acacggatga gtgagcaggg gaaaactcac tttctgagtt atcatatatt tcttaccggc    1440
tgggatgaaa atcaggctct tcacatagct ttacactggg acgaaaatac tgacgtgatt    1500
acaggcttaa agcagaagac cttctatggg aggcccaact ggaacaatga gttcaagcag    1560
attgcctaca atcaccccag cagcagtatt ggcgtgttct tctgtggacc taaagctctc    1620
tcgaggacac ttcaaaagat gtgccacttg tattcatcag ctgaccccag aggtgttcat    1680
ttctattaca acaaggagag cttctag                                        1707
```

<210> SEQ ID NO 3
<211> LENGTH: 568
<212> TYPE: PRT
<213> ORGANISM: Mus musculus

<400> SEQUENCE: 3

```
Met Pro Val Cys Trp Ile Leu Asn Glu Ser Gly Ser Phe Val Val Ala
1               5                   10                  15

Leu Leu Trp Leu Ala Val Asn Ala Tyr Leu Phe Ile Asp Thr Phe Phe
            20                  25                  30

Trp Tyr Thr Glu Glu Ala Phe Phe Tyr Thr Arg Val Ile Leu Gly
        35                  40                  45

Ser Ala Leu Ala Trp Ala Arg Ala Ser Ala Val Cys Leu Asn Phe Asn
    50                  55                  60

Cys Met Leu Ile Leu Pro Val Ser Arg Asn Phe Ile Ser Leu Val
65                  70                  75                  80

Arg Gly Thr Ser Val Cys Cys Arg Gly Pro Trp Arg Arg Gln Leu Asp
                85                  90                  95

Lys Asn Leu Asn Phe His Lys Leu Val Ala Tyr Gly Ile Ala Val Asn
            100                 105                 110

Ser Val Ile His Ile Val Ala His Leu Phe Asn Leu Glu Arg Tyr His
        115                 120                 125

Leu Gly Gln Ala Lys Asp Ala Glu Gly Leu Leu Ala Ala Leu Ser Lys
    130                 135                 140

Leu Gly Asp Ala Pro Asn Glu Ser Tyr Leu Asn Pro Val Arg Thr Phe
145                 150                 155                 160

Tyr Met Gly Thr Thr Thr Glu Leu Leu Met Thr Val Ser Gly Ile Thr
                165                 170                 175
```

Gly Leu Gly Ile Ser Leu Ala Leu Val Phe Ile Met Thr Ser Ser Thr
            180                 185                 190

Glu Phe Ile Arg Arg Ser Ser Tyr Glu Leu Phe Trp Tyr Thr His His
            195                 200                 205

Ile Phe Val Phe Phe Ile Ser Leu Ala Ile His Gly Gly Arg
210                 215                 220

Ile Ile Arg Gly Gln Thr Pro Glu Ser Leu Arg Leu His Asn Val Thr
225                 230                 235                 240

Tyr Cys Arg Asp His Tyr Ala Glu Trp Gln Ala Ala Leu Cys Pro
                245                 250                 255

Val Pro Gln Phe Ser Gly Lys Glu Pro Ser Ala Trp Lys Trp Ala Leu
            260                 265                 270

Gly Pro Val Val Leu Tyr Ala Cys Glu Arg Ile Arg Phe Trp Arg
            275                 280                 285

Ser His Gln Glu Val Val Ile Thr Lys Val Val Ser His Pro Ser Ala
            290                 295                 300

Val Leu Glu Leu His Met Lys Lys Arg Asp Phe Lys Met Ala Pro Gly
305                 310                 315                 320

Gln Tyr Ile Phe Ile Gln Cys Pro Ser Val Ser Pro Leu Glu Trp His
                325                 330                 335

Pro Phe Thr Leu Thr Ser Ala Pro Gln Glu Asp Phe Phe Ser Val His
            340                 345                 350

Ile Arg Ala Ser Gly Asp Trp Thr Glu Ala Leu Leu Lys Ala Phe Arg
            355                 360                 365

Val Glu Gly Gln Ala Pro Ser Glu Leu Cys Ser Met Pro Arg Leu Ala
370                 375                 380

Val Asp Gly Pro Phe Gly Gly Ser Leu Ala Asp Val Phe His Tyr Pro
385                 390                 395                 400

Val Ser Val Cys Ile Ala Thr Gly Ile Gly Val Thr Pro Phe Ala Ser
                405                 410                 415

Leu Leu Lys Ser Val Trp Tyr Lys Cys Cys Glu Ser Gln Ser Leu Pro
            420                 425                 430

Glu Leu Ser Lys Val Tyr Phe Tyr Trp Ile Cys Arg Asp Ala Gly Ala
            435                 440                 445

Phe Glu Trp Phe Ala Asp Leu Leu Leu Ser Leu Glu Thr Arg Met Ser
            450                 455                 460

Glu Gln Gly Lys Ala His Leu Leu Ser Tyr His Ile Tyr Leu Thr Gly
465                 470                 475                 480

Trp Asp Glu Asn Gln Ala Ile His Ile Ala Leu His Trp Asp Glu Ser
                485                 490                 495

Leu Asp Val Ile Thr Gly Leu Lys Gln Lys Ala Phe Tyr Gly Arg Pro
            500                 505                 510

Asn Trp Asn Asp Glu Phe Lys Gln Ile Ala Tyr Asn His Pro Ser Ser
            515                 520                 525

Ser Ile Gly Val Phe Phe Cys Gly Ser Lys Ala Met Ser Lys Thr Leu
530                 535                 540

Gln Lys Met Cys Arg Leu Tyr Ser Ser Val Asp Pro Arg Gly Val His
545                 550                 555                 560

Phe Tyr Tyr Asn Lys Glu Asn Phe
                565

<210> SEQ ID NO 4
<211> LENGTH: 1707
<212> TYPE: DNA

<213> ORGANISM: Mus musculus

<400> SEQUENCE: 4

```
atgccggtgt gctggattct gaacgagagt gggtccttcg tggttgctct cttatggctg    60
gcagtaaacg cctatctgtt tattgacaca ttcttctggt atactgaaga ggaggctttc   120
ttttatacac gagttattct gggttccgca ttggcatggg cccgggcatc tgccgtgtgc   180
ctgaatttta actgcatgct aattctgtta cctgtcagtc ggaacttcat ttcactggtg   240
agaggaacaa gtgtgtgctg tagaggacca tggagaagac aactagacaa aaacctcaac   300
ttccacaaac tcgttgccta cgggatagct gtcaattcag ttatccacat tgtggcacac   360
ttgttcaacc tggagcgtta tcacctgggt caggccaagg atgctgaagg ctgctggct    420
gcactttcca acttggcga tgccccaaat gagagctacc tcaatccagt ccgcaccttt   480
tatatgggca caaccactga gctattgatg acagtgtcag gaattactgg cctgggtatc   540
tctctggctc tggtcttcat catgaccctc tcaaccgaat tcatcagaag gtcctcttat   600
gagctcttct ggtacacaca ccatatcttt gtcttcttct tcatcagtct ggccatccac   660
ggaggaggtc gcatcattcg aggccaaact ccagagagtc tccggctgca caatgtcacg   720
tactgcagag accactatgc tgaatggcag gcagctgcct tatgccctgt acctcaattt   780
ctggcaagg aaccttcggc ctggaaatgg gctttgggtc ctgtggtctt gtatgcgtgt   840
gaaagaataa ttaggttctg gagatctcac caagaagttg tcattaccaa ggtggtgagt   900
cacccatctg cagtcctgga acttcacatg aagaagcgag acttcaagat ggcacctgga   960
cagtacatct tcatccagtg cccatctgtc tccccctgg agtggcaccc cttcactctc  1020
acctccgctc cccaggagga cttcttcagt gtacacatca gagcctcagg agactggaca  1080
gaggcgttat tgaaggcctt tagagtagag ggacaggctc ccagtgagct ctgtagcatg  1140
ccgaggctag cagtggatgg gccctttgga ggctctctgg cagatgtatt tcactacccc  1200
gtgagcgtgt gcattgcaac gggaattgga gtcactccct tcgcctctct tctgaagtct  1260
gtgtggtata agtgttgtga atcacagagc ctgcctgagc tgagcaaggt gtacttctat  1320
tggatctgcc gggatgccgg agcatttgag tggtttgctg atctgttact gtcactggaa  1380
acacggatga gtgaacaagg gaaggctcat ttactgagct accatatata tctcactggc  1440
tgggatgaaa accaggcaat tcacatagct ttacactggg atgaaagtct ggatgtgata  1500
acaggcttaa agcagaaggc tttctatggg cgacccaact ggaacgacga attcaagcag  1560
attgcctaca atcaccccag cagcagcatt ggcgtgttct tctgtggatc caaagccatg  1620
tcaaagactc ttcaaaagat gtgtcgtttg tactcatctg tggatccgag gggcgttcat  1680
ttctattaca acaaggaaaa cttctag                                     1707
```

<210> SEQ ID NO 5
<211> LENGTH: 568
<212> TYPE: PRT
<213> ORGANISM: Rattus norvegicus

<400> SEQUENCE: 5

```
Met Pro Thr Cys Trp Ile Leu Asn Glu Ser Val Ser Phe Val Val Ala
1               5                   10                  15

Leu Leu Trp Leu Ala Ile Asn Ile Tyr Leu Phe Ile Asp Thr Phe Cys
            20                  25                  30

Trp Tyr Ala Glu Glu Glu Ser Phe Phe Tyr Thr Arg Val Ile Leu Gly
        35                  40                  45

Ser Ala Leu Ala Trp Ala Arg Ala Ser Ala Val Cys Leu Asn Phe Asn
```

```
            50              55              60
Cys Met Leu Ile Leu Leu Pro Val Ser Arg Asn Phe Val Ser Leu Val
 65              70              75              80

Arg Gly Thr Ser Val Cys Cys Arg Gly Pro Trp Arg Arg Gln Leu Asp
                 85              90              95

Lys Asn Leu Lys Phe His Lys Leu Val Ala Tyr Gly Ile Ala Val Asn
                100             105             110

Ser Val Ile His Ile Val Ala His Leu Phe Asn Leu Glu Arg Tyr His
                115             120             125

Leu Gly Gln Ala Lys Asp Ala Glu Gly Leu Leu Ala Ala Leu Ser Lys
                130             135             140

Leu Gly Asn Ala Pro Asn Glu Ser Tyr Leu Asn Pro Val Arg Thr Leu
145             150             155             160

Tyr Thr Gly Thr Thr Thr Gln Leu Leu Met Thr Val Ser Gly Ile Thr
                165             170             175

Gly Leu Val Ile Ser Leu Ala Leu Ile Leu Ile Met Thr Ser Ser Thr
                180             185             190

Glu Phe Ile Arg Gln Ser Ser Tyr Glu Leu Phe Trp Tyr Thr His His
                195             200             205

Ile Phe Ile Phe Leu Phe Ile Ser Leu Ala Ile His Gly Gly Gly Arg
210             215             220

Ile Ile Arg Gly Gln Thr Pro Glu Ser Leu Arg Leu His Asn Val Thr
225             230             235             240

Phe Cys Arg Asp His Phe Asp Glu Trp Gln Glu Ala Ala Ser Cys Pro
                245             250             255

Val Pro Gln Phe Ser Gly Lys Glu Pro Ser Ala Trp Lys Trp Thr Leu
                260             265             270

Gly Pro Val Val Leu Tyr Ala Cys Glu Ile Ile Ile Arg Phe Trp Arg
                275             280             285

Ser His Gln Glu Val Val Ile Thr Lys Val Val Ser His Pro Ser Ala
                290             295             300

Val Leu Glu Leu His Met Lys Lys Arg Asp Phe Lys Met Ala Pro Gly
305             310             315             320

Gln Tyr Ile Phe Ile Gln Cys Pro Ser Ile Ser Pro Leu Glu Trp His
                325             330             335

Pro Phe Thr Leu Thr Ser Ala Pro Gln Glu Asp Phe Phe Ser Val His
                340             345             350

Ile Arg Ala Ser Gly Asp Trp Thr Glu Ala Leu Leu Lys Ala Phe Gly
                355             360             365

Ala Glu Gly Gln Ala Pro Ser Glu Leu Cys Ser Met Pro Arg Leu Ala
370             375             380

Val Asp Gly Pro Phe Gly Gly Ser Leu Ala Asp Val Phe His Tyr Pro
385             390             395             400

Val Ser Val Cys Ile Ala Thr Gly Ile Gly Val Thr Pro Phe Ala Ser
                405             410             415

Leu Leu Lys Ser Val Trp Tyr Lys Cys Cys Glu Ser Gln Ser Leu Pro
                420             425             430

Gly Leu Ser Lys Val Tyr Phe Tyr Trp Ile Cys Arg Asp Ala Ala Ala
                435             440             445

Phe Glu Trp Phe Ala Asp Leu Leu Ser Leu Glu Thr Gln Met Ser
                450             455             460

Glu Gln Gly Lys Ala His Leu Leu Ser Tyr His Ile Tyr Leu Thr Gly
465             470             475             480
```

-continued

```
Trp Asp Glu Tyr Gln Ala Ile His Ile Ala Leu His Trp Asp Glu Ser
            485                 490                 495

Leu Asp Val Ile Thr Gly Leu Lys Gln Lys Thr Phe Tyr Gly Arg Pro
        500                 505                 510

Asn Trp Asn Glu Glu Phe Lys Gln Ile Ala Tyr Asn His Pro Ser Ser
            515                 520                 525

Ser Ile Gly Val Phe Phe Cys Gly Pro Lys Ala Met Ser Lys Thr Leu
        530                 535                 540

Gln Lys Met Cys Arg Leu Tyr Ser Ser Ser Asp Pro Arg Gly Val His
545                 550                 555                 560

Phe Tyr Tyr Asn Lys Glu Asn Phe
            565
```

<210> SEQ ID NO 6
<211> LENGTH: 1707
<212> TYPE: DNA
<213> ORGANISM: Rattus norvegicus

<400> SEQUENCE: 6

| | | | | | | |
|---|---|---|---|---|---|---|
| atgccgacgt | gctggatttt | gaacgagagt | gtgtccttcg | tggttgctct | cttgtggctg | 60 |
| gcaataaaata | tctatctgtt | tattgacacg | ttctgctggt | atgctgaaga | ggagtctttc | 120 |
| ttttatacac | gagttattct | gggttccgca | ttggcatggg | cccgggcatc | tgccgtgtgc | 180 |
| ctgaattta | actgcatgct | aattctgtta | cctgtcagtc | ggaacttcgt | ttcactggtg | 240 |
| agaggaacga | gcgtgtgctg | tagaggaccg | tggagacggc | aactagacaa | aaacctcaag | 300 |
| ttccacaagc | tcgttgccta | cgggatagct | gttaattcag | ttatccacat | tgtggcacac | 360 |
| ttgttcaacc | tggagcgtta | tcacctgggt | caggccaagg | atgctgaagg | ctgctggct | 420 |
| gcgctttcca | aacttggcaa | tgccccaaat | gaaagctacc | tcaatccggt | ccgcaccttg | 480 |
| tatacgggta | caaccactca | gctattaatg | acagtctccg | gaattactgg | cctggtgatc | 540 |
| tctctggctt | tgatattgat | catgacctct | tcaactgagt | ttatcaggca | gtcctcttat | 600 |
| gagctattct | ggtacacaca | ccatatcttc | atcttcctct | tcatcagtct | ggccatccac | 660 |
| ggaggaggtc | gcatcattcg | aggtcaaact | ccagagagtc | tccggctgca | caatgtcacc | 720 |
| ttctgcagag | accacttcga | cgaatggcag | gaagctgcct | cgtgccctgt | acctcaattt | 780 |
| tctggcaagg | agccgtcggc | ctggaaatgg | actttgggcc | ctgtggtctt | gtatgcgtgt | 840 |
| gaaataataa | ttaggttctg | gagatctcac | caagaagttg | tcattaccaa | ggtggtgagt | 900 |
| cacccatctg | cagtcctgga | acttcacatg | aagaagcgtg | acttcaagat | ggcgcccgga | 960 |
| cagtacatct | ttatccagtg | cccatccatc | tccccgctgg | agtggcaccc | cttcactctc | 1020 |
| acgtctgctc | cccaggagga | cttcttcagt | gtacacatcc | gagcctcagg | agactggaca | 1080 |
| gaggcgttac | tgaaggcatt | tggagcagag | ggacaggctc | ccagtgagct | ctgtagcatg | 1140 |
| ccgagactgg | cagtggacgg | gcccttcgga | ggctctctgg | cagatgtatt | tcactaccct | 1200 |
| gtgagcgtgt | gcattgcaac | aggaattgga | gtcaccccct | tcgcctctct | tctgaagtct | 1260 |
| gtgtggtata | agtgttgtga | atcacagagt | ctgcctggac | tgagcaaggt | gtacttctac | 1320 |
| tggatctgcc | gggatgctgc | agcctttgag | tggtttgccg | atctgttact | ttcactggaa | 1380 |
| acacagatga | gtgaacaagg | gaaggctcat | ttgctgagtt | accacatata | tctcactggc | 1440 |
| tgggatgaat | accaggcaat | tcacatagct | ttacactggg | atgaaagtct | ggatgtgatt | 1500 |
| acaggcttaa | agcagaagac | cttctatggg | cgacccaact | ggaatgagga | attcaagcag | 1560 |
| attgcctaca | atcaccctag | cagcagcatt | ggcgtgttct | tctgtggacc | caaagccatg | 1620 |

-continued

```
tcaaagactc ttcaaaagat gtgccgtttg tactcatcct cagatcctag gggcgttcat    1680
ttctattaca acaaggaaaa cttctag                                         1707
```

<210> SEQ ID NO 7
<211> LENGTH: 371
<212> TYPE: PRT
<213> ORGANISM: Homo sapiens

<400> SEQUENCE: 7

```
Met Ala Gly Pro Arg Tyr Pro Val Ser Val Gln Gly Ala Ala Leu Val
1               5                   10                  15

Gln Ile Lys Arg Leu Gln Thr Phe Ala Phe Ser Val Arg Trp Ser Asp
            20                  25                  30

Gly Ser Asp Thr Phe Val Arg Arg Ser Trp Asp Glu Phe Arg Gln Leu
        35                  40                  45

Lys Lys Thr Leu Lys Glu Thr Phe Pro Val Glu Ala Gly Leu Leu Arg
    50                  55                  60

Arg Ser Asp Arg Val Leu Pro Lys Leu Leu Asp Ala Pro Leu Leu Gly
65                  70                  75                  80

Arg Val Gly Arg Thr Ser Arg Gly Leu Ala Arg Leu Gln Leu Leu Glu
                85                  90                  95

Thr Tyr Ser Arg Arg Leu Leu Ala Thr Ala Glu Arg Val Ala Arg Ser
            100                 105                 110

Pro Thr Ile Thr Gly Phe Phe Ala Pro Gln Pro Leu Asp Leu Glu Pro
        115                 120                 125

Ala Leu Pro Pro Gly Ser Arg Val Ile Leu Pro Thr Pro Glu Glu Gln
    130                 135                 140

Pro Leu Ser Arg Ala Ala Gly Arg Leu Ser Ile His Ser Leu Glu Ala
145                 150                 155                 160

Gln Ser Leu Arg Cys Leu Gln Pro Phe Cys Thr Gln Asp Thr Arg Asp
                165                 170                 175

Arg Pro Phe Gln Ala Gln Ala Gln Glu Ser Leu Asp Val Leu Leu Arg
            180                 185                 190

His Pro Ser Gly Trp Trp Leu Val Glu Asn Glu Asp Arg Gln Thr Ala
        195                 200                 205

Trp Phe Pro Ala Pro Tyr Leu Glu Glu Ala Ala Pro Gly Gln Gly Arg
    210                 215                 220

Glu Gly Gly Pro Ser Leu Gly Ser Ser Gly Pro Gln Phe Cys Ala Ser
225                 230                 235                 240

Arg Ala Tyr Glu Ser Ser Arg Ala Asp Glu Leu Ser Val Pro Ala Gly
                245                 250                 255

Ala Arg Val Arg Val Leu Glu Thr Ser Asp Arg Gly Trp Trp Leu Cys
            260                 265                 270

Arg Tyr Gly Asp Arg Ala Gly Leu Leu Pro Ala Val Leu Leu Arg Pro
        275                 280                 285

Glu Gly Leu Gly Ala Leu Leu Ser Gly Thr Gly Phe Arg Gly Gly Asp
    290                 295                 300

Asp Pro Ala Gly Glu Ala Arg Gly Phe Pro Glu Pro Ser Gln Ala Thr
305                 310                 315                 320

Ala Pro Pro Pro Thr Val Pro Thr Arg Pro Ser Pro Gly Ala Ile Gln
                325                 330                 335

Ser Arg Cys Cys Thr Val Thr Arg Arg Ala Leu Glu Arg Arg Pro Arg
            340                 345                 350

Arg Gln Gly Arg Pro Arg Gly Cys Val Asp Ser Val Pro His Pro Thr
        355                 360                 365
```

Thr Glu Gln
    370

<210> SEQ ID NO 8
<211> LENGTH: 1116
<212> TYPE: DNA
<213> ORGANISM: Homo sapiens

<400> SEQUENCE: 8

```
atggcaggcc cccgataccc agtttcagtg caaggggcag ccctggtgca gatcaagagg      60
ctccaaacgt ttgccttctc tgtgcgctgg tcagacggca cgacaccttc cgtgcgcagg     120
agttgggacg aattcaggca gctcaagaag accctcaagg agaccttccc ggtggaggcg     180
ggcctgctgc ggagatctga ccgcgttctc caaagcttcc tcgatgcacc actgttggga     240
cgcgtggggc gcacgagccg cggcctggcg cgcctgcagc tgttggaaac ctattctcgg     300
aggctgctgg cgactgcaga gcgcgtggca cggagcccga cgatcactgg cttcttcgca     360
ccgcaacccc tggacctgga gccgcgctg ccacccggca gccgggtgat cctgcccacc      420
ccagaggagc agcctctttc tcgcgctgcg ggccgcctct ccatccacag tctggaggct     480
cagagcctgc gctgcctgca gcccttctgt acccaggaca cgcgggatag ccttttcag     540
gcgcaggccc aggagagcct ggacgtgctg ctgcggcacc cctcaggctg gtggctggtg     600
gagaacgaag accggcagac cgcctggttt ccagcgccct acctggagga ggcggccccg     660
ggccaaggcc gggagggagg cccgtcccta gggagcagcg gtcccagtt ctgtgcttcc      720
cgcgcctacg agagcagccg cgcagatgag ctgtccgtgc ccgcggggc gcgcgtgcgc     780
gtgttggaaa cgtcagaccg cggctggtgg ctatgcaggt acggcgaccg ggcgggccta     840
ctccccgcgg tgctgctgcg gccggaaggg ctgggcgctc tcctgagcgg acggggttc     900
cgtggaggag acgacccggc gggtgaggcc cggggcttcc ctgaaccctc ccaggccacc     960
gcccctcccc ccaccgtgcc cacccgacct tcgccgggcg ccatccagag ccgctgctgc    1020
accgtcacac gcagggccct ggagcggcgc ccacggcgcc agggccgccc tcgagggtgc    1080
gtggactctg tgccgcaccc cacgacggag cagtga                              1116
```

<210> SEQ ID NO 9
<211> LENGTH: 349
<212> TYPE: PRT
<213> ORGANISM: Mus musculus

<400> SEQUENCE: 9

```
Met Ala Ser Pro Arg His Pro Val Ser Ala His Ala Val Ala Leu Val
1               5                   10                  15
Gln Met Asp Arg Leu Gln Thr Phe Ala Phe Ser Val Cys Trp Ser Asp
                20                  25                  30
Asn Ser Asp Thr Phe Val Arg Arg Ser Trp Asp Glu Phe Arg Gln Leu
            35                  40                  45
Gln Lys Thr Leu Lys Lys Thr Phe Pro Val Glu Ala Gly Leu Leu Arg
        50                  55                  60
Arg Ser Glu Gln Val Leu Pro Lys Leu Pro Asp Ala Pro Leu Leu Thr
65                  70                  75                  80
Arg Arg Gly His Thr Gly Arg Gly Leu Val Arg Leu Arg Leu Leu Asp
                85                  90                  95
Thr Tyr Val Gln Ala Leu Leu Ala Thr Ser Glu His Ile Leu Arg Ser
                100                 105                 110
Ser Ala Leu His Gly Phe Phe Val Pro Lys Pro Leu Asp Leu Glu Pro
```

```
                115                 120                 125
Met Leu Pro Pro Gly Ser Leu Val Ile Leu Pro Thr Pro Glu Glu Pro
130                 135                 140

Leu Ser Gln Pro Arg Gly Ser Leu Asp Ile His Ser Leu Glu Ala Gln
145                 150                 155                 160

Ser Ile Pro Cys Val Gln Pro Phe His Thr Leu Asp Ile Arg Asp Arg
                165                 170                 175

Pro Phe His Thr Lys Ala Gln Glu Ile Leu Asp Ile Leu Leu Arg His
                180                 185                 190

Pro Ser Gly Trp Trp Leu Val Glu Asn Lys Asp Gln Gln Val Ala Trp
                195                 200                 205

Phe Pro Ala Pro Tyr Leu Glu Glu Val Ala Thr Cys Gln Gly Gln Glu
                210                 215                 220

Ser Gly Leu Ala Leu Gln Gly Ser Gly Arg Gln Phe Cys Thr Thr Gln
225                 230                 235                 240

Ala Tyr Glu Gly Ser Arg Ser Asp Glu Leu Ser Val Pro Ser Gly Ala
                245                 250                 255

Arg Val His Val Leu Glu Thr Ser Asp Arg Gly Trp Trp Leu Cys Arg
                260                 265                 270

Tyr Asn Gly Arg Thr Gly Leu Leu Pro Ala Met Ser Leu Gln Pro Glu
                275                 280                 285

Gly Leu Gly Ser Leu Leu Gly Arg Pro Gly Phe Pro Asp Ser Ala Gly
                290                 295                 300

Ala Asp Lys Val Ala Glu Asp Arg Thr Ile Pro Pro Val Pro Thr
305                 310                 315                 320

Arg Pro Cys Met Ser Ala Ile Gln Ser Arg Cys Cys Ser Ile Thr Arg
                325                 330                 335

Arg Ala Leu Gly Gln Glu Gln Gly Thr Arg Val Pro Arg
                340                 345

<210> SEQ ID NO 10
<211> LENGTH: 1050
<212> TYPE: DNA
<213> ORGANISM: Mus musculus

<400> SEQUENCE: 10
atggcaagcc caagacaccc agtatcagcc catgctgtag ccttggtgca aatggaccga      60
ctccagacat ttgccttctc cgtgtgctgg tcagacaaca gtgacacatt tgtgcggagg     120
agctgggatg agttcaggca gctccagaag acccttaaga aaaccttccc agtggaggca     180
ggcctgctac ggagatctga acaagttctt cccaagcttc ctgatgctcc attgctgaca     240
cgtcgggggc atactggtcg aggactggta cgtttgcggc tgctggacac ctatgtacag     300
gcattgctgg caacctcaga acacatattg aggagttcag cacttcacgg cttctttgta     360
cccaaacctc tggatctgga gcccatgctg cctcctggca gctggtgat cctgcctaca     420 ccagaggagc ccttatccca acccagaggc agccttgaca ttcatagcct ggaggctcag     480
agcattccct gtgtacagcc tttccacact cttgacataa gagacagacc tttccacacc     540
aaggctcaag aaattctgga catattacta cgacatcctt caggctggtg gctggtggag     600
aacaaggatc agcaggtagc ctggtttcca gctccctacc tggaggaggt agcaacgtgc     660
caaggccagg agtcaggcct ggctttgcaa ggaagtggga ggcagttctg cactactcag     720
gcctacgagg gcagtcgctc tgatgagcta tccgtgccct caggggcacg tgtccatgtg     780
ctggagacct cagaccgagg ctggtggctg tgcaggtata atggccggac aggcctactc     840
```

```
cctgcaatgt cgctgcaacc tgaagggctg ggctcgctcc tgggcaggcc agggttccca      900
gacagtgctg gggcagacaa ggtggctgag gacaggacca ttcccccgt agtaccaact       960 cgtccctgta tgagtgccat ccagagtcga tgctgctcca ttacccgcag ggcactggga    1020
caggaacaag ggactcgggt tccccgttga                                     1050

<210> SEQ ID NO 11
<211> LENGTH: 482
<212> TYPE: PRT
<213> ORGANISM: Homo sapiens

<400> SEQUENCE: 11
```

Met Ala Ser Leu Gly Asp Leu Val Arg Ala Trp His Leu Gly Ala Gln
1               5                  10                  15

Ala Val Asp Arg Gly Asp Trp Ala Arg Ala Leu His Leu Phe Ser Gly
            20                  25                  30

Val Pro Ala Pro Pro Ala Arg Leu Cys Phe Asn Ala Gly Cys Val His
        35                  40                  45

Leu Leu Ala Gly Asp Pro Glu Ala Ala Leu Arg Ala Phe Asp Gln Ala
    50                  55                  60

Val Thr Lys Asp Thr Cys Met Ala Val Gly Phe Gln Arg Gly Val
65                  70                  75                  80

Ala Asn Phe Gln Leu Ala Arg Phe Gln Glu Ala Leu Ser Asp Phe Trp
                85                  90                  95

Leu Ala Leu Glu Gln Leu Arg Gly His Ala Ala Ile Asp Tyr Thr Gln
            100                 105                 110

Leu Gly Leu Arg Phe Lys Leu Gln Ala Trp Glu Val Leu His Asn Val
        115                 120                 125

Ala Ser Ala Gln Cys Gln Leu Gly Leu Trp Thr Glu Ala Ala Ser Ser
    130                 135                 140

Leu Arg Glu Ala Met Ser Lys Trp Pro Glu Gly Ser Leu Asn Gly Leu
145                 150                 155                 160

Asp Ser Ala Leu Asp Gln Val Gln Arg Arg Gly Ser Leu Pro Pro Arg
                165                 170                 175

Gln Val Pro Arg Gly Glu Val Phe Arg Pro His Arg Trp His Leu Lys
            180                 185                 190

His Leu Glu Pro Val Asp Phe Leu Gly Lys Ala Lys Val Val Ala Ser
        195                 200                 205

Ala Ile Pro Asp Asp Gln Gly Trp Gly Val Arg Pro Gln Gln Pro Gln
    210                 215                 220

Gly Pro Gly Ala Asn His Asp Ala Arg Ser Leu Ile Met Asp Ser Pro
225                 230                 235                 240

Arg Ala Gly Thr His Gln Gly Pro Leu Asp Ala Glu Thr Glu Val Gly
                245                 250                 255

Ala Asp Arg Cys Thr Ser Thr Ala Tyr Gln Glu Gln Arg Pro Gln Val
            260                 265                 270

Glu Gln Val Gly Lys Gln Ala Pro Leu Ser Pro Gly Leu Pro Ala Met
        275                 280                 285

Gly Gly Pro Gly Pro Gly Pro Cys Glu Asp Pro Ala Gly Ala Gly Gly
    290                 295                 300

Ala Gly Ala Gly Gly Ser Glu Pro Leu Val Thr Val Thr Val Gln Cys
305                 310                 315                 320

Ala Phe Thr Val Ala Leu Arg Ala Arg Gly Ala Asp Leu Ser Ser
                325                 330                 335

Leu Arg Ala Leu Leu Gly Gln Ala Leu Pro His Gln Ala Gln Leu Gly

```
                    340                 345                 350
Gln Leu Ser Tyr Leu Ala Pro Gly Glu Asp Gly His Trp Val Pro Ile
            355                 360                 365

Pro Glu Glu Glu Ser Leu Gln Arg Ala Trp Gln Asp Ala Ala Ala Cys
        370                 375                 380

Pro Arg Gly Leu Gln Leu Gln Cys Arg Gly Ala Gly Gly Arg Pro Val
385                 390                 395                 400

Leu Tyr Gln Val Val Ala Gln His Ser Tyr Ser Ala Gln Gly Pro Glu
                405                 410                 415

Asp Leu Gly Phe Arg Gln Gly Asp Thr Val Asp Val Leu Cys Glu Glu
            420                 425                 430

Pro Asp Val Pro Leu Ala Val Asp Gln Ala Trp Leu Glu Gly His Cys
        435                 440                 445

Asp Gly Arg Ile Gly Ile Phe Pro Lys Cys Phe Val Val Pro Ala Gly
    450                 455                 460

Pro Arg Met Ser Gly Ala Pro Gly Arg Leu Pro Arg Ser Gln Gln Gly
465                 470                 475                 480

Asp Gln

<210> SEQ ID NO 12
<211> LENGTH: 1452
<212> TYPE: DNA
<213> ORGANISM: Homo sapiens

<400> SEQUENCE: 12
atggcctctc tgggggacct ggtgcgcgcc tggcacctgg gcgcgcaggc tgtggatcgt      60
ggggactggg cccgcgcctt gcacctcttc tcgggcgtcc ggcgccgcc cgccaggctg     120 tgcttcaacg cgggctgcgt gcacctgctg gcgggggacc ccgaggccgc gctgcgggca     180
tttgaccaag ccgtgaccaa ggacacctgc atggcggttg gcttcttcca gcgaggagtg     240
gccaacttcc agctggcaag gttccaggag gctctgtctg acttctggct ggccctggag     300
cagctgaggg gccacgctgc catcgactac acgcagctgg gcctgcggtt caagctgcaa     360
gcctgggagg tgctacacaa tgtggcgtcg gcacagtgcc agctggggct ctggacagag     420
gcggccagca gcctaaggga ggccatgtcc aagtggccgg aggggtccct gaatggcctg     480
gactcagccc tggaccaagt gcagagacgg ggctcactgc cgccacggca ggtccccagg     540
ggcgaggtct tccggcccca ccggtggcac ctgaagcact ggagcccgt ggatttcctg     600 ggcaaggcca agtggtggc ctctgccatc cccgacgacc agggctgggg cgtccgccct     660
cagcagccac agggaccagg agcgaaccat gatgccaggt ccctaatcat ggactcccca     720
agagctggca cccaccaggg cccctcgat gcagagacag aggtcggtgc tgaccgctgc     780
acgtcgactg cctaccagga gcagaggccc caggtggagc aagttggcaa acaggctcct     840
ctctccccag gctgccggc aatggggggg cctggccccg ccctgtgg gaccccgcg      900 ggtgctgggg gagcaggtgc aggggctcc gagcccctgg tgactgtcac cgtgcagtgc     960
gccttcacag tggccctgag gcacgaaga ggagccgacc tgtccagcct gcgggcactg    1020
ctgggccaag ccctccctca ccaggcccag cttgggcaac tcagttacct agccccaggt    1080
gaggacgggc actgggtccc catccccgag gaggagtcgc tgcagagggc ctggcaggac    1140
gcagctgcct gccccagggg gctgcagctg cagtgcaggg gagccggggg tcggccggtc    1200
ctctaccagg tggtggccca gcacagctac tccgcccagg ggccagagga cctgggcttc    1260
cgacaggggg acacggtgga cgtcctgtgt gaagagcccg atgtccccct tgcagtggac    1320
```

```
caggcatggc tggagggcca ctgtgacggc cgcatcggca tcttccccaa gtgcttcgtg    1380
gtccccgccg ccctcggat gtcaggagcc cccggccgcc tgccccgatc ccagcaggga    1440
gatcagccct aa                                                       1452
```

<210> SEQ ID NO 13
<211> LENGTH: 444
<212> TYPE: PRT
<213> ORGANISM: Mus musculus

<400> SEQUENCE: 13

```
Met Ser Ser Leu Gly Asp Gln Ile Arg Asp Trp His Arg Gly Val Leu
1               5                   10                  15

Ala Val Ala Arg Glu Asp Trp Asp Ser Ala Leu Cys Phe Phe Ser Asp
            20                  25                  30

Val Arg Glu Pro Leu Ala Arg Met Tyr Phe Asn Arg Gly Cys Val His
        35                  40                  45

Leu Met Ala Gly Asp Pro Glu Ala Ala Leu Arg Ala Phe Asp Gln Ala
    50                  55                  60

Val Thr Lys Asp Thr Cys Met Ala Val Gly Phe Leu Gln Arg Gly Val
65                  70                  75                  80

Ala Asn Phe Gln Leu Gln Arg Phe Gln Glu Ala Val Ser Asp Phe Gln
                85                  90                  95

Leu Ala Leu Ala Gln Leu Arg Asp Asn Ala Val Ile Asp Tyr Thr Gln
            100                 105                 110

Leu Gly Leu Asn Phe Lys Leu Gln Ala Trp Glu Val Leu Tyr Asn Met
        115                 120                 125

Ala Ser Ala Gln Cys Gln Ala Gly Leu Trp Thr Lys Ala Ala Asn Thr
    130                 135                 140

Leu Val Glu Ala Ile Ser Lys Trp Pro Glu Gly Ala Gln Asp Ile Leu
145                 150                 155                 160

Asp Ile Ala Met Asp Lys Val Gln Lys Gln Val Pro Leu Gln Leu Gln
                165                 170                 175

Gln Val Pro Lys Gly Glu Val Phe Gln Pro Pro Arg Arg Tyr Leu Lys
            180                 185                 190

His Leu Glu Pro Met Asp Phe Leu Gly Lys Ala Lys Val Val Ala Ser
        195                 200                 205

Val Ile Pro Asp Asp His Asn Ala Gln Pro Gln Arg Ser Gln Ala
    210                 215                 220

Glu His Ala Gly His Gln Pro Ser Ser Met Cys Lys Arg Val Leu
225                 230                 235                 240

Ser Thr Thr Gly Gly His Thr Ser Pro Gly Leu Tyr Asp Ser Leu Leu
                245                 250                 255

Ala Ser Arg Arg Pro Gly Pro Gly Pro Ser Glu Val Ser Ser Gly Ser
            260                 265                 270

Glu Gly Ala Ala Thr Lys Asp Pro Glu Ser Leu Val Thr Val Thr Val
        275                 280                 285

Gln Cys His Phe Thr Val Pro Leu Lys Val Pro Arg Gly Thr Gly Leu
    290                 295                 300

Ser Ser Phe Gln Thr Leu Leu Ala Gln Ala Leu Leu His Gln Thr Gln
305                 310                 315                 320

Thr Gly Gln Leu Ser Tyr Lys Ala Pro Gly Glu Arg Ser Trp Ile
                325                 330                 335

Pro Ile Ser Thr Glu Glu Ser Leu Gln Ser Ile Trp Arg Asn Val Pro
            340                 345                 350
```

```
Val Gly Pro Gly Gly Leu Gln Leu Gln Cys Gln Gly Val Trp Gly Arg
        355                 360                 365

Pro Val Leu Tyr Gln Val Ala Gln Tyr Asn Tyr Arg Ala Gln Arg
    370                 375                 380

Pro Glu Asp Leu Asp Phe His Gln Gly Asp Thr Val Asp Val Leu Cys
385                 390                 395                 400

Glu Val Asp Glu Ala Trp Leu Glu Gly His Arg Asp Gly Cys Val Gly
                405                 410                 415

Ile Phe Pro Lys Cys Phe Val Pro Ala Gly Ala Tyr Val Glu Ala
                420                 425                 430

Met Leu Val Leu Gly Pro Gln Pro Gly Asp Gln Asn
            435                 440
```

```
<210> SEQ ID NO 14
<211> LENGTH: 1335
<212> TYPE: DNA
<213> ORGANISM: Mus musculus

<400> SEQUENCE: 14
atgagctctc tagggatca gatacgggac tggcaccggg gtgtgctggc cgtggcacgc    60
gaagactggg actctgcgct gtgcttcttc tcagatgtcc gagagccgct ggctaggatg   120
tactttaaca gggctgtgt gcatctgatg cagggatc ccgaggctgc gctgcgggca     180
tttgaccaag cagtgactaa ggacacctgc atggctgttg cttcctcca gcggggagtg   240
gccaatttcc agctgcagag gttccaggag gctgtgtctg acttccagtt ggccctggca  300
cagctgaggg acaatgctgt cattgactac acacaactgg gtctgaactt caaattgcaa  360
gcctgggagg tcctatacaa catggcatca gcacagtgcc aggcagggct ctggaccaag  420
gctgccaata ctctagtgga ggcaatctcc aaatggccag agggggctca agacatcctg  480
gacattgcca tggacaaagt gcagaaacag gtacccctac agctacagca agtgcccaag  540
ggtgaggtct tccagcctcc caggcgatac ctaaaacatc tggagcccat ggatttcctt  600
ggcaaggcta aggtggtggc ttctgtcatt cctgatgacc acaacgccca gcctcagcag  660
aggtcccagg cggagcatgc tggccaccag ccatcctcat ctatgtgtaa agggtcctg   720
agcactacgg tggtcacac gagccctggc ctatatgata gtttgctggc atccagaagg   780
cctggtccag gccctctga gtttcctca ggatctgagg gagcagctac aaaggaccct    840
gaatccttgg tgactgtcac tgtgcagtgc cactttactg tgcccctgaa ggtcccaaga  900
ggaactggcc tgtccagttt tcagacacta ctagctcaag ccctccttca ccagacgcag  960
acagggcagc tcagttacaa agccccagga gaggagagat cctggattcc catctccacg 1020
gaggagtccc tgcagagtat atggaggaat gtgcccgtgg gcccaggagg gttgcagctc 1080
cagtgccagg gggtctgggg ccggccagtc ctctaccaag tagtagctca gtacaactat 1140
cgtgcccaaa gaccggagga tttggacttc caccaagggg acacggtgga tgtcctgtgt 1200
gaagtggacg aagcatggct ggagggacac cgagatggct gcgttggcat tttccctaag 1260
tgctttgtgg tccagctgg cgcctatgtg aagccatgc ttgtactggg accccagcca  1320
ggagaccaga actag                                                  1335
```

```
<210> SEQ ID NO 15
<211> LENGTH: 526
<212> TYPE: PRT
<213> ORGANISM: Homo sapiens

<400> SEQUENCE: 15
```

-continued

```
Met Ser Leu Val Glu Ala Ile Ser Leu Trp Asn Glu Gly Val Leu Ala
1               5                   10                  15

Ala Asp Lys Lys Asp Trp Lys Gly Ala Leu Asp Ala Phe Ser Ala Val
            20                  25                  30

Gln Asp Pro His Ser Arg Ile Cys Phe Asn Ile Gly Cys Met Tyr Thr
        35                  40                  45

Ile Leu Lys Asn Met Thr Glu Ala Glu Lys Ala Phe Thr Arg Ser Ile
    50                  55                  60

Asn Arg Asp Lys His Leu Ala Val Ala Tyr Phe Gln Arg Gly Met Leu
65                  70                  75                  80

Tyr Tyr Gln Thr Glu Lys Tyr Asp Leu Ala Ile Lys Asp Leu Lys Glu
                85                  90                  95

Ala Leu Ile Gln Leu Arg Gly Asn Gln Leu Ile Asp Tyr Lys Ile Leu
            100                 105                 110

Gly Leu Gln Phe Lys Leu Phe Ala Cys Glu Val Leu Tyr Asn Ile Ala
        115                 120                 125

Phe Met Tyr Ala Lys Lys Glu Glu Trp Lys Lys Ala Glu Glu Gln Leu
    130                 135                 140

Ala Leu Ala Thr Ser Met Lys Ser Glu Pro Arg His Ser Lys Ile Asp
145                 150                 155                 160

Lys Ala Met Glu Cys Val Trp Lys Gln Lys Leu Tyr Glu Pro Val Val
                165                 170                 175

Ile Pro Val Gly Arg Leu Phe Arg Pro Asn Glu Arg Gln Val Ala Gln
            180                 185                 190

Leu Ala Lys Lys Asp Tyr Leu Gly Lys Ala Thr Val Val Ala Ser Val
        195                 200                 205

Val Asp Gln Asp Ser Phe Ser Gly Phe Ala Pro Leu Gln Pro Gln Ala
    210                 215                 220

Ala Glu Pro Pro Arg Pro Lys Thr Pro Glu Ile Phe Arg Ala Leu
225                 230                 235                 240

Glu Gly Glu Ala His Arg Val Leu Phe Gly Phe Val Pro Glu Thr Lys
                245                 250                 255

Glu Glu Leu Gln Val Met Pro Gly Asn Ile Val Phe Val Leu Lys Lys
            260                 265                 270

Gly Asn Asp Asn Trp Ala Thr Val Met Phe Asn Gly Gln Lys Gly Leu
        275                 280                 285

Val Pro Cys Asn Tyr Leu Glu Pro Val Glu Leu Arg Ile His Pro Gln
    290                 295                 300

Gln Gln Pro Gln Glu Ser Ser Pro Gln Asp Ile Pro Ala Pro
305                 310                 315                 320

Pro Ser Ser Lys Ala Pro Gly Arg Pro Gln Leu Ser Pro Gly Gln Lys
                325                 330                 335

Gln Lys Glu Glu Pro Lys Glu Val Lys Leu Ser Val Pro Met Pro Tyr
            340                 345                 350

Thr Leu Lys Val His Tyr Lys Tyr Thr Val Val Met Lys Thr Gln Pro
        355                 360                 365

Gly Leu Pro Tyr Ser Gln Val Arg Asp Met Val Ser Lys Leu Glu
370                 375                 380

Leu Arg Leu Glu Gln Thr Lys Leu Ser Tyr Arg Pro Arg Asp Ser Asn
385                 390                 395                 400

Glu Leu Val Pro Leu Ser Glu Asp Ser Met Lys Asp Ala Trp Gly Gln
            405                 410                 415

Val Lys Asn Tyr Cys Leu Thr Leu Trp Cys Glu Asn Thr Val Gly Asp
        420                 425                 430
```

```
Gln Gly Phe Pro Asp Glu Pro Lys Glu Ser Glu Lys Ala Asp Ala Asn
            435                 440                 445

Asn Gln Thr Thr Glu Pro Gln Leu Lys Lys Gly Ser Gln Val Glu Ala
        450                 455                 460

Leu Phe Ser Tyr Glu Ala Thr Gln Pro Glu Asp Leu Glu Phe Gln Glu
465                 470                 475                 480

Gly Asp Ile Ile Leu Val Leu Ser Lys Val Asn Glu Glu Trp Leu Glu
                485                 490                 495

Gly Glu Cys Lys Gly Lys Val Gly Ile Phe Pro Lys Val Phe Val Glu
            500                 505                 510

Asp Cys Ala Thr Thr Asp Leu Glu Ser Thr Arg Arg Glu Val
            515                 520                 525

<210> SEQ ID NO 16
<211> LENGTH: 1581
<212> TYPE: DNA
<213> ORGANISM: Homo sapiens

<400> SEQUENCE: 16
```

| | |
|---|---|
| atgtccctgg tggaggccat cagcctctgg aatgaagggg tgctggcagc ggacaagaag | 60 |
| gactggaagg gagccctgga tgccttcagt gccgtccagg accccactc ccggatttgc | 120 |
| ttcaacattg ctgcatgta cactatcctg aagaacatga ctgaagcaga aaggcctttt | 180 |
| accagaagca ttaaccgaga caagcacttg gcagtggctt acttccaacg agggatgctc | 240 |
| tactaccaga cagagaaata tgatttggct atcaaagacc ttaaagaagc cttgattcag | 300 |
| cttcgaggga accagctgat agactataag atcctggggc tccagttcaa gctgtttgcc | 360 |
| tgtgaggtgt tatataacat tgctttcatg tatgccaaga ggaggaatg aaaaaagct | 420 |
| gaagaacagt tagcattggc cacgagcatg aagtctgagc ccagacattc aaaatcgac | 480 |
| aaggcgatgg agtgtgtctg gaagcagaag ctatatgagc cagtggtgat ccctgtgggc | 540 |
| aggctgtttc gaccaaatga gagacaagtg gctcagctgg ccaagaagga ttacctaggc | 600 |
| aaggcaacgg tcgtggcatc tgtggtggat caagacagtt tctctgggtt tgccctctg | 660 |
| caaccacagg cagctgagcc tccacccaga ccgaaaaccc cagagatctt caggggctctg | 720 |
| gaaggggagg ctcaccgtgt gctatttggg tttgtgcctg agacaaaaga agagctccag | 780 |
| gtcatgccag ggaacattgt cttttgtcttg aagaagggca atgataactg ggccacggtc | 840 |
| atgttcaacg gcagaagggg cttgttccc tgcaactacc ttgaaccagt tgagctgcgg | 900 |
| atccaccctc agcagcagcc ccaggaggaa agctctccgc agtccgacat cccagctcct | 960 |
| cctagttcca agcccctgg aagaccccag ctgtcaccag gccagaaaca aaagaagag | 1020 |
| cctaaggaag tgaagctcag tgttcccatg ccctacacac tcaaggtgca ctacaagtac | 1080 |
| acggtagtca tgaagactca gcccgggctc ccctacagcc aggtccggga catggtgtct | 1140 |
| aagaaactgg agctccggct ggaacaaact aagctgagct atcggcctcg ggacagcaat | 1200 |
| gagctggtgc ccctttcaga agacagcatg aaggatgcct ggggccaggt gaaaaactac | 1260 |
| tgcctgactc tgtggtgtga aacacagtg ggtgaccaag ctttccaga tgaacccaag | 1320 |
| gaaagtgaaa aagctgatgc taataaccag acaacagaac ctcagcttaa gaaaggcagc | 1380 |
| caagtggagg cactcttcag ttatgaggct acccaaccag gaccctgga gtttcaggaa | 1440 |
| ggggatataa tcctggtgtt atcaaaggtg aatgaagaat ggctggaagg ggagtgcaaa | 1500 |
| gggaaggtgg gcattttccc caaagttttt gttgaagact gcgcaactac agatttggaa | 1560 |
| agcactcgga gagaagtcta g | 1581 |

<210> SEQ ID NO 17
<211> LENGTH: 525
<212> TYPE: PRT
<213> ORGANISM: Mus musculus

<400> SEQUENCE: 17

Met Ser Leu Ala Glu Ala Ile Arg Leu Trp Asn Glu Gly Val Leu Ala
1               5                   10                  15

Ala Asp Lys Lys Asp Trp Lys Gly Ala Leu Glu Ala Phe Ser Glu Val
                20                  25                  30

Gln Asp Pro His Ser Arg Ile Cys Phe Asn Ile Gly Cys Val Asn Thr
            35                  40                  45

Ile Leu Glu Asn Leu Gln Ala Ala Glu Gln Ala Phe Thr Lys Ser Ile
50                  55                  60

Asn Arg Asp Lys His Ser Ala Val Ala Tyr Phe Gln Arg Gly Met Leu
65                  70                  75                  80

Tyr Tyr Arg Met Glu Lys Tyr Asp Leu Ala Ile Lys Asp Leu Lys Glu
                85                  90                  95

Ala Leu Thr Gln Leu Arg Gly Asn Gln Leu Ile Asp Tyr Lys Ile Leu
            100                 105                 110

Gly Leu Gln Phe Lys Leu Phe Ala Cys Glu Val Leu Tyr Asn Ile Ala
        115                 120                 125

Leu Met His Ala Lys Lys Glu Glu Trp Lys Lys Ala Glu Glu Gln Leu
130                 135                 140

Ala Leu Ala Thr Asn Met Lys Ser Glu Pro Arg His Ser Lys Ile Asp
145                 150                 155                 160

Lys Ala Met Glu Ser Ile Trp Lys Gln Lys Leu Phe Glu Pro Val Val
                165                 170                 175

Ile Pro Val Gly Arg Leu Phe Arg Pro Asn Glu Arg Gln Val Ala Gln
            180                 185                 190

Leu Ala Lys Lys Asp Tyr Leu Gly Lys Ala Thr Val Val Ala Ser Val
        195                 200                 205

Val His Gln Asp Asn Phe Ser Gly Phe Ala Pro Leu Gln Pro Gln Ser
210                 215                 220

Ala Glu Pro Pro Arg Pro Lys Thr Pro Glu Ile Phe Arg Ala Leu
225                 230                 235                 240

Glu Gly Glu Ala His Arg Val Leu Phe Gly Phe Val Pro Glu Thr Pro
                245                 250                 255

Glu Glu Leu Gln Val Met Pro Gly Asn Ile Val Phe Val Leu Lys Lys
            260                 265                 270

Gly Ser Asp Asn Trp Ala Thr Val Met Phe Asn Gly Gln Lys Gly Leu
        275                 280                 285

Val Pro Cys Asn Tyr Leu Glu Pro Val Glu Leu Arg Ile His Pro Gln
290                 295                 300

Ser Gln Pro Gln Glu Asp Thr Ser Pro Glu Ser Asp Ile Pro Pro Pro
305                 310                 315                 320

Pro Asn Ser Ser Pro Gly Arg Leu Gln Leu Ser Pro Gly His Lys
                325                 330                 335

Gln Lys Glu Pro Lys Glu Leu Lys Leu Ser Val Pro Met Pro Tyr Met
            340                 345                 350

Leu Lys Val His Tyr Lys Tyr Thr Val Val Met Glu Thr Arg Leu Gly
        355                 360                 365

Leu Pro Tyr Ser Gln Leu Arg Asn Met Val Ser Lys Lys Leu Ala Leu
370                 375                 380

```
Ser Pro Glu His Thr Lys Leu Ser Tyr Arg Arg Asp Ser His Glu
385                 390                 395                 400

Leu Leu Leu Leu Ser Glu Ser Met Lys Asp Ala Trp Gly Gln Val
            405                 410                 415

Lys Asn Tyr Cys Leu Thr Leu Trp Cys Glu His Thr Val Gly Asp Gln
        420                 425                 430

Gly Leu Ile Asp Glu Pro Ile Gln Arg Glu Asn Ser Asp Ala Ser Lys
        435                 440                 445

Gln Thr Thr Glu Pro Gln Pro Lys Glu Gly Thr Gln Val Val Ala Ile
    450                 455                 460

Phe Ser Tyr Glu Ala Ala Gln Pro Glu Asp Leu Glu Phe Val Glu Gly
465                 470                 475                 480

Asp Val Ile Leu Val Leu Ser His Val Asn Glu Glu Trp Leu Glu Gly
                485                 490                 495

Glu Cys Lys Gly Lys Val Gly Ile Phe Pro Lys Ala Phe Val Glu Gly
            500                 505                 510

Cys Ala Ala Lys Asn Leu Glu Gly Ile Pro Arg Glu Val
        515                 520                 525

<210> SEQ ID NO 18
<211> LENGTH: 1578
<212> TYPE: DNA
<213> ORGANISM: Mus musculus

<400> SEQUENCE: 18
atgtccctgg ctgaggccat cagactctgg aatgaagggg tgctcgcagc cgacaagaag      60
gactggaagg gggccctgga ggccttcagc gaggtgcagg accccactc gaggatttgc      120 ttcaacatag gctgcgtgaa caccatcctg aaaaacttgc aggcagccga gcaggccttc      180
accaaaagca tcaacagaga caagcactct gcagtggcct acttccagag aggaatgctc      240 tactacgaa tggagaagta cgaccttgct atcaaagacc ttaaagaggc cttgacgcag      300
cttcgtggga accagctgat agactacaag atcctggggc tgcagttcaa gctgtttgcc      360
tgtgaggtat tgtacaatat tgctctcatg catgccaaga agaggaatg gaagaaagca      420 gaagagcagt tggcattggc aaccaacatg aagtccgagc ccaggcattc aagatcgac      480 aaggccatgg agagcatctg gaagcagaag ctgttcgagc ccgtggtgat ccctgtgggt      540
cggctgttcc gtccaaatga gaggcaggtg gctcagctgg ccaaaaagga ctatctgggc      600
aaggctacgg ttgtagcatc tgtggttcac aagacaact tttctggctt cgcccctctg      660
cagccgcagt cagcagagcc tcctcccaga cccaaaaccc cagaaatctt cagggctctg      720
gaaggtgagc acaccgcgt attgtttggc tttgtgccgg agacgccaga agagctacag      780
gtcatgcctg ggaacatcgt ctttgtcttg aagaagggca gtgataactg gccacagtc      840 atgttcaatg gacagaaggg gcttgtcccc tgcaactacc tggagccagt tgagcttcgg      900
attcaccctc agtcgcagcc ccaggaagat acctctccag aatctgatat tccaccacct      960
cctaattcta gtccccagg aagactccag ttgtcaccag gtcacaagca aaaagagccc      1020
aaggaactga agctcagcgt gcctatgcct acatgctca aggtgcatta caaatacaca      1080
gtggtcatgg agacgcggct tggcctcccc tacagccagc ttcggaacat ggtgtctaag      1140
aagctggcgc tctcgccaga acacactaaa ctgagctacc ggcgtcggga cagccacgag      1200
cttctgctcc tgtccgaaga aagcatgaag gatgcctggg gccaagtgaa aaactactgc      1260
ctgactctgt ggtgtgagca tacggtgggt gaccaaggtc ttattgatga acccatacaa      1320
```

```
aggggaaaact cagacgccag taagcagact acggagcctc agcctaagga ggggacccag    1380
gtggtagcaa tcttcagtta tgaggctgcc cagccagaag acctggaatt tgtggaagga    1440
gatgtaatcc tggtactgtc acatgtgaat gaagaatggc tggaagggga gtgtaaaggg    1500
aaagttggca ttttcccgaa ggcttttgtt gaaggatgtg cagccaagaa tttggaaggc    1560
attcccagag aagtctag                                                  1578
```

<210> SEQ ID NO 19
<211> LENGTH: 390
<212> TYPE: PRT
<213> ORGANISM: Homo sapiens

<400> SEQUENCE: 19

```
Met Gly Asp Thr Phe Ile Arg His Ile Ala Leu Leu Gly Phe Glu Lys
1               5                  10                  15

Arg Phe Val Pro Ser Gln His Tyr Val Tyr Met Phe Leu Val Lys Trp
            20                  25                  30

Gln Asp Leu Ser Glu Lys Val Val Tyr Arg Arg Phe Thr Glu Ile Tyr
        35                  40                  45

Glu Phe His Lys Thr Leu Lys Glu Met Phe Pro Ile Glu Ala Gly Ala
    50                  55                  60

Ile Asn Pro Glu Asn Arg Ile Ile Pro His Leu Pro Ala Pro Lys Trp
65                  70                  75                  80

Phe Asp Gly Gln Arg Ala Ala Glu Asn Arg Gln Gly Thr Leu Thr Glu
                85                  90                  95

Tyr Cys Gly Thr Leu Met Ser Leu Pro Thr Lys Ile Ser Arg Cys Pro
            100                 105                 110

His Leu Leu Asp Phe Phe Lys Val Arg Pro Asp Asp Leu Lys Leu Pro
        115                 120                 125

Thr Asp Asn Gln Thr Lys Lys Pro Glu Thr Tyr Leu Met Pro Lys Asp
    130                 135                 140

Gly Lys Ser Thr Ala Thr Asp Ile Thr Gly Pro Ile Ile Leu Gln Thr
145                 150                 155                 160

Tyr Arg Ala Ile Ala Asn Tyr Glu Lys Thr Ser Gly Ser Glu Met Ala
                165                 170                 175

Leu Ser Thr Gly Asp Val Val Glu Val Val Lys Ser Glu Ser Gly
            180                 185                 190

Trp Trp Phe Cys Gln Met Lys Ala Lys Arg Gly Trp Ile Pro Ala Ser
        195                 200                 205

Phe Leu Glu Pro Leu Asp Ser Pro Asp Glu Thr Glu Asp Pro Glu Pro
    210                 215                 220

Asn Tyr Ala Gly Glu Pro Tyr Val Ala Ile Lys Ala Tyr Thr Ala Val
225                 230                 235                 240

Glu Gly Asp Glu Val Ser Leu Leu Glu Gly Glu Ala Val Glu Val Ile
                245                 250                 255

His Lys Leu Leu Asp Gly Trp Trp Val Ile Arg Lys Asp Asp Val Thr
            260                 265                 270

Gly Tyr Phe Pro Ser Met Tyr Leu Gln Lys Ser Gly Gln Asp Val Ser
        275                 280                 285

Gln Ala Gln Arg Gln Ile Lys Arg Gly Ala Pro Pro Arg Arg Ser Ser
    290                 295                 300

Ile Arg Asn Ala His Ser Ile His Gln Arg Ser Arg Lys Arg Leu Ser
305                 310                 315                 320

Gln Asp Ala Tyr Arg Arg Asn Ser Val Arg Phe Leu Gln Gln Arg Arg
                325                 330                 335
```

Arg Gln Ala Arg Pro Gly Pro Gln Ser Pro Gly Ser Pro Leu Glu Glu
                340                 345                 350

Glu Arg Gln Thr Gln Arg Ser Lys Pro Gln Pro Ala Val Pro Pro Arg
                355                 360                 365

Pro Ser Ala Asp Leu Ile Leu Asn Arg Cys Ser Glu Ser Thr Lys Arg
        370                 375                 380

Lys Leu Ala Ser Ala Val
385                 390

<210> SEQ ID NO 20
<211> LENGTH: 1173
<212> TYPE: DNA
<213> ORGANISM: Homo sapiens

<400> SEQUENCE: 20

```
atggggaca ccttcatccg tcacatcgcc ctgctgggct ttgagaagcg cttcgtaccc      60
agccagcact atgtgtacat gttcctggtg aaatggcagg acctgtcgga aggtggtc     120
taccggcgct tcaccgagat ctacgagttc cataaaacct aaaagaaat gttccctatt    180
gaggcagggg cgatcaatcc agagaacagg atcatccccc acctcccagc tcccaagtgg   240
tttgacgggc agcgggccgc cgagaaccgc agggcacac ttaccgagta ctgcggcacg    300
ctcatgagct gcccaccaa gatctcccgc tgtccccacc tcctcgactt cttcaaggtg   360
cgccctgatg acctcaagct ccccacggac aaccagacaa aaagccaga gacatacttg   420
atgcccaaag atggcaagag taccgcgaca gacatcaccg cccccatcat cctgcagacg   480
taccgcgcca ttgccaacta cgagaagacc tcgggctccg agatggctct gtccacgggg   540
gacgtggtgg aggtcgtaga aagagcgag agcggttggt ggttctgtca gatgaaagca   600
aagcgaggct ggatcccagc gtccttcctc gagcccctgg acagtcctga cgagacggaa   660
gaccctgagc ccaactatgc aggtgagcca tacgtcgcca tcaaggccta cactgctgtg   720
gaggggacg aggtgtccct gctcgagggt gaagctgttg aggtcattca caagctcctg   780
gacggctggt gggtcatcag gaaagacgac gtcacaggct acttcccgtc catgtacctg   840
caaaagtcag ggcaagacgt gtcccaggcc aacgccaga tcaagcgggg ggcgccgccc   900
cgcaggtcgt ccatccgcaa cgcgcacagc atccaccagc ggtcgcggaa gcgcctcagc   960
caggacgcct atcgccgcaa cagcgtccgt tttctgcagc agcgacgccg ccaggcgcgg  1020
ccgggaccgc agagcccgg gagcccgctc gaggaggagc ggcagacgca gcgctctaaa  1080
ccgcagccgg cggtgccccc gcggccgagc gccgacctca tcctgaaccg ctgcagcgag  1140
agcaccaagc ggaagctggc gtctgccgtc tga                                1173
```

<210> SEQ ID NO 21
<211> LENGTH: 390
<212> TYPE: PRT
<213> ORGANISM: Mus musculus

<400> SEQUENCE: 21

Met Gly Asp Thr Phe Ile Arg His Ile Ala Leu Leu Gly Phe Glu Lys
1               5                   10                  15

Arg Phe Ile Pro Ser Gln His Tyr Val Tyr Met Phe Leu Val Lys Trp
                20                  25                  30

Gln Asp Leu Ser Glu Lys Val Val Tyr Arg Lys Phe Thr Glu Ile Tyr
        35                  40                  45

Glu Phe His Lys Met Leu Lys Glu Met Phe Pro Ile Glu Ala Gly Glu
    50                  55                  60

Ile His Thr Glu Asn Arg Val Ile Pro His Leu Pro Ala Pro Arg Trp
65                  70                  75                  80

Phe Asp Gly Gln Arg Ala Ala Glu Ser Arg Gln Gly Thr Leu Thr Glu
                85                  90                  95

Tyr Phe Asn Gly Leu Met Gly Leu Pro Val Lys Ile Ser Arg Cys Pro
            100                 105                 110

His Leu Leu Asp Phe Phe Lys Val Arg Pro Asp Asp Leu Lys Leu Pro
        115                 120                 125

Thr Asp Ser Gln Ala Lys Lys Pro Glu Thr Tyr Leu Val Pro Lys Asp
130                 135                 140

Gly Lys Asn Asn Val Ala Asp Ile Thr Gly Pro Ile Ile Leu Gln Thr
145                 150                 155                 160

Tyr Arg Ala Ile Ala Asp Tyr Glu Lys Ser Ser Gly Thr Glu Met Thr
                165                 170                 175

Val Ala Thr Gly Asp Val Val Asp Val Val Glu Lys Ser Glu Ser Gly
            180                 185                 190

Trp Trp Phe Cys Gln Met Lys Thr Lys Arg Gly Trp Val Pro Ala Ser
        195                 200                 205

Tyr Leu Glu Pro Leu Asp Ser Pro Asp Glu Ala Glu Asp Pro Asp Pro
210                 215                 220

Asn Tyr Ala Gly Glu Pro Tyr Val Thr Ile Lys Ala Tyr Ala Ala Val
225                 230                 235                 240

Glu Glu Asp Glu Met Ser Leu Ser Gly Glu Ala Ile Glu Val Ile
                245                 250                 255

His Lys Leu Leu Asp Gly Trp Trp Val Val Arg Lys Gly Asp Ile Thr
            260                 265                 270

Gly Tyr Phe Pro Ser Met Tyr Leu Gln Lys Ala Gly Glu Glu Ile Thr
        275                 280                 285

Gln Ala Gln Arg Gln Ile Arg Gly Arg Gly Ala Pro Pro Arg Arg Ser
290                 295                 300

Thr Ile Arg Asn Ala Gln Ser Ile His Gln Arg Ser Arg Lys Arg Leu
305                 310                 315                 320

Ser Gln Asp Thr Tyr Arg Arg Asn Ser Val Arg Phe Leu Gln Gln Arg
                325                 330                 335

Arg Arg Pro Gly Arg Pro Gly Pro Gln Ser Thr Asp Gly Thr Lys Asp
            340                 345                 350

Asn Pro Ser Thr Pro Arg Val Lys Pro Gln Pro Ala Val Pro Pro Arg
        355                 360                 365

Pro Ser Ser Asp Leu Ile Leu His Arg Cys Thr Glu Ser Thr Lys Arg
370                 375                 380

Lys Leu Thr Ser Ala Val
385                 390

<210> SEQ ID NO 22
<211> LENGTH: 1173
<212> TYPE: DNA
<213> ORGANISM: Mus musculus

<400> SEQUENCE: 22
atgggggaca ccttcattcg ccatatcgcc ctgctgggct tcgagaagcg cttcatcccc    60
agccagcact atgtgtacat gttcctggtt aagtggcagg acctgtcgga gaaggtggtc   120
tacagaaaat tcaccgagat ctacgagttc cataaaatgc tgaaggagat gttccccatt   180
gaggccggcg agatccacac agagaacaga gtcatcccac acctcccggc acccaggtgg   240

```
tttgatggac aacgagccgc tgagagccgc cagggcacgc tcactgagta cttcaacggc      300
ctcatgggac tgcccgtgaa gatctcccgc tgcccacacc tgctggactt cttcaaagtg      360
cggcctgatg acctgaaact gcccactgac agccaggcca agaagccaga gacgtacctg      420
gtgcccaaag atggcaagaa taacgtagct gacatcacag gccccatcat ccttcagacc      480
tatcgggcca ttgctgacta cgagaagagt tcgggaacag agatgaccgt ggcaaccgga      540
gacgtggtgg acgtcgtgga agagagcgag agcggctggt ggttttgcca gatgaagaca      600
aagcgaggtt gggtccctgc atcctatctg gagccccttg acagtcccga cgaggcggag      660
gatccggatc ccaactacgc aggtgaaccg tatgtaacca tcaaagcgta cgctgctgtt      720
gaagaggacg agatgtccct gtctgagggt gaagccattg aggtcattca taagctcctg      780
gatggctggt gggtggtcag gaaaggggat atcaccggct atttcccatc catgtatctg      840
cagaaggctg gggaggagat aacccaggcc cagcgacaga tcagaggccg cggggcacca      900
cctcgaaggt cgaccatccg caacgcacag agcatccacc agcgttctcg gaagcgtctc      960
agccaggaca cctatcgccg caacagcgtc cgattcctgc agcagcgcag acgcccgggg     1020
cgacccgggc cgcagagcac ggatggcaca aaggacaatc catcgactcc gcgcgtcaaa     1080
ccacagcccg cggtgcctcc gcgacccagc tcagacctca tcctgcaccg ctgcacagag     1140
agcaccaaac ggaagctgac gtccgctgtg tga                                  1173

<210> SEQ ID NO 23
<211> LENGTH: 60937
<212> TYPE: DNA
<213> ORGANISM: Mus musculus

<400> SEQUENCE: 23
atgccggtgt gctggattct gaacgagagt gggtccttcg tggttgctgt gagtatcact       60
cttcttactt ggctctaaga gtcctccatt cttagaatga tatttctaaa atggtttaag      120
tttggaaata ttactttaga tatgagacta aaaacttgtc agcaaacact cattgaatgt      180
atttaactta cccttataga atcatgcaaa gttgttttcc aagtccattc attttttgagc     240 attttttaaag tcaactagtt tgttttgtat ggcacgtgtc tatcaaatga agtctgtgaa      300
tcagcctgtg aaactagcat ttttttttcc tagagtgctt taaagatgcc ctgactcttc      360
acaccatggt caattcctgt tgactaagaa gatcctgtgc ttgtcagtaa atactttgaa      420
gttgacagcc ttatttaaa ataatgtatt tgtaatccct gctgtaatgt aatctgtaag       480
aaataaatgt atagagtgat tctgaggaat actgacaact tctgcatttc atctgaaaag      540
aagtttagtg tcgaatgatc ttgagtaggc gaggggtggc ccatagcagt gatctcatct      600
cttttctccc tacccctagct cttatggctg gcagtaaacg cctatctgtt tattgacaca      660
ttcttctggt atactgaaga ggaggctttc ttttatacac gagttattct gggtgtaagt      720
agatttaatg acaatctgtt attgtttcaa aaaagaaaat gcattctact ttctcaagct      780
tcaatgtttt catcatcctc ctttttttcta tttctaactt atggatagtc cgcattggca      840
tgggcccggg catctgccgt gtgcctgaat tttaactgca tgctaattct gttacctgtc      900
agtcggaact tcatttcact ggtgagagga acaagtgtgg taagtactaa aaaattttaa      960
gcaagctcag ttgttgacag cctgcaacta aagactggaa agatggctta gcaggtaggt     1020
gctggccagc aaaccttggg aacctgagtt caaatggcca gaatccatgt taaaaaaaaa     1080
aaaaagcagt gtgtacttgt gtgtttgtga caccagcatg gttgagggtc agaggcagga     1140
ggataatcag ggactagctg gccaccaacc taactccaag ttcaataagg ccctgatctc     1200
```

```
aagagaaaaa aaaagcagag agtgataaaa caggtaacct ggttggtgtt ctctggcctt    1260
ggagtgtgtg catgagtata catatgcaca tgcactcaat atgcagaccc catgcttaca    1320
cacacacaca catacacaca cacacatgca cttttttacag gtatgattga aacatgtatt   1380
ttcctatgaa actcccagca actgtgctta cactagttaa agctaaagat caggacattc    1440
cacttgacgt tggctttcca acaacactg gactcaactt tttcccacat ggagatgcag     1500
gggttatgac tgtttgaacc acaatcattt ctgattgaag aaagataaat aaatcattga    1560
gatgagagcc actcaggaaa cacccccaatt ccttccataa tcaaaatcac aaggcccaga   1620
ttgaacctgg tgattttaac actgatccat ggtaacaccc ctcctaatca tatttatttc    1680
aatatgctta attaccactt cctctgttac tgaaaacagc atgcagaaaa ataagattgt    1740
cagtaacctt tatcagaaga aataacttat tgtgaaatca tcacaatagt aaatactagt    1800
tatagatgca aaacatcttt ctttgtgtaa taaggaacag tgaacaagtc attcaaaata    1860
catgactgga aatggtaatt attacttctt tattctatat caataagctg actaaggcat    1920
gaccataagg tttacttaag cactgtgagt tagagccaga gacctaagaa atcccacttt    1980
tagattgagt tgctattcca gcaaaatagc taaagaaaaa tcttttgcct tgctgtgatc    2040
aaatgccact agttttttaag tcccgtgtcc ccacttgaag caacacagag atcagttgag   2100
cctgagtcat atcctcttag atcttgtagc attgttagct ctgtgtccat tttcctaatt    2160
catttattca tttattttgg tactttagtg ctgtagagga ccatggagaa acaactaga     2220 caaaaacctc aacttccaca aactcgttgc ctacgggata gctgtcaatt caggtgagtg    2280
cttaccaatt gtctttagca ctggctaaga tctaacttca tagttttttg tttaactcct    2340
cccaatcgtg cctttagata atagaagctt tcacccttca tctgaacaca tgaaaccttg    2400
catttacatt ctttcaattc ctaatctata cttaaatgag ttttttccata ataatctctc   2460 aaagatcaaa agaaagttgg tcagatttcc ctttgtgaat aagtagcttc tttgtaatgc    2520
agtgataaat acctatttaa atgaaaattt tgctattcgt atcattcaga actaaaattg    2580
agttatagca aaaacctcat tcatataata ggaaaattga attgtcattc aatgaatgtc    2640
aatatagatg ggatagtgtt cttctttgtg tggtaaggat gtcttaatct ttgccctgac    2700
attagagtct aaaaaaggag gaaaaaaaag aagaagaaga aaagcttggt catgtgacct    2760
gggttcagaa ttgtgttgag ttagtggaca tagaagagcc tttaaaggta gagattgtag    2820
gttgtatagg aactgctact gttacggtta cacttgtcat ttaaggagaa attagtatct    2880
ctgagcaagt ttagacaccc acaaagaagg aaagaatgaa aggagaggta gcaatcaact    2940
ggcttgtggt tttgccgggc aacaaagtca ttgaaataaa agaccattgg aaagataaag    3000
agttatgatt cggtactctt tctctcaaac taatttcact ataaaatgtt ttcctcattt    3060
gtttttcatc ctctcatgca ttaaaaaaat gcagagtaaa aggaacactc gaaccaaatg    3120
ggaatttaat taagcaacaa gacatgacag acggtgcccg agtgccaatt aacacaactc    3180
tgggtgtgta gtgagacatg tggggaagac tctccccatt gattgtctta aacaccggag    3240
caaattaacc cgagataagc gttgcagagg gtctttgtgg tttgtctttt taaaaaaaaa    3300
agtgttaaaa gaaaaatcaa gtcctagctg aaacagctag taaatggggc ggttagggac    3360
aaggttggtc tagctgtatg tctcaggacc tgaagtggtg cagaatacac ctgtgtacat    3420
agagcctttg aaaacaagta ccattaccag gaagtagact ttggcttgca aacggaagcc    3480
gtttccacac tttgaaaaga tacaaaagca gagctcagt gctcacagag ctctgagctc     3540
cctgtggtgt gtggaatcag gcacagggca caaccaccga gctccttggt aaacttgtca    3600
```

```
gagaaggaat tctaggacat ttctgggctt cctttaaacg cttcaaaagt ccttatttc   3660
tcattaagaa tagagattaa acactctaaa gaggcaagaa gaatcttatt accatgcata   3720
gcttaaaggc agagtcagac tttaaaagag agttgtaaag atataaagaa aaaggggat    3780
catcaaaatt catcagaaag gagcacagag catacacgaa aacatgagtt gtgaaaggct   3840
ttcttcttaa atctctgggt acatatcctt tctatgtcct catacatccg tagtataaat   3900
ggatagataa tatacattga atgtatccca tgagcagggc accctgtggg taagacctgt   3960
tgaaccccct gtggcccgtg ctgtttcagg gcactgtgaa attgagagtg agcaagattt   4020
gactagggtc atatgaccag cttcttttat agccctgctg ttgctgggtg tgtgagctca   4080
ggtctcttca gctggctgtg gaatcttgaa agcatcaata gccgtttgat ttctctacct   4140
tggtgagata ctgtagatta ccttcaggac taaatctgat atagcaatct gaaaaataca   4200
aggccattca ttcacttgtt gttattgcga gtgaggtcaa gtccactccc ccaaagcatg   4260
gcggatggac tcacagctct aaccaagttt ttggttctcc acatcctcat ggccttccc    4320
cttgggtacc cttaagagca agtgttctca acctgtgggc tgtgtgaccc ctttgtaggc   4380
cacatatcag acatcttgaa tatcagatat cactattaca attcacaaca ataggaaagt   4440
tacacttacg tagtagcaat ggaaatcatt ttatgattat gggtcaccac aatattacaa   4500
actgtattaa agggttgcat cattaggaag attgaaaacc actactccaa agtcttctct   4560
ttccttgctc agatgaccct tctgctgaaa ttcctccccc ttcatcgtgc ttcctgggag   4620
gttaagactt gtctatatca ggaacccact gtctgtccta aatgccatca cctacaaggc   4680
tcctgcctta ctcgatagct caagagtggc aatcctcagt ttctgagagg ctcagaggca   4740
gggagcatct cttgcatttt agtaacctgt gtctctaaca caagtagact ataacagact   4800
tgaccaaacc agggcaagtg gcatgtagcc atgtgtgtga ggctaaaaga attgatagga   4860
aaggaacaag acacaaattc tgggcatcgt gtggatgaaa cagcgtttgg gaaatgaatg   4920
gatttagaat gatactaatc attcaagatt ataaattcac attctgctgc aaggagaaga   4980
aacaggatgt tctttctcca tctttccctc ccaagtctgc aaaggacatc agttttcttt   5040
ccaacccacg tctcttgaat tgctgctact ctgagctgct cctgagcatc tactgggct    5100
caccccagca gggtcagagc tgtatctccc agcaaagtag cctcatccgg tctgtcatgg   5160
caaccaaccc cagggctgtg gtttccagcc cgacaaaggc aggaaggtgg aaaggaaact   5220
ctttaccttg tccaatcctt gaaaaagcaa ttactgcatt tcacattaac taagaaatgt   5280
ggctggcaac tgtgctttta gagagaggag aaaaaaatgc taagcctggg tttcattgct   5340
acaccttgct cttctcattt gtccttctgc tgtattcacg gaggagcagc tgcaatgtcc   5400
ctgggcttat tttattagcc tcgcccatta tgctgctttt gaaatagcca actggcttaa   5460
tagggggtgtg taaccttgga agaaatgcat gcacagagaa gtttgcatgc cagcctctaa   5520
tttcttatcc gttcccctag atgttgaact gcaggctcta attggtcgga taattaaagg   5580
atgtaattag agactggtgg atgtaggcta gggaatgggg ttggggaggc aaaacagtgg   5640
tatctctaat caagggcatc accgaaaatt cagtgccagg agcccttctt cttgccttcc   5700
tgcttgcctg cctgtgataa gcaggagccc cctccaacca ctaaataaat tgtgttcagg   5760
gacctgtaac tccactggta taaaaatcgt tgtctcacag cctttacgtt cttattaatg   5820
tggatctttc tgggttccct ggtccatggc agaccttgaa gaccccagca attgaaaagc   5880
agtatgtgga gcctgggctt ccatcaacgg aggttgtaaa ttgtgaccta tgcagctctt   5940
tccgcaaatt ctgcaacttg tgtctgccag atttcagtgg tgtaagatca ccctgattgc   6000
```

```
aactcctgat gagttgctaa aattagttca caaacatcga taaacagaag aggggcaggc    6060
tgagaagaga gggtacagca taaaggtcct gagaaaataa tgattcggag ctcccaaggt    6120
agagatggtg tcaaaggcac cagttccttg ggatctgaca cctaacaagt tgctaccaac    6180
cagttcctca gttccactga aagtgttcaa agctccaaca gggctccttt atgattttt     6240
ttgtctgctt ctcaataaaa gtttcatatt tgaactcaga agtccacaga ccacttaaaa    6300
gagtgtgtgc agcattgcca acataactgg tctctgtaaa agtacttggg tgagaaaata    6360
gaattacagg aagagccacc ctcttacagc ttggatcatt tgggtgagtg atggagagac    6420
gtagcttgag cttttaccaa tatacagcgc tgtatagcat aggaagtcca caggggcaca    6480
caaagagctt gttttcagat attaacccag ttgtcacaaa gctgccatgt atggttatgg    6540
gtatttttc caagtctacc cattttacgg atgagaaaat agagacagga aaaaaaatta    6600
ggtaatcaag aagcatccac tttgctattc ttcctgctag acaccaacat ccagtctaac    6660
atcatggaag tatcacagtg gctgggaagg tgagaattca cccacagcag catcttcaac    6720
ccatttcaga gatagctgtg gccataccac aatagtttgt ttgctcatac taaaaaggat    6780
aagacatata taaagaaaaa aaatagaat gtctgtaagg gaccaaaagc aatacttctc    6840
ctgttactta tcctgcctgg gcagtcctag gtttaacagc ttttatattt ctagttttta    6900
gccatgatca aatctaagag gaacatagag tgtttacgca accaaaatgg cctcaggtgg    6960
tttttacccct taggatctgt cttagtcagg gtttctattc ctgcacaaac atcatgacca    7020
agaagcagtt ggggaggaaa gggtttattc agcttacact tccatgctgc tgctgttcat    7080
caccaaagga agtcaggact ggaactcaag caggtcagga agcaggagct gatgcagagg    7140
ccatggaggg atgctgctta ctggcttgct tcccctggct tgctcagcct gctctcttat    7200
agaaccaagt ctaccagccc agagatggca ccacccataa aggaacctcc cccttgatc    7260
actaattgag aaaatgcctt atagctggat ctcgtggagg catttcccca actgcagctc    7320
ctctctctgt gataactcca gcctgtgtca agttgacaca aaattaacca gtacaggatc    7380
cctgggataa ctaggatatt acaggtttaa tctactttgt gaagcaaaaa caagatggag    7440
agtactgaag gaaaggaatg tatattatat aaaccttaaa gcacataaaa gctacaggta    7500
acagagctct agcttagtcc cgtggagatg gtctcttgag aggctacttg gacttccctc    7560
ctccagtgtt gtcttccgag ctaaaggaag ggaggaggcg gtaaacatga atgagcgctc    7620
cgggtcctaa gtcatctatt ccacacacgc caatctaggt tagctctgtc agattctcct    7680
gtggaagcta acctaagagg aaacagactg agatctgcag ctcattacaa ggaagagggg    7740
tgtcataaaa acaggcgaag acaaagagaa tttgttcatt gctttcttcc tgactgttag    7800
gtatagatga cacattggga aatcagtcct ataatagaaa atgaaaacca gcgtctaatt    7860
ctgtgaaatg gaaatgcccc agtctccatc tccataaaag atttttttgg ttaatcttgt    7920
attcagccac tttggtgaaa gtgtttatca gctacaggca ctccctggtc gaattttgga    7980
ggttgcatgt gtatattatc atatcatctg tgaatagcaa tactttgact tctttctctc    8040
caatttgaac caccttgatc tccttttagtt gtcttactgc tctggctagg acttcaagtg    8100
ctatattgaa tagatgtgaa gagagtagac atcttcatta agacatgaat ttggttgagg    8160
accctggaag gactgttctt ctctgaggag ggttgaagaa agggtagatt gaggaaaggg    8220
gagaagaggg agagactggg gggaagggaa actgaagtca ggatgtaaat atgacagaat    8280
aaataaaaaa gggaaaagga aataagaaa attcttctaa ataatagttg acattgtgca    8340
gctatgacca caggcacaaa attacctgca atattctcaa aggttctgtg tgtgtgcaac    8400
```

```
atacatgcat gaatgtgcat acagaggcca gatgttggca ttgctggtgt cctcagtggt   8460
tttctgtctc tctgtctctg tctgtctctc tctctcagcc tggagctcac              8520 tgtattttt ttttaaatag actaactggc cagcatctcc aagtatctac ctctttcctt    8580
accacctctg cctcaaccag tactgaggtt ataaacctgc attactgatt atgtacatgt   8640
tgcagataaa actcaagtct ctgtgcttac atggcaagcc cttaccgact tctctgtctc   8700
cccatcccca gtattctcag ccttacatct tccacacctc caatcataaa gaacaaccat   8760
ggaggatgct gtaacacacc cacaatattt atagccatgt acatgttagc ctatacacac   8820
gtacatatat ccatatgtat atatacatag tagccagcac agttacttct tcccattgca   8880
gatgcagaag aacgtgtggg aaattaacta tatcctgagt aatgagtcct ttgttcacac   8940
ttgagtctga tcccaatggt gtgtgtcgac tggcagctca tccaggtctc catggaggtg   9000
gcatgactgc tggcttttcca atggagtttc caagctagga aagagcagca cagaggtaga  9060
atctccaggc cagatcacac agtgtccttg aatttgtcct ctttatctaa aatttaaatg   9120
tactaactct cagaatcaga tatcacactt tccttaagag tatagaaaaa atatgttggt   9180
tccacaaata ctggctcatt tcaatgtgcc tgatgatttt gtaagagtta tctatgcaaa   9240
tgtgtgtgta gttgtataaa tgcacatatg tgtatgtacc tatacatata catgtacata   9300
catacatact acatacatac acacatgtat gtgttaaaac atatgaagag aagaacagaa   9360
aatatttctg gaaatgtgtga agaaaatatc cctgaaattt tcctgatatc aacctgtgtg  9420
tcaaataaac atatattgct gtgtatgatg catggtattc taagataatt ctttctgaat   9480
tctttaggaa gcttcatatt ctacacccgt catatgccat ctttctttaa gaattatatc   9540
tatattatag tatcctatat tatattatgt tatattatat tatattatat tttgtctgta   9600
attacaataa tgctatgata aaatactgtg accaaaaaag caagttgaag aggaaaaggt   9660
ttatttgtct ccatcattgt aggaagtcat ggcaggaacc tggaaggaag acctgatgca   9720
gaggccatag aggggttctg cttactggct tgttcctcgt agcttgctca ttacagaaac   9780
catcctagaa gtggctccac cccacaatgg ggcaaaagct ctcacatcaa tcactaataa   9840
agaaaatacc ctacagcctg atctgatgaa ggcattttct cagatgagcc tcccttagcc   9900
aacacaacaa caatgttctg atataataac ttcatcact tccaaaatga gtagaaattt     9960
aatatcaaat catgaattaa gatgacttta tttgttaata taattaaaca cttataataa  10020
gccatacact gtatgttcta ctccattcaa gacactggga gagatgcaca aataaatcac  10080
aattccttgt agactgccag agcagagaca cttaaggtag cagcacagta ttttgaatga  10140
actaaaaaga tgtctctgac acagcctctg tccgatgtct cctcatccct agttatccac  10200
attgtggcac acttgttcaa cctggagcgt tatcacctgg gtcaggccaa ggatgctgaa  10260
gggctgctgg ctgcactttc caaacttggc gatgccccaa atgagagcta cctcaatcca  10320
gtccgcacct ttgatatggt gagtcagtcc ttgcacgtta accagtctca cccctgcgga  10380
gtcatttctc ttcccatccc tatatcaaga gcaatagatt tcaaaagctt cacataaaag  10440
agctggataa aagaggtttc tgccaaatgc taatatcaat ttcacctttc tgttttaaca  10500
gctagttttt ccaaccatta atatggctgg aaggatatga gcaaggagaa aaacatactc  10560
ggcttaatta atttatagtg aatatatatc cgtgatattt taggtacgca aaaacctgtt  10620
aaagccttaa tattatggat tttagaagca gctcccgatc aaatttcctt cactgatgtg  10680
agattcataa agcaagcacc acccaaaccc agattgaatg cttcattttc aacctgcaaa  10740 ttgtttttctg ggtctgttct ctgtgccttg tatcttggca caagtgtgag cagctggttt  10800
```

```
gccaagccat acactgactg atggccattt caaaaagaca agtatgtgac tcatgacacc   10860
atcactgcta atgtctaggt gcacagaaca gcagtgtctc tgggaagaaa aaatacagtc   10920
agcctcggca tcctatcctt agaggtaaac acttccctag gcctcagcat cctatcctta   10980
gaggtaaaca cttccctagg cctcagcatc ctatccttag aggtaaacac ttccctaggc   11040
ctcagcatcc tatccttaga ggtaaacact tccctaggcc tcagcatcct atccttagag   11100
gtaaacactt ccctaggcct cagcatccta tccttagagg taaacacttc ctaggcctc   11160 agcatcctat ccttagaggt aaacacttcc ctaggcctca gcatcctatc cttagaggta   11220
aacacttcct taggcctcag catcctatcc ttagaagtaa acacttccct gagccactc   11280 ttacatctct cttactggtt catctaaata tcttccatgg actaccatat tggaattgag   11340
actatatatt tttaatctat tttctaaaaa aaatctcaa ggccacacac cccatcaata   11400
ggattctctc gggctgctgt gacctaggcc cttttttataa gtgatagttt tgttcacatg   11460
tttatttgag aaggaaaatt cagattctag ttatgaggac attcttccaa gtcaaaatct   11520
tgatttcctc gggaaggctt acaattcaag gccattaata aactgaattc cctttttctt   11580
aactgacacc aattagaagc acatatttca tagctacaaa tcaaaactgc agatgcccga   11640
agcaggcaga gatgtgttta ataccatttc cttgaatctc agaatttatc tggccacctg   11700
tttagatcta catttcttcc ccaataaagc ttaacaaaat tcactgctca caaaagaccc   11760
aagaataaat ctcaacatct tgaataaact atgcaataaa tagtatttat tataaataac   11820
ctttaaagca atttaacaag ctaattaagc tacttcaaac acagttgttt caaaaatttt   11880
agaagcaata tactttgtta gtactaatta ggctcagaag cccctctaat ttgggtattt   11940
ggagagatga ttatcaataa cttgaagcat acattaaagc aattcataag taatgcagtg   12000
gggttacatt agacaactgc cggcaactca gaccagtctg taaatacatt gcagggaaat   12060
gaggagaaat agtctttaat agtcaaaaca gaatgatttg aaattaacac accatgtgct   12120
gttaattgac ttctaaagtg cctgagtata cttacaaaac aaatatttta aatgttctac   12180
gtgtaccctc tttcaatttt attcttctct tctcttctgt gaagagaaga aaataaacaa   12240
tggagaagtc cctgtccaaa ttacttccag atctcatagc agcctaaatt aatgaggttt   12300
tactgacaaa agatatagtg tgagtttatt gagctggtag ttggctcaga tgagagca    12360 cggggtatga atactaatga ctaagcaagg aatatgggaa ctcacaataa aaacaaaat    12420 gctttgcaat taatattctc aaaggctatt taactgtccc ttgcactcat gggtcagaat   12480
catgctcgtt ggagagtgct gatcagataa gaatagctgt gtccttattg atcacagagg   12540
ctttaccaag ctttattcca agaccctg aggttatttg aaggaaatgc aagtcatggt    12600
tcttccaatt aaaaagccag aacaaggcat agccaccaag ggaagagtgc atgaaactgc   12660
tttattagga gtgcccctaa ggaaactctc cttcaccccc caaaaagtg tttattaatg    12720 ttaagatgca attaaacatg gtgagccaca ctttttaatc ttaaaaagt aaaaacctcg    12780 aatttgagct gattctgcca tgttgttctt ctaatgctct ctggtactga ttcaaaatag   12840
tagctttgac aagaaaatta actcatgcaa atggaaaagt tgtgcttaat ggcacagtat   12900
tttataaaat ttgaacaaag taaatatcca tggtgacaca ggggagaagg aagaatttca   12960
cacctagttt cttgaagtgt gtatggactt tggtgaggtc ctgtgtgttg gcacaaaaca   13020
tcctgaattg ctctttgttt ggatcatcta atactgatcc taaaaatgca aaatccaaa    13080 atatgaattt ggcggtactt tgtgatcttc tagggcacaa ccactgagct attgatgaca   13140
gtgtcaggaa ttactggcct gggtatctct ctggctctgg tcttcatcat gacctcttca   13200
```

```
accgaattca tcagaaggtc ctcttatgag ctcttctggt acacacacca tatctttgtc    13260
ttcttcttca tcagtctggc catccacgga ggagggtaag cccatttttat aatgaggtgt   13320
tcagatgtat gtctctgtgt acacgtgccc tgactatagt gaatagagca tctgtggaca    13380
ttgttgaaca agcatttgag gcgtggaatg tcaggtttgt tgagcacatg caaagagtgc    13440
tatatctggg tagtatggct gcttctgctt ttagttatta aaggattctc cacacttatt    13500
tccttaatgc ctgtaccagt tacaaccttg ccaatggtga atgaaggttc ccttcctcca    13560
cacccccat tctcagcaat attttaacta tcttgacagg cataaggtga aatctcagag     13620
tggtttaaat ttgcatttct ctaactgtta agaatatcaa ttccttatct gttttttattt   13680
cttcttttga gatctctctg ttcagataca tagccctttt ttaaattggg ttgtttgttt    13740
tcttgactct agtttttgaa tcctttgtat ggagtgggta ttaatcactt atcaaatgta    13800
cagttagcaa acattctctc ctactctgta gatttcctct tctagctatt cttttcctttc   13860
ctggacagag catcttagtt ttttgttgtt tgtttgtttg ttttgttttg ttttgttttg    13920
ttttgttttg ttattgtcaa tggctggtct tgcttcttta gtaaaagaaa ctctgtttag    13980
aaactcctct ccatcacatc ttgtaggagt ctgcctatgt tttcagcttc acattgagat    14040
ctttgatcca tttgaagttg atattcatac agagtaagac atagcccata tgggtctaat    14100
tttacccttc tacatgtagg caacctcttc tccgagcatc agttgttgaa gatgctatat    14160
gttctccagt gtgcatcttg gcatctgtca gatgtgaggt ggctgtaatt atgtgcaatt    14220
ttgtctgcat cttctacgtc attccattgg cccacatgtc tgtttttatg tcagtgccat    14280
gctgttttta ttaccatgtc tctgtaacat agcttgaaat acggtgtggc aaccccttg     14340
cccagcattg ttctatttgc tcagcattgc tttgactaac cagagttttt gttgttgttg    14400
ctgctgctgc tgctgctgtt gttttttgttg ttgttccatg tgaactttag gattttttttc  14460
ctgtttctgt gaatagtgtc ttgaaaagat tgatgaggtt tgtgctgagc ctgtaaacta    14520
cggttaccat cttcacagca ttaattctac ccacctgtga acccaagagg tgtttgcatt    14580
tcctagagtc ttcttccgtg tctttcttca aagacttaaa attctctctg taggtctttc    14640
acctccttgg atgggtttaa tcctacacat ctttgatact attgctaata gtgctttaat    14700
aacctctttt tcagcttctt tgcttttcttt tgctgtatat aggaaggcta ctgattttg    14760
taagctgact ttagaaatct tagtgcaatc ctctttttaac atggaaagta ttcctataat    14820
cccctaaatc cacattttct gcactcacac cctgggtatt gaaccacaag tccatctcaa    14880
tgggcagtaa cttggctgaa gttaggattt aatgcacaaa taatatttca caaggagaat    14940
tgttgagtta tttcaacatt gctgaaaggc ttatttatgg ataaaaacct atttaatctt    15000
ctcagcttga catattctac aactactatt tacatcaaaa gcgatttgca aattctataa    15060
aaaaaatgcc aagtagacat aagattgttg gaaggcataa agctcactag tctgcctatt    15120
atcccaatgg tataagtgaa aaaattaaac tttttaatat ttttaacagc atacatatgg    15180
aatgacctgg aatctcttct agatagcatg gggaaagtta tcaaacatct aaggatatag    15240
gtactgaaat gtatgacatc cacaatctgg ctcccattta ccactcatcc acccgggcat    15300
catttggcct ggaggttcac agattgtcct gcttacctga ttcaaagtga tgtcatcaag    15360
cttgcatgac ttgcatggaa cagagtcaaa gcctaacata tcttctgtag ctgacaccag    15420
gcagtttcca agagcattga ccactactcc acagacaaac acagcatctc tgtgatgttg    15480
atgttgccca gtctaggaga acctaatttc tcaaaacaaa ccagcgcatc ttatcccataa   15540
gtacctagga actgagccac tccagggttc tattatctag gtgtatggtt ctttgccgta    15600
```

```
agaatacaag ccagtaaagc catcctgaga gttgatgcct aagcaatttg cagaggtcaa   15660
cagactcaag ccagtaagat tacaggactc tttatctagt gctccatcca ttcagacttc   15720
tctttctact tttaaattta tcaatacagc ctcaaagaca catttcaaag tgacctgttt   15780
tgaccttgtc taagcctgct agtaatcact aagcctgcta gtgatcaccg ggggaaaaa    15840 taccattatt ctgggcactt cttttgactt attcacttga aacttctaag tgctcagaaa   15900
caagctaaga agggtagaag ttaaatcaat ccgcagaaga agccaatcgt acaaagttgg   15960
ccaattagcc caaatcagca atcagaatga gatgaaacct aattaaattc aacagtctac   16020
aaaaggatgt gttcaaacaa tttccttcat tatgaattct ctaatataga cactttcaat   16080
gtgacacagg ataccacaga ggggcacttc tttttctggga tcttcaaagt tacccaaagc   16140
tttctaatgc ctattttaa agatgctggg ggaagtgagt gacagcccaa gttttaagag    16200
atgggagtgt tgttttggaa cccactactg agtataaatc tgtgtaaaga tatcgcacaa   16260
aatcagcttg acattttat gctttcccc ccctctctct ctctgcatgt gtgtgtgtgt     16320
gtgtgtgtgt gtgtgtgtgt gtgtgtgtgt gtgtttctaa gtcgcatcat tcgaggccaa   16380
actccagaga gtctccggct gcacaatgtc acgtactgca gagaccacta tgctgaatgg   16440
caggcagctg ccttatgccc tgtacctcaa ttttctggca aggaaccttc ggtaagagtg   16500
aatccaggag ctttttaaaa ataactgtcc ccacagttaa ataactaga gctttaatag    16560 gcttgaaaaa aataaccgcc catgtcacca cttgacgaag ccatctcttt attaagtggg   16620
ctaatggaga aatcgagtta tggataattt caaaagagat ttactgccaa aagcactttg   16680
ttcagctttg aaatgtattc tactccggct taaatatgga tgtctgatat tgcaaggctt   16740
cataacagca gagtaatgac tctgagggca ttagcctcat ggttcaccac ccgctacacc   16800
cttgctattc ctcagtctat ctcccgggta actggagga cccagtctt tcctaggttt      16860 actgtgtctc tttctacaac tttggtgatc aaaagaatta agggtgccca gttacttttg   16920
ctataactaa tttctgtttt agccaaaaat agatttacc aacttaagta ttaatttagt    16980
gatagtgtcc acagattttg aaagtaatgt tttctgtttt ctgggtatgc agcagttgtt   17040
gacttaggta aacaaaaata atactcccat ctggactctg atatattagg aaagtacaaa   17100
cctttggttt aactggtggt tgatatatga cagataataa atgaagtgac tgcattacaa   17160
gtaggaagag gttggcatgt gacttaggtg atggaatgct tgcctaacat acacaaagca   17220
ctgagtttga tccccagcac cacacaaact atgcctgtaa tcccagtaca cagaaagtgg   17280
aagcaggaaa gtcagaagtt caagttcatc agcagcaaca tagggagttc caagagaacc   17340
taaccatcct aaagacagga gactttgtct cagaacaaac aaaaatagaa aacaaaaaag   17400
ttggagagaa caagtaccca agatgtgtta ctctttaaaa tagggtaat ggactatggt     17460 cacgcataag ccatcagaag aatggaaata gccatttctt taaaaattta caaatacaat   17520
aaattcaatg ccatatttta agggtaaaag tagtaggaga aatgtttaaa actgagagat   17580
gtgaaataga tgtgcccatt agactgtggt tcctttaatg gccagtatag attgtctctg   17640
tcttaaactc agctctctgt agccactacc tggcctgtat attaatgaag aaaatgaata   17700
cctctctaaa attttcagcc acagcatctc catttaaaaa aaaatcaata ctctcccaca   17760
cttcatgaat acagaccagg gcctgctccc accagtgtgc gctagcatta attatgatta   17820 aaaggggggaa cttggccatc tcttgctaac tcccctgcta cacctccttg cacatccaaa   17880
ctcacaccat cactcttttc cattatttt aatggatcct gattcaaagc atgtgtgggc    17940
tgtgcaatta ccgtttggct agactgtacg atactccctc tgatgtctta ttgactctga   18000
```

```
atcagaaagg cattccaagg acatgggggg ggggggttccg tgctccacta cactggacct   18060
agctcatctt agtaaggctt catatagtcc tccttgcctc tcttttcctg gggcactttt   18120
ttaatgaaga ttttatctgt agaatatttg tcagctgatg ccatgttgaa tctgagaatc   18180
ttttttctgt caccttgtat aagctggcca gagaaatctg ctgccctagt ttctacctca   18240
atctcacagg cacacaaacc tgcagatctg agagttgctc atgcagtcag tctaatgtca   18300
aaagatgctt ggtcctcctt agccaagaaa ttagctcatt tacctgtaga gaataatcat   18360
atggctctgg gtttcctttt ttagttgttt gttggtttgt ttgggttttt tgtttgtttg   18420
tttgttttt cactttctat ggatgatatt aatggtcaaa gggaaatctt gaatgagggt   18480
agagtcaatc actgaatttc atcaagtggt gagttctcct gcttgctcat ctgtagacag   18540
acacaggact ctgacatggg ggcctgcccc tggaaagctt attgtctaca gcaatcatct   18600
attcataacc acatacataa aataaactca aagccagcct gaccttattt tctggaagga   18660
ataaaagtag aggaatcatg tttcattgct atcactgtta agtcaacacg attttatttc   18720
tgtaataatg caattgctgt actatggttt ttctgcgtgt ttttggagac tagaataaga   18780
aaactaagaa gccatatgaa ttttcagtac taaaaaaact gacacactaa acaattattt   18840
ttttcttatg actaatattc tttttttatt agatatttc tttcactaaa caattcttac   18900
cctttgttta agagctagag aaagtaaggt ggagggtttc aaagggttgc ctctgataca   18960
gagggcattc caagcaaagt cacacctggc gtaaaaagc tcctgacttt gtggcaagtt   19020
gtaacacttc ttttccatat cctatggcct tccttcggat tctctgacct tcttccaaga   19080
attccttagc cagtcctctg cagctatctg caagtacgtt ttcccagcgc cattttatc   19140
cttgtaaata aacccaaaac atttaagagc ttggcaagaa cttcaatgag aattttctcc   19200
aatcatctcc cggtttgaaa aatacaaaac tcaaatatga aaataaagca tgagatgtga   19260
gccagggaga tagtgtctta gtcagggttt ctattcctgc acaaacttca tgatcaagaa   19320
gcaagttggg gaggaaaggg tttattcggc ttacacttcc atactgctgt tcatcaccaa   19380
aggaagtcag gactggaact caggcaggtt aggaagcagg agctgatgca gagaccatgg   19440
agggatgttc attactggct tgcctccctt ggcttgctca gcctgctctc ttatagaacc   19500
caagattacc agtccagaga tggtcccacc cacaagggc cttgcccct tgatcactaa   19560
ttgagaaaat gccttgcagt tggatctcat ggaggcattt cctcaactga agctccttcc   19620
tctgtgataa ctccagctgt gtcaagttga cacaaaacca gccagtacaa ttgaccccctt   19680
gtcaacttga cacacaaaca catcactagt aagcctcaac ccttacattc ttattcatcc   19740
caagatctag acaactttaa aagtcccact gtctttacat attaaaagtc aatccccttta   19800
aaatgtccaa tatctttaa aatccaaagt ctttttacaa ttaaatgtct cttaactgtg   19860
gggtccacta aaatagtttc ttccttcaag agggaaaaca tcagggcaca gtcacattca   19920
aaaaaaaat caatctataa ccatccaatg tctgggatct aactcacgat cttctgggct   19980
cctctaaggg cttggatcac ttctccagcc tgcccctttgt agcacactcg tcgtcctcta   20040
ggctccagat gcctgtactc tactgctgct gctgctcttg gtggtcatct catggtactg   20100
gcatctccaa aacactgcat gaccccttca gtcctgggcc ttcaattgca actgaggctg   20160
caccttcacc aatggccttc catggcctct cacagtgcca agcctcagct gcttttcgtg   20220
accccttcat gccttcaaaa ccagtaccac ctgggtgacc cttacatatt accaagtccc   20280
gctgcagcag gaatacaaac ttggccatct ctggaacaca gcctctttgt gctttcagaa   20340
aacacttccc agaaaatgtc acctcaatga tgctggtctc tttgtttgtt tgtttgtttg   20400
```

```
tttttgtttt ttgagacagg gtttctctgt gtagccctgg ctgtcctgga actcactttg    20460
tagaccaggc tggcctcgaa ctcagaaatc cgcctgcctc tgcctcccaa gtgctgggat    20520
taaaggcgtg tgccaccacg cctggcttgc tggtctcttt ttaagcaccg ctaatttctt    20580
agctccagct aaccagcatc aatagtccca gtaatgcaaa gttttttgctt tagtagttct   20640 ggtatcttgt taatcacagc tgattcttca gccccagcta accagaacta cagaatcttc    20700
acaatcaaaa cagcaatggc cctgaaaagt ctttaattt ccctctgaaa tttcacaagc     20760
caggcctcca tcttctgcac tgttctcaac attatcttcc aagctcctac aaaacatctg    20820
acagagctct taacaatgaa tggatcttca agcccaaagt tccaaagtcc ttccacagtc    20880
ctccccaaaa catggtcagg ttgtcacagg ataccccac tctgctggta ccaatttgtc     20940
ttagtcaggg tttctattcc tgcacaaaca tcatgaccaa gaagcaagat ggggaggaaa    21000
gggttgattc ggcttatact tccatactgt tgttcatcac caaggaagt caggactgga     21060 actcaagcag gtcaaaaagc aggagctgat gcagaggcca tggagggatg ttcattactg    21120
gcttgcttcc cctggcttgc tcaccctgct ctcttataga acccaagatt accagtccag    21180
agatggtccc acccacaagg ggcctttccc ccttgatcac taattgagaa aatgccttac    21240
agctggatct catggaggca tttcctcaac tgaagctcct tcctctgtga taactccagc    21300
tgtgtcaagt tgacacaaaa ccagccagta cagatagctt agccaataaa gtgctttta    21360 tgcaggtata aggactaaaa gtataaaagc ctggcacaat agagagtgca tgtaatctga    21420
acactggcag gagagatggg cagatccttg gggctcacag agcaattgtc ttagtctgat    21480
cagtaaacct agtgagagat gctatttcaa aaaaaaagt agaaggctcc aaagttcaca     21540
cacacacaca cttcacgatg tatctgatta tacagaataa aagatgggag catggtctcc    21600
ccatctgtac agtgttgtct atgctgatgc tgatccccac agctggacca cttttctagc    21660
atcacttact ggctatatct caccctcact cctgaacttt caagggactc tgggagcatc    21720
acagtataaa taagccgccc tatctcctca tggagcaatt tatatagtag aatagagata    21780
gagcctagga ttaatggctt acattctcct tcctgactaa ccatggaaag aaaaataacc    21840
cttttcattt catcaatgtg gagaaatcag aggccgtggc tgatttggcg ccaacaaaat    21900
gagctatgtg atgtctaaag catgtgtttt caaatggata cggaagatta tttgtgaaaa    21960
tacacaaaga ccatgtgaat atctttgcaa atctttctgt cctgcagaaa gaattgttgc    22020
ctgcattcct ctacatgtcc aaaccatttc ttaaaatact ttcaagcata aggaagctct    22080
ggctttgctt acttggtcca gctccatcct tctgctactt ccctgttttg ccttctctga    22140
ccatcttcac tgccttaccc tagcacgagt ggacctaagg ctttattctc ccctccattc    22200
tgaacgtgtt gttgaatccc actaaggttg aaatgagtaa gtaggtcaac ttgctttgta   22260
ttgcccgaat aaatcatagc ctttgtcaag caagcaagag gaccttagga agaagcaga    22320 gagagctgat gggtgaagac agagatcctg caaacagcca agactgacga aaacagaaag    22380
gaattaaaaa taggaaagat aatttaaaag aaattaaaaa gttatgtcaa agagctggtg    22440
aacttggcga cagagccaag gccagtaagg aaataatcaa tgaccagagt tgaaataaaa    22500
cacaaactct aatcagcttc caaacgctga caccattgca tacactagca agattttgct    22560
aaaaaggacc ctgatatagc tgtctgttgt gagactatgc tggggcctag caaatacaga    22620
agtggatgga tcacagggcc cccagtggaa gagctagaga aagtacccaa ggagctaaag    22680
ggatctgcaa ccctataagt ggaacaacaa tatgaactaa ccagtacccc cccccccca    22740 gagctcgtgt ctctagctgc atatgtagtc ggccatcagt ggaaagagag gcccattggt    22800
```

```
cgtgcaaact ttatctgcct cagtacagga gaacaccagg accaagaagt gggagtgggt   22860
gggtggggga gtgggtgggg gagcaggtga gggacttttg ggatagcatt ggaaatgtaa   22920
atgaaataaa tacctaattt aaaaaataaa taagtaaaaa cacaaactaa aaaaaaaaag   22980
gaggtgtcct ccccgttccc atgatcttat gaaagaacta aggtcgtggt agatttggaa   23040
tggcaaaggg gaaatttaag aacctctccc aagacttgag atccaataag gaactgagaa   23100
ccagcccagc ctcccaagat aactcaaatt gattcccaga gaaccatagt ttatttttg    23160 ttttgttttc ctataagatt aaagcaggat taaaaaacaa aaaacaaaaa ccttgacatt   23220
ctaaaattca ataagctcag gaggctgatg ttttacaaag caagtctctg gacatacct    23280 ggtgttagat agcacacagt aggactccat ttctgctgta tggtaaatat tcaggcaagg   23340
cagctgagac cctgtgaaaa caggctgtgt accaagcctg tctaggccca catcttctcc   23400
acatactttc tcatgtccaa gggatcattt gatcagactg tgcctcagtt tctttctcta   23460
tgaaataaat aggctatcat ataccttgca agattgtttg acattgaacg acaaaaatca   23520
tacattccca tccttcctgt ctactggaga aagacccctc gtgttatatg caacacctga   23580
ggcaagtgta ggctttaaaa tatggtcatt cataatgcag aactcaagaa ataagagtag   23640
taacattttt aagcatgaaa atattcctaa tcatatctct ccagatgatt gttgatgtct   23700
ttgttctgat cctctgagac aaaatctagc ttgatctttt tcattccaca taacattata   23760
gaaggtagag gtatgcacag gggaatgtgg cagtgtgagt gtctgtattc agacagattc   23820
cctacttggg aggcattatt ggcccccaga attactattt gaaactcctt atgttggcta   23880
aaaggatgct ttttctataa gcctttgact ttggctgctt gggagcattt acaacgctag   23940
catacagaac ataacatca acctgctttc ttatttcttt acaaattcaa ttatttctaa     24000
ttacataaag gcatcattga tcaaggaagc ataaaaacca atagaggaga atttaatctc   24060
ttaaataagc ttgtagactt taaggaataa ttaaatgcta ttgtatttag tacatggaga   24120
catctttgct gttgatagct gggccaaagt tgagggaaat atcttagtcc cgtcatgcta   24180
tatattgata tagttcgaac tagaaatttt ggattctatt ttaacttatc tctctgtgtc   24240
tctgtctctc tgtttctctc actgtctctt attttctgtc tgtctatgtg tctctcccac   24300
ctccctccct gccccctcccc ttttctctc catctctctc ttttccccac tctctctgca    24360
ggcctggaaa tgggctttgg gtcctgtggt cttgtatgcg tgtgaaagaa taattaggtt   24420
ctggagatct caccaagaag ttgtcattac caaggtatgt gtgtagcttt atgtctgaat   24480
aaaagcctga gtgtagatga aaattttta ttagcccaag ttttaattt gccattttta     24540 ttgcagaact gcccgtaatt tagaggctca tcttctggtc taataattgc ttgtatcggg   24600
agcatctttc agtgtgacca attttactgg agacagggat caaagctcca tgctgttatt   24660
cggaattctg ataaaggctt acagcgtaga actggagtta gccatatttc tctttattat   24720
ggtttctctc tagtgaggaa aagacaggaa actactaaga atgctttaca atgatcgtag   24780
taactttaaa tagcccatag aggtgggatt tcgcaaacat gccagcatca tccacacagc   24840
ttcaagcata tgcgttctta acctgggtac tgagcatggg cttggaatgc agccacaggt   24900
tcagagcatg gagggatgct aaggttcaag atgacaatga tggaatggca tgctgctcta   24960
ccctgtttag tgttatgtgc cttggaggca cttctctgcc ttgctgtatt tcatgctgga   25020
ggaagatagg aacagataga cagaaaaagc atatctcaca ggttaacaaa agtacaaatg   25080
ccaggtgtag tggcacacgc ctttaattcc agcacttggg aggcagaggc aggcagattt   25140
ctgagttcta ggccagcctg gtctacagag tgagttccag gacagccaga actacacaga   25200
```

```
gaaaccccgt ctcggaaaaa aaaaaagtac aaagtatgct acccactcct gagtgttagc   25260
tagtgcagtt ttaaccaaat acgtacaccg ttcactgtca cattgaaaga agatggacag   25320
gcattcctat ttctgctttt acatgtttct gtgtttctga gtttaagctt agaaccgtag   25380
aaggtcaatc aagcctggaa caagtgtgga aacctagatc tgttagcagg aaagcacata   25440
gtaggtcctt tagaggcagt gtcgggaggg caagcagaaa tctggaagta aagataaaaa   25500
tgctgtgaag gactcttcat gtagaaaagt gtcataccag tatccacata ctggatcgtg   25560
ttctcatatg catttactac aaaagacacg aaggtgtaca gatatttttt cataaggtaa   25620
tggatatata tgaagggcaa atgttccttc cctcagatga tcgttagtgt aaagtccttg   25680
gagaagcttc acggggcttc cctataccaa aaacttagca ccaagacaat atttagtcaa   25740
actgaacaag taaacatttt gggagagaa taaaagatca atatttttcc cctcagcatg   25800
aagaaaatct caaattattg ctacatttttt ttacatgaag atgatgtggt aactatttta   25860
ataaatgcaa gtaaaattat gagatctcct tccatgacag cttatattca gttggaaatg   25920
gttagctggg ctcagggacg cttggtcacg tggggcatgg agtcatgtgc tgccctactg   25980 cttttcctgca cagttattaa aagtcaagtg cagcaccctg cgccatgaac gctgttatca   26040
ctcaaattgc aagcctaggc ataaaagtgc tgacaaatta tacatcaaaa aaaaatccaa   26100 ttaaagatttt cgtatggaca gaagaatgtg ctcttgtcat tttacctgag tgagaatccc   26160
cttggctatc ttgctctgtt gtaggtggtg agtcacccat ctgcagtcct ggaacttcac   26220
atgaagaagc gagacttcaa gatggcacct ggacagtaca tcttcatcca gtgcccatct   26280 gtctccccc tggagtggca ccccttcact ctcacctccg ctccccagga ggacttcttc   26340
agtgtacaca tcagagcctc aggagactgg acagaggcgt tattgaaggc ctttagagta   26400
gagggacagg ctcccagtga gctctgtagc atgccgaggt gagacctgcc ccgcctcccc   26460 gccccaccc gccccaggtc actgttatat acaagctgtg ctacttcaaa cgggaaaaat   26520
atctaaatgg atgaataaac tgtccagttt ggcaatagct ttatattaag ctgcaagctt   26580
gagttcgttc aaaaaaataa taataattga gagtcttcat cagatgtata atttaggaga   26640
agcgaataca tttctgtaaa aataaataaa tgttcaacaa aagtaggtga tgatccaggg   26700
agacggaaga gtttccttttc cagatccaaa agcagctcta gtctaattat gtgcagcctg   26760
ccatgagtca gacaactccc tctgcaagct ctctcccagc acagactgag ttttcaggct   26820
gtgtttgcaa aggttggtct ctggaagaag gatagtttat tctgctcatg ctggacttaa   26880
cccataccat tcctgtatga ctgcatagta acatatagga agcttatata aagactcctc   26940
gtttctgtag ccctctttttc agatacacag tataagttcc tggagttagg gcttctttat   27000
attcatcaga gggaggcatg attctggccg taccactacc ctattcagaa aagcctacac   27060
gtttgaccca agtcactgtg agaatgatca tgtcttgcct catttaagtg aacaagcagg   27120
ttagttccca atcctatagg accattaaat agtacatgaa gtccacagat aggacccccag   27180 aaaaacaaga agacataaaa aaatatgaa aaaaataaat taaaaacaaa atatttcaat   27240
gaagcatgag aaaaaataat gtctatttgt accattcttg ggggacattg gccaccacgc   27300
atttatttag ttaaaaacac agttgtacat acatacatgg aagttcctgc agatgactat   27360
cttccttctg tatctacaca aatgccagac acataaggat aacataacag aaaaaagtta   27420
acatgttcac caaatatgta tccttttagct cattgaactt gacaaatctt tttgtcaact   27480
gctagcctct ataggcatgc acaaacacac atgtgtgtat ccccactcac ataccaacac   27540
atatgcagac acacactcac atatacgcac atagatagag cacacgaacg ataaaatgat   27600
```

```
agaaaagttt tccaaagagt acctattcca attgcaaggg tgagataaat gtagaccacc  27660
cctccaaaat aaatctaata atgaggttca gagcttgata cataggaagg aagaaatata  27720
taaaatatat tctaaagaaa gcaaaaggta agatccttac agactgcagt aagtcactga  27780
gaagaattgt ctcaaactga accctgccgc tggtataaca aagtgtcttg caggttgaca  27840 cttttgcagag tatgagcagg cctcagacaa gggcatggaa aagctctcaa ttctaaataa  27900
ttagacagat atatgtatgt gtgtgtgtct ctgtgtgtgt atgcttctgg taagatggcc  27960
atttttccta tattaaccct accaatccat gagcatggga gatctttcca ttttctgata  28020
ttttcctctg gcattggatg ctctttctct tacctggact gcctggttgg acctcagtgg  28080
gaaaggatgt gcctagttct gctgggacaa gatgtcccag ggtggggtgg tatgcaggga  28140
aggctcccct tctcctcaga aaagaagaga aacaattttg gaagggattt ggaagggtgg  28200
gacagggagg agaggaggca gaggctgtgg ttgggatgta aagtgactag aaaataaatt  28260
attgaaaaaa taatggagca aaaaaattaa gttttatata tatatttctg caggctttga  28320
gacataggtc tcctctgaat ttaatggata tctttttaaa atttgtgtca ataatcact  28380 gattattaat tataataata accaacaata agatgcctta atcaatggat aaagtttcta  28440
tttgtcaatc tatttatcta attatttata aaataatcaa cgtgggctaa gatactagca  28500 cttctctggtt aatgaccttt attttattct tctatttcca tatatcaata tgtaattaag  28560
ccttattatt taagattaat tcaaggacag tttatttaaa ttattaggaa gtctgggata  28620
tggaatattt ttaaattaat ccatttgaac tttcatgaac acatactaaa gcccaaatgg  28680
gttaaccccc acccgctctg tgcaggtgac gggctctcct cagggaatgg ttatgaatga  28740
cttagaaacc ttttcattag catatctttg ttcatatgta aatgtgtact tttggaataa  28800
taggagttat ttaatacatt cggcctactg aaatgctcta aatattccct ttacagttga  28860
ctcaacaaat tgctgttgaa cagttccaga ctgtatcgta agcaagacac caaatacgaa  28920
atgagcaaaa tcagacctgt ttcccacatc caaaacctgg aaacgtagag gtcgtgatag  28980
acaggactaa atcctgagca cccatcgtat aaacgctaat attcagctat gggaaggaag  29040
ggcatatgag ggagtttctc tgagtcacag gggtccaggc agacttccct agggaaataa  29100
agattagaca ggacctagag gaaaggtatt atgtcagcaa gtagaaagag gggaaatttc  29160
aggtattcca tgggaaaaga tcttgtgtgt cagaaggcaa tactgtgtgg tatttaggta  29220
atacaagaaa agccaacatg gagaaccagg aaaaagattg agaggaaccc agtggccggt  29280
ctgcataaga acatcttatt tattcaaaga acatgtttat cattataaag aaaaattgct  29340
aaggaaaggc aaaacatttt actgcccctg gactgatgag cataaaggat tttttttttag  29400 caaatatgat ggaaaataga gagttttaca agttgtactt aactgacaaa ttattttaaa  29460
attatgttta ctctgaacaa atcgcctcca ttagactaaa atgatataaa tatataaaca  29520
tgcaaacaaa caaatgaaaa tgaggggggg agttcaccat gaaaagaaaa cacatatcct  29580
ctaagcccct ttgaagtatc tcctttgcct ttgattggca actgagggaa agacagtcat  29640
ggaggctctt catgcaggcg tcccaatgct cacagttgac aggagctccc agaactctaa  29700
caggagcaag ccatgttgac gaggagccac agcaggcgat gacaagcttt gccctccctg  29760
gctcacgtgg agcgtgtgtg tgtgtgtgtg tgtgtgtaca tgagtacaca tgttcatggg  29820
aaggctggaa ggttgcctcc ttgattactt ctctacccta gttttttgaga caggttttca  29880 tttgcctgag acttaccatt aggatagctt ggcttgccag aaagctagaa ggatctgcct  29940
gcttctgcct tcctcaccct gggatcacag gcttgctgcc atgcttggct ttttatgcag  30000
```

```
gtcctgggaa ataaactgag gtcctcatga tgatgtagaa agcacacaac taaccaattt   30060
atccttttcc caccccaaaa gagggaatct ttaaatgccc tagcaacctt cagcccacat   30120
ttgctgaccc acactatgaa attgactagc ttgggatgtc tttgtgtcca agagggagac   30180
gttctgaagg tcaaccgaac tgcattctat gattccaggc tagcagtgga tgggcccttt   30240
ggaggctctc tggcagatgt atttcactac cccgtgagcg tgtgcattgc aacgggaatt   30300
ggagtcactc ccttcgcctc tcttctgaag tctgtgtggt ataagtgttg tgaatcacag   30360
agcctgcctg agctgagcaa ggtatggaaa aatcattagg tcacccttcc atagagtgaa   30420
aggttcaaca ccctcaaatc tctcctctgc cgattcttgg ggaggatttt aattaactat   30480
gagggataaa ctcaaggatc cttaactata cttatgttct taaaaatctc cattcagtgt   30540
tacatttatg agcagggtta tgtctaatct tgttaaagat gacaagacat aaattttatt   30600
gcttcattgc cattacagga catgtaattg ctcatctcga taaaatgtgg acaggctgca   30660
aatggctatg tgactgggct gcagttagtc atattaacag gcgggcttcc ccctcacctc   30720
tttagctcca ctcagtggct gatggtattc aattccacat cttttctcca tggcctctac   30780
taatagacgt tgttattctt ttcacaatgg tgttgccaca tggcaccgag tcctctttgt   30840
gatttcttgt atgttcttgg actaggcttc tccatttctt tgtcctatcc agtgtgagaa   30900
accatctcat actttgactc tcccaaggtg aaatgagcct tcttttccat ctcctgaaag   30960
tttaataatt gactctgtaa gatactctgt aattaacaga agaaaagata caccaattta   31020
ttgatgtgtt agctgatagg aaccatgcaa agttcaatac tcagagaggg caggtggtgg   31080
aagcctcaat agcctttcct ttggctccta tgggcaagtt tatagtaagt gacttttagg   31140
ggagatgaat gagcctaaag aacaaatatt tggaacaaac cttgccgtgt tctgccaatg   31200
gtgtcaactc cctattctcc gtgagacctg gtattttaga aaattcagcg tctaggtcag   31260
cagcagagtt acacagaaag acccttccct gccctcagta gtggcaaagt ggggcaggtg   31320
atgaaggtca ggggaggaat tggttatcct cagctcagac cactcatcat gctaatatgc   31380
cacactctgg actttcattc tctgaaccta aacagtctta ggaccaacat ggggtactac   31440
aagagcagac gaaaagttgg atatgtatct tagggtttct attgctatga cttgagaggg   31500
aaagatttat ttcatcttag agatccatgt aatagtccac cttggaagaa agtcaaggca   31560
ggaagtcagg gaacctggag tcaggacctg aagcagaagc aactctaatt actggcttgc   31620
tcacctgtcc agggatagca ccacacacag tacactgggc cctcccacat caatcacgaa   31680
ttaataaaat atacaacaaa tctgcccaca gaccaagaca gtgggatcat tttctcaatt   31740
gagatttcct ctgccaaatt aaatctagct tgtatcaagt tgaaagaac aaacagacaa   31800 acaaacaaaa aactagacag cacaccgtgt gaacagaaag tatggaaaca catgaggaag   31860
cagggcactt ggcaagttta gaactaatcc tggtctgccc atatctgctc tgtgtggccc   31920
ttggtcatgg cttcctacca gacctaaaga aaacgctgaa gtcagtaagt ggatcccagt   31980
gaatagtcat tacttttct ttttgggggg gggagtgagg ggggtcgaga caggatttct   32040
ctgtatagct ctggctgccc tggaactaac tctgtagact aagcaggcct tgaactcaga   32100
aatccacctg cctctcaagt gctgggatta aaggcatgca ccaccactgc ctgtctcatt   32160 acttttctt attgctctga tcaaataact gtcaaaaaa caagggaagg gggacttgtt   32220
ttggatcatg acttgaggat ttagtccatc atggtaagaa aaatgtggca gtgagtggcc   32280
ctgtggcagt ggaagaatgt aagagctgtt ctctcatatc ttaacaggcc agaaagcaga   32340
ggctgtacag gatgcaggac gcagcaataa gccttaagct cctctcccaa cacaactcct   32400
```

```
ctaggaaagt ccaacctccc aaagatccca caacctctta aaacagctaa ggaccaagca   32460
taagaacaca tgagcctgtg gcaaacattt tacactcaca ctgttgcaca gcacccattc   32520
tatgggacat tagctgtatg atgtgatatg ctaaacagaa ttttaacacc taagaattgt   32580
tccttcaata cagaattcta gcagattcta gaattatctg caacccttc agacagtgct    32640 tatagaaaaa gaatcttaag aagtcttgat ccacccattc ttcccaaacc aatttagcca   32700
ttgaaccttc cttcatcagc tacatactag ggaattgtgt tctgtgaagc actgagaaaa   32760
atgtaaccca acgacccaaa aattggtgtc ttacctacta agaagaaga gaaaattaa     32820 ctgtttcctc aggtccaaag tgacagatgc tggacatctg tttttccttt ggtcttggag   32880
ctaatcttca cagctgggga tcaggtgtca ggacacaaga gcctgtgagt aacattttat   32940
actcagacta caacacagta taagaattaa agttctttct cttggataca gaacttgatg   33000
tttagaaaga gtagagggag cttccaaaaa tattcaaaca atcaaaggca gaatccagat   33060
ataggtctga ttagttcttt atatgtcata gaatcagcac cttgtagaca tgacaccata   33120
tgaccctgga actcacctct ctctctctct ctctctctct ctctctctct ctctctctct   33180
ctctctctct ctctctctct ttctctctct ctctctctgt ctctctttct ctctctcaca   33240
cacacacaca ctcctgctct tgctctcctg ctctgtgtgt atatttgtgc acacatgcaa   33300
gtacatggaa tgcacacatt cttggaagtg catctgtaga ttcaagtttc aagtacagtt   33360
gcctacgttc ccaacacata catcagagcc agaggaaaga ctcaaacacc agccctcaga   33420
tatctctact ttttgtttca gacaggatct cctcagcaga ctatttggcc tataagcttc   33480
tagagattca tctatcttac agggaacaca ggcacacact gtcatactgg ctttttcttc   33540
gtaactgacc tcagaccctc ataccctgcag ggcaataatt gactgactaa gccaaccct    33600 cagctccact ggtactgatc agagaatctg tacctgaatt ctgctctccc agaggctctg   33660
actgacagct atcactgaaa aaccataact tgcagtgcct ccattcacct ctttagattg   33720
ggattcctat tccatccagt gaagaagtaa gaattcatat gaaacatgga gggtattttt   33780
ttaatagaag aaggaggagg agaaggagga ggtgaaggag gaggaggaga aggggaagga   33840
ggagggggag gaggaggagg agggaaggag gaaggagaag aagaagagga ggaggagaaa   33900
aagaggaaaa gaggaagaaa agaagaagaa aagaaggagg aggagaagaa gaggaggaga   33960
aggaggagga gcaggaggag gaggagaaga agaggaggag gaggaggagg agaaggagga   34020
ggaggaggag gaggaggagg aggaggaaga gacgaatact atgaaatgca gaattactgt   34080
ggggctagta actaccagaa ccagtctaca gttactgaag attttctacc caaacagtat   34140
agagctggac attgtacata ttttataatc acaattttta agtaatttct ctttatttcc   34200
tttattccca tttacagag acaaaataa acaccaatct caaagctaac aagaataata   34260
gattaggctg tcttgatgaa ataactact accctcactt caccaatgga ggacatgaaa    34320
cacagagggc aggtgaacag tagaattagg atttggaccc ttttggtacc caagccactc   34380 attttaatt gttatttatt attattgtac tatgatgggg gtggtgccac agcatgcatg    34440
tggcagtcag agagcagcta ttgagagttg gttatctgta tccaccatgg gtcccaggaa   34500
tcaaaactgg atcatcagac ctataccaca aacactttca cccaccgagg caccccagtg   34560
gcgccaagcc tttctgtcct tcacagccag tttagcaaag caagcagaat agctttaaac   34620
tgcaggtttg aatctcagag tgaggcctta ctcaccttga tctttcagtc taccaaggaa   34680
aacccctgta tagggtgtctt gctgcatccc cgtttccatg acactcgagt cacatcatgc   34740
ttctcacaga gatggtatag cctgtgagcc tcactttcac ttgcccattc acacaacata   34800
```

```
tattcagcat ctactataag ccagattctc ttgggctaac acgtctctca catctgtatt   34860
gggacccagt ccagagctga cttaaaataa cttctctgct tttcacctcc cttcctttgc   34920
actgtgctac tgtttcagct agctcccttt tttgtattag catccataaa gcatcttatt   34980
gctctgaaca caccgtgagc tctttaaaac catcctatcc tcttcattag tcaatatgta   35040
gtgcatatct acaccagtga gccactaagt cagcaccaga gtgtgcgatt ctgatatcca   35100
cttcaatagt ctctgttaaa agaagtggca ttctcatact attcaaaggt taggctgaaa   35160
aattatactt aatacctaac tcctaagggt tgacctgcct ggtcacaggg ttaagatgtt   35220
tctgctcttt gaagcagctt tgtgtgtgtg tgtgtgtg tgtgtgtgtg tgtgtgtgtg   35280
tgtgtgtgtg tgcagctatc atcaggatta tgcaattaat atttgtcacg gctgtctaca   35340
tgcttttgag atataaatac tattccttcc actgaactgt cagcatctat ataattttga   35400
aagtgcagca gagcaaagtg gtgtgtattt atctaacagc atcttcacaa ttttaggtct   35460
aggccacagc ttccagattg ttatcattca ttacaggaag agagaaacat agcatagaaa   35520
ctcagagctg aaattttcag tgtaaattgt caactgcgat taagtagaat ttttctccta   35580
tggatacaaa aaaaaaaatc tggcatacat atttctatgt tgaagcctca agttgtaact   35640
gcacagcaga ggaaggctgc tgcagctttt tgccagtgtt actgctgtac acaatatctt   35700
ctccttcccc tcttccccc cctcctcctc ctcttcttcc tcttcttctt ccttagtaca   35760
cttttttttg agacagggct tatccctgca gtccagattg gtctggaact cactacacgg   35820
cccaggctgg ccccaagcgt ccagcaatca ttttgccttt gcctctgcct cttaagtgct   35880
aagattccag gtataagtca ctacgtccag ctacacagta gcttccttac tcttctcttt   35940
tgctgtgtaa ttctaaagtc cttctaggga aagacagact cctaaccaaa aaagatggag   36000
gttgtttctt tggctgatat aaagaagcac tgtctattta aatcaaacat tttaaaataa   36060
ttttctgtct tggtatttca agatataaag ttggttggga agatgatgtg gggaacaaag   36120
tgtttgccac acaggtatga ggacttgggt ttgagctccc agggcccag aaattcaatc   36180 cttgtcacaa gtgtctgtag tcccattgtt cctactgtga gatgggaggt agagatggca   36240
gacttcttgg aagctagcct ggagtacgta gttgtagggt taccgggtcc catgtccact   36300
ctgccacagg actctgccag ttggggaggc aggatgcagg agttttgact gcccttaccc   36360
agaactgttg ctggacgggt atcaaccgat cctggggtag gggagagcaa tctgaggaga   36420 ggacaacaa gacaaagcca gggctgtctg gttctcaggc tctctgacac tcaggcgctg   36480
ctagatgctg tggaaaggct gagaacagag tgggggccct caggctggag ctgagaacag   36540
agtgggggcc aaaggggaaa gaggagctcc agctgggtcc cttggggata gagtccttgg   36600
cttgtcggtc acagctggct tgagtttggc ttagtggcca tggctgggga cacagagagg   36660
cattctacgg gaagttacac agtggctctt taagcaaagg ccttctccgt tgttccccac   36720
aacggatccc actgcaaaga ggcagtccat ggttttaagg tatttattgt catagcagga   36780
gcctggttcc caggagctgg gtgaagaaac gctttcaaga cctccaggct tagcacacag   36840
cttactccac tttgcaccag agccttcttt ccaactctca tctcttccct caccttacag   36900
ccttctagcc ttagctcaac caggctgcct ttcagggtac tacaacatga ccaacaaaat   36960
aagaccctga tagtaaacaa actggaaggt gaaaacctga cctaagttgt tctctgacct   37020
ctacatatac ccaggcatct gcactcatac acacaaacac ccagcacatg cacacacatg   37080
atgatgaggg gggtggtagt ggtggtggtg gtgatgatga taatttaaaa gaaaaagaca   37140
gagagtaaat aggaagggac aaaattaccta aggaagaaaa atacccttaa gcataatgga   37200
```

-continued

```
gaattgcttg aaagaagtga aaataaaagt tgttatgcgt tgaagagcta ttttagcac    37260 agaagcatag tcatcactag gttaaaggga gacaagagca gtggccctgt aaggtgaggg    37320
aagggatgag agctggaaag agggctctgg tgcaacgtgg agtaagccgt gtgctaagag    37380
tagaaaggcc ctgtagtggt aaagttttc cgactcccag ttactggctg tgattaattc     37440
tacatcacac ccgatttgtg agaagaactc ttgaaaaaac ttaggacagt ttgcttgtgc    37500
aaactgtcaa gatgatgaat gaaataggtg tgtgtatgtg aatggggagg ggggaggctg    37560
ctgacataaa tatatcggct tacacatttt agttctcttg atatcacctc agtgtagacg    37620
gctctgaggg aagtgccaac tgggagattt ggttcatttt cttaactgca tatgtaatca    37680
tcagaataca ataaaataga ttatagaaaa gctgagataa tctaattcct tcataattgt    37740
ctctcttcat cagctcaata atagataaca gtgataatgg gtatttatag tgtgtcctgt    37800
gcaaaatggc ctttgggttc ctaacctaat ataataaaca gataattcaa ataaaaagac    37860
agcacgggcc agtgggagca aggcaagaac gccaagaagg acaaaaatcc atactctgct    37920
taaagatatt aataaaacaa agagggcct gctcccttc ctaatgaatg aaaaatgcat       37980
ttaatttaat ccgtttactt tgagaaatta tttacttgca ctctccctca cactggagct    38040
ctggctaccc ctggaattga tcacctctcc cagccacaga aatcaacaat caattgagca    38100
aggtggctga agccatgttt gcttgtcata agcctgtgta ggagccctac tttcattagg    38160
tgacctcaaa agactccagt gccccactag gccttactct tgtcctatgg gaaggtagca    38220
gccctaaccc ttgcagtgcc ttgatttatc acacttgcaa gctttggtga ttattctcct    38280
tgtataagaa aagaattaaa taaaatgtat catttaaaag ctcccttttat tgatctcagt    38340 tctcaaatta aatatagccc tggaagtccc caggggagtcg tcctgaagct tgtctcaaaa    38400
ccattctttt cattaccttc acatagtaga tggaatagct ggggtttgtt tgtttgtttg    38460
tttgtttgtt tgcttttaac atatacattt gtaggtgtac caagaagaga gagggagctg    38520
taaccaaagc acttgctttg gtttggacct ccattatacc atggcttgaa gctctgcagt    38580
atcgctatct aacaatctcc ttcatttttcc tttttgtttt tattttttgca ttgagacagg    38640 gccttaatat gtagaccaga ctagctcaaa ccacagagat ctacctgtct ctgactgcca    38700
aggacagatc tgtacattga tggaatgcct ctgtgtgtgt gtgtgtgtgt gtgtgtgtgt    38760
gtgtgtgtgt gtgtgtgtgt gtgtgtacac caaggagaga gaggcaattg taccatttgt    38820
attaaaagta tgtgccacca cacccagcta tatctcattt tatttaagta ttccatagaa    38880
tactagtcca ccatcaagat aatcattggt gaatgcttca gtaaggatta ataactataa    38940
ttacagtagt cacaaagatg tctagtcatg gatcagatga caaactggta ataaagttct    39000
gagatggata acatgcagaa tagcagcctt aagaaaaga atcttggggt gaaaaatgat     39060
ttacaatagc tgatctcagt cttattagta gtataccata aaaataattt tataatttta    39120
ttgctttaaa gcagtacatt tttcatgttg gaaagtcttg taaataagaa ttttttaaa    39180 gtttttgtc tctgttatat tcattcagga ttgctctgac actaaaaaca gcagaataga    39240
acctgggaaa aaatagcagc tatttactgg ggagatggaa cattttctaa atggcattgc    39300
agtctctatc tttccaggga taaacgttct tattgctcac aattgtcact atgcagaata    39360
tccatcctag acctggcatg gagcttctct ttgttctatg tcatatgctc agtgaagaga    39420
cagaggtgta ctgtcagatg gaagcaggtc acactgctac cactgctctg ctccttggga   39480
agaggccatg gccaaagtac caagatcaag gccccctgtg gaatgctgcc acagagattt     39540
agcacacaag catcctgggg tcccctttcc ctagtgaagg gatactctta agagactaca    39600
```

```
tcattggatt cataccaaaa tttcaattct acgactcaaa aataaggctt tgcctcctct  39660
caatggctcc atctctaaaa ttatttatta gatagtgaga aaaagaccaa gaagggccag  39720
tgtgcctgtc tgctctgagg tataaatacc ttatacctac tccactcatt tctcaaatga  39780
caggaagaga ctaccaatag tggcaaccac cttagcagct acagcttccc tcagacactg  39840
agaaggcgct cacaggctta tactctctac tttcacagaa acatcatgag tgatactatg  39900
cttatggaca tttattacac agtaagagag gctttagcta cacagctagc cccagttcca  39960
ccgcgcctac atggtgaagc caggatccca ggccaggaca caaaacctga ggtcccattg  40020
tgtttagtgg cagtgtcgtg cttctgtgtc tccctggaca cgccccttct ttgtatcagg  40080
ttataaacaa atacttctcc cactcattca tggttaacca acttggggcc taaagaatca  40140
catgttataa atgtaactgg actgttgtgt ggacttctga gatagtatgt cctggaaaga  40200
taaattagca gttttccctt tctttttttt tttttttttg tttataaata attttctttt  40260
tgcaaagatc tctctcctac ttactctgga tcattctgac cattacacaa gtgctacttg  40320
ggaacccttta cagaggagcc tgggctttgg aacatggaaa ggagttgaga caggacagac  40380
tatatcatta tgtatgtagc tcagacccag acataggagt tggatcagac cataagtgcc  40440
agcaaaagat agaaccgtga aaacctgatc caggccatgt gcacagagaa ctgtgtgatc  40500
tcagaatgaa ttcctctaac agctgaacct acactgtctc tccaaaaatg tagggtagct  40560
cttgttgcca cagaagttca aaactttatt ttaccgactt tctgcttact gaaatctttt  40620
aaccttgggt attttagacc tctaatatcc acctcgagtt ctcaaagcca gctttgtgc   40680
agggagctgg ttttaggttt gttttacttt tggagagtaa ggtggagaag gcacagatca  40740
cagctttgca gcccattgtt tgggacattt gttcttccag tgtctgtgtc ctttctcctg  40800
ggccaaatac aggggtggaa ttctgatgtc tcttcacagt aagtgtcccc accatcagaa  40860
acatgaaaga gagttgaagt aaatagcccc ttcttctgtt caaagtctcc tctttccttt  40920
gtctccctga agcacttcta cagggccaat gcattttctc ttcattgcct cttgcaccaa  40980
aaaggccagt gtccctaaaa gtcagttatg gggtgtgggg ggcagctcac aaggcaacaa  41040
caaggaagca aaggcatgag gcatgaaagg attcacaaac tcgaaggata ctggcacact  41100
gctatgccct gtgaaagcaa ggacaggaat atttctatct gaaaaaaaaa aaaaaaaaa   41160
agattagaat gtgaagaaag ttaagatgca ggcatctttt caagtgagaa aggtcaaagc  41220
aggctctgat atgagttttt attgttgttg ttgtttcaat aattattttt ggattaccag  41280
gctaacaaag tcagtgagtg ctccaagctt aatgaatcta agcttagaag gagattctgg  41340
gagaaacgtg aattgtggac tcgttgctcg tgaggtttta aagatggca agagtgtaat   41400
taataataga tggtggggtt ttggtgtgat aattttggcta aaaattgtga acgatgtcat  41460
gttggaggtg aagaaacaac catgattatc aaaaaaaaaa aaaaaagct gtggttccac   41520
tgaggtaaaa gccaaacaca attcactaag acagtggacg ctggccatct ggggctacag  41580
agtcagctgt gatgaatcag atttcagtgg gtgggcacca ttcgggtgat atcttggaag  41640
tgtttcctca gggtcagccc acagatgctg tggtgcacag ctgtatctca agcctgtaac  41700
tgaacctaac actgggtgag agtcacccac ctagtagcca ttttgaaggc ataagagatg  41760
caagactggg gagccatgaa acaggctaa ggcctacagt ttgtgccagg gtcacacaga   41820
gaggtcatta gggaagctat agccttagtt gtagtggagt ggagacccca ggatatcaga  41880
aatgccaagg ctccaagaca gagtgggtat agtagaccct gagactgagc caagctcttt  41940
gtgctaagga cagagaagtg ggaaaatggt gcttgcccaa gctctctaaa atctgtaagc  42000
```

```
tcatgagtga gtccaagatt ttggacacag agctacagac cttaaattta tgctactgaa    42060
tttgtgttat tcttttttc tagttgattc tcattctctc tctgtctctg tctctgtctc    42120
tctctgtgtg tgtgtgtgtg tgtgtgtgtg tgtgtgtgtg tgtgtgtgtg tctgtctctc    42180
tctctccccc actacatttt ttgctttat tgaaaatata ttgtgactgt ggtttcctct    42240
ccctctactc ctcccagttc ctctccacct tctgtactat gcagacctcc tccctttctg    42300
tctctcatta ggcttctaag agataataat aaaataaaat aaaataaaat aaaataaaat    42360
aaaataaaat aaaataaaat aaaataaaat aaaaatataa taatagaaaa ctacagtctc    42420
catgagaggg cctgtattct ccattccctc tggctctaat actctctttg tctcatctct    42480
tctgtagatt ttcctgagct ctgaagaaag ggatttgatg aagatattcc caattagggc    42540
tgaggttcca aggtctctct ctctccctcc ctctctctct ctctctctct ctctctctct    42600
ctctccctcc ctccctccat ccgtacccac ctctctctct gtctctctct ctgtctgtct    42660
gtctctctgt ctgtctctct gtttttttctt tctctccctc tgtgtgtgtg tgtggagggg    42720
gattctttgt atttgttctc atctgctgca ggaggaagtt tctctgatga tggttgagca    42780
agacgctgat ctataagcat agtagaatgt cattatgagt cccttatca ataggttttt    42840 ctattttag ttttggttg attggttggt tggttggttg gttggttggt tggttggggt    42900
tttgttgttt gtttggtttt ggttttggtt ttggttttg gcttttggtt ttttgagaca    42960
gggtttctct gtgtagcctt ggctgtcctg gaactcactc tgtagatcag gctggcctca    43020
aacttagaaa ttcacctgcc tctgcctcca agggctggga ttaaaggcat gtgccaccac    43080
gcctggcttt agttttgttt taaggccact agtatttggt cccagagaga tctagtctct    43140
gactcttggt cacccaagca atgttggata tgagttccat cttgtagagt gggccttcag    43200
tcaaatcagt tactggctgg tcactaccat aagcattgtg ccaccattgc cctagaatat    43260
cttgcaggca gtacatctgt tcaaagactt tatggctggc ttggtgtgca tatttctcct    43320
tttttagttg tttgctgggt acatttctgt atcaaagatg ctgaaacata gttctatgta    43380
ggcactagtt tgacgttttc atgttcaatg caatgtgtag gtgttttctt cagcaatgag    43440
acctcactgt caaatagtgg agtgcagcct gttgtcttgg aaacagcttc agttgttgga    43500
gatttccatg agactccttt ggccaacaac tcaattactt gctacccaat cctggtactg    43560
gaagcttcat ttgaagacaa aagttgggac tcggtttccc cccaaaattt ggtgatttca    43620
cttagagagc actcatacat gtatatattt tatggagttt ctactgtatt atatcaaatg    43680
gcccttaatt ttcaagtaag agctagtgag ttagccagag agcaagccag ccagcagtgc    43740
tcctccatgg ttcataattc aagatcctgc ttgggtcctt gcttggtgc ccctcagtga    43800 tgggcagtga cctgaaaagc cagatcaacc atcccttcac catgcttctt ttgatttgag    43860
tgttttgcca cagcaatgac ataaaactag aacatcatct gacacctccc ctgcagggtt    43920
gtgctcaagt gtctccatct cagtgaggtc cttttgccac tgtgaccatt cccagattgc    43980
cttttttcta cactgcactg attaccatct aacatagtat atactttata tatttataca    44040
tcaccctcct tttccaagac acaaactcca tgaggatgga caatgtgtgt gtgtgtgtgt    44100
gtgtgtgtgt gtgtgtgtgt gtgtgtgtgt gtgtatgtgt gtgtgtgtgt gtgtgtgtgt    44160
gtgtgtgtgt gtgtgtgttt cggtctgtct gtctttctat ctgtgtacat gtgtatgtgt    44220
ctgtgtttct ctgtgtgtgt gtctgtgtgt gtgtatatat gtttgtgtgt cttgtgtgtc    44280
tgtctgtctg tccatccatc tgtctgccag tccatccatc tgtctgcctg tttgtctcag    44340
acattacgat tattccagag tgcaatttgg tatctgccca tagtaagcat tagtgctgcc    44400
```

```
ctttgttagg gaggactctt gggatattca acattaggca ctttaggctc tgttctgctt    44460
tgaagctatc tggaaggact atgaactata cactccaagg aatattatgg aacatgggag    44520
acgtctttca gtgataataa ttgtgtttaa ggtctatgac aggacttctc aaccttccta    44580
atgctgtgac cctttaatat agttcctcat gttgtagtga tcccaatgat aacatcattt    44640
tcattgcttc tttatagttg taatgttgct agttgtgaat cataatgtca atatctgata    44700
tgcaagatat ctgatatgtg accctcccaa agaaagggat ccagacctac aagttaagaa    44760
ccactgttta agggatctct ccttggatta atattttgaa ttttcatctg agcaggagct    44820
atccagcaaa taggcaacct ttgattctga gatgaaagga gattctcacc tcctgtcctt    44880
cctaactgct aacactacaa atcactgcgt aaatccaaag agaacccgca agatactgag    44940
ccttgaaata cattccttga tttctttttc cttgtgatac taattaaatc tcacttataa    45000
atctgattat atgatggtga gcttacaaac tgagagagag agagagagag agagagagag    45060
agagagaggg agggagggag ggagggaggg agggagagag agagagagag agagagagag    45120
agagagagag agagagagag aggcaaacac tggctctcag agggcgtgtt ttaggtgtta    45180
acacaccaga cagcacctag agtgcagacc aggctccata gaaactgttg cgcccctcag    45240
atgttccttt gagtggacag cagagaatag aaatgtgaac agatttgtgt cccatggttt    45300
cttctagcta gatacaatta tctgaaactc aaagcacaaa gctaagcctt tcttttagca    45360
accccaagct gcttgtcacc tgccatttgc tcaacacaaa gagagtgttt taaaaataaa    45420
taaataaata aataaataaa taaataaata aatatgaaaa caaaccccca gaaacaattt    45480
cactgcgtct gctgacacat aggcacaacc tccacccacc tgccttggag gacactgaca    45540
tgtctcactg aagggaaatt tcagtcttgt gagactgcat tctgtaatta ccctaatctc    45600
cattctcaag aggctgtagc aggggaagtg gattagcgcc tgagcctttg ggggtctctg    45660
gagaagagag ctgaaatctc aagcttaggt cataagcaaa gatgaagggg atggcctgct    45720
ggctcatccc ctttgggaag caatgaaagg cacagagagt tgggattatt aatcttgttc    45780
agaagaagct tgtccagaag ctcggaaagt tgattctcat acaaagaggt tggcaaagtc    45840
catggaaacc ctgactcctt gaattcactc tgggcctttt caaatacaat gggatttttt    45900
tttctctctc aaaagaaatc tcggtgtgat tgttcactga tagagaaaaa catatggttt    45960
tgcagaagtg ccaatttggg ctcaaataat ataatggatg taaagtagcc tgtgattatc    46020
agcacattat ggaaagggga acagatgcac cctcctgtct tctctcctga caggtgtact    46080
tctattggat ctgccgggat gccggagcat ttgagtggtt tgctgatctg ttactgtcac    46140
tggaaacacg gatgagtgaa caagggaagg ctcatttact gagctaccat atatatctca    46200
ctggctggga tgaaaaccag gtatcagaaa aaccgaggat ctccattact gcttccattc    46260
ttaaaagaaa cccatttcca taatgagctg gggacttatc aggcaggagc aaagaattat    46320
cctaaagttc cttaaaggga gagggaacg gaatcaagcc agactgaaaa caactactta    46380
agatgtagca ataaaaagac ctctagctgt tgggtaataa actgcagccc agatattagg    46440
actcttaaag ttcgaatttg tcatttaaat agaagaatca gtgtcttgtc attaattgcc    46500
tgggtcatct gctgaattcc taattgcttc tgattctatg ctgctcaaag gaaaacagaa    46560
aagattccat gttgtttctc tacagccttt catattgaaa agtgtgtgag tcagaaaatg    46620
actctggata catgatttac atagagagtt cttttctttta aaacatgcac cctgaatctt    46680
gccaatgctg aggtgacttc tgcttgggta ggtgttccac aagccgttgt agtaatgaag    46740
tataaaagct gagtttgaca aaaatgatgt gtgtcaatgt actgacagta ctgtttcaat    46800
```

```
cctgataaaa gttaccatga ttgggatata aatgacaact agggaatcag agtccagttg    46860
gaatctcaat atagccatga cactagttta tgaaaggcat gttttaaact gtgcatctga    46920
agaagatatt acatggtact gttgatgatg aagataatat tacatggtac ttttagggaa    46980
aatagattca agccaaggag ctttgaccaa atttacagat gattactcta tgagttctgc    47040
aaatattctc tctttctctc tctccctctc tctctctctc tctctctctc tctctctctc    47100
tcacacacac acacacacac acacacacac acacacacac acactgtcta cctccaacca    47160
ttgttataac ttgtctttct cttcttctgt aaatgagtaa gactctgctt gaggttcaaa    47220
atatgttttg gactttatg gccttaattc cagtccttct taaatattta accttctggg     47280
ataatttgaa attgcaggtt tcttgggaac tgggcttgat agatctcaat gagttatatg    47340
gtgttaatta ggttttccaa acaaacattt tccctatcca agcaggattt ttgactgatg    47400
atccatttgg tgaagcacag acgtggcttt tgtcgtttgc ttctgagccc ctgcctgttc    47460
ttccactgct gaagtaaatt ggtcccaagt gttcacttag ccaatccctg tcacttggga    47520
tttatgagac ttggaactct gaagtggatt ttgtgacagc acaactctgc cctgccctgc    47580
cctatctttg ccccttttcaa gactgagata taaaatgtcc ttttttttcct taaatgaacg   47640
taaattaaag ttggtagctt cttaagttttt cccatggcat gtcagaaatt cttcagactt   47700
ccaaatttca accaggaaat cactaatctc aacattgaaa gagttggtgc atttctgtca    47760
gttaactcaa gcactgaggg gctgtttag aaatagccca ttcttaaact gaatccaaca     47820
acctcagaat ggcaaattga caagaacaga agggacagat gggagtggta ctataaaggg    47880
caactcaaaa gagttggaga ttaattgaac attgggctga gaattatgga acagatataa    47940
ttccaaatgt ttgaacacca gagactgagt gttaccaccg tcttaagtag agaaggcctc    48000
cccgctatga gttaatacca gaatgtctta acaagcactt taaggaccat cttaacctaa    48060
cctgtttcaa ggcaagcctc actgtttttc tatggcccca gaactgtcga ctaatggatg    48120
cttatgtatc cttcagtgtg cattcaggtt ttcaagtctt ttgctcctgt tgggtccact    48180
ctccaacatg tcaatcaaga cccccctcca tttccccacc ctcacacagc atggagtact    48240
gttcccaaac tcttttgcaa ttacaaacac tgttacctaa gctcagactt gcttggtagc    48300
agtatctgca gcctgacatt ctgaaggcca gtctgccctt gtccactggt ctgttagggt    48360
agccaccata acttggatat gaacctccag cactagctgc cttcttgtac taggaacaaa    48420
accattcagg ctagtcatat tcaaagcagg tagccacagc tcgagttggg catagcaagg    48480
ctattattga aactgtcaaa actaagcaag atttagagag tgagagaaaa actgacacat    48540
gagttttcag agctgatggt tcccaggaac agctcagagc acacatacct gaggcagggg    48600
gaacaaggta gcttctagaa ttcacagcag ctaaagtcaa tggtagacct ggagtagatg    48660
tttataatga gtattgtgcc ccgggctctc atatacaaac ctctaattac acggtgactg    48720
gatgagttca ctgggtttga aggcagtcac tttcagagct ccaagcagac cctgcaatgt    48780
tccctgtccc caacatcaca tcaccacctt caagtatagc ccccaacact tgaaacctaa    48840
tactatacaa gttggctatc catattgttg agttccacat ctgtgtgttt aaccaactga    48900
agactgaaaa tgttgggaaa aaaatacatc tgtgttgaaa acatatgtcc atcttattcc    48960
tttacattat tccctaaaca gtcgaggaca actcttttcc tagttgttgt atggaagtaa    49020
ggttttatag accatctaga tggttttgag aggatgtgag tagcttacac acaaaattctt   49080
ttgaacctct gaagacgttg gtatctggag aagaggacag tcctaatatt tggggatgac    49140
cacccatcaa accatgtcaa ctcaataggc agatctgact gtaagacaca gcttcttccc    49200
```

```
gggtacttca tggcacttta gtctggaaat ccccaagtcc cctgaattaa atgaatggga   49260
ccatgaggag aagactgatt tttgagatgt tatgcaggaa gaaaactaac ttgggtaacc   49320
acatttactg tattaccctc atcctttaag aaaaaaaaaa tcttttcaag ctctgcctct   49380
gcttatctac tatgtacaca aaagtgtttt gtcccaacaa agacagatga tacctaacac   49440
ttgtcctaaa gcacaacatt gaaggcagct gttaataaag catttcaagc cgtgtttaaa   49500
atattttgaa cacacaagtg atgatagtga gtttatcttt tatttataga tggttctcat   49560
acgttttata atgtcatcta aaactacaat ttttaattta ggcaattcac atagctttac   49620
actgggatga aagtctggat gtgataacag gcttaaagca gaaggctttc tatgggcgac   49680
ccaactggaa cgacgaattc aagcagattg cctacaatca ccccaggtga gcaaagcaag   49740
ctctctctct ctctctctct ctctctctct ctctctcctc tgtctgtcag gatcctccct   49800
gaagtccaga caagctgtca ctggggagag agggggatga gggagggggg ttaatctgaa   49860
gtcataactg agaattttga tccaagactt ttttaaaaaa atatctacct tagaaaatat   49920
gtccatgact ctcttatatt tcagaaacca caaacctctg tttaactggc tgacagattc   49980
agacaattat cgattatgtt cacacttaac ctcaatttaa agttggtatt tcttaaacag   50040
catatgtctt caaaaaaatc ttttcagcag acttagtctc taattaccca gctagagaat   50100
tcatttctcc ccagctctac agtgtgtcta gcacatctag caaaaaagca aagagaaaaa   50160
gtgttctcag acagagtgga ggtttgacat ggtgctaaag aacccagatc tggagctggg   50220
gtatttaagg gtctaccctg gctctgccat tcccatgggt ataccttggt catctaataa   50280
ccctgtgatg acctagtctc ctcctcctct aaaaaactgt aactaatact gcttgcctcc   50340
caggattctg caagaaaaaa atgaatgaag catctaaagt gcctgataca acatctcggt   50400
tagggtttta ccgctgtgaa caggcactgt gaccaaggca actcttgtaa ggacaacatt   50460 taattgggc tggcttacag gtcaggaggt tcagtccatt atcatcaaca caagaacatg   50520
acagcatcca ggcaggcatg gtgcaggagg agctagaatt ctacctcttg ttccaaaggc   50580
aaacaggaga agattggctt ccaggcagct agggtgaggg ttgtaaagcc cacatccaca   50640
gtgacacact taattcaaca aggccacgtg tattccaagg ccatacctct taatagtgcc   50700
acttcttggg tcaagcatat acaaaccaca catacagcaa tctttctcaa ctgccactgc   50760
cattgcttcc atcaattcga ttatcactac tatcatccta accatacaat gtacttcaat   50820
gcatggagga ccttgccatg gggccacaag actagggtac aacctctgac tcccggttct   50880
agaattttcc atctacatga cctgggttga acaaggtagc ttatttcagt gtatttaact   50940 atattttgg tgtaaatgca aaacacaagt gataaattca tgctcagtgt tgttttctta   51000
agttagcaca tacagtgctg aagagctggg taaagtgtaa gtcgctacga caaagcacta   51060
tccttgctcc taggtcagtc tttgtctgga accttcatca tctatagcat gcactgtctt   51120
catatttgag gaaagagtga aagggaggaa agggagcaac tagaaatgaa caagagccaa   51180
ggccctgagg caagggacat tgttcctgtt gtgattcgat ttgggaggcc agtgggtgga   51240
acagaggcca caagaggaag tatccccaaa gatatcattt aaataggggtg acaggggata   51300 cctgcaagga atcataagac tttggatatg attctcagag gaatagtcac ttagaggtac   51360
aagctcaaga ctggcatgaa agtcacccett gttactataa gaaaacagac tgcagtgggc   51420
ctaggagaga ggtgaggagg acgatgggga acaggcaggt ggggagcact ggaggaagtt   51480
gtgaagagcg gtttgattct gaacatttta tggaggctga acgggcatga gttatagatg   51540
gactggggca cggacccaag ctggaatgaa ttcccactca ttagcatgga catgaccgtg   51600
```

```
agaattgctg tgtagaagac acaggatatg agaagtttca tttttgatct ttagcttaag    51660
atatgcctta aaaattcaaa tatccagcaa atgatgcctt cagcaggatt tggggtgaga    51720
acctcagctg aaggtatctg catgtaaact gtgtgtggaa ccacaacacc aggataagtg    51780
atcaagagtt ccaagataca ttatattcac gaagcaagaa accataattt ctctctctct    51840
ctctctctct ctctctctct ctctctctct ctctctctct ctgtgtgtgt gtgtgtgtgt    51900
gtgtgtgtgt gtgtgttaca aagtttaaag acattactg atatttacct tagcaatcaa    51960
gccatctggg gctttctgac ttttaatct gtccttttta tcgctaaatt aaaatctact    52020
cctgtgtctc tgacgacttt ccgttcttcc tgattgcctg tgtgttttct ctttggcttt    52080
ccttctgaga actcatgctt cattaatctc tctctagttc cctgatacct ttttctactc    52140
agtggaattc tttatggtg agtataaatt catcttttgg tcaattcagc tccttttccat    52200 attttccctt atattttctt tgtgctagaa ctatgccttt ctatctttat gagctgcctg    52260
tgtgtctgtc tgagttcact ttggatgagc aagggaagaa ggaagtatcg agtagcattc    52320
acagttcata agcatccaat tgcagtatcc ttggtccatg tgaagtcact tggcttctac    52380 taccctagt gctgagagac agaccctctg caaaccagga gtacagcttg tgctatgaca    52440
gccttctgtg gaaaccctg cattccgaga atgttctgtg agtgagtgtc tcaggcctcc    52500
tggtcataca gcagaggaga gaaattagta gtgacttcca tcagcctaag aggggcagaa    52560
ttctaagagg agagacagga aacatcttaa cttctagctg aaaagtcaag aggaggtaga    52620
tccatcgcac aatgtggcag tctagctttt tcccaccaa ctcagcttta ggtgccctca    52680
cagaactgct gaccccaagg caagtggcct tggcagctct tctttgtcat caaattctgg    52740
tgccctcttg tttactttgc ttccttcctt ggctcttgtg gatgctcagc cttggatcca    52800
gttctggagc accaccttgt ctctaaacaa gagactccat tccaaacacc accccatcc    52860 cacaagagtc ctctaagcat ccgctcaaca atggatgctg gatgtcaacc tcgtaagacc    52920
ctctaagccc tgggagaagt gttccttcac ctgcacctac ctcgttcttg accagagcaa    52980
atgcagtaat ttcatgaata tgcctatatg taagacctaa gtgggtttgt tactattttc    53040
tcctttggga gaaaaatata gttttgaaca aatttatacc tcttgttttc actgatgaca    53100
aaatagattt cttggctccc tatgggtggt ggggtggca tgtacacata catgtggagg    53160
ctggaagaca acagtgtgtg tcattcctta ggcaccgcat atacctagta tttttggacag   53220 ggtttctcct tactagccca gagacctgtt ttccaagtgg gttgggatgg ctggctaatg    53280
agcctcaaaa attcacctgt ctttacttcc ctagcagctg ggataacaaa cactcatcat    53340 tgttttttg taaaaacaaa cctggttttt atcatatagg ctctgaggag caagctcagg    53400
tctccatcat ttcaaggcaa gcattttctc tatgagatac caccctaccc caacttcaga    53460
ctgcaggctt ctgaaacata catctttaaa ttcatgtaaa tagctccagt cttcacagtg    53520
atttccctac attgatactg cattgtgttt gttttatca taatataaac ttgatggccc    53580
aatgcagaaa gcctttcaaa tcaattcact taatcatctt tcttcacttg gagagtgtga    53640
gccagaagta caagaaatca aaggcaaaaa cgagccttgt gcaatccctg ttcagaaaaa    53700
tgctatttca ggtgagcctg tcccatgtgc atagtgactg tccaggacag ttttatctaa    53760
gctgggaaac atgttcaccc cataccgaaa cacccctc ccccatcaaa gcacacaatt    53820
gcatggaata gctagctatg tttctcatta tggtagctgt gcaaactctc tttctctggt    53880
gcatgattct atgtcgtcca ggagagaaga gactcctggg gttaagtcat ttcagaacca    53940
agacactact gactacttcc tacctgaaaa aaaaaaaatt taatatcaga tttgtaaaag    54000
```

```
cttgagactc cggaacacgc tggcttatta aattgcttca agcatcaata taattaatat   54060
tagataaatc gatgcaaaat caatcattgt ttcatctctg gaatgccagg tccctggaag   54120
cctgcaaatc tccagcatca agctcagcac tgcccgtcta aagactttt aaaatgacct    54180 cccgtaaaat aatttttgt ttttcttctg cgtaaaagga gatttatgct taatgaagct    54240
tttaatgaag aaattacaga aggagaatgc caataaaatc taattcttaa acaagaaaat   54300
ctaatattga gaagcattgc aatatgctgg cctttgtcca gattgaaatg aaacacaatc   54360
caatcactgt tcggcacaaa ggacaaaata acattaattt tcttcaagat ggttattaga   54420
gagataaaca gtatgttctc ccctatcgt gtcacagaga tgtttgttcc caagcccact    54480
tggctactct cacaaggccg gcttgtcctg caatattagc ttgtatcttt tggcaaagat    54540
aggccaggaa gaattgctgg atttgttagt agcctcagaa aagatccttt gttccccagg   54600 gccttttgaag taggctctcc accatcggag cacaaagctg ggccttctta gcactaactc   54660
ctgtaatcgc atttacctgt tcactcaaag ctggagtttg ctcctgtcct aagaaagagt   54720
tgaatcaaaa gaatggaggg gaaaggaatg caaaaaaatt ttataggaca tgaaaaaaca   54780
ccaccaaaaa taaagctgga agggaagcag atcaaagcgg attgagcaag ttctgaagga   54840
accagaaaat tgcaaaaata acagtaatag agaaacaaat tgatggcatt agaacgaata   54900
caaatgagga acaggagagg cggttttaaa atagatcaaa ggctggaagc agaaaacagg   54960
gaagcacggc ctgctgtttt cttcggtaat taattttggt aattatacca gttgatttac   55020
agaaacacga ggatagtgct aaaagacagt caacaaatag caaatgagtg tacatttaaa   55080
gaggtcattt cttgctctgc ccaaactctc atacatgtga caattgtcaa ttacatcaat   55140
tatacaagca cagaaaagta ttcccagcat acagtgggag tcgccctccc attaaagtac   55200
aataggctaa ttagtgcatg cattgacacc taggacttat gaatctatag aaatgtgtct   55260
tatacaaaaa tggaagctct gtttcatttt ctgtaagcat tcttgatatg ctgccaacct   55320
ttagacaagt gttcagaatc agaaaatcat tttcaagaag acaggcagag tgaaaataaa   55380
catagttttg tcatttctag ctattttttt tgacaaacac acattgtaca tccactcacc   55440
catgtggacc tgtggctcag ctattgttag ttaattgact aagaagcttt tctgtatggt   55500
ttcagtcttt gatcttacac ttcggaaaat atttatagtt ttctacttct gacttatctg   55560
ctgatatctt caccatgcct tataggtgtg aactttatgt aattaattag cataaaaact   55620
tttgagattt ttcccagttt tcataacttt aataagaact attgtttaat aatgaagagg   55680
aacagagaaa gagggatgtc agcacttgtc aggacacagc cacccggccc agacatgaac   55740
aaggtgtcag cttactatac aaataagggc acttctaatc catatgacat gaatgtattt   55800 tagacccca ttgttttcaa atatgtaaaa aaaaatacc taccttttta ctaaattgag    55860
taaatgtgtc catctggagt tacatttgct tgtgtgcata cccttcagtt ctcatttgta   55920
catgcatatg tgcaaatatg ttgtaaagtg atatttttag gaaattagca ttctgattat   55980
agtataccag gtcctttatc taacagggta tcctaaacat tcattatatg actaaaatgt   56040
gcagaatact caaagaaata gatttaaatg caaatccagc acatgataaa ttatagcttt   56100
ataagaaaag taaagcccca taatgcacat tggaaatatt gtccccacag ctaaatgcta   56160
ccttttccac cagagaacat ccagctcact ggttatagcc gagtaaaaat tccatgaaaa   56220
ttactagcct tgtttgtcgt caggggacta agaacataag taaatagaaa gtggagttat   56280
tactctgtta acttactttg atggcattat tccagtaaat taaggattgt agaaaatctt   56340
ttgatatttt ataggtttac atgtcttagt agagcaagga taagggaaaa gataggatgg   56400
```

```
agaaaagttg ttccaccatt ttctgggacc caatactatg aatcaactag ttttctcctt    56460
ttccccctcc tcctcttcct cctcttcctc ctcctcttca ttctcttctt cctcctcctt    56520
ttttctttct tctctttctc ctccttttt cttttcctcc tactcttctt cccctactct     56580
ttctcctctt ctttctcctt ctcttcttcc tcctcttcct cctcctcttc ctcctcctct    56640
tcatcctcct cctcgacctc cttcccaccc ccatcccata agggcaactg ctttattcac    56700
tcatatctac tgctcagcat gaacaagtga aaggatgatg acgtagagga aacagggatg    56760
agaatcctaa gtgtgcagtg acagtcttat ctgtcaaaag ggacagtttg ttggaaagtg    56820
ggaaaagaag aggcacatgt aagttttgtt agtaacatct gcagcccag ataaacaact     56880 cagtaaggag aacactgcat tagttacttg tcttgttgtc acgaccaaat atctgacaag    56940
aagcagctca gagagaagga gtttatctgg gtccgtggct tgtggaagca gctcatcatg    57000
gctgcagaag caggaggtgc ttgctcacat taatccatag tcaggaagca gaaagcagta    57060
tggatgcctc tgctcaactc gcttcctcct ttgtgttcag tctgagaccc tagcccatgt    57120
ggtcagtctt tcttcctcct cagttaattt tctctaaaac attccttcgg acctccccct    57180
aaggcgtgtc tcctaggtga ttatataagc caagttgaca atcaagattg accaccatac    57240
actgtgagaa ggtcaataca gctggctgct gggcagtgac tatgatgtgg gttagaaagg    57300
gagagaactg accagcacaa ctatcatctg tagttatgaa aaagatggtg ttgtataaaa    57360
tgtaattatg tgataaatca tttggaggca tttctaatga aaaacattcc ctgggaaaga    57420
ttaagcagaa cttgtgtgtc cactgtctga aaccgagttt gtagctctcg ctgctgtcgt    57480
cctaagcctt cataaatcca caggaagctc ctgtttatcg atttatttg cagaacacac     57540 tccgagtata aagtaatttg atttttttta acagggttta gggtctgccc caacagggtt    57600
ataacttacc aagcataaaa gccaacacat aaaagcaaac atacaattta aggagaaagg    57660
ggctcatgcc agcagaatca gcgaatcagg gggtggtgag attaccccca ggcatatcca    57720
tgcacccatc tatctgtctg ggaatctggg ggtgaggctg gcaagattat tcccaggaac    57780 accccccatgc cctctaactg ctgggctgaa atctcctggt gagtgatctt ttggatgcct   57840
ttcatgcata gtgttgctca actcttttga gagaaaaaac aataataaat cccacagaga    57900
aaaacatagt ggttatttaa cagacacggg gcgggtagag agagaacctt ctttcctgtt    57960
tatcagagca ggaaccgttc tgtggatgtt tttaaccatt ttttttcact ctctgtgaaa    58020
tcttcccttt tgtcatcaaa gtcagccact cagactggtc agtgccatct atgagtgtta    58080
tccatgatcc aggtctgcac gcgtgtgcaa gctctgcttg caggctgtaa actgaggat    58140 aaatggtgtc tcacgatttt atacttcttt tgcacagagt cttcgttttt aactctaagc    58200
aattgtggat aattaaattt ttatagaagg aatttttttc tttagcaatc ccattagggc    58260
tctgttgtac ttgtccattg cctcataaag gaaaaggaa gaaaaaaaaa aaaaactgcc     58320
acatctgtgc cttaaccatt ttgtgcagat tctctcccgc tccatagttt atgggatgcg    58380
ttcatgaccg gggaacccta tattggtgcc ataaatgcca aggctggtaa aagcaggaga    58440
gcagcagaat gccttacttg tgaagagaga cggaataagg gatgagtgcc aggtcactga    58500
gggcagatag caaatggcct ctgtgagact ttctggtgac cacataaccg tggtagctat    58560
gagccccaag gacagaacag tttggttta gctggacagt gcaagagcca gagcctcagc    58620
ggagcagggg agttgtgaac cactggaaat cccagtggta cacctgatgg cccaccatca    58680
gaatgctttg aaagggactc ataaaggcag ggcatcaaag aacaccatca acttctcaaa    58740 cttttgactct ggctataaat gaaagggcag tcccaatctg tgggaatagg caacctcttt   58800
```

```
gttgactttc acactaatgg ggaaaatttc aaccccccac cccataacag cacctttgaa    58860
acagagtaca aggacaccct ggcaggatac ccacagcaaa ggtatgactc ctcatcagga    58920
aggacctcca tctgacctct tccactcaga tgtttttgtc cagtgctcaa aaggccaatc    58980
cccataattc tcctgcagcc tctgtgtcca cccctactt cccatcttct gttcagctct     59040
gtgaacatgt gtgatactga tatctgagca cgaacagcta cagagaccac catgtaccaa    59100
gtacagggcc acagcagggc cggccatgcc tcccttcatc ctcagagaaa gcttgggac     59160
acagaggaga ccttgagagg aaaggtctct aatgctcctg attatatcta catgacgtga    59220
tagaactttg aggagataat taatgtgtcc aaagctcatg gcagccaaat gatgaaaca     59280
tcagtctcct taccagttgc ctcctggttt gagaaacacc tggaaattac ctcaagtcaa    59340
attattcagt ataaaacatt tggggggggg ggaaagatac tttcacaaat taagtcccag    59400
atatcttgga aagtgacact tagacatttt aaatgtgttc tcatttgtag gtgaagccat    59460
ttagtgaatt ctcttgaagg tagttttaaaa tgtggttaaa ccatcaccgt ctaccatggg   59520
catcatggtc tggggacatg ttgttaaaat aggactctgc tatatgatag agaaccacac    59580
tactatataa gctagggagc aaggctatac acgaacttac taacaaaagt caggtggaag    59640
gaagagaagc agtagagcgg gctggccttg gatctgaaga atttctgagg cagtatgtct    59700
catagggcca tctgtctcag tattaactgg cttcatacca aacatattct ccatggatct    59760
caaccaaaga atctcaatta taacaagctg cctaatgatt ttatacatgg taatgtgggt    59820
acttttgatc taggctagag taagtagttt agcttatgct gaagattagg aaaagaaagc    59880
accacagggc acaatgatgt agacaacaag ggaggaaagc ttcggtcttt gtatttttca    59940
atagggactg gtgtgacctg aacacttgaa ccagtccttg gcctacacag gagactggag    60000
tgctcttgca atgcgaagca aatctgtgcc ttctacacta tttttggaag tgcaaggatc    60060
aaaggtcaca ctgttttggaa gactgggtgt tcagcaatgc ttgtctctgc catcttgtac    60120
tttaagcctc ctttgcaggt tgaattctag taggagaaat aagtaagttg ttgttacttt    60180
agatatacat tttattatct ataaaaatgc caaggttgaa caagatatta gtcataacaa    60240
acccttctat aataccttt gaatatactg ttttattttg ctttcattaa aacacacaat    60300
gtaattgtta gctttagatt acatatgtaa gacctccagc cctgcccaaa actatgcagg    60360
taataaccca catgaccatt tacacattcc ttcagcaaat gtatggtttt tgtctactta    60420
agctagacac tatcccaggt tctgagatga agatgatgag tcggaagttc tgatttacac    60480
tttagccaca gatccaagaa gatgttgacc aacttcacct gaccaaaacc cgactgtatc    60540
acaaatcccc tgtgctatta tcaagtacct gcccagcctc tgccttcttg agtttctagc    60600
tcctgtgagt ctggggatca cagggctccg gaaagcttgg ctggagcaat gtactgcaaa    60660
caggaaggac tcttacaaaa gaagtggaca gataagaaaa taagcaaatg gcctcgctag    60720
catgtctgct tcctaattga ctaggcctat cttggcttcc tgctggcctt gcccaggtaa    60780
cactctctcc ttttcttatc cccctccag cagcagcatt ggcgtgttct tctgtggatc     60840
caaagccatg tcaaagactc ttcaaaagat gtgtcgtttg tactcatctg tggatccgag    60900
gggcgttcat ttctattaca acaaggaaaa cttctag                             60937
```

<210> SEQ ID NO 24
<211> LENGTH: 58965
<212> TYPE: DNA
<213> ORGANISM: Homo sapiens
<400> SEQUENCE: 24

```
atgatggggt gctggatttt gaatgagggt ctctccacca tattagtagt aagtatcatt    60
tttgttattc aactttaaat atatagattg aatagtcttt gattttttagg aaaacttgta   120 taggaacgct aaatagcttg aagtattact ctagttaaaa gactaaaact tgttagaaaa   180
cattcagtag atgtatttaa tttcccctta tagaatcatg caaagttgtt ttccgattga   240
gctcattttt aattattttt aaagtcaagt agtttgtttt tgcataatgt atgagtgttt   300
ctctaaatca aatgaagtct ttgaattaga ctatgaaatt ggaactttc tagagaactc    360 tcggagttgt ttttaaagat ttcttccttc ttgacatcat tgtcaagcaa cgttgattaa   420
gaaggttttg tagtttcatt aaatcactta aagttgactc atatgtgttt aaaatctttt   480
taataaaggt aataatgtat taccatcata atcctattaa aaactaatct atgagaaata   540
aatatgtgga gtaattctga ttaatattga gaagctcttc attccacttt aaaagaagaa   600
ccccaagtga ttttgaatag agaaaaagct tgaaggtagt aatcattggt tctctttcct   660
ttctactcta gctctcatgg ctgggaataa atttttatct gtttattgac acgttctact   720
ggtatgaaga ggaggagtct ttccattaca cacgagttat tttgggtgta agtacagttt   780
atgattaaac attattttttt cagaaaacaa aatgcatttt attttccctg gatccttgtt   840
ttccctgaat ctctttttta tgtctttaca tgtggacagt caacactggc ttgggcacga   900
gcatccgcac tgtgcctgaa ttttaactgc atgctaattc taatacctgt cagtcgaaac   960
cttatttcat tcataagagg aacaagtatt gtaagtacta aaatatctga ataatctca   1020 actgttacga cttcctcata taagtgccat tgaaaaaaaa tgtactttat tatgaaattc   1080
tcagtaattc tgtttaaact tgggtttctt tgttagagat aacagaaagg ctaagacaga   1140
aaaacggtaa tcagtacatc tatctgattt ggctttggct gttgccattg atttcctaca   1200
tgacactcaa ctcattgcta aacagttttcc tgatatattt gccccatgaa gatggaagca   1260
ttataatagc tggaaccatc attgtttctg actgaaagaa gacagataag cttttgagac   1320
aaacgccacc aggaaacatc tctctgggtt ctcacccaca aaagcataat cacagtacat   1380
agattttatt atgtagattt taacctctac caaacataat gggatatttc tcaattatat   1440
tgatttcact gtgttgggaa cttacctgtg cttcctgtca aacaaaatag catgcagaga   1500
atgagacctt caaaaacttt taccaggtaa aatactgtat tatgcaggca tccctcattt   1560
tattgcactt ccccttattg ttcttctcag atactatggt ttttacaaat tgaagacttc   1620
tggcaaccct gtgtggagca agtatactag cgccattttt tccaatacca tgtgctcact   1680
ttgtgtctct gtgtcttttt tagcaataaa gtgtttttta attaaagcat gtactttttt   1740
tagacataat gctattgcac acttaataga ctacaggatg gtataaatat aacttttata   1800
tgcactggga aatcaaaact tttgtgtgac ttgcttattt gcaatatttg ctttattgca   1860
gtggtctgaa atcaaaccca caatatctcc gaggtatgcc tgtataatca tcatcatgat   1920
tttatgaata tttatatata gatgcatatt tgcctttgta tatgtaggaa taattttcag   1980
actacctaaa acacatgaat gaggatgatg gctattacct taaattttta aacaaagaag   2040
ctgagtgagg catgtatttt ggcaggctta ttcaagagtt ttgaattata aacagagaac   2100
taataagtca atcattttg agttgagagt tcagcaaagc aactaataac cttttgattt    2160
gcctgtttga ctaatggcca ttaacttttg tgtcacatag ccccacttta agcagtttag   2220
aggcagagcc tgattcctac tctcttaact ttcatgagat tgttttcact gcaattttc    2280 cataaatcag gcatattttt ttgttactct agtgctgcag aggaccgtgg aggaggcaat   2340
tagacaaaaa cctcagattt cacaaactgg tcgcctatgg gatagctgtt aatgcaagta   2400
```

```
agtacttatt aattgctcaa tggattttac aatatctgat gcctaacttc atagttttgt    2460
tttaactctg ccttccccaa gtctcaccct caggtaaaag aaaactttgc cctttatctg    2520
accctgtaaa ccttacacaa atgggttttt acattttcaa tttatactta cctatacgtt    2580
ttcccctacc aagacctcaa ttggtcaaag aaaagttggt gaaacttcat ttgcgaatag    2640
ttaagcttgt taataataca ataataaata cttacttgaa aaagggacac tttgttattc    2700
aatataattc actttggaaa taaaattgac ctctgttcaa aatctcattc acagtcgtag    2760
gaaaatgact gtcaaatagt attgtgggca ataaaaaaga aaaagaaaaa gaaagatcat    2820
gtgagccaag ttctgaatca tagtgaggta atggacataa aagggtcttg aaaagacatg    2880
aagctttatc ggcatataaa gtgttattgc tattattata tttctaattt aagaggaagg    2940
cactagaaat tagcacccaa ggccaaggtt aaactctgat gaggaagaaa ggaggaggag    3000
cagtcatcaa ccagcttgtg gttttgctgg aaaacaaaga cattgaaata aaaggctatc    3060
tgagcgataa ggagttatga ttcaggactg tttctctcaa actaatttaa ctataaaatg    3120
ttttcctcat ttgtttttat cctctcatgc ataaaaaaaa aagcagagta aaggaacac    3180
tcaaaacaaa tgtgaattta attaagcaac aagacatgac agacggtgcc cgagtgccaa    3240
ttaacacaac tttgggggtg cagtgagaca tgaggggaag atgctcccag tgactgtctt    3300
caacgctgga ttaaaccaac ctgagaactg ctttgtaaaa ggtctttgtg gtttgttagg    3360
aaataagagt aaaaagacat cgtgtcctag agaaaaccag ctcagagata aaggggagga    3420
aataaggctg gttcatcttt gtattccaag gcccacagta gtgctgagta tgcgtaggca    3480
ccaataaccg ttcatgaatg agcgaatgca tgaaggaata aagactcagg gaaagaaatt    3540
ttggctcagg aatggaaatc ttttccgcac cttgaaaatt atctaaaatt agaatgaagc    3600
tcccctaaga atactgaatt ccccatcatg ggtgatgtcc aaacagagac cagatcgctc    3660
cttgataggc tcatcacaga agcaattcaa ggaatctcca ggcttccttt aaaatcttaa    3720
atagcttgat ttctgcataa cacagtaaaa tggcaagaat attatcacaa tacaatagct    3780
ttaagacaga cttgaactct aagagaaagt tttaaagata ttacagagag aaggggggaaa    3840
aaaacagcca gcatcaaaag acatcagaaa agaggccggg catggtggtt tacgcctata    3900
atcccagcac tttgggaggc tgaggcaggt gaattgcttg agctcagaag ttcgagacca    3960
gcctgggcaa catagtgaaa gcccgtctct accaaaaatc caaaaatat tagctgggcg    4020
tggtggtgca tgcctatagt cccagctact tgggaggctt tggtgggagg atagcttgag    4080
cccaggaggc gaaggttgca gggagctaaa attgtgccac tgcactccag cctgggcagc    4140
acagtgagac cccatctcaa aaagaaaaaa aaatacaaca gaaagaaag caagaataa    4200
gaaaaatgtg ttatgaaata gttttctcct taaacttttg ggcatgtaca tttcttata    4260
tgtaatcgtg tatcaataat accaatgcat tagaaacgta taatgaatat ccccgtgtt    4320
aaagataccc tgaaagcagc tataactttc tgaaactagt gtggtcaggg ctgttttagg    4380
atggagtata atttagtata agcagctgtt gactaaaatc aggtaaccaa attattttat    4440
accctgcta ctgattggta gtgtgatatc tgagaagttc ctcatgctct ttcttctgtg    4500
gagttaaaag aatactaata caggccgggc gtggtggctc acgcctgtaa tcccagcact    4560
ttgggaggcc gggcgggtg gattacctga gatcaggagt tggagaccag cctgaccaac    4620
atggtgaaac cctgtctcta ctaaaaatgc aaaaattagc caggtatggt ggttcatgcc    4680
tgtaatccca actactggg aggctgagga aggagaatca tctgaacccg ggaggtggag    4740
gttgtagtga gccgagaatg ccccattgta ctccagcctg gcaataaga gcaaaactct    4800
```

```
gtctcaaaaa aaaaaaaatt tttcaatgag atgtgcagat tattgtcagg atcagagtta      4860
gttggaagtt tgcagaatac agggttattc acttgctgct attgcaaata aaatcaaatc      4920
caaagccctt agcctgacca agggctccaa tgaccatgca tgtgccccct gcctgtgccc      4980
cctgccacag tcttatctcc tgccatatcc ccctggcttt tcccttggg cacacccagc       5040 tcctaggagt tcctaagcat tctgtgcctt tgatccaggg atcccctttg cctgaaatgc      5100
tctgtcctcc tcatggtgct aaatgggtga gatatggcca tgcccaggac tcatatcctg      5160
gcctacctcc cccagcgcag cctctgaggg gtctaaggtc atactttcta ccacagagtg      5220
aaattcattc cccagaagct gatcacctcc agggctgagc ctgtgcctta cgcctcttgg      5280
ctgccctggt ccctggcgca caggaggtcc tcaagaaatt tggtgaaaac tgaggatgag      5340
tgagagccag caggcaagag aggttgaagg aatcactggg aatggtacag acacatatg      5400 catgagttgt tcagggagtc atgagcagtc tggggtggac tgaacagagt gtggggaggg      5460
aaaagattca acaatgtca attgtccaag ataatacatt cacattctgc tgcaaccaga       5520
gaaagcaggg tgctctttct ccctctttcc ctcacacatc cctggagaca atcaagtgtt      5580
ctctccggcc cccttcctcc tgaacccac tgctttgcca ggctcccaga tatctcctgg       5640
ggctccccca gcagggtcag aactgcaacc cagagcaaag tgcccctcat cccactcctc      5700
catggcgacc agcagagctg cggtgtttcc actccctgca aatgcaggag ctggggaga      5760 aagctctctg cttctcccaa accctgacaa agcaattatt acatttcaca tgaacgaaga      5820
aatgcgtctg gcaactgcgc ttttgggagg aaaaaaaatg ctaagccttg gtttcatgca      5880
aacacctctg cttttcacat tttcttcttc tggtagattc acttgggagc agctgaaaat      5940
gtccctgcgc ttattttatt agcatcgccc attatgctgc atttcaaata gcctgctggc      6000
ttaatagagg tgtgtaacct tggaaaaagt gcgaccacat cgaagtttgc atgccaacct      6060
ctaatttctc atccgttccc ctgtaagctg aactgcaggc tttaattggt caaatcatta      6120
aaggatgtaa ttagagactg gtggaagaag gcgagggagg aggagggaag aggcaaaaca      6180
atggtatctg taatcaagga catcacggaa aatgcagtga caggaactct tcttttggct      6240
tcctgccttc ctgcttgtct gcctatgata agagctgccg gagcattctt caaccactaa      6300
taaatcattt tcagggacct ataaccccat gggtataaaa atcatagttt cacagcctct      6360
tcgttcttat taatgcagat cttttctggag tccctggtcc acagcagacc ttgaagaccc      6420
ttccaattga aaagtagtac tttgagctcc agcttccatc aagggtgtc taaatagtga       6480 cccaggcagc tctccctggc agagtcggca gcttgcttct gccaggttcc aggagtgaac      6540
aattagccga gtgcagctcc tgatgagttg ctaaaattag tctacaaaca tcaataaaca      6600
taacaagggc agggtgagag gagagagcac agaataaggg tgcccagaaa ataaagattt      6660
ggagacccag gcttgagaat agccctaaag gcacaaactc ttcagtcctg accccctcaag     6720 gattgctcct aaccagttcc ccctgaggct ctggagcctt cagggaagct gcatcccag       6780 ccctgcctga caggatttaa tgtgatttac aaatgcgtgg cacacacagg gtgccagagt      6840
caacgatcct tctacagaaa tcagaccaca ggtttaaaag tttgcagcca aattctggct      6900
gcagaagcag agccagaatc tgtccctggg tccttgtttc tgaaggctgc ttaattagga      6960
ggtgactaac tccaaaatga ctgttatcac tgacaggcag gcagaaagac agcaaggaca      7020
gaccacactt ccaagattcc ccccaattat gctcactttg atctcctgaa aaataaaatg      7080
aaagaaggaa ggtaaaagaa cttctcagg gcaactggct ctaatagtag cctttatgat       7140
tttttttttt ttttttttg gttcactctt caatggaaag ctccttattt gaactcagaa      7200
```

```
gtccacatac caattaaatg cgcatgtgta gtgtttccaa aattgctgct ctcttaaaag    7260
tactttgggg agaacacaaa attgtagaaa gatccagcta tagcacctt tagcctggca     7320 caattgagtg ggttatggaa atgtgtgtct tgcggtcctc caagggcaga gaagtgcgta    7380
ctgtagaaag tccacagagg cccaggaaga gctcccccgc atagctaatg gcgttggatt    7440
tactgcaaga ctgaagagcc ccaattaagc cagagttggc tttggaaaca tgaaaacatg    7500
agctttgtgt ttgcattact tccatattgg tctacaaatc cctttagat gataaatatg     7560 ctcccagtta acttcagaga aagacacagg agccacacag ctggaagggg cttagataa     7620 ccttgtttag tacaatctac ccatttcaca gatgggaaaa aaagggccta aaagaagtta    7680
ggtgactgag aagtatcctc ttcagtattc tttctgttac atactaatat caaatctaat    7740
aacatgaaat gatattgatg actaagggag ggagaaatca aaccatatca ctgtttatc     7800 ccacctctgt agcccttgtc cctgtaacat aaacagcatg gctacttata ttttaaaag     7860 cctaaaatgt agaagggaag gaatagaaaa tacaatgtct aaagaagaac aaaaatagta    7920
tctcccctgg tgtctatcaa gtcacaacaa ttctgaattt agcggttggt atatctttag    7980
ctccaagcca agattgctgt aaaattagga tcagatctaa gaggaaaata aaatgtttag    8040
acaaacaaaa tcggcataag cagttttctc tctgagaatg cctgagataa ataaaatatt    8100
ccactttgta tgttctacct tgtgaaagaa aacaaaatgg aggtagcgag agcaagggaa    8160
catgtaagac atgaacttta aagtgtgtga caaatactgg agagaatagt ttttacaaat    8220
tccctcagaa gctgcctctt gaaaaccatc tggggctttc tcgtactcct tcattagttt    8280
cttcagctct gttatgggag acctggcaac aagaataagt aaatagttta atatctttgt    8340
tcattcaatc aacatactta aatttagttt aacagtgtca aattctcatg tggaaatcaa    8400
tctaacagaa aacaaattgc aatcaacaac tcattacaga gaagaagaac gttataaaat    8460
ataaagccag gcgtggtggc tcacgcctgt aatcccagca ctttgggagg ccaaggaggg    8520
cagattgcct gagctcagga gtttgagacc agcctgggca gcatgatgaa accccatctc    8580
tactaaaaat tagctgggca tggtggcgtg tgcctgtaat cccagctact tagaggctga    8640
ggcagaagaa ttgcttgaac ccgagaggca gagtttgcag ttagctgaga tcgcgccatt    8700
gcactctggc ctgggtgaca gagggagact ctgtctcaaa aaaaaaaaa aagttataaa    8760 atataaaaac ttatcctgca aaaagaagt tataaaatat aaaaaacgta tcctgccttc     8820
tctttctgac tatcatatat ggattatgca atggtaaaca catcagttaa cttggtccga    8880
agctcagttt ctatttctgt aaattgggaa cagcttcact ccctgtctgg agtgccctag    8940
tctatggaga gagaattaaa gaaagctagg aggagaggag taagggtcaa ggggcagaat    9000 ataaaggag catttacacc aacctacaat gaggactcca aatgttgtga tcagccagaa     9060
gccttagaaa cggttggact ctagattaaa gacaccaggt aaaccattca gagttttatc    9120
taagcccata gaaaaactg ttttcaatt aaaaatcagg tatgataatt gctcattagt       9180
caaacgaagc aatacagctt gatggtcaaa agatggggca ccgagtcacg caaatcacta    9240
aaccactttc atcacgaatc aacagcaaat tccttaactc tttgaatact ggtctgtcga    9300
atgagaagaa ggctgatacc tgaggagggt taaatcaggt aatatgccta cagcatttac    9360
aacagtgtct gttgtatagt aaatattcaa tatgtttgct atgagacgta ctacctgctt    9420
tttaaagacg tcgagataat tatcagaaaa cagcaattag gaatactgga caatgtttgt    9480
gttcaattta gcaaatagtt tccattttgc atgtagcata ttggaaaaga ctcctgctag    9540
ataagccttt ccagctttgt ggatgctgag gctaaacaag gcagcacctt catagacatg    9600
```

```
gctgtatatt ttgacaaagc acctagggag gaaacatagt acttcgtggg tgctaacctc   9660
tctgaagcca taaggaagca gtaaacatca cgatgcggaa acactatcga gtgctttgcc   9720
ttccttgggtg agcctcaacc tgaagtatat ttgacttgat tttcaactta aaggctaaag   9780
aaaaatgtgc aatatatata tattatatat atatatatag catatatata ttatatatat   9840
atagcatata tatattatat atctatagca tatatattat atatctatag catatatata   9900
atatatatat atagcatata tatatatata tgtatatgtc agcagagaaa acactactcc   9960
aacaaggttg tatttataga ttgattttcc tacccttca ttaccccttc tacctttctt    10020
taatctcatt gtcactaagc aaataattgt caaatacaaa ctggtgctga ggtttcaagg   10080
atgaataaag tccatccttg agaagtcaaa gttcatcagg ggtgcaggga taaatagata   10140
ctgcaacagt aatatctgag aaatgctatg gtcatactat catttgtgct ggtgaaattg   10200
aagaatgtgt gatagaagtc aacttttgaa gtgagttgta aggcatgcgt agaaaatttt   10260
gcaaatcaga aaagggagtg atagcaggaa ctcaggtgac aaagaaaaga ggttgcatag   10320
aagatagcat ttctaaataa atctgctcct aggaccacag ggaccaaaat gacacgaata   10380
ttctcagaag ttcttgctgt ttcttttttcc ccatcacatc ttcttccaca cctcaaccca   10440
caatgtacaa ccacggagga tcccgtaact cactcacaac ctgtatagac tttatgatag   10500
tcataggccc tgctacttct cactgtgggt gcagaagaaa agaagatatc aactgggaaa   10560
ttatctatac cccgggcaat gaattctcat ttcacacacg aatctgatcc caatggcagt   10620
tatcaactgg ccacccagcg ggagtttcat ttgcaggaaa agcatcggta tgttgttgtc   10680
tagctgtgac tgctggcttc ccaacagatt tggaaagagc agcatcagac acagaatcct   10740
caggccagac gatgctgggt tcttaagctt gttctcttca tttagaattt agacaccacc   10800
aagtcccaga attagaaagc tccatttact tcttaagaat atacagaagg tacatttagt   10860
tccataaata atggcttatt tcaatccacc agaaataaca catgcaaatt tatgtgtgaa   10920
tgtgtatgtg caggggtata tatacatata gagtagtccc tccttgtctg cggggtatac   10980
attccaagac ccacagcaga tgcctgaaac aggggatagt actgaccccg actgccatcc   11040
atcagaacat gttcctttc atgtcttcca cccacaaatg taatgctttt ttcatcataa    11100
ataagcactt atcatgcatt gtggctgtaa cttttgcagt ttgaggtgtg acagcgaaac   11160
tagcacaaat gtcttttttc ttcttcacaa tttcagatag aagatttgtt cttaccgtag   11220
atcttagcaa cttccacata cagttttttt cctttcctta ttaagtagag aactttcacc   11280
ttttcactta aaggaagcac ctgatggctt ccctttggtg tagccgaatt gccagcatca   11340
ctacttttcc gctttgaggc catttttaag taaaataagg atgactcgca cacaaacact   11400
gggataccgt gacagttgat ctgataacca agagggctac tggatatgct ggacaaaggg   11460
attattcaca tcccaggtgg gacagagcgg gatggcatga gatttcatca tgctactcag   11520
aatggcatgc agtgtaaaac acaaattgct tattcctgga attttccatt caatattttc   11580
tgattgtggt tgacctcagg taactgaaac tggagaaagt gaaactttag actgggggga   11640
ctactgtata ctaaaatgtg gaaaggaata aacagaaaat agagtggctg aaagagaaca   11700
aaaacaatat ctctcctggt atctatcatt tacattatat acatacatat cagcatgtat   11760
aatgtacagt attctagaat aatgctttcc gatttcttaa gaagttatat atacttgttt   11820
cttttagaat tatttcatat ataattatgc tgagatatca taacatttat tccacttcca   11880
tgataactat acactttaaa ttatgatgaa ctgagattta ctttatttat taatataact   11940
taaataaatg tggagatttt tgtacagtat catatacata catatcagca tgtataatgt   12000
```

```
acagtactct agaataatgc tttccaattt cttaagaagt tatatatcat tatttctttt   12060
agaattattt catatataat tatgctgaga tatcataaca tttattccac ttccatgata   12120
actatacact ttatgatgaa ctgagattta ctttatttat taatataact taaataaatg   12180
tggagatttt tgtacagtat ctttggaagt attcaatcca ctccactcaa agcactggga   12240
aagatgtgta aatacatcac ttttccttgg agattacaaa aaccagaaca gagaaacttg   12300
agcacagaga cactgtatTt tttagtaact agggagaaag caagccacag ggtgcatgtt   12360
tggtgtcatc tccttgtcct agccatccac atcgtggcgc atttcttcaa cctggaacgc   12420
taccactgga gccagtccga ggaggcccag ggacttctgg ccgcactttc caagctgggc   12480
aacacccccta acgagagcta cctcaacccct gtccggacct tccccacagt gagttcctgc   12540
atgctaacaa gcttctcccc tgaaaaatcc gtccttttcc agtcctctaa tcaggaacgc   12600
tatattgaaa agctttttaat aaaagagctg gagaatgaat ttatatgtga atttgttttc   12660
aatttcacat ttctaaaaa gttatttttt tctcattaat gttgctggga agttatgagc   12720
aaggagaaaa agatatgtca cctaattaat ttatatatat atacacacac acactagaaa   12780
cgcagtaacc tgttaaattc ctaatatttt aaaatttaac attttaaaag cagttcagga   12840
ttagatattt tttcactgat gttagactca taaagaaggt gaagtgccag ctaaacacag   12900
agattataaa ttggatgtct tcatttttcaa tctgcagatt gttttccgga tctgttctcc   12960
gaatgcctca tacattggca catatgtgaa tagctgcttt gccaaatcag atactgggca   13020
aagcagctaa tttcataatg agacctgcat ggccagtgac atcattaatg ctaattacct   13080
gtgtgcacag actgtcagca gctatgggga acaaaaagaa aaccaaaaat gtagccacag   13140
caatctatgt tccgagatga agacggtcgt ctcccttaat tcaccectac ctctttcttt   13200
gtggttgatc tcagtttttt tccacatacc accatattgg catatgtgtg cagcacgttg   13260
accagactaa aaatatcttt attgcccaag aaaagccgta aggcaataca cttcagcaat   13320
gaaaatccct ccattcttat ccaggccatc tctttaagtg accatttccc catgcagcct   13380
tatttaaaga acaaaaactc aaaatctggt tttgggacac ttgttccatg tcatgtcccc   13440
taattagcct aagataattt tcaatatcag gccattgatc aggtttagtt gagctacctt   13500
ttctttttatt tttttatttat atttatttat tttttttgag acagagtctc actctgttgc   13560
cagagctgga gtgcagtggt gcgatcacgg ctcactgcaa gctccgcctc ccggattcac   13620
gctattctcc tgcctcagcc tcctgagtag ctgggactat aggcacccgc caccacgccc   13680
agctaatttt tgttattttt agtagagacg gggtttcact gtgttagcca ggatggtctt   13740
gatcgcctga cctcgtgatc cgcccacctc ggcctcccaa agtgctggga ttacaggcgt   13800
gagccaccgc gctcggcttg agctaccttt tcttagctga cagctattgg aagcaaaaat   13860
ttcacacttc cgaatcagaa ctacagctgc ccttatgagt ggggatgcct ttgtgtccgt   13920
ccattgaatc acagcatttg tctaggcacc tactgaggtt gctgtttttc cccactaaga   13980
cgctggaaaa tccattgcta cacacactca agaataaatc tcaacatttt gcatagtcta   14040
tataataaat agtatttatt aaaaatactt ttcaagcaat gtgattatat atcttactag   14100
aaaaataata aagctactac caatgcagta atttcaaaat tttagaagca atatactatg   14160
taagtactaa ttaagctcag gaaaccctct aatttagggt attggagag atgagtat   14220
caataacaca gagtgtacat tatagagcat ttttagagat gcagtgggat tgttttggag   14280
gatacattgc aactgtaacc agtctataaa tgtgttgcaa gaaagagaca tggcgatttg   14340
ccttaatagg caaggaagaa tgatgtgaaa ttagcatatc atatgatgta aatggatttc   14400
```

```
taaaatgcct gaaggtactt gagaagaaaa tattttaaat gtttgagaca tacccctttc    14460
aattttattt ccactctttg ctctatgaag aaaaaataat gaagaagtcc ctgtccgaat    14520
tacctccaga tctcaaagcc gcccaaatta atgagatttt actgacaaaa gatatagtga    14580
gtttattgag ctcatggccg tctcaacgat agtaacacaa tgtatgaata ctaatgactt    14640
ggcaagaaca tgggaaactc acaatgaaaa taaactgctg tgtgatgcta ttctaaaagg    14700
ctattttact gtcccttgca ctcacaggtc agaattctgg ccgtttagcc gtgtccacca    14760
gataagaata gctgtacctt tattgatcac ctaggattta ccaagcctta ttccaggccc    14820
ccggagatgg cgtgaaagaa atgcaagtca tggtctttcc aattaaaaag caagagcaag    14880
gaacaactac caagggaact gagtgtgcag ctgctttatt aggaacgccc caagggacct    14940
ctcaaaaaaa tgtgtttatt aatgttaaaa tgcaattaag catggtgatc cacatagtta    15000
ttttgaagat taaaaactta aaactcagat ttattttgca atattttatc ttaaaatgct    15060
cttttcatgc tgccctaatt tcaattcaac ataatcactt tggtttttt tttttttgtt    15120 ttttcttttt tcccattttg ttattgttgt tgttgtttta gacacagggt ctcactctgt    15180
ctcccaggct ggaatgcaga ggcagcatca cggctcattg cagcctcaca ctcctgggat    15240
caagtgatcc tcccacctca gcctactgag tagctgagac tataggctca aaccaccatg    15300
cccagctttt tttttttaat ttatttatgt gggttttttt tccagtataa taactttgat    15360
gtgaaatgat atatacaaaa ataaaaaaat gtgattgatg aaatggtatt ttacgaaatt    15420
ttagcaaagc aagtaaccac cgtaagctgg tgggaagggg gtggaagagt aagctcgctt    15480
cttgagttgc acctgcatcc tcgctgaggc taacgtgctt ctgagtgaaa cattgtgaac    15540
ggctccctgc ttgaaatctc aagtactggt cctaaaaatg aaaaaaaaaa atatgccagg    15600
atatttaatg tcaaggtgtt ttttttgtt tgtttctttt tttgttgttg ttgttttttt    15660
tagaacacaa ccactgaatt gctaaggaca atagcaggcg tcaccggtct ggtgatctct    15720
ctggctttag tcttgatcat gacctcgtca actgagttca tcagacaggc ctcctatgag    15780
ttgttctggt acacacacca tgttttcatc gtcttctttc tcagcctggc catccatggg    15840
acggggtaag tccatactgc gctcctctgc aaggatttta tctctgagag tcccaaaata    15900
atcttagaaa gtcctttaga tgaaggagcc ggcgtgcggt gactacagga ctcgtataat    15960
gtgtgaaaag cacattgact gtggcaaacg ctttttcagt aacactgaaa ataagctaca    16020
tagatggtga agtattatat ttattttcc tctctgactc tgttagtgag tcttggcatg    16080
tttataaaat tcaggaatcc taatgaatgc aggatgacag tagatctatg tttcattcag    16140
tacctgttct gccatccaat ttatgtgaga ttactcagga tatatattt tgacaccaag    16200 atttcacttc tgcttaacca aaaccgtcaa ctaggaaacc cactgttcgg gcagggacaa    16260
tgtgtggcat gggcagtctg tgtgtggggtc cagaagcagc tctgacacca gttatcagag    16320
tgagcccttc aggtcctctg agcctcagtt tccccatttg acctctagga ccccattttc    16380
ctcagacatc ccgtaaaaca ctgttctggt attcaatacc tgcctgatat ggttcatctc    16440
ttcttcagga agctagcata gcccctgatg tgttcaccct caaatataat gcttttcaat    16500
cctttaaata ttaataaatg gccctggact aatacatcaa ttgctgtctg tgaactagct    16560
tgtcccttta attatttcaa aaactgattg ccttttttc catttacaa ttttcaaagc    16620 acattcatat acatgatcaa cttgaccccc acaacagtcc tgtcatgtag agaaggtgct    16680
gctgtcccca tttcataaag aggaaaaagg tgttctgagg gttaagtgat gccctcaagg    16740
tcccatgatg aataaacagc agagtcagat ccaggacgcc agtctttaga ctatcaatca    16800
```

```
gacctttact ctggtttgca agcccctgaa gaacaagtct tccattttag gaattaaacc   16860
ttcctcaaca ccagcaagaa tgtggccagc aatgttgcta atgccctttt tggcttgcca   16920
gcagcaactc ctctgttccc gcaccacaga ataccctctt ccaccoctca ttctcccacc   16980
attgccaccg ctgagcatgg agggtcctgt cccggaggtg gcctccgact ctgcgcggac   17040
ctggaagagc aagcgcatag ctgcagagtg gcatggccta ggaagtcaca cctgccttgg   17100
tgactctggg tccatgtag ggcccacaga caacgctttg ggatttgccc ttccacaagt   17160
caacaacgcc tccaatctcc ctcctcaccc ttaatgctcc tgtcttctca gcccoctact   17220
tctggaaggg ggtggcagtt ctgccgctgc cactgcctgt gcctaagact ctcccgtgg   17280
tccctcagct ggtggacaga aacacattct ccacggaaga agtgcccctg agggtgcatt   17340
ttaccctaaa agactgcctg tgcctctgct gagccttagt aaccgggtca gtccacattc   17400
acccgtactc tgctgcctgg ctagaggctt tccattctct ttcagctaga ggtctctggg   17460
attggctctt ctgaatgtgg aaatctcaac attccttttt gtacttggga tgggcaaggt   17520
ggatggtgtg tagacccagt gtgttccaac tcagagactg tcagtcctcc ctttctactg   17580
ctgattctgc ccccgacgcc ggggttgtta acccctgaag cacatttatg aggctatcta   17640
taactcaggg gaatctagaa gccctattca cagacatgat gtgcttaccc ccctaaacat   17700
acgtcccccca catccacacc ctggtgcatt gtagaagcac aagagaattt caatgggcag   17760
tgtttcgttg gagatatttt tgatatccaa ataacatctc ataagatgaa atttttagtc   17820
attttaacct agttgaaaag cttatttag gataagggcc tcatttaatc ttctcagtgt   17880
gaagtattct acagctactg tttacagcga aagcaatttg caaattctac acaaagtgcc   17940
aagtgaaagt aggattattg gaatgtgtta aggcccacta atcttcctat tatgggatgg   18000
catagatgaa gacatttcaa acgttaaaa tgtttaaaag atacagcatt tgtggaatga   18060
tatgaggctt cttttagaca ctatggggaa tgctgcctac agcctgagaa tgaaagtgtt   18120
aaagtatctg gaatctttcc tctgactctc acttactatt caccctgcct atgtctgggc   18180
atcatttgta cattggagat ttacagatag ttttttctcat ctaactcaga gggatgttat   18240
caagtttgga tggcttccat aaaacagact gggacaaaag ccaagatgtc agttctagct   18300
gacaccaggc tgttttccaa gggcgtatta ctgctccttc ctcccatgcc ctgtgatata   18360
acaggggcca caccactcca caggctgtcc aggacataag tctgtgtgat gctaaggttt   18420
ctcagtctag agtagcatgt ttctcaaaac agatcaatgc atttcattca caaacaccta   18480
ggaactgaac aattcccaga ttccctgacc ttgatgtctt gggctttgct gtctgtgcac   18540
caagaaggaa ccctaggagc ttgtaccaaa gctacttgtc aaaggtcagt caggagtgca   18600
ctcatggcaa atataatata gcaggattat ggactcttc gtccagtgct ccggtcatta   18660
ggactgcctt ctcttttccat tcctaaatgt atcaataccg tcttgaagac acactccatt   18720
gtgacctgtt ttgactgagt caaacactgg cttgctggtg gtcactagga ggaaaaatac   18780
cattcttccg gtattttgac tccttcactt gaagacttct gagcattcag aaacaaccca   18840
aggagggtag aagttaaata aatctgcaaa agaaccaaat agtacaaagt tagccaatta   18900
gcccaaatca gcaatcagaa caagatgaaa cctaattaaa ttcaacagtc tacaaaagga   18960
tgtgttcaaa caatttccct tcattatgaa ttctctaata tagacacttt caatttaaca   19020
caggatacca cagaggggcc cttcttttct gggatcttca aagttactcg aagcttctta   19080
aatgcttatt tttaaagaag ctgggggaaa tgaatgacag cccgagtttc aagaactgga   19140
agtgatattt cagagctcac tgtaggatat ataccctgtgg gagaacaaga ctgctcaaaa   19200
```

```
tcagtttgac gttttttgct ttttgttttg ttttgctttt cttaaataac aagtcggatt   19260
gttcgaggcc aaacccaaga cagtctctct ctgcacaaca tcaccttctg tagagaccgc   19320
tatgcagaat ggcagacagt ggcccaatgc cccgtgcctc aattttctgg caaggaaccc   19380
tcggtaagaa tgaacccagg agcttttaaa aataaatgtc accacagtta aaatacagag   19440
tttttatagg cttggaaaaa agaaagcaca tttcaccact agacaaagcc aactctttat   19500
taagtgtgct aatggagaaa tcaagttaca gataatttt aaagaggttt actgccaaaa    19560
gcactatgtt cagctttgaa atgtattctt ctacttacct ttaaatacta gtgtctgata   19620
tggtgggaat tcataacagc acaatgatgt ccctggagga gtcagccttg ggcctcacca   19680
cccttctttg tgctccctgc atccttagcc acctgtcctc tgcataactt ccatcccagt   19740
ctgagaatta ctggcacccc tgctcaaacc taggtcaatg aacagccaaa tgaggctcag   19800
ggcttcttta taagcttgcc ttctttcttt tgacaacttc aaggatcaaa aacttagtgt   19860
gtcaaacgca tttacttctt gttctaatta agctcctgta actgaaataa tgatgatgtt   19920
agccaagaag atacttaatt aatttgtgta gatgataatg tccacagatc tgaaaagtca   19980
gatttcccgg gtaggtggta accattacag ttggtagcat agggaaagag aagtaatatt   20040
cctatctggc ctcttctggt atcttagaac agtgcaaatc tttgggacaa ccaagtgatg   20100
cttgaaagaa aataaatgca tctggcagat aaacagtagg aggaaataag tgtccaaaaa   20160
tacatcactt aaaacatgga ataacagggt ataatagtat acaaatgatg aagatttagg   20220
aaattaagtc atcaacatat gaagaatata agtgattgcg ttgtttaaaa aaaaaccct    20280 caaatatatt aaattaagca ctggatttta agggtgaaag tactaggagg aatgattaaa   20340
accgagagaa ccggaataga tatgcccatt agactgtggt tcttttaatg gccggtatag   20400
attgtctctg tcttaaactc aactctcagt agccactatc caacctgcat attaatgagg   20460
aacatgaata cctctctaaa attttcagct acagcatctc cataaaaaaa tcaatactcc   20520
cccacacctc atgaatacag accagggcct gctcccagca gcgtttgccg gcattaatta   20580
tcattaagag ggggccttgc tcatctctct ctaactctcc cctgctccac ttccttgcac   20640
acccaaactc agggtgtcac tctctcccat tatttgtaat ggatcctgat tcaaagcgtg   20700
tgtgggctat gcaattaccg cttggctgaa ctgtacgata ttctctctga tgtcttatag   20760
acactgaatc cgaaaggcat cccaaggaca aggaagggtt cctgcgcttc actgcaccac   20820
acctactcgg tctctacaaa gctccatttc tcttcccttg cctctcttaa ctcagggcgt   20880
tttcacggtg ctctgatcaa tagaatatgt atcatttctc cttcagcggt tcactgttcc   20940
cagtgttagg acagataacg ttttgtacct cacctcgtgt aaatggaact gattaaagaa   21000
accaactata cccggcagtc cctcctcccc tacttgtctt acgtggaaaa tatcagagac   21060
caggtctgat ttgacatcac caaaatgaag tgtgtgatgc cccaaactct ctaaaatggg   21120
tggggaagat tatttgtaaa aatatatgaa gactgagtgt cttgtccaat atctcttctg   21180
gcccatttag aaagaactgc attcttgctc tcatttctgt aaacatccaa agcaattctc   21240
aaaaagcttt ctggttcatt caagcataag agacctaagg attccttgc tcggtccaac    21300 cccatccttc ccagggacgc ttcctacatt tcccttactc tgttcatctt cgcagcttgt   21360
ctcagtctcc ctttccagcc caaatgcact gacaaaatca ggactccaga ttcctggttt   21420
gctgctgatg caatccagtc tcaaaagatg cctggtcgtc ctaggccgga gaagcacttt   21480
atgtcattta accacagcat caactcatcg taaccataag gctgacactt tgtaattact   21540
agggaaagct gttagtggta aaggagaaag ccctgatgga ggtagagtca attcagcgaa   21600
```

```
cttcaccgag tgcctaagtg cattgcttgg caatgcagta gacaggattc agacacgtgg   21660
gacctgcccc aggagatctg attgtctaga aaaagaggct attcataaac acacacataa   21720
aataaaatca aagccagcat gttcttattt tctggtagga atgaaaaacc aggagtgaaa   21780
gtgaaggaaa caagtttcat tattgctgct tttgaatcaa catcgtttta tttctatcat   21840
aaaatactca ctgtagcgtg acttttgag cattttttga agaagaagaa aagaaagcca    21900
agaagccacg gagtatttta gcattaagga aacttagata ctaaatagtt cttccccatt   21960
atttaatagc tgaggaaatt gaggtccaag cagtttcagt gtcttaccca tggtcacaaa   22020
aagcattccc agtaaagcca ccttaaagaa ccagagcccc taactctgtg gccatgaact   22080
ttctcctcca ttcacagcat tcactctaag tctctggctt ccataaccgc cattttgtca   22140
gcactctgct gctagctgct acaagtacat agccccaacg ttctacttat ctctgtgaat   22200
aaagccaaag tgtttaagag cttggaggga actaataat aattttctcc agctagttcc    22260
cattttacaa acaggacgt tatgaacata ataaatctca agatgtgcct agtggcacag    22320
agtgaggggt ggtggcccca aggccagaat ccaggtcttc agacacccag cctagcatct   22380
actttgacac acggccctct tgctctgaat caaggcctcc ttgtcttgat tctctcttgt   22440
ctgtcccggg tatcactgca aggacagttt cctaatattc atccctggcc atctctccct   22500
caggccctga cttccagggg ctccaggcac aacacaggta acgacactgg ctacttcctc   22560
ccggagcaaa ggatatacta agattgagat ggagtcgggg attaatagct tatattctcc   22620
tacctgaacc atggaaagaa aaataatcca ttacatttta tcaacgtgga aaatatcaga   22680
gatcgtgtct gatttgacat caccaaaatg aagtttgtga tgccccaaac tctctaaaat   22740
gggtggggaa gattatttgt aaaaatatat gaagactgag tgtctttgcc agtatctctt   22800
ttagcccatt tagaaagaac tgcattcttg ctctcatttc tataaacatc caaagcaatt   22860
ctcaaaaagc tttctggttc attcaagcat aagagaccta aggattcctt tgctcggtcc   22920
aaccccatct ttcccaggga cgcttcctag atttccctta ctctgttcat cttcaccacc   22980
tcatccacag catagggga caaaaggttt attctctttg ctgttctgaa cacattgctg    23040
ggccctactg aggcagaaaa aataagtggg tcaaattgtg ttgccttgtg ttgcccccat   23100
aggtctagct tttatgaggc caagagcccc cccaggaaaa aaagcagaga gggttgatgt   23160
aggtgagaag agggaccatg cgaagagacc cagaaatcaa caaaaagcaa tagacaaaac   23220
gagaaaggtg actcaaagga agtaaaaata atgctaaaag acttgtgacc catcaacaga   23280
agagacagag ccagatgact ggtcaggag cactgagtaa tgagtcaatc ggggaggggt    23340
ggtgaatgtc tgagttctga agaccgagac atccttcctg cccccacccc ccgccccaga   23400
tactattcaa ggagtaaggt ggtggattta gaaaacctag gaggaagtgt agggacatat   23460
gaaaaggctt gagttctggc cctggctatc tctggtccac ctcagactct ccaggcaact   23520
cagacccatt cccagaatgt caggattttc cttcttttaa ttctaaaaga attagaggat   23580
attgaatgtt cccaatacaa agaaataatc agtgtttgag atgatggata gagtaattta   23640
ccctgacctt atcatgatac attgtatgta tcaaaacatc actatgtacc tcgtgaatat   23700
atacaattat tatttgtcta ttgaaaacaa taaaaatttt aaaagaaaaa aaagaattaa   23760
gagtagattt ccaagagcat gcagtatcct aaaattcaat gagttcatga gtttctaatg   23820
ttttggaaaa caagcctcag tatcaattta gcgctggaca gaaaggacca cgataaatatg  23880 gcaatgcaca tggaggtag cctgggtcc tggtaagaac tcaggctggg tagtcaggca     23940
tacctgagtt cacatctcta cgaaacacct tcgtcccttt atgaccttgg acaatttggt   24000
```

```
tgatctgact gagtcttaac tccttcctct gtaaaatcaa ggtaatacat atgcctcatg   24060
ggattgttca gtacaaatag aactcttcaa aaattgtaac ttcccatttc ttcccttcca   24120
ctgaggaaga caccttatgt tgtacagagc tcctgataca atagcctgct ggtaaattga   24180
tcatcagtaa tgcacattat actcatcaaa agttaacata gcatctgatt tgtttaaaat   24240
ggacattttc accatcacaa ttctctagac aattattgag ccttttgctg tgattagata   24300
aacttaaatt taaggtgcca ggaaattgac tttatatttt actccaaata actgtgtgtg   24360
tgtgtgtgtg tgtgtgtgtg tgtgtgtttc tgtgtttatt caggcagacc ctgtagttgt   24420
gatgcattct tggcccaaaa aattactatt tgagattttta aaatgtaatt tcttatgtcc   24480
tgtgttgggt gagtaatgta gctttgactt tggcttgagt ttgggagcat ttacgaccct   24540
atcatatgta atataaacat caatctgctt ttttatttct ttgcaaattc aattatttct   24600
aattacataa aggcatcatt gatcaagtaa gcataaaaac caatatagaa gagtttaatc   24660
tcttaaataa gcttgtagac ttcaatataat aattgaatgt tatagtatat aatacaagga   24720
gacatctttg ttgctgataa ctggcccaaa gttaaaggaa aaatatctaa tccccatcat   24780
gttgtatatt gatttggttc aaattgaaaa tatttggatt ctattttcat ttcctttttc   24840
tctctctctc tgctactctc ttcaggcttg gaaatggatt ttaggccctg tggtcttgta   24900
tgcatgtgaa agaataatta ggttctggcg atttcaacaa gaagttgtca ttaccaaggt   24960
atgcatgtag ctttatgtct gaataaaagc ctgagtgtag atgaaaattt tttattagcc   25020 caaatttta atttgccatt tttattgcag aactgtctgt aatttagagg ctcatcttct   25080
gttctaataa ttgcttgtat cctgagcatc ttttagtgtg actaattttg ctgaagacag   25140
ggatcagggc tccagacggc acacagaatt ctgataaagg tttattgtac agcactggaa   25200
tgatctgctt tgtctttatt ttgctttctc tctaggggga aatgcaaggg gagtgagtgt   25260
actttacatg ggtcatagtg acttgaagga taatcacttc ttcaccacgt aaaggcacaa   25320
attttgcaaa caaataacat tttcaaatct atacactctc actggggact accaagcaga   25380
ggaaagggaa acagtcacca taaggttcag agcaagaggg accactgtgg ggaagaaaaa   25440
tggagatgaa ggatgaagat agagttctac cctcatgagc agcatgctcc tggtagcatt   25500
tttcagtctt gctccccatc ctcacatctc tacgtcctca caatgtttac ctcttgctgg   25560
aggaagacgg gaaggggtag accaagacca aaaaaatgca tgcctaggag agtgaaaagg   25620
tgccaaatac tctcccccag cttttgaaat gtccaagaag aaactctccg ttagccaagc   25680
ctatcccact ttgctaatac aatttttaaca gaatcctgta tctctgtagc cgccttcatg   25740
aaagcagatg tatagaaatt gcttcctatt tctgctttaa gctgtttctg tgttgctgtt   25800
tttaagttaa gcaccaaagg atgtcaggct gtatcaaaag ctagactgta aaacttctgg   25860
aaacctactc gagctgttac gagggagacc atttaacagc aatgtcagaa cagataccag   25920
tagggagagg gaaaacttag aaccaatgat gaaaatgctg tgaaattctc ttttgaacgg   25980
aaaaatactg tcacagtatc tagatgctag attttgttcc cttatacctc ttgtcacaaa   26040
agaagacagg agggcctgga gagatttttc aggaaacaag attgaaatct aagaagggaa   26100
attagctctt tccctctgat aagcagtaag tcataaagct tttataaaca ctactagaaa   26160
ccttgtccaa tgcttcccta catctaaaac tcagagcgga gtcaggacac aggatgagac   26220
tcaaccaaaa agaaaacaaa acaagaaaag agtttgaagt gagtttgaag attgttttc    26280 acttagcctg aagaaataag aggggttaatt cacaagacat tgagaaaaga tgcagatcat   26340
tgaaaaaggt aacaaaatgt tcctagatgt taaaaacaca gagataatgt ggtgacttat   26400
```

```
tttaataacc ctaagcataa taatatgcaa gcttctactg tcttgggtct ggttgactgt    26460
gctgtggaaa gcctggccat tggacacatg gactcacatg ctgggcacca attgcacctg    26520
ggtgcagcta tttcaaatgc caccctctga aggagaggag catcattctt gctggagttg    26580
caaacacaga tgtgaaagcg atggcacata tctttgggag ctaacagcag atgggatatg    26640
taaattacac ctgaaacaag ctgatctaaa attttcaaca cctttgatgg aatgaaaggt    26700
gtttctttat tatttcgagg acaaaggcaa acaactctct cactctcaca taggtggtaa    26760 gccaccccctc tggagtcctg gaacttcaca tgaaaaagcg tggctttaaa atggcgccag    26820
ggcagtacat cttggtgcag tgcccagcca tatcttcgct ggagtggcac cccttcaccc    26880
ttacctctgc cccccaggag gactttttca gcgtgcacat ccgggcagca ggagactgga    26940
cagcagcgct actggaggcc tttggggcag agggacaggc cctccaggag ccctggagcc    27000
tgccaaggtt cgtgcccatt tctctcatgt ataaattgca gtattataaa aagtaaggta    27060
tcttaatgta tcaacatgct acctgattca gcaatatctt tattaaatgg tgagtttgag    27120
actgtgtcta aatttgagaa tgtgtgtaaa aagtataatt ttgtagactt ctaggagaca    27180
cacatctgtt cctgtaaaaa aaaaaaaaaa aaagaaaaa aagactaatg ttcagccaag    27240
agagggtgat ccaggaagga ggtttctctt ccaggtccta aagcatcacc tggttacttc    27300
tatgcagcct gcaatgagtg agacaactct gggcattttt ttctatcaca gtctgagttt    27360
tttttattgt atttgtaaag tcaggtcttc ataacaagga tgctatgttt ctgtgtcctc    27420
ttcttataaa gacccaagtc atattggata taagggccca taccactcca gcatgacctc    27480
atcttagctt tattcattat gtctgcaacc ctatttctaa ataaggtcac atcctaagta    27540
ctgaggttag gactttaaca tatcaatggg ggacacactc aacccacagc atcactctat    27600
tcagaaaagt ctgggctcac gcctgttatc cgagcacttt gggaagccaa ggcgggcgga    27660
tcacttgagg tcaggagttt gaggccagcc tggccaacat ggcaaaaccc catctctact    27720
aaaaatacaa aaattagccg ggtgtggtgg cacatgcctg taatcccagc tatctgggtg    27780
gctgaggcag gagaattgct tgaacctggg aggcagaggt tgcagtgagc cgagatcgcg    27840
ccactgcact ccagcctggg tgacagagtg agaccttgtt tcaaaaaaga agaaggagga    27900
ggaggaggag gaaagaaaaa gaaaaagcct gggcacataa cagaagtccc aaagtaaatg    27960
accactcctc agctctgttc agtaaacaat ggcttcgggt caattcccac tgttcataca    28020
gggttaccca aaagcatgca aagcacacat ttggggctct ggaagaacag ggacaccaaa    28080
aaaaatgaga aaaacatttt tggaagaatt tcatatttga aaagaagcat caagagattc    28140
ctacttctgc catccttgga gggtatcagg aactaccaag aagcagccac tgtcatgagc    28200
actgtggtag ggagctcggt agagacactt caaatgaag ttcctgaggg caggacattg    28260
tctttcctcc tcggaatctc cagtgcctac aacagtgtct gacatgcagt gcgtacagag    28320
gaaagatttg acaaaagaat taatgaagcc ctggggccaa tatggattct ttatctcatt    28380
tagtttgaca aatatttatt ggtgacaaac aaggtaccac aataaatttg agacacaaaa    28440
tgtagtcagc ttattgtcct gctttccctg ttttcgtagg ctactgagct gtaactgcac    28500
cctgggcttg gttgtatttta gtgggtagga agagtcacag gcctcctttc agacactggt    28560
cctgaagaat ggtatgccaa gccaagtaga agcatcatct gctcaagcca gagccccaaa    28620
tcagatgaga acacatgact attttctttt ttataatgga aaggaagcaa tgtaataaaa    28680
ttttaaggtt cagagtgcag agcaaatgcc taaaatcaaa aataaaagta gatgcactgc    28740
acagcacccc caccctcacc aacccccca gcacacacac acacacacac acacacacac    28800
```

```
acacacacac acacacgcca cagtgtctaa ctgctttctc ggtccctgct ctccccttgg   28860
catcgccaag gcaaaagttt tcatccttt tgctaactgg cttctgccct gtgtgtatac    28920
acttatctgt tctatcaacc accttcccc ttcacaaacc agatagcatt tcaaccagtc    28980
ccccaagaag aactcagtac tggttactca gtagctgaca tgctttctgc ctatggagtg   29040
catcgccagc tgcaagttcc aacaggatcc ccagggcctc cctgggctca tctgttccac   29100
ctcctgctcc ctcatgggct tagctcttcc agctttcttg ttgttcacac acactgagaa   29160
tgtagtcctc agtgcctttg ccattgctgt tccctccacc tggaatgctg ttccccacat   29220
ctctgctggg cagctccctc tcttccttca ggtctctgtt caaatgtccc cttcagtga    29280 ggcctttgct tcccactgca catgaaacaa cccccagcag tcactcaatc gccatgatgc   29340
cacatgctga ctttattttt ctttatagta cataccacca cctggcatgt aaatattta    29400 tatttgcttg attgtttact gtctatctct ccacactaga atggaagctc tatgagaaaa   29460
gggcctctgt ttgcttcact ttaccatcca cagggcctag aacaggccct gactgtcagt   29520
cactcagtaa gtcattatgg gctcgataaa aatgagttgt cataaacaga gctgcttccc   29580
tccattcact aatttgtttc gccctctgcc tctgtatgtg tgtaggcata tgtattagtg   29640
gcaaagcctt ccaaaaaact agaatttgtt taaatcttca acatacaaag aatcaggatg   29700
ttattggact tccttggatg atttacagt tccccactgt tttaattttg aattaaatca    29760
tattggggag agcactatat cttttactg ctttggatcc cagacaaatt taatccagcc    29820
cctggaattt gtgagtgaga tgcccaggag gggaagcaag cccaaaaaaa gaacagggaa   29880
acctcttcct ctaaacccaa gaaaaaggga gagaatgtga gctctttcaa aagactagac   29940
cttctgaagg aaaacagagg aatttctcag ttgatggagt ttccagctat cctttgccca   30000
gagctggggc ccacactgtg agaggagctg ggttcaaagc ccaactttgt gtgtgatctt   30060
ggagaatgta tgtaacacac tgcctcagtt tcctcatctg tacaatgaag atgcaataa    30120 tagtactcat ggctttgttt aggatcacac ataacagtcc ataaaaacac ttaacataat   30180
acttagcaca cggtaagtgc tcaaagagtt agctactatt attattaaca acataagaat   30240
ggtcacctac cacagaaata gcaatggaag tgtttgttag aggagtaaat gcagtcagtt   30300
cagagagctg agactggaac ttaatggggt agggtggggt gctgctgaac tacccagcaa   30360
ggactcacag gacagggatg caggcaagac aaatcatttt ctgagcctca ttattagaaa   30420
cgctgtgtct aaatcaaggc agggatagct gcataaacgt gataaacaag aatttgtgca   30480
aatgaagctg attcagattg ttaaaaatct ggagaaatgg agaaatttgg gcccaaaaaa   30540
gaacaactgg gatgtcatga tagctatgtt caactattta aaggcctgag atgccaaaaa   30600
ggaaaaagat ctggaatgtg cttctcagaa aggcaaaaga tgagagttgt cagaagacag   30660
atttcagtaa gacatgagaa caaattgtct aatatttaga attgccccta agtggaacaa   30720
ggtgccccgc agtttaacat aggtatatga gcatctctca ggaatgtggc aggaggatta   30780
ctgtattagc agggaactta gaccaaatat tttctcctgt agctttgagt ttcaattcta   30840
aagatgtaga aatttgttta ttgtatattt ctgtggatta atttacaaaa ttcttcttgg   30900
gatttaattg acatcttttt aaatcagtgt caaataaatt cccaatatga ctgattattt   30960
tttaaaaatg aacagtaaga catttgaatc tatggacagg ttttcttttct ctctttctct  31020 caatttcctt tatgtaatta tttatggaat aatctacagt gggctaagat actaaccatt   31080
tctggttaat gacctttat tttattctt ccatttccat atatcaatat gtaataaagc     31140
cttattaatt aagattaact tgaggagagt tcatttgaat tattaggaag tctggcatat   31200
```

```
agaataattt aaaataaacc caattgaact tcatgaaca catagtaaag ctcaaatggg    31260
ccaacctccg gtgtcttcaa cagacacccc ttagggaatg gttatgaata actcagaaac    31320
cttttaatta gcatatcttt gttcatatgt aaatgtgtgc ttttggaata gttgaggtta    31380
tttaatacat tctgctgact gaaatatttt aaacattccc tttacaattt attcaaccaa    31440
ttgttattga caacttcat gtcagggagt gctgggatta cagcagtgag caaagacagc    31500
cctgactcct actttcctag acctcacagc tctacacaga aatcaatcag atcacgcata    31560
cacaccaata aattgtaaaa ttacagctgt gatgaggact atagaggagg gaaacatgga    31620
gctataaatt ataagagg ggatttaacc taatctgagg ggttcaagaa ggcttccaca    31680
ggaaaggaat gattgggata agacctacca gagaaataac tattaaccaa ctaaggagag    31740
agggaaggaa ctggagaaga tgccaggtgc agtggctcac gcctgtaatc ccagcacttt    31800
gggaggccga ggtgagcgga tcatgaggtc aagagatcaa gaccatcctg gccaaaatgg    31860
tcaaacctcg tctctatgaa aaatacaaaa aaattagctg ggcgtggtgg cacgtgccta    31920
cagtcccagc tacttgggag gctgagtcag aagagtcgct tgaacccagg aggcaaaggt    31980
tgcagagagc ggagatcgca tcactgcact ccagcctggt gacagagcaa gactccatct    32040
caaaaaaaaa aaaaaagaa aaagaaaaag aaaagaacag aaactggaga agattattcc    32100
aagggaaaat ggtatcgcat gcaaaggccg tgtggcagta gggagtactg tgtatttaat    32160
attttaagaa tattaatatc tcaccagtgt gagaaccagt gatgagtgat ggaaaagaac    32220
tcagggacca gtctgcatag gaccatgcta aggaccctct tatttattca atgaatatac    32280
tttatcctta ttaagaaaaa tttgctaagc aaagaaaaat accagtgcta cccaaggcct    32340
aattaccaca gattttgagt cagtataatc taaaataatg ggttttagaa gttccacata    32400
actgacaaat gacttcaaaa ttatatttat tccaaatgaa tagcttccat tagactaaaa    32460
ttacataaac ctactaagat gtgtgaccaa atgtaaacag gggagaatga cattaggaag    32520
aggaaataga agcctgctaa gcttccttga tgcttccaga ttttttccctc tgatggcagc    32580 tggggtggaa agggaaatag ctcttccagc agcctcaatg atacttggag ccaaaacaag    32640
cttctaagcg ctgtaaggag agcatgccac atggacgagg cctgagctat agcgagagat    32700
gtcaggcttt gtccttccat gaacagtgcc tgggccagga caacctcgtt gtctcccaat    32760
aaggcagagc tggaaatcct catgctaacc ccaggctctc caaatagggc attttcaggc    32820
acagagtcaa cctctgcatg cactggcaaa cacgtcctgt aaaaagcacc agctccggat    32880
ggttctgggt tcacgagcaa ggtgttctga aggtcaaata ggctgcattc ctctatgatt    32940
ccaggctggc agtggacggg ccctttggaa ctgccctgac agatgtattt cactacccag    33000
tgtgtgtgtg cgttgccgcg gggatcggag tcactccctt cgctgctctt ctgaaatcta    33060
tatggtacaa atgcagtgag gcacagaccc cactgaagct gagcaaggta cggaaaaatc    33120
attagttcac ccttccatgg attaaaaggt tcaatgtcct tatatctatc atctgccgat    33180
tcttggggag gattttaatt aactatgagg gataaactca aggatcctta actatactta    33240
tgttcttaaa aatctccact cagtattaca tttatgagta gggttatgtc taatcttgtt    33300
aaagatgaca agacataaat tttattgctt cattgccatt acaggacatg taattgctca    33360
tctcagtaaa atatggacag gctgcaaatg gctatgtgac tgggtggcag ttcgcaatat    33420
taagaggcaa cctctcctta gtctctttag cttcagactg tggttgcaag tgtacaattc    33480
gatgtcctcc tctcgtggac tcagtcctaa caagaagcca caattgggat ttattggccg    33540
gcttgctgtg gggtggccat cccgctctga atctcccttt tgtcatttcc tgtatgtttt    33600
```

```
acaactagat gcctctagaa tttctttccg tcctttgtcg tatctagaca ctccatccga   33660
tacttggacc ctcttaggac cagcagcagg cactagagca atggtaggca aagagccctg   33720
ataacccaaa gccgtatgaa tgcaggagga gtgaggatgg cagacgagct tggtgctggg   33780
ccgtcctgca tatcttctct gcttaaccct ttgtccacag tgtcctcatc tatcaaaggg   33840
agacgcttga cttaaccacc aggtctcaat gtgtaaacca tgggacatct gtcacctgac   33900
atgatccact agagagaatt ccgtagtcaa aggaacttaa gcaacgctcc tgcaacatcc   33960
cactctagaa gacatcatcc actagccatt aaataagttc tgcggggggtg gggcgcagta   34020 gctcatgcct gtaaccccag cactttggga gattgaagtg ggaggatcac ttgaggccag   34080
gagtttgacg ctagaccagc ccgggccgca tagagagaca tcatctctgc aagaaaatta   34140
aatattaggg agttcaaagc agtgagccgt gatcgcacca ctgcactcca gcctgggcaa   34200
cagagcgaga ctctgtctct aaaaaaagtt ccgcagaaaa gatcctcatt cagttttgtt   34260
tcatctatct ttcccaagct tatttagcta cagaacctt cctcacctaa cacctatcaa   34320
gaattcgtat tctgtgaagc atcccaggca atgagggcta aagatctct aaactcgggt   34380 ctctgccaac taagaaacag cagttaacta tttcatgagt ttccaagtga caggtccttg   34440
acatacattt tctcatttga attttttaat ctccccaaca accttataaa gtaagtaaca   34500
caaggcctgt tttccaggta aggaacctga agcttggaga gattaaattg attttcctga   34560
aaagacatgg gtaatcaaag gcagaatcag gattcaaact taggttcatc tggctctttc   34620
catgacaaaa ccaacacatg gtagacgtga ccccagctc ctcctgcaac cctggagcaa   34680
tattttagga agacggtggg attcctgctc atagaatcgg cacctgaatt ttgctgtcat   34740
caaagaacat gcctgattcc accctgactg aaatactgcc tgcagttcac ctctctgagc   34800
tgagtttcct gatccacata acggagaaat aagaatccat atccaacagg gagttttaat   34860
gctaaataag acaaataata tggaaatatt accatagaaa tgtgtataca gaaatataga   34920
tgattatcta aatgctgatt gtatctacca aaggtataaa taggttacca gtactgctat   34980
tactaatggc ctagatttat caagcactga ctacctaaca ggaaggaaac tgggcatttt   35040
acatgcacta tctcatgcca tcttttcgtc atacttatca ttttattcc cattttacag   35100 atgagaaaac taaggcctga tcacaaagct aatagaaatg acagtcattt tactaaatgc   35160
tcataatagc tcattcagat aggtaatatt ctcaatactg atgaggaccc tgacacacag   35220
agagctaaat aatactagaa ctagagtttg aatctagatc cttctggcac caaagctcat   35280
cttctttcct ctacgccata atatatttaa caaagcaagc aaaacagtga ctgggatatt   35340
tggacctcac agcaatgctt tgttttggtt cgtgatgatt tttcagccac cctaagttct   35400
tccttccctc ttgctgccta ccaagtaaat cccactcaga gaggtggctc actgcttcat   35460
ggtttccacg acactaaaag tcacttcatg cttcacagga agatggtggt ggatagcgtg   35520
tctcattttc attcactcac taatccaact aatatttcaa gtcctgctca gagacatgca   35580
aagtctcatt gtcattacac ccgactcaca atcacctccc ccttctctta acctccacca   35640
ctcctttgct gccctactgt tatgtcacat atctttcctg tattaagatt cgtgaaataa   35700
tcttattttc tctaacagac tgtgagttcc ttgaacatag cttctctgga tatcttcata   35760
catatatata tatacacata caacatgtga taactatata tatagtaaaa atattgaata   35820
aatcaatgag tgaataaatg tctacatgtc caaaaagaat aaacaatggc ttctgtacac   35880
aattttcttt aaaatttaag ggtattaagg ttttgtttat gtaaccaaaa aaattcttca   35940 atgatttta ctaaattcca attatttac taggaatata gaggaaaaat cttataagaa   36000
```

```
cccccaaaaa ttttaaaatt catacaggag cctacaaaat cttaattttg cctcctttct    36060
cagcattcca ttgtcattcc tgggctctgc ttgtggcgtt tctcaaggct ttcagcactg    36120
cagtcaccac aaaaccataa aatagggaca ttgatctcta ttccaagaaa cagaaacagt    36180
agagtaaaaa atataaaagc aatgttttca tcgcttataa aaatgtgagg gactatttgg    36240
acacgactca ggtgaaaata agggcagaaa taatgtcata tgggagaaag gaagctaaag    36300
tgtggaatca taaaataact taaaggtcct aatctcctag ctttgcatag gaccatgaaa    36360
gtcagtatct gcacctcgag cggagatgat ttgtccaaag tcacccagct tgttcaccac    36420
tgagtcagga cctgagcatg tgtttctgat ttctgcttca aagttctttc atggaagaag    36480
tgaggttttc atgctattga aagtttgggc tgaaaattac agttcagatc caattcctta    36540
agcgtctgca ggcatgagaa caggtttagg aagtttctct cttttaaagc aactttgtgt    36600
tggtttgagt atagctacta ttaggcttat gtaactaata tttgtcaggg ctacctacat    36660
gcttttgaga tataaagact actccttcca ctaaactgtc agagtctata aattttttga    36720
agtgccacag agcaaagcag tacatattta tctaacggtg tcttcacaat tttaagtctg    36780
gactatagtt ttcagattgt cctcttttgt aataaggaag gaaaggacaa ctcgcatagg    36840
cgttgagagc cagaatttta agcttaaatg gttaactgcg attaggtggg atttttttt    36900
cctccatgtg taaaaacact ggttggcata aggcatacat ttttacacac aaaactcaag    36960
ttgcaagtct ataggaaaaa atgtgcacca aagttttctc aattgtcacc gttgcaaact    37020
agaacttctt taccctctc ctctgttgca ttattctaga aaacttctaa gtaaaatgca    37080
ggagcacaac caataaggcg cctgccactt cctcagtggg aagcgtcata agtagtactt    37140
tccatttgaa gctgatgtct taaaatatct ttgtttctaa gtacttttgt tttgaaagat    37200
ctgggagggg gcggggagtg aaggggagg gggaagaatg ggcaggaggg gatttcccaa    37260
gaaggccaaa taacaagaag tataatgatg gcttgctgtg atgaaaatgg aaaaagttg    37320
taatacatga aagaaatatt ttcaacgcag aagtaagagc caaacttcac tgagttgaag    37380
gcagctgaga acgctgtgcc cctgtgggat gagggaaggc tgagggtggt tgagaattct    37440
ctgtgatgca atatggagga agctgaatgc tgggggtgaa aaatgccctc tagcaataaa    37500
gtcctccacc tcctgcctaa cgggtatgat taattctaca tcacactcaa tttgtgaaaa    37560
gagctcttga aaaaaaatta ggacggtttg cttgtgcaaa ctgtcaaaat gatgaatgaa    37620
ataggtgtgt atgaatgggg agggaggggg aggattgctg acataaatag attggcttac    37680
acattttagt tctccctaat atcacagctg tgcagtcagg actgagacaa ctgccaactg    37740
caagatgcgg ttcgttttct taactgcata tgtagtcttc agactacgat acaacagatt    37800
atacaagaac tgagataatc tcatttcttc ataaattgtc ttccttcatc agctccataa    37860
tatataacca tgataatggg tatttatagt gtgtcccatg caaaatggcc tttgggttct    37920
taacctaata taataaacag ataattcaaa taaaagaca gcacgggcca gtgggaacaa    37980
gggaaagagg ccaaaaaaga caaaaaatcc atactctact aaaatatatt aataaaacaa    38040
aggagggcct gctctctttt ctagtgaatg aaaaatgcat ttaatttaat ctgtttactt    38100
tgagaaatta tttactttca ctttccctca cactggagct ctgactactc ctggaactga    38160
tcatctctac taatcaccaa gattcctgcc atcagttggc ctctttagga ggggccattc    38220
atgcttctcc taaagaaatg tatgcttctt gtctttcctc ggagggcctc aaaaggcctc    38280
agtaccccat cagccctcac cattgctctg tgcggaagtg accagtatta atatgtttaa    38340
tatcttggtt tattaaccac agattgcgtg actacagtct tcttgcaaaa gagtccaatg    38400
```

```
aaatacacaa acattttaaa atctcccttc acctccctcc ccaaactaaa cacctcccca   38460
actttgctcc ctaagaaact caccattaaa cagttgaata tgtctcattc cattcctttt   38520
ccatgcattt atatgcatat acctatacac attcatgcat aaataggggt gtgtgtgtgt   38580
agaaggcaga ggaagtgtaa tttgttttgt ttttcattaa agcataactt cgggcaccgt   38640
cagtgtcaat acctgatgat ctatttcatt ttgtttggtg tctttagagt attccatagt   38700
gtggataggc cacaatttat ggaatcattc tgctattaaa taatgttttca ggccaggtgt   38760 ggtggctcac acctgcaatc ccagcatttt gggaggtcga ggtgggcgga cacctgagg    38820 ccaggagttg gagaccagcc tgaccaacat ggcaaaaccc catctctact aaaaatacaa   38880
aaattagccg ggcgtggtgt caggtgcctg taatcccagc tactcgggag gctgaggcat   38940
aagaattgct tgaacctggg aggtggaggt tgcagtgaac tgagattgca ccactgcact   39000
ccagcctgga ggatagcgcg agactccgtc tcaaaaaaaa aaaaaaaaaa aaaaagaat    39060 gtttcagatg tttcagttgt ccaacaagga ttattaactg taattagacc aaacggaggc   39120
ccaaaagaga tcagtcctca gccacagggc gaagtagcaa tatagtcatg aaatagttaa   39180
cattgaggat aatcacattc agaaaatgtc ttaaggatga aaaattattg acaaagcctg   39240
gtcttggcct tataatggtt caccagaaaa acaattttat aactgtatca ctttaaacta   39300
gaacttttac acattaggta ggcttatcat taagaagaaa tatttcttct tttatttctt   39360
cttatttgct attgtattaa tccaggattc ccttaacaaa aacaaaataa aaaccaggac   39420
aataagagtg atcatttatt gaggaggtaa tatattttct aaacaccagt ctttatcttt   39480
tcacagagag aaattctcct tttggaaaat gatcctgatt cccctctatg cagagcttct   39540
gtcatcctgc tggtttcaag cttctgtctg ttctgttctt tcttttgcac agtgtggggt   39600
acagaggcgt gctgcccagc aggaggcagg tggcactgca agccactgcc cttctccttg   39660
aggaggcgat ggtcaaggtg gcccctggc tccctgtaaa acgcctctag gtgagtttag    39720
cacacaccga gcctggtgag gggcttcccc ttcatggagc acatcttcat gatgaatgct   39780
gagattctgc ttctgacact ggtgctagag gtcaagtttg gcttcccttc tcagtgacca   39840
ggagtgacca gtgggaacac atgccaagca aggcgcatgt ccctctttgc tctataatat   39900
actgtcttca ttcttcattc tctaagctcc tccaaatgac aaacaaggat agtaacaata   39960
gcagctaaca tcttctgagc acttactgtg tctgccagac gttgcattaa atgcttcagt   40020
aaaacatatc ctttcatcct cacaataacc tcaggagcta ttgttctgtg tttattgcca   40080
ttttacatac gcagtaatct aggttggagt taaataactt tgcccagtt gcacaagtta    40140 tttgcaactt ctacctgcat ggtgaagcca gcagcagtct accacagcag atgggcttca   40200
taggctcaca acgctgagct gttgtaccat gctacactat atcctaaacc tgtattcttg   40260
tgtacacttt ccttgtttag aggggttctg ggccataaat aaatacatag gtaaataatt   40320
ttttttctgt ttcattctct ggaaatttat tttggatata aagacataca gattgcattt   40380
gtgaaagtgc cctctgcctg tgttcatgga tatctattca agatacggca caagttttgg   40440
agatgtaatc gcctgaaagc atccaacttt gattagagag tctgagctct catagtaaca   40500
cagattggta gtgcttctca attcattttc tgaaactgtt tatcaaaatt tagcacagtt   40560
ccatttccta ctggccccag acctctttga cctggtccct atgtgctgct gaagaattct   40620
taaagagaag ccttggcttg ggaaaacatg aaaatgagaa gggacacaca gagagcccaa   40680
acttgtgact gtcgctcaga cccaagcccc ttgcaaatgg acatggctga gtttgggctg   40740
atcattagcg cttgggaatg atgtgaaact aaggtctatg acgggccaca tgcacacaga   40800
```

```
aaccctcaac gccatgacag tcccagagtg gtctcccaaa acatctaggc atccactata   40860
tctacaagaa tgtggctggg cacgatggct catgctggta atcccagcgc tttgggaggc   40920
cgaggtgggt ggatcacttg aggtcaggag ttcgagacca gcatggccaa catggtgaaa   40980
tcccatctct actaaaaaat aaaaacttcg tcgtgcatgg tggcacatgc ctgtaatccc   41040
agctacttgg gaagctgagg caggagaatc acttgaaccc gggaggtgga ggttgcagtg   41100
agccaagatc ccaccattgc actccagcct gggcaacaga gagagactcc ctctcaaaaa   41160
aaaaaaaaaa aaaaaagaa agaaagaaa agaaaaaaa gtgttggatg agtcctgtaa    41220
aaaaaaataa ttttattact atgaaagttc agaacttttg ttattttact gagaatgact   41280
ttctatttaa taaaatcttt taaagtaaac tcaggtattt ttggtctctg agatcagcta   41340
tgaaattctg aaaaggcatg ctttctacag gtagctgatt tcagggttgt tttatttttg   41400
gagactaagg tggggtgagc attggaaagc acagatcaca gagttgtagc ctattgtttg   41460
ggatacttgg tctctcattg accaggtcct ttctcatggg cgaaatgcag acttggaact   41520
cttatgtccc ttcccagtga gtgtccccca ccattagaaa gatgaaagaa agtcaaagta   41580
aatacctttt gcttctgttc aaagtcccctt tctttctttt tctgcctgaa acacttctac   41640
tgagcctatc cattttcct ccatagcctc ttacaccaaa gctgcccagt gtcacttaca   41700
agtcaattac ggagggaaaa acacacaaag ccattacgag gaagcaaaaa gtataaaagg   41760
cttgacaaac cctaaggacg ctgacatgca gctaggccac gagaaagtaa ggaaggattt   41820
ctatttgaaa agataaagtt tcatgtacgg aggaagctaa gatggggata gttttcaaga   41880
aaggacgact gggactagat ttgaaattgg aggattttt tataaagcaa atgttctggt    41940
ttattatcca tctatgaatg tgttttaagc atgttcctta aagaatggga aagagagaaa   42000
ataaatcaat gatatttgct ctatgcccaa tgccaactct gagatgaaac aggctaccaa   42060
ggccagggag gaggggtca tgcataggtg agcactgcat taattcagcc agtagatttt   42120
tcatttccac ccagagcaaa gcaaggcaaa atgaaagcta aggttttcaa agagtaattt   42180
agattaggca caatacaaag cgaaaagaaa gcagatagtg gtattcatca ccaacctcga   42240
atataaaatc caccctaac tggtctcctt tcctcctccc ccacccctcca taccctgggt    42300 ctattctcaa tacagcagcc agagagatcc tgccacctgc tgcgggccat ggaactccct   42360
gctcgccaac tccctgtgct ttcctgtctc tcggagggaa agtctacaac ggccccaaag   42420
ccctacaacg ccatggctcc cccagccctc ccctcgccca tctccttgct ctccccaccc   42480
tctctgggct ccagccacac aggcctccag gctcttcctg gaaaggtctc actcaggacc   42540
tccgcacttc ccaccatctg catctgcact tcccacctaa gcatttgact ccctcaactt   42600
ttccaggtct ttgctccaat gtccccttct catgaagagg ggacatgaat ctccacgaat   42660
tgatggttca tgtccatcca ttactgattc aacaaatatg tgttgaatgc ctcctatgtc   42720
tccagactgt tctactccct ggaattataa aagtgaacac aagaggccaa aaacaagaga   42780
gggctcattg agccccgtt tgaccattca acttaatatt gcaacacttc taacccgcct    42840
ggggtttctg catgcacttc tcaccatctg acataaccta tattctactt atctatcatc   42900
ttccttctcc ctctaagatg caaattttaa gaggacagca ttttttttg gccctgtctt    42960 gttcacttgt atagttccag agcacagaag agtctggaca ggtaggaagc actcaataca   43020
tatttgttga atcagtgaac ggatggatga acgtgagccc cttgctcatg ggattcaga    43080 gggtgtcaca aagggaaccc cggcttagct ctgcctggag aggctgtgca gagatcatcc   43140
ctaggaagaa ataagtgtca ggaaaggaaa ggcaacccctc tctcttcctg agaaaagcag   43200
```

```
gtcattgtgc ttagagactg agggattatt tgtcctgaaa ttagtatctt aagtcccctt    43260
gtgaacagga gctgtccaac aaatatgtgg gcccagtttt tgaaagaaga ggccttattc    43320
tcagcatctt ttactcttac aaataattaa tattataaag tcctgcctaa acatgaagag    43380
aatagacaag atgtttagct ttgagataaa cttttttatt tttgtctcat gaatttgatc    43440
tattcattaa atctcattta tatctctgat tatatgatcg tgagcttaca agctggccgg    43500
cagagaggga gagaagagaa cattgatcac tggatgaggt atttccaggt ggggatttac    43560
caggcagcag ctggaatcaa gaccagccct catggatatt gttaagccat acagatgtct    43620
ctttggggag aaggcacgag agagagaggt gtgggcagca aggggtggga gtgtgagaaa    43680
aatgggagaa ttaatagatt tatctcctgt ggtttcttct agatgcaatt atttgaaact    43740
cgcagcacaa aaactaagct tttattttag caaacccaag ctacttttg tcacatgcca    43800 tttgcttaat accgagagtt aaaaaaataa ttcttcccag tcataatttc attatagcag    43860
ttgacacaca ggcacagccg ccacccacca gctttcttgg acaccgatat gtttcactga    43920
gaggaaattt ctggcctgtg tgacttgatt ctgaaattac cataatctcc actctccaga    43980
ggccgtagct agtgaagtgg attagtgtcc aagcctttgg ggtctctgga gaagaaagtt    44040
caaatccaga gcttaggtca taagtaaaga tgaaggggtt ggtctaacgg tttatccccc    44100
tttgggagca gtgaaaggca cagctagtta tgattattaa tcttgttcag aagcagcaca    44160
gccagaaatg tggtgagttg atcctcatcc agagaaactg gcacggccca caggctcctg    44220
actctctgaa ttcactctgg cttttttcaa acacattgtg aatttttca aaagaaatca    44280 cagtgtgact gttttgttcac tgacacacac aaaaaaaagc atgttatttt gcagaagtgc    44340
ccatttgggc tcaaataatt taatggagat aaagtagtct gtgattatca gcacatatga    44400
aaagagaata gatccgttca cttgccttct ctcttgacag gtgtatttct actggatttg    44460
ccgggatgca agagcttttg agtggttttgc tgatctctta ctctccctgg aaacacggat    44520
gagtgagcag gggaaaactc actttctgag ttatcatata tttcttaccg gctgggatga    44580
aaatcaggta ctgataagac tctgagaata agcaatattg ctgaactcat ctaatagcaa    44640
tgaggaacaa tttcaataat gagctatgta gcactctgat agcatgacag aattattttt    44700
atgttcttaa aagggaaagg agaataaaat aaaaccagat tagcaagagt gattcaagtt    44760
gtaacaatca aagaaccaaa aaaagaagct acagttaact tgctgaggaa tagaaagggt    44820
cagacaatgg aagacaatcc agaggctgga aatcccaaac aaatttgcat ttgtcccttt    44880
aaaagtgaca tcaaatgaat attactgatt ggctgtatca tcttgttgag ttcctgactg    44940
gttctgtttc tgtgccttga gctgttcaga gctaagcaaa aaagattcct aggtgtttac    45000
attcaacatt ttgtattgtg aagtatgtga gcatctatag aaaataatta ttatgaatac    45060
atgatttgtc cagagtttgt tctcttaagg tgttcttaga aattgtgtgc acgtatgttt    45120
atttacctaa gatgaagatg atcttttgtt ttggcaggtg ttctgcagta tattgtatta    45180
atgaaatatt aagattgaat ttaccaaaaa taatgtatac caaaatattg actatggtag    45240
tatttcaatg ttgatactat tgaatgataa ctactacatt gtaatccatt ttaactcctc    45300
aaacagggga attaacaacg aagtgattac taggttacac aatatatatt ctaatcagca    45360
gctattattg atatatactt ttaaggaaag tgtatttgag cctgggagat tgacattaat    45420
cactacattt acaaatgaat gctctgtgta tgtacatcac acatacacac acatgcgtgc    45480
gcacacacac acacacacac acactggcct tatagaacat cactgtaatt tgactctgct    45540
tctgcaaatg aataagactc tgctagaaat tcagtagctt aatgaatttt tatggtctta    45600
```

```
tttgcagtcc ttcttaaata tttaatcctt tgggataatt tgaaatgtag ctttcttggg    45660
aactaggctt gaaacatctt aatgaattat atagtgttaa ttatgttttc caaacaaaca    45720
ctttccttat tcaagtggga ttttttgactg atgaacagtt tggtgaagta gagacagctt   45780
ctgtcttctg ctctcaagta ctgtgcctgc tcttctactc taaggtgcat tgatcccagt    45840
gtgcacctag gtattccttg ccaactggga gctgtgggac tgaggttctc ataactgaga    45900
actgaagttg atttggcgac aacacaatcc tgcccctcc cgtctctact acttccaaga    45960
atatgctata aaacatatat ttttttttcta aacacaagta gattaaaata gatgtcttac   46020
atttttgcca tgacatgttg aaaattattt cgactcctaa atttcaggca gaaaaatcac    46080
taatttccac atttaaagga aaaataattg gtgcattctg tcgggaaaga atcaagaggc    46140
tgttttagaa atacccaatt gttaaactga attcaacaac ctcaaagtgg caaaatgaca    46200
agaacagaag ggacagatgg aagaggtatt gtgaagggta aatcaacaga gtttggagac    46260
taattgaaca ttgggctgag aaatatggga caaatatcat tccaaatgtt tgaacatcag    46320
tgattggcgg taccacaagt gtaagtaggg aaggcccttt ttgtgtgtga aatggtgccc    46380
gaacttctca gcaaggacct taagacccctt cccagcctga ctcccactca ctagctgtgt   46440 cccacccca tcggtttcct ctggcaccag agccaccaaa ggatgcgtgt tcacccatca    46500
cactgtgcac agtcacacgt ccatggcttt gctcgttctc tccccacacc tggcgtgtca    46560
cttaacaccc tctgccactg ttccccacct tcttttgct cggagtccta taccccaact    46620
cttttccagc agtagctctg ccacctggtg tcagacttgc ctgctcacaa cttcctacga    46680 cctggattc tttttatatt ttctttattt tttagattca gagggtgcgt gtgcccattt     46740
gttacatggg tatagcgcat actggtgggg ttacccatta cccaaacagt ggatatcata    46800
cccagtaggt tctttgtcaa ccctcactcc cttctcaccc tccccccctt ttggagcccc    46860
cagtgcctgt tattcccatc tttatgtcca tgtgtgccca ttgttgagct gctgcttgta    46920
agtgagaata tagagtattt cgttttttgt ttctgagtta gttcacttag gataatggcc    46980
tccagctcca cccatgttgc tgcaaagaac atgatttcat tcttttatg gctgcatagt     47040 attccacagt atgtatataa cacgttttct ttgtccagtc aactgttgat ggacactcag    47100
gttagttcca tgattttgct attgtgagta ctgctgtgat gaacatatga gtcttttta    47160 tataattggc ctggatttct gagatctaac ctaccattgt ctcctgacct gttgggacac    47220
ttccactatt ttcagctgaa cctccctaga ttcaactact tttttagact ggagagaagg    47280
tcagccagga aagtcaggct tacagtggga acctggggca tgagttgcac ccagcaaggt    47340
tgttagccaa actggtcagg gtcaggatga gtcagagggt gagaatgaat agagcaccac    47400
ataggggtct aagggatgag cactgggaac acagatcccc agaagtgaga agcaaggtag    47460
ctaccagaat gcagaagggg ctaaaataaa tgacagcaac ttaaaacatg atcatggcca    47520
ggtgcagtgg ctcatgcctg taatcccaac aatttgggag gccaaggcgg gtggatcatg    47580
aggtcaggag atcgagacca tcccggctaa cacagtgaaa ccctgtctcc aataaaaata    47640
cacacacaaa aaaaattagc caagcatggt ggtacacacc tgtagtccca gctactcgag    47700
aggctgaggc aggagaatcg cttgaactca ggaggtggag attgcagtga accgagatca    47760
cgccactgca ctccagcctg ggtgacacag caaggctctg tctcaaaaaa cacaaaaaca    47820
tacaaacaaa caaaaacaaa caaacaaaaa tgatcacaag ggattatgct gtgggctgtc    47880
atttattgac cactagctac atgacgcctg gatggagttg cttaattcca aggcaaatga    47940
ttaggcacag atctccagcc aagccgcctg ccaggctctg gccaccattt tccgcctgcc    48000
```

```
aggctccaca tcctcccagc acttgaaact ggacagtata catcacaccg tttaaaccca   48060
ctaggcaggt ctcattgtaa gatgcagttt cttcccagac atttcatacc actttaatct   48120
ggcaatgccc ttctcaactc cccaggagcc aatgttaagt gaaggggat agcaggtaga    48180
cattaattgt tgaaaagttt ggcaggaaaa gaaggaagtc gtttagtgct tgctttctct   48240
taaccacatt tactatatta ctttcatcct tttaaaggaa aatattcttt ctaggttaat   48300
gttattgcac atctactagg tataaagagg cacttggttc caacaaggcc tgattcagac   48360
ataaatgaga tatgatgctt gccctaaagt gcagcattgg agacatctgc aaatagtgat   48420
aagcattgcc agccctgtac acatttttaa ttaaatctac aaatgaacat gattacttta   48480
ttctttattt atagaagtct tatttttttt ttctaaatgt catctaatgc cacaaattta   48540
ctttaggctc ttcacatagc tttacactgg gacgaaaata ctgacgtgat tacaggctta   48600
aagcagaaga ccttctatgg gaggcccaac tggaacaatg agttcaagca gattgcctac   48660
aatcacccca gtaaggcaa gctcttgctc ctctccctgc caggctcttc tctgagaaa     48720
tgcaagggct gctggagtga aaagttaatc tgcagtaccg tatatctcca ttagagacaa   48780
aacatctacc ttagaaaagg tgatcaatgg tatatttcag gggccacaag cctctcctga   48840
actggcttac aacctctgac agttattgat tatgttgcaa ttttcacac ttaacctcca    48900
tttaaagatg gtatttcttc aactacatat gctttcaaga catctttggt gggtacagtt   48960
gatctctaat tacccaactg gagaattcac tcctgtccaa ctgtacacta tctagcatgt   49020
ctagcaaaag cagagagaaa atgttagaag acaaagcagg gatttcgggt ggtggttaag   49080
aacccagcat ctggctgtaa atcctggttc tgcctttacc attggttgac cttggacagg   49140
ttatctaccc tggtactgac tctgtctcct cctctgcaaa ctgcagaaaa taatagtgct   49200
ttcctcctaa gagtctgcaa ggataaaatt aatgaatgca tgtaagaggc ttaaaacggt   49260
gctttgtatg gagtttgcaa gaagcactag ctgctatcac tgctattatt attttattta   49320
tcgtttccat tattactatt attattatca ttatataata aatttcaata tagaaaagca   49380
agaatacttg ttctggggtc acaaaactga agtgaagcct gcacttcctg gttctagaag   49440
ttactggctg tgtgaccttg gaagaggcag cttatttgag ctttcgcacc ccattgaaaa   49500
atatggatga taatatccat tcacagtgtt gttttcataa cgtaaatata cttgtagtat   49560
ggggcactaa tgcaaacagt tatcattgtt atgatgtctc ctaagtcagt cttttgctttg  49620
aaccttcatt gtctacggct cttaaaagtc ggcatgtcct aatattgtct tcattaaaga   49680
acagttccca tatttgagga aagatctgaa ggcagtgaag gagtgtgcca tgtgggcaac   49740
tggagcatgt gccaaggccc tgaggcagga gacatcattc ctggcatgat cccagaacag   49800
aggaggtgag agggagagca gcaagagcca tgctgtagga gaggtaacaa agacagctgc   49860
gagtcattgt aaaactttgg atttttattca cacaggggaa ggcacttaca ggtttgagca   49920
gtagagtgac gtgggatcac tctgcaagag aatggaacgt gaggggcctg ggacagaggt   49980
ggagaggcca gagaattcag cagtggtggc agtttggatt agggagcagc agaggaggtg   50040
atgagaaatg gttagattcc ggagtctttg cgggttgagc tgaattgact atggatggga   50100
tgtgaggtgt gacccaagct attcaataga gtggaatccc cacttaccat atggtgatga   50160
ctttaagagg agcagctggt tggcagacat ggggtgtcag gagttcagtt tgtgacatgt   50220
ttagcttatg atgcctgtca tacatccacg tggaattttg gagtgggcag atgaatataa   50280
gaagcaaacg ttcaggggag aatttcagcc agaggtgtga gcacatggac tgtttggagc   50340
cgtgaaactg gatgagatga ccagacaggc agatatagat ggacaagagt tccaagaact   50400
```

```
gcactgttgg atggtcaggg aacagacact gtattgacag gtcacagagt ttaatacgtg   50460
acactcatat ctgccttaat aatcatgccc cttgggtctt ctataccctg accttctttc   50520
catccacttt ctctgtattg caccagtaag agtacattaa agcccactaa ggtacctctg   50580
actgcttcca tatccccggc gatgttccca ttgtcttgca tccttcaaag cctcagtcct   50640
tgcatttctg cctcgtgggc ttcctgcaga gacagcatgc ttcattaaac tctttgtact   50700
tccttcatat ttgttctgct tcacagagta ctttctctggt gaatattatt tatcttatgg   50760 tcatttggc tgctccttttt taacatttttt ttcacactct ttctgtacca gaaagatgcc   50820
attttctttt ttatcagttg tcatggaatt cattagactc cctggaccag ctatttgaag   50880
gaggttaatg aggagggaga tgtggaagga gtgatcaggt agctgtccaa gattcataac   50940
catctgattc cagtcaccat cttgcctgtg aagttactca gacctcaact gccctgtgct   51000
ctgtgagacc cctgccaacc ctctctgcac cctgcaccca gcaacctgta gagaaacagg   51060
agtgtttaca ccctgggaag agatggtttg aaggcatgct tgtggggatt actcctgacc   51120
cacattcagc cagggagtaa aggctttcca gcaggagacc ccaagaaaag catcactttg   51180
agcatagggt tggggaggga gggcgtggac cagctgcaca acctcacaat cttgctcttg   51240
ccccacgggg ctcattctga tgcctcataa gctgtggcag tggccttgga gacttttcca   51300
ggtgtcactt cctgacacct ccttgctcca ttttgcttct tgccctgact cctgctgaca   51360
tatggcctag aatccagttc tggttctacc ttctctccaa atgaggtgct tccaacccat   51420
cctggcttct gcagccacag aatccggttc tctgagctc ctgctccaca cccagccctg   51480
gctccagggc ccccagtgct tctgagtcta agtcaccaca cccacctcac acccacccag   51540
aggagagacg agatcatttc atctgccatt tccttgaaaa gattgtaggt agaaactaac   51600
aaaatattaa aagcttatat gagaaaactc aaggggtttt tgttgctatt ttctcctttt   51660
gggaaaaaaa aaatatatat atatatatat tcactgataa atgttttacg ttcggttttc   51720
agtcatcatg gaataaatgt tctcacttcg caggcttttg acatggacat ctatatcttg   51780
gttttcagtt cttctagata gtctcagtct ttattaggat tgtccctttt tgacatctca   51840
tatggtgttt gtttgtttat tatttatta tttatttatt tattttaca cacaaagctt   51900 gcagcccagt gcggaaggcc tttaaaacca aactatttaa ttatctccct tccctcaaaa   51960
aggcatgagc caggaacacg gagcatcaag agaccaagga taaaactggg tttgcacaaa   52020
ctctgcctag aaaattatgt aactcagtgc tgagaagtgg gcctgtccaa ttttttcgca   52080
gggagtaaag agtaatcagt tttaaggtgg caaaactgta ttaccatcac tttccctgtt   52140
gctcatacct ttctagaagc cataatcaaa gtgaagtgcg gaaacgtact taatgctcaa   52200
ttgtattttg cagcacggta gctatgcaaa ctctctctcc ttgatggatg acttcatctc   52260
ttccagagta gacgaggccc ccaaggtttg gaatcactga atcaaacctc tacagcatac   52320
ttcccagtcc caaatttttt aatatcatat ttgtaatagc cttagactct agaacatggt   52380
aacttgttat atagcttcaa gcatccatgt cattaatatt agacacatga aggcaaagtc   52440
aatgattttg tccctggaat gccagatccc tgggaaaaga caagccttcg gtcaaaagct   52500
tagcaccacc ctttcaaaag gcttttaaaa tgacctcctt aaaataattt tgttttctgc   52560
tgtgtaaaag gagatttatg tttaatgaag ctttttaatga agaaatctcg gaaagagaat   52620
gccaataaaa tctaattttt aaacaagaaa atctaatatt gagaagtatt tcaatatcct   52680
ggcctttgtc cagatgtaaa tgaaacacac aatccaatta ctgttctgca caaaggacaa   52740
agtaacatta attttcctcg ggatggttat taaagagata aacagtatgt tttcccctta   52800
```

```
ttatgtcaag gatatgtttg ttcccaagcc tgcctggcta ctcttacaag acggttctgt    52860
cctgtcgtta gctcatatct tttggcaaag atgggtcaga agaaattggt ggatttgtta    52920
gtggcctcag aaaaggttct ttgttcttga gggcctttga agtaggctct caaccatttc    52980
tattcatcga cacgaagccg aggattctcc ggacttactc tttcaaaaat atttacctgt    53040
tcactcaaag ctggagtttg ttcttgttct aagaaggagt taaatcaaaa gaataaagtg    53100
aagaggggca aaaagatttt ttatagaaca tgaaaaacag gaccaaaaat aaagcttgaa    53160
gggaagcaga tcaaagagag tagtacaagc tataaaggaa ccagaaaatt gcaaaaataa    53220
cagtaataga gaaacaaatt gatgggcatc aaaatgaata caaataaggg agagagaaga    53280
aaaattaaaa atagatcaaa ggctgacaga aaatagaaaa gtgtgttcta ttgttttttgt   53340
ttgtaattaa ttttggtaat tatattagct atattacaaa aacacaagta tagttttgaa    53400
agacagtcaa caaatattaa gtggatgcat tataagcctt ttattgatat attcaaattc    53460
acatgcatgt gaaaattgta tagtatttca gttagataaa gcacagaaaa gtactatgaa    53520
acaaaaacat taaaaattat tctcccaatt aaaatatagt aggctaatta aatacattca    53580
ttgccatcta tgtcttacta atctagagaa aggtatcttt ttcaaaaatg gaaactgtat    53640
tgcattttttt gtaaacattg tcaatacgtt cacaagcttt aggtaaatgt tcagaaaatc    53700
aggaaaatat ttccaagaag gtagacagaa tgaaaataaa ataccgttg tcacatctag     53760
ttactttttt gataaacaca cattgtacgg atactcagct ttctgaattt gtggatcagt    53820
tgcttttaat taattgaata aaataatttt ccataggcct taaatctttg atcttaccct    53880
tcagataata tttgtagttt tctacttttg acctatctgt taataacttc accacgcctt    53940
ttaggtgtaa atttgatgta attaattacc ataaaaactt taaagtttgg tcattttttt    54000
ttttttttttt gtaatttcag tagacgtatt tcttttaact ttgaagaaaa aaaaatagaa   54060
gagtactacc atttgttaga acagtttaac ccaacctaac gatgaagaaa ggtgtcaact    54120
taccatatga ttgggggctt ctaatccata ttgcatgaat gtattttaga ccacctattg    54180
ttttcagaaa cgtgaaaata cctttatact aaattgagta aatgtgtcca tctggaccca    54240
catttgcttg tgtatgcacc cttcaattct catttgtatg tgcatatgtg caaaatgttt    54300
taaaatgata ttttttaagaa attagcattc tgattatagc atacagggcc ctttatctaa   54360
caggatatcc taaacattca ttatgtgact aaaatgttca gaatactcaa agaaatagac    54420
ttaaatggaa atacaacaca tgataagtta cagcttcatg ggaaaaataa agacaccata    54480
aacttatgat gaggaaattg tcagcatatt cccatagttc cttcccatga gagggcatca    54540
atctctctgg ttagacccaa gtgaagattc aataaaaatt gctgaaatta ctccatttgt    54600
ggtagggggg attggagaga tgggtgagta cagggtggat ttatcattat actgcaaaat    54660
ttcttcaatg gcattaccta tctatcaaat tattagtttg gcaaaatatt tggttactta    54720
tgcatgaagg catatatatg ttactgtttt attggggtgg ggaagggttg gcaaaaatgg    54780
ctctaccatt ccctgggatc ggatgctaca agtcatctgc tttcatttttt cttccccatt   54840
tgaccataag cttctcaagg gcttatagct ataagcaact ttatctatgc acctcagagc    54900
ctagcaaaat ggccagtatg tgcaagtggc agcaccatga gaccaatgag ggagctggga    54960
caagtgtccg aacagcacag ttctggctgc caaagaaaac agagcctgtg gagtgtgggc    55020
aggagcagaa tcacaacagt gagcctggtt agggacatct gcagcaactc atgagcaact    55080
gagtaattag gacacagaga aaagtaatgt cgtaggctgc tacaaattaa ctgggagata    55140
ggttaaaaaa aaaaaaaaag ctggccagca caattatcat ctgcggttct gaaaaagaa    55200
```

```
ggtgttgtac aaaatataat tatgtgatga atcatttgga ggcatttcta atgaaaaaca    55260
ctcactagaa aggattaacc agaagttgtg tccattgtct gatacagagt ttgtagctct    55320
catcttcttt ctaagcctcc ataaatccac gggaagcttc tgtttatcga ttttatttgc    55380
agaatgcact cagggtataa agtaatttgc ttttttttaa atagggttta gggtctgccc    55440
ctacagggtt ataacttacc aagcataaaa gccaacacat aaaacaaac atacaattta     55500 aggagagaag gctcacggc agcagaacct gggaattcag cgaggtggtg ggatcactcc     55560
cgggcgcacc cacacgccca tatatctgct gggctgaaat ctcctggtgg gtgatatttt    55620
ggatgccttt catgcatggc atcgctgaac tgttttgaa aaatgcacca accccacaga     55680
gaagagcaca atagttattt agcagacata gagagggaaa ggagaatttt ctttattgtt    55740
tatcagagct aaaaataatg ctgtgaatgt tagccatctt tgcagcttgt gtaaaatttg    55800
tccttttctc atcaaagtca gcagcccaga ctgatcaatg ccattaacat tgtccccgat    55860
ccagctcccc catgcgtgtg caagctctgt ggcttgcagg ctgtaaactg aagaatagca    55920
ccttgcgttt ttatacttct tttgcggaga atctctattt aattccaagc gattgtgggt    55980
aattaaattt tatagaagaa ttttttcttt accaacccca ttagggttct gttgcacttg    56040
tccgttgcct cataaaagaa aaaaaaaaa gggaagctgc cacatctgtc ccttaaacac     56100
ttggcttgga ttctctgccc tgtgattcac agtatgcatt tgtgacaaga agttctccat    56160
acttggagtc acaaatgccg agaagagtaa gccaggcaaa ctgcttgtgc tgtctgtggg    56220
gacagtgatg cacagagagc cagtgaaggg ctgacctttc cacctttagca gaaggtagat   56280 aataaatggc cttttgtgaga ctttttggtg attgcatcac cacggcggat atggcccctg   56340
agtaaagtgt ggacttagct gtgcagtgtg atagccacaa cttcaaaaga ctcaggggag    56400
ctgtgaactg ctggggacac caggagaaca ccaggcagca gcaatcagaa tcctttgaaa    56460
tggagtctta aaggcagagc atcaagggc accatcaggt ctgcagttac tgttgctgca    56520
aacgaaagag cagtcttagc ccattggagt gggccagtgg gcaatctctt tggtgacatc    56580
tacactaatg gaaaaatatc accacccata acagcatctt tgaaaataga tgcaaggaca    56640
cctctgggca tcagacacaa agcaaagctg tgactcctca ctgggaaggg tctcgcctga    56700
tccatctacc attcaaaatg tttcagtcca gagctcaaaa atctagtgct gatctcagta    56760
agtctacata atcacctctg tgttaacacc ccgcaccacc tcttctgttc agcttcacgg    56820
agcaggcaga caccaatagc catcgcgtgg gaaaataata tcaggaagct agccattcct    56880
gagagcacac catgtgccaa gcacaggacc agcggccaga cctgcaatgt cttgcttgat    56940
cctcacagag attctcggag ctagattcta taattctccc catttttatag atgagaaact   57000 gggggctttg tgaaggtaat tgacatgccc aaagttaccc agcaacgaag tggtggagcc    57060
aagagcactc ttaaccattg cctttattt ccataaacac ctcaaaatct cttcattaag     57120
ccataaactc atacctttcc atgggaaata ttttctgaaa aattactttc tcaaatttag    57180
ccatgggaat gatttctttg aaagtagtac tgctacattt taaacatatt gtcatttgta   57240
aattaagcca ttgataagtt cctttgaagc tggagtttga aatgcagggg aaccatcaat    57300
ttctactgtg gatgtgatgg tcctggaaca cacagttaaa atgtggctat gacacatggc    57360
agagaaccat gttaacatat gagctaagaa gaactaggct ctataggcac ttcccagcaa    57420
gatccatgtc tgaagaaaca gagatggtat agtgagctgg tcctgaagcc caaagaatgt    57480
cttgatgaca gtgtttctca aagtgaggct cacagggcga tctgcctcaa caccacccga    57540
gatcctcact aaacatgcat tccttggatt cgagcctagg aatctacatt tcaacaatct    57600
```

-continued

```
gcctagatga tttatgcac agtaaagctt gagaactttt gatccacact agagtaacta    57660
attcagctta tactagagat tggaaaaaat gctacaaaga atagtaatat tcaagacaag    57720
agaaaaaaga catggtctct aaaaatctct atagagactg atgcaccccca acttccagaa   57780
acaactttga aaccctgtgc agatgtggtg tttatatgta ggctaagttg caaggcattt    57840
gagcagctct gggatagcca ctatatgcaa aaagtatctc tctgacatag ttttctgaaa    57900
tgtcaagatt agagatgaca acgtttgggt gactatattt tcagcaatgt cttttctttt   57960
tccagctctc ccttctggcc ttcttgtgaaa attaaagtaa ttccaacagg agaaattaat   58020
taaattgcta ttactttagc attaatttta ttatctataa aaaggcaggg ctgaacagga    58080
tattagtgat aactaacctt tttaaaaccc ttttgaatgt attatctcat cttgcttttg    58140
ataaaacata caacgtagtc cttatcatct tttccacatg cagaaactga ggtcagtga    58200
cttgcccaag accacgcaga tactactcag gaaagccatt tagtcattca ttcagcaaat    58260
gtgtgttgat tgtccactgt atgccaggca ctgttccagg tgctggaata aaacagacca    58320
ggtttatgtt ctcaggaagt taacatctgg tcacgtatcc aagaagacat gaatcaaggt    58380
cacctggcca aaaaggaggt caagtccagg cattgtgtaa gtggctgcaa tcatataggt    58440
cagggattgg gaaactcttc ccataagggg ccaaatagta atcattttag gctctatgga    58500
ctgtatggtc ccactctcaa ctactgaact ctgccattgt aaagtgccaa cattgcaggg    58560
tgttgtatca aaccccctca acagtttcat ggcccctttc cagcctcagt cttcttggct    58620
ccacctccct gattaattta ggggaggatg ctgggaacct aggagagagc atggtgctga    58680
aagtaggtag aaaaaaagaa tctaagaaaa aacgacatgg agggagaaaa ataaataagt    58740
aaagccacaa ccacttcatt aatcttatca ttgtcttggc ttctggctgg ccttgcctcc    58800
tggtgacatt ttatttcctt tcttaccccc tactgcagca gcagtattgg cgtgttcttc    58860
tgtggaccta aagctctctc gaggacactt caaaagatgt gccacttgta ttcatcagct    58920
gaccccagag gtgttcattt ctattacaac aaggagagct tctag                   58965
```

```
<210> SEQ ID NO 25
<211> LENGTH: 16
<212> TYPE: PRT
<213> ORGANISM: artificial sequence
<220> FEATURE:
<221> NAME/KEY: source
<223> OTHER INFORMATION: note="Description of artificial sequence:
      synthetic peptide"

<400> SEQUENCE: 1

Arg Gln Ile Lys Ile Trp Phe Gln Asn Arg Arg Met Lys Trp Lys Lys
1               5                   10                  15

<210> SEQ ID NO 26
<211> LENGTH: 18
<212> TYPE: PRT
<213> ORGANISM: artificial sequence
<220> FEATURE:
<221> NAME/KEY: source
<223> OTHER INFORMATION: note="Description of artificial sequence:
      synthetic peptide"

<400> SEQUENCE: 26

Lys Leu Ala Leu Lys Leu Ala Leu Lys Ala Leu Lys Ala Ala Leu Lys
1               5                   10                  15

Leu Ala
```